US012697330B2

(12) United States Patent
Burke et al.

(10) Patent No.: US 12,697,330 B2
(45) Date of Patent: Aug. 4, 2026

(54) THERAPEUTIC METHODS USING VADADUSTAT

(71) Applicant: Akebia Therapeutics, Inc., Cambridge, MA (US)

(72) Inventors: Steven Burke, Cambridge, MA (US); Ajit Chavan, Cambridge, MA (US); Zeeshan Khawaja, Cambridge, MA (US)

(73) Assignee: Akebia Therapeutics, Inc., Cambridge, MA (US)

(*) Notice: Subject to any disclaimer, the term of this patent is extended or adjusted under 35 U.S.C. 154(b) by 417 days.

(21) Appl. No.: 18/259,897

(22) PCT Filed: Jan. 7, 2022

(86) PCT No.: PCT/US2022/011666

§ 371 (c)(1),
(2) Date: Jun. 29, 2023

(87) PCT Pub. No.: WO2022/150621

PCT Pub. Date: Jul. 14, 2022

(65) Prior Publication Data

US 2024/0325360 A1 Oct. 3, 2024

Related U.S. Application Data

(60) Provisional application No. 63/177,104, filed on Apr. 20, 2021, provisional application No. 63/177,098, filed on Apr. 20, 2021, provisional application No. 63/135,316, filed on Jan. 8, 2021, provisional application No. 63/135,327, filed on Jan. 8, 2021.

(51) Int. Cl.

*A61K 31/4418* (2006.01)
*A61K 31/4412* (2006.01)
*A61P 17/06* (2006.01)

(52) U.S. Cl.

CPC ................................ *A61K 31/4418* (2013.01)

(58) Field of Classification Search

CPC .. A61K 31/4418; A61K 31/4412; A61P 17/06
See application file for complete search history.

(56) References Cited

U.S. PATENT DOCUMENTS

| | | | |
|---|---|---|---|
| 2016/0143891 A1 | 5/2016 | Shalwitz et al. | |
| 2018/0092892 A1 | 4/2018 | Smith et al. | |
| 2023/0071553 A1 | 3/2023 | Smith et al. | |
| 2024/0325361 A1 | 10/2024 | Smith et al. | |
| 2024/0335434 A1 | 10/2024 | Shalwitz et al. | |

FOREIGN PATENT DOCUMENTS

| | | | |
|---|---|---|---|
| JP | 2016521747 | A | 7/2016 |
| JP | 2018510178 | A | 4/2018 |
| TW | 201534302 | A | 9/2015 |
| WO | 2014200773 | A2 | 12/2014 |
| WO | 2016161094 | A1 | 10/2016 |
| WO | 2021087144 | A1 | 5/2021 |
| WO | 2022150621 | A1 | 7/2022 |

OTHER PUBLICATIONS

Pergola, P., B. Spinowitz, C. Hartman, B. Maroni and V. Haase, "Vadadustat, a novel oral HIF stabilizer, provides effective anemia treatment in nondialysis-dependent chronic kidney disease", Kidney International, vol. 90, No. 5, Nov. 2016, pp. 1115-1122, DOI: 10.1016/j.kint.2016.07.019. (Year: 2016).*

Haase et al., "Effects of vadadustat on hemoglobin concentrations in patients receiving hemodialysis previously treated with erythropoiesis-stimulating agents", Nephrol Dial Transplant, vol. 34, No. 1, Jan. 1, 2019, pp. 90-99, DOI: 10.10193/ndt/gfy055. (Year: 2019).*

Haase, et al., "Effects of vadadustat on hemoglobin concentrations in patients receiving hemodialysis previously treated with erythropoiesis-stimulating agents", Nephrology, dialysis, transplantation: official publication of the European Dialysis and Transplant Association—European Renal Association, vol. 34, No. 1, Jan. 1, 2019, pp. 90-99, DOI:10.1093/ndt/gfy055 (10 pages).

International Search Report for PCT/US2022/011666 dated Apr. 8, 2022 (5 pages).

Nangaku, et al., "Vadadustat, an oral hypoxia-inducible factor prolyl hydroxylase inhibitor, for treatment of anemia of chronic kidney disease: two randomized Phase 2 trials in Japanese patients", Nephrology Dialysis Transplantation, vol. 36, No. 7, Jul. 2021, pp. 1244-1252, DOI: 10.1093/ndt/gfaa060, (9 pages).

Pergola, et al., "Vadadustat, a novel oral HIF stabilizer, provides effective anemia treatment in nondialysis-dependent chronic kidney disease", Kidney International, vol. 90, No. 5, Nov. 2016, pp. 1115-1122, DOI: 10.1016/j.kint.2016.07.019, (8 pages).

Haase, Volker H., et al., "Vadadustat maintains hemoglobin (Hb) levels in dialysis dependent chronic kidney disease (DD-CKD) patients independent of systemic inflammation or prior dose of erythropoiesis stimulating agent (ESA)", Akebia Therapeutics Press Release, Jul. 14, 2020 (1 page).

Sanghani, Neil S., et al., "HIF-prolyl hydroxylase inhibitors in renal anemia: current clinical experience", Advances in Chronic Kidney Disease, vol. 26, No. 4, Jul. 2019 (pp. 253-266).

Wu, Yue , et al., "Small-molecule inhibitors of HIFPHD2: a valid strategy to renal anemia treatment in clinical therapy", Medicinal Chemistry Communication, vol. 7, May 25, 2016 (pp. 1271-1284).

* cited by examiner

*Primary Examiner* — Kamal A Saeed
*Assistant Examiner* — Sagar Patel
(74) *Attorney, Agent, or Firm* — Proskauer Rose LLP

(57) ABSTRACT

This invention provides methods for the treatment of anemia in patients with chronic kidney disease (CKD) using vadadustat (Compound 1). Methods described herein provide alternative dosing regimens for patients having anemia. In addition, methods herein are suitable for patients converting from a previous anemia treatment including erythropoietin stimulating agent (ESA), patients who are on dialysis (e.g., peritoneal dialysis or hemodialysis), or CKD patients having certain hemoglobin (Hb) levels.

21 Claims, 28 Drawing Sheets

ESA: erythropoiesis stimulating agent; HD: hemodialysis; R: ramdomizad;
TIW: three times weekly SD: Standard Deviation ESA: erythropoiesis-stimulating agent; IV: intravenous; SD: Standard Deviation
Note: IV ESA: darbepoetin alfa or epoetin alfa Stratum: High Epoetin >90 to <300 U/kg/week

| Number of Patients: | 0 | 1 | 2 | 4 | 6 | 8 | 10 | 11 | 12 | 13 | 14 | 16 | 18 | 20 |
|---|---|---|---|---|---|---|---|---|---|---|---|---|---|---|
| Vadadustat 300 mg (N=18) | 18 | 12 | 14 | 16 | 14 | 12 | 11 | 9 | 8 | 7 | 8 | 7 | 7 | 7 |
| Vadadustat 450 mg (N=21) | 21 | 16 | 19 | 20 | 19 | 18 | 15 | 15 | 15 | 12 | 14 | 11 | 14 | 13 |
| Vadadustat 600 mg (N=21) | 21 | 16 | 13 | 15 | 11 | 12 | 14 | 10 | 12 | 10 | 13 | 10 | 8 | 8 |
| Vadadustat Total (N=60) | 60 | 44 | 46 | 51 | 44 | 42 | 40 | 34 | 35 | 29 | 35 | 28 | 29 | 28 |
| Epoetin Alfa (N=13) | 13 | 12 | 12 | 13 | 13 | 11 | 9 | 12 | 10 | 12 | 12 | 10 | 11 | 12 |

Treatment Group: Vadadustat 300 mg; Vadadustat 450 mg; Vadadustat 600 mg; Vadadustat Total; Epoetin Alpha Week 0 is the baseline
N: number of subjects; SD: standard deviation Stratum: Low Epoetin <= 90 u/kg/week Week 11

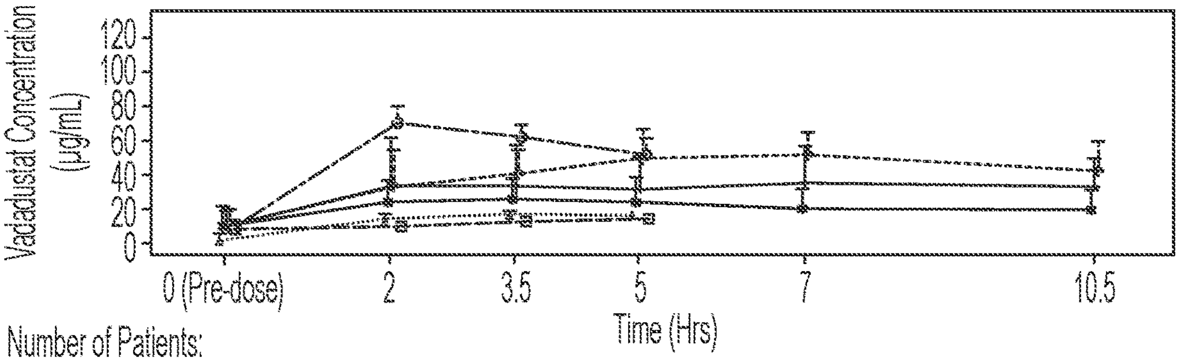

| Number of Patients: | | | | | | |
|---|---|---|---|---|---|---|
| Vadadustat 150 mg | 2 | 2 | 2 | 2 | 0 | 0 |
| Vadadustat 300 mg | 12 | 12 | 12 | 12 | 6 | 6 |
| Vadadustat 450 mg | 15 | 15 | 15 | 15 | 6 | 6 |
| Vadadustat 600 mg | 10 | 9 | 10 | 9 | 2 | 2 |
| Vadadustat 750 mg | 3 | 3 | 3 | 3 | 0 | 0 |
| Vadadustat 900 mg | 1 | 1 | 1 | 1 | 0 | 0 |

Treatment Group: Vadadustat 150 mg Vadadustat 300 mg Vadadustat 450 mg Vadadustat 600 mg Vadadustat 750 mg Vadadustat 900 mg

FIG. 15C

Stratum: Low Epoetin <= 90 u/kg/week

Week 13

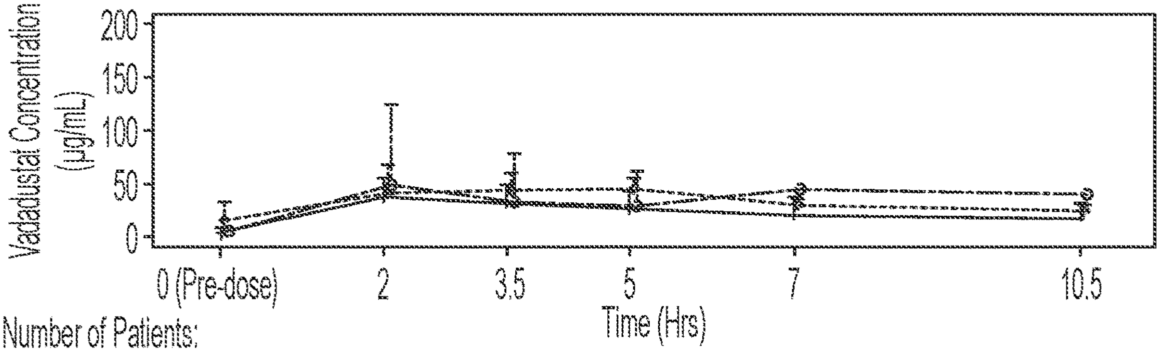

| Number of Patients: | | | | | | |
|---|---|---|---|---|---|---|
| Vadadustat 450 mg | 4 | 4 | 4 | 3 | 2 | 2 |
| Vadadustat 600 mg | 5 | 5 | 5 | 5 | 4 | 4 |
| Vadadustat 750 mg | 3 | 3 | 3 | 3 | 1 | 1 |

Treatment Group: Vadadustat 450 mg Vadadustat 600 mg Vadadustat 750 mg

FIG. 15D

Number of Patients:

| | | | | | | |
|---|---|---|---|---|---|---|
| Vadadustat 150 mg | 2 | 2 | 2 | 2 | 1 | 1 |
| Vadadustat 300 mg | 5 | 5 | 5 | 4 | 2 | 2 |
| Vadadustat 450 mg | 4 | 4 | 4 | 4 | 1 | 1 |
| Vadadustat 600 mg | 8 | 8 | 8 | 8 | 1 | 1 |
| Vadadustat 750 mg | 4 | 4 | 4 | 4 | 0 | 0 |
| Vadadustat 900 mg | 3 | 3 | 3 | 3 | 0 | 0 |

Treatment Group: Vadadustat 150 mg, Vadadustat 300 mg, Vadadustat 450 mg, Vadadustat 600 mg, Vadadustat 750 mg, Vadadustat 900 mg Number of Patients:

| | | | | | | |
|---|---|---|---|---|---|---|
| Vadadustat 300 mg | 1 | 1 | 1 | 1 | 0 | 0 |
| Vadadustat 600 mg | 2 | 2 | 2 | 2 | 1 | 1 |
| Vadadustat 750 mg | 1 | 1 | 1 | 0 | 0 | 0 |

Treatment Group: Vadadustat 300 mg, Vadadustat 600 mg, Vadadustat 750 mg

THERAPEUTIC METHODS USING VADADUSTAT

CROSS-REFERENCE TO RELATED APPLICATIONS

The present application is a 35 U.S.C. § 371 National Stage Application of International Application No. PCT/US2022/011666, filed on Jan. 7, 2022, which claims benefit of U.S. Provisional Application No. 63/135,316, filed Jan. 8, 2021; U.S. Provisional Application No. 63/177,098, filed Apr. 20, 2021; U.S. Provisional Application No. 63/135,327, filed Jan. 8, 2021; and U.S. Provisional Application No. 63/177,104, filed Apr. 20, 2021, each of which is incorporated by reference in its entirety.

BACKGROUND OF THE INVENTION

Treatment of anemia associated with chronic kidney disease (CKD) using erythropoiesis-stimulating agents (ESAs), such as epoetin alfa, epoetin beta, darbepoetin, or peginesatide, often results in prolonged, supraphysiologic erythropoietin (EPO) levels, which are implicated in increased unwanted cardiovascular side effects, including hypertension and thromboembolic events. Therefore a need exists for treatment of anemia associated with chronic kidney disease (CKD) without prolonged, supraphysiologic erythropoietin (EPO) levels.

SUMMARY OF INVENTION

Described herein are methods of treating anemia with vadadustat (Compound 1), including methods for increasing and/or maintaining hemoglobin levels in a patient having anemia.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

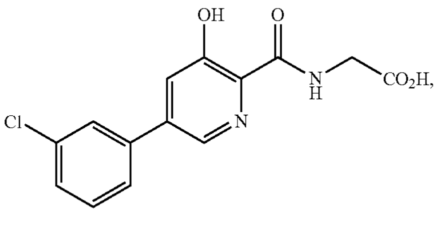

or a pharmaceutically acceptable salt, solvate, or hydrate thereof, wherein the dose comprises about 450 mg to about 1200 mg, or about 450 mg to about 1800 mg of Compound 1.

In another aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

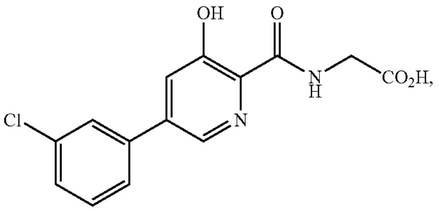

or a pharmaceutically acceptable salt, solvate, or hydrate thereof, wherein the dose comprises about 450 mg to about 1200 mg, or about 450 mg to about 1800 mg of Compound 1, and wherein the hemoglobin levels are increased to about at least 10 g/dL from a baseline hemoglobin level.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

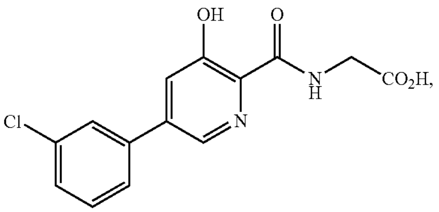

or a pharmaceutically acceptable salt, solvate, or hydrate thereof, wherein the dose comprises about 450 mg to about 1200 mg, or about 450 mg to about 1800 mg of Compound 1, and wherein the hemoglobin levels are maintained at about 10.0 g/dL to about 13.0 g/dL.

In embodiments of any of the methods described herein, the dose comprises about 600 mg to about 1200 mg, or about 600 mg to about 1800 mg of Compound 1.

In embodiments of any of the methods described herein, the dose comprises about 600 mg to about 1200 mg, or about 600 mg to about 1800 mg of Compound 1 three times weekly.

In embodiments of any of the methods described herein, the dose comprises about 750 mg to about 1200 mg, or about 750 mg to about 1800 mg of Compound 1 once daily.

In embodiments of any of the methods described herein, the dose is administered to the patient for at least about 12 weeks. In embodiments, the dose is administered to the patient for at least about 12-260 weeks.

In embodiments of any of the methods described herein, the patient has anemia secondary to or associated with chronic kidney disease (CKD). In embodiments, the CKD is dialysis-dependent CKD (DD-CKD).

In embodiments of any of the methods described herein, the patient previously has been treated with an erythropoietin stimulating agent (ESA). In embodiments, the ESA is epoetin, darbepoetin alfa (DA), and/or methoxy polyethylene glycol-epoetin beta (epoetin beta pegol).

In embodiments of any of the methods described herein, the patient is a hyporesponder wherein the patient is resistant or refractory to ESA treatment.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

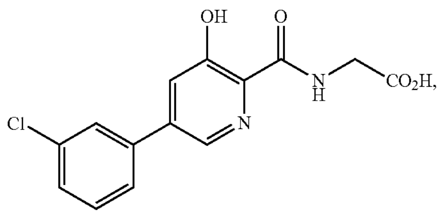

or a pharmaceutically acceptable salt, solvate, or hydrate thereof, wherein the dose comprises about 750 mg to about 1200 mg, or about 750 mg to about 1800 mg of Compound 1 once daily.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In an aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

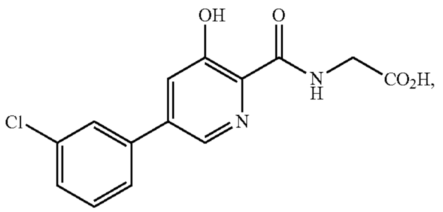

or a pharmaceutically acceptable salt, solvate, or hydrate thereof, for at least about 12 weeks, wherein the dose comprises about 750-1200 mg, or about 750-1800 mg of Compound 1 once daily.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

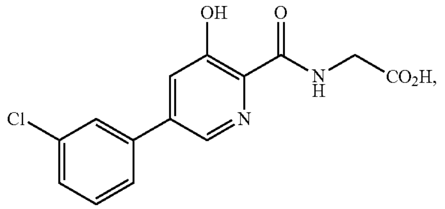

or a pharmaceutically acceptable salt, solvate, or hydrate thereof, wherein the dose comprises about 750-1200 mg, or comprises about 750-1800 mg of Compound 1 once daily, and wherein the patient was previously treated with an erythropoietin stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

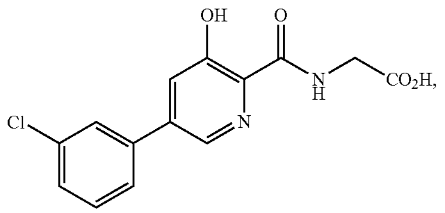

or a pharmaceutically acceptable salt, solvate, or hydrate thereof, wherein the dose comprises about 750-1200 mg, or about 750-1200 mg of Compound 1 once daily, and wherein anemia is anemia associated with or secondary to dialysis-dependent chronic kidney disease (DD-CKD).

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

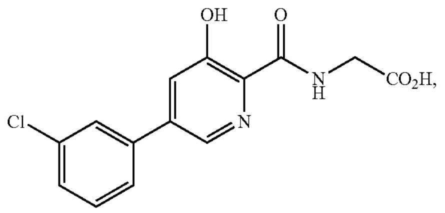

or a pharmaceutically acceptable salt, solvate, or hydrate thereof, wherein the dose comprises about 750-1200 mg, or about 750-1800 mg of Compound 1 once daily, wherein the patient was previously treated with an erythropoietin stimulating agent (ESA), and wherein anemia is anemia associated with or secondary to dialysis-dependent chronic kidney disease (DD-CKD).

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

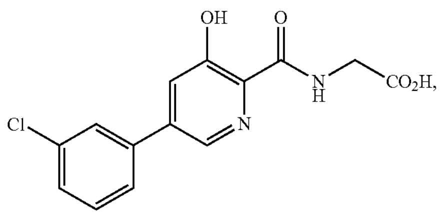

or a pharmaceutically acceptable salt, solvate, or hydrate thereof, wherein the dose comprises about 600 mg to about 1200 mg, or about 600 mg to about 1800 mg of Compound 1 three times weekly.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

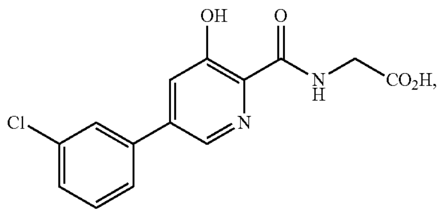

or a pharmaceutically acceptable salt, solvate, or hydrate thereof, for at least about 12 to about 260 weeks, wherein the dose comprises about 600-1200 mg, or about 600-1800 mg of Compound 1 three times weekly.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

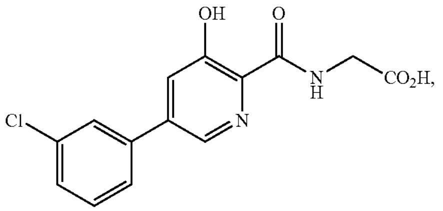

or a pharmaceutically acceptable salt, solvate, or hydrate thereof, wherein the dose comprises about 600-1200 mg, or about 600-1800 mg of Compound 1 three times weekly, and wherein the patient was previously treated with an erythropoietin stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

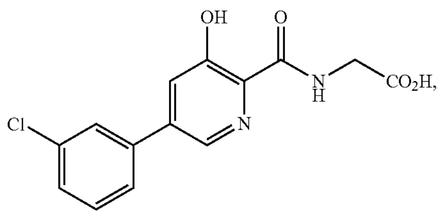

or a pharmaceutically acceptable salt, solvate, or hydrate thereof, wherein the dose comprises about 600-1200 mg, or about 600-1800 mg of Compound 1 three times weekly, and wherein anemia is anemia associated with or secondary to dialysis-dependent chronic kidney disease (DD-CKD).

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 µg/kg/week and ≤1.5 µg/kg/week DA.

In embodiments, the patient previously has been treated with epoetin beta pegol at a dose of about 0.3 mcg/kg of body weight to about 1.2 µg/kg of body weight once every two weeks or about 0.6 µg/kg of body weight to about 2.4 µg/kg of body weight once a month. In embodiments, the patient previously has been treated with epoetin beta pegol at a dose of about 0.6 µg/kg of body weight once every two weeks or about 1.2 µg/kg of body weight once a month. In embodiments, the patient previously has been treated with ≤250 µg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

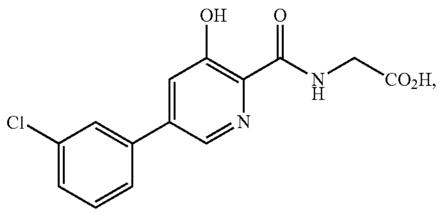

or a pharmaceutically acceptable salt, solvate, or hydrate thereof, wherein the dose comprises about 600-1200 mg, or about 600-1800 mg of Compound 1 three times weekly, wherein the patient was previously treated with an erythropoietin stimulating agent (ESA), and wherein anemia is anemia associated with or secondary to dialysis-dependent chronic kidney disease (DD-CKD).

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

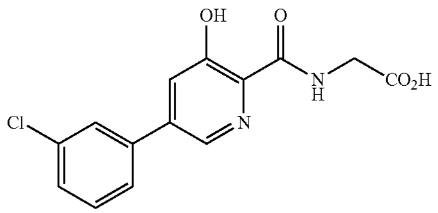

or a pharmaceutically acceptable salt, solvate, or hydrate thereof, wherein the dose comprises about 150 mg to about 1200 mg, or about 150 mg to about 1800 mg of the Compound 1 three times weekly, and wherein the patient was previously administered a daily dose of Compound 1.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

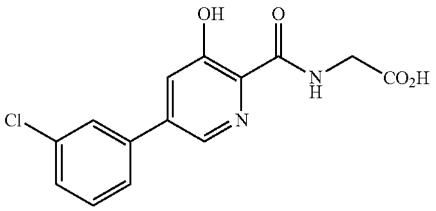

or a pharmaceutically acceptable salt, solvate, or hydrate thereof, for at least about 12 weeks, wherein the dose comprises about 150 mg to about 1200 mg, or about 150 mg to about 1800 mg of the Compound 1 three times weekly, and wherein the patient was previously administered a daily dose of Compound 1.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

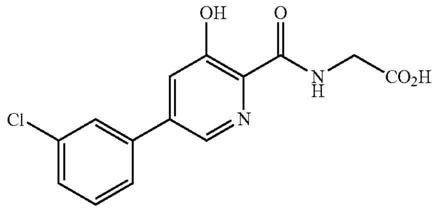

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, and wherein the patient was previously treated with an erythropoietin stimulating agent (ESA).

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

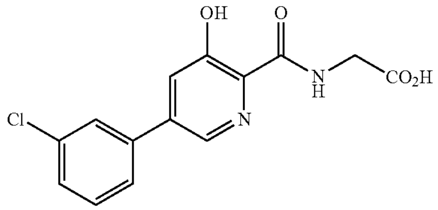

or a pharmaceutically acceptable salt, solvate, or hydrate thereof, wherein the dose comprises about 150 mg to about 1200 mg, or comprises about 150 mg to about 1800 mg of the Compound 1 three times weekly, wherein the patient was previously administered a daily dose of Compound 1, and wherein anemia is anemia associated with or secondary to dialysis-dependent chronic kidney disease (DD-CKD).

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to A method for treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

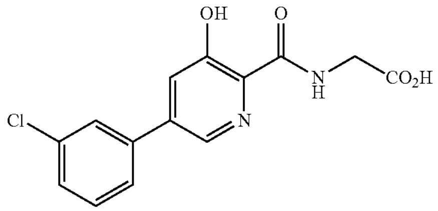

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein the patient was previously treated with an erythropoietin stimulating agent (ESA), and wherein anemia is anemia associated with or secondary to dialysis-dependent chronic kidney disease (DD-CKD).

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly In embodiments, the dose comprises about 1500 mg three times weekly In embodiments, the dose comprises about 1650 mg three times weekly In embodiments, the dose comprises about 1800 mg three times weekly In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of treating anemia, comprising administering to a patient having anemia a starting dose of a compound that is {[5-(3-chlorophenyl)-3-hydroxypyridine-2-carbonyl]amino}acetic acid having the structure of Compound 1, (Compound 1)

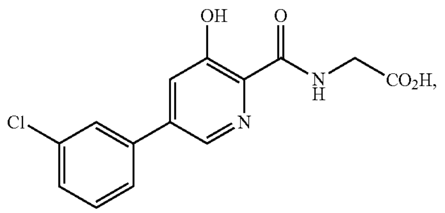

or a pharmaceutically acceptable salt, solvate, or hydrate thereof, wherein the starting dose comprises about 750 mg to about 1200 mg, or about 750 mg to about 1800 mg of Compound 1 once daily, or about 600 mg to about 1200 mg, or about 600 mg to about 1800 mg of Compound 1 three times weekly; and adjusting the dose by about 150 mg to about 300 mg of Compound 1 if the patient has a hemoglobin level of <10.0 g/dL or >11.0 g/dL following administration of the starting dose.

In embodiments, the starting dose comprises about 750 mg to about 1200 mg of Compound 1 once daily. In embodiments, the starting dose comprises about 750 mg to about 1800 mg of Compound 1 once daily. In embodiments, the starting dose comprises about 750 mg of Compound 1 once daily. In embodiments, the starting dose comprises about 900 mg of Compound 1 once daily. In embodiments, the starting dose comprises about 600 mg to about 1200 mg of Compound 1 three times weekly. In embodiments, the starting dose comprises about 600 mg to about 1800 mg of Compound 1 three times weekly. In embodiments, the starting dose comprises about 600 mg of Compound 1 three times weekly. In embodiments, the starting dose comprises about 750 mg of Compound 1 three times weekly. In embodiments, the starting dose comprises about 900 mg of Compound 1 three times weekly.

In embodiments, the starting dose is administered to the patient for at least four weeks. In embodiments, the starting dose is administered to the patient for at least six weeks. In embodiments, the starting dose is administered to the patient for at least eight weeks. In embodiments, the starting dose is administered to the patient for at least ten weeks. In embodiments, the starting dose is administered to the patient for at least twelve weeks.

In embodiments, adjusting comprises adjusting the dose by about 150 mg of Compound 1 if the patient has a hemoglobin level of <10.0 g/dL or >11.0 g/dL following administration of the starting dose. In embodiments, adjusting comprises adjusting the dose by about 300 mg of Compound 1 if the patient has a hemoglobin level of <10.0 g/dL or >11.0 g/dL following administration of the starting dose. In embodiments, adjusting comprises increasing the dose by about 150 mg of Compound 1 if the patient has a hemoglobin level of <10.0 g/dL following administration of the starting dose. In embodiments, adjusting comprises increasing the dose by about 300 mg of Compound 1 if the patient has a hemoglobin level of <10.0 g/dL following administration of the starting dose. In embodiments, adjusting comprises decreasing the dose by about 150 mg of Compound 1 if the patient has a hemoglobin level of >11.0 g/dL following administration of the starting dose. In embodiments, adjusting comprises decreasing the dose by about 300 mg of Compound 1 if the patient has a hemoglobin level of >11.0 g/dL following administration of the starting dose.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In one aspect, the invention relates to a method of treating anemia, comprising administering to a patient having anemia a starting dose of a compound that is {[5-(3-chlorophenyl)-3-hydroxypyridine-2-carbonyl]amino}acetic acid having the structure of Compound 1, (Compound 1)

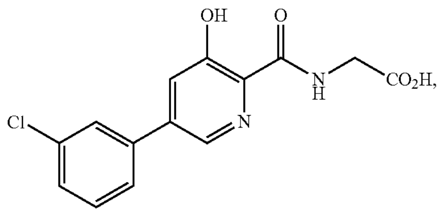

or a pharmaceutically acceptable salt, solvate, or hydrate thereof, wherein the starting dose comprises about 750 mg to about 1200 mg, or about 750 mg to about 1800 mg of Compound 1 once daily; or about 600-1200 mg, or about 600-1800 mg of Compound 1 three times weekly; and decreasing the starting dose by 150-300 mg of Compound 1 if the patient's hemoglobin level increases by >1.0 g/dL within a 2-week period.

In embodiments, the starting dose comprises about 750 mg to about 1200 mg of Compound 1 once daily. In embodiments, the starting dose comprises about 750 mg to about 1800 mg of Compound 1 once daily. In embodiments, the starting dose comprises about 750 mg of Compound 1 once daily. In embodiments, the starting dose comprises about 900 mg of Compound 1 once daily. In embodiments, the starting dose comprises about 600 mg to about 1200 mg of Compound 1 three times weekly. In embodiments, the starting dose comprises about 600 mg to about 1800 mg of Compound 1 three times weekly. In embodiments, the starting dose comprises about 600 mg of Compound 1 three times weekly. In embodiments, the starting dose comprises about 750 mg of Compound 1 three times weekly. In embodiments, the starting dose comprises about 900 mg of Compound 1 three times weekly.

In embodiments, the method further comprises decreasing the dose by about 150 mg of Compound 1 if the patient's hemoglobin level increases by >1.0 g/dL within a 2-week period. In embodiments, the method further comprises decreasing the dose by about 300 mg of Compound 1 if the patient's hemoglobin level increases by >1.0 g/dL within a 2-week period.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

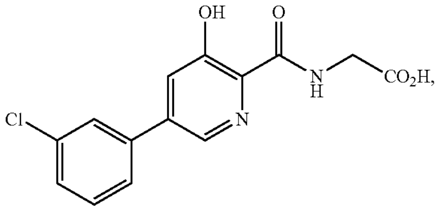

or a pharmaceutically acceptable salt, solvate, or hydrate thereof, wherein the dose comprises about 750 mg to about 1200 mg, or about 750 mg to about 1800 mg of Compound 1 once daily, and wherein the hemoglobin levels are increased to about at least 10 g/dL from a baseline hemoglobin level.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

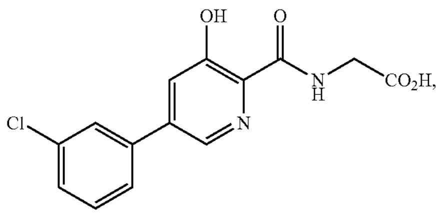

or a pharmaceutically acceptable salt, solvate, or hydrate thereof, for at least about 12 weeks, wherein the dose comprises about 750 mg to about 1200 mg, or about 750 mg to about 1800 mg of Compound 1 once daily, and wherein the hemoglobin levels are increased to about at least 10 g/dL from a baseline hemoglobin level.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

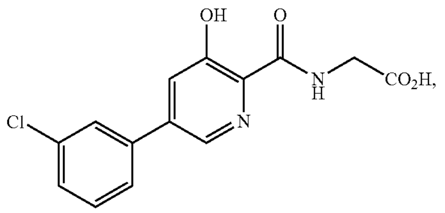

or a pharmaceutically acceptable salt, solvate, or hydrate thereof, wherein the dose comprises about 750 mg to about 1200 mg, or about 750 mg to about 1800 mg of Compound 1 once daily, and wherein the patient was previously treated with an erythropoietin stimulating agent (ESA), and wherein the hemoglobin levels are increased to about at least 10 g/dL from a baseline hemoglobin level.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

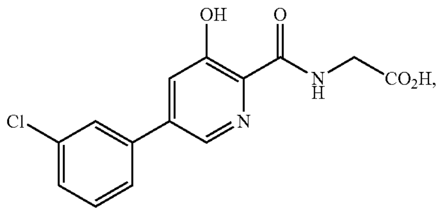

or a pharmaceutically acceptable salt, solvate, or hydrate thereof, wherein the dose comprises about 750 mg to about 1200 mg, about 750 mg to about 1800 mg of Compound 1 once daily, wherein anemia is anemia associated with or secondary to dialysis-dependent chronic kidney disease (DD-CKD), and wherein the hemoglobin levels are increased to about at least 10 g/dL from a baseline hemoglobin level.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week. In embodiments, the patient previously has been treated with epoetin alfa at a dose of about >7,700 U three times weekly.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

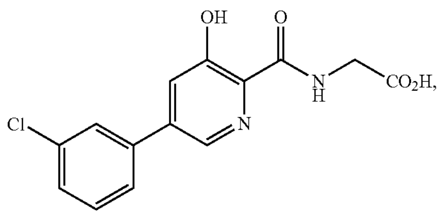

or a pharmaceutically acceptable salt, solvate, or hydrate thereof, wherein the dose comprises about 750 mg to about 1200 mg, or about 750 mg to about 1800 mg of Compound 1 once daily, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

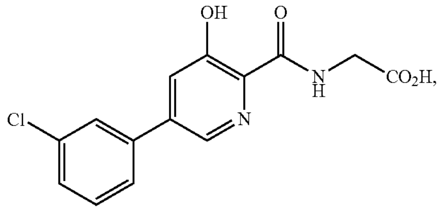

or a pharmaceutically acceptable salt, solvate, or hydrate thereof, wherein the dose comprises about 600 mg to about 1200 mg, or about 600 mg to about 1800 mg of Compound 1 three times weekly, and wherein the hemoglobin levels are increased to about at least 10 g/dL from a baseline hemoglobin level.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

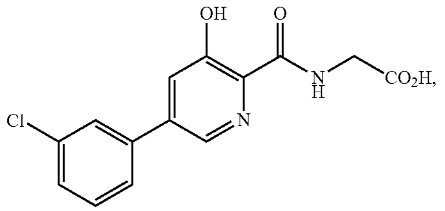

or a pharmaceutically acceptable salt, solvate, or hydrate thereof, for at least about 12 weeks, wherein the dose comprises about 600 mg to about 1200 mg, or about 600 mg to about 1800 mg of Compound 1 three times weekly, and wherein the hemoglobin levels are increased to about at least 10 g/dL from a baseline hemoglobin level.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

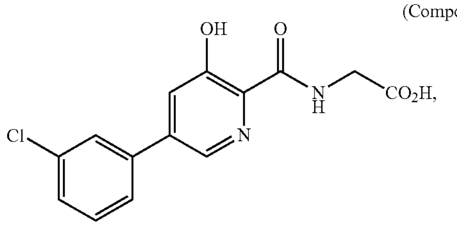

or a pharmaceutically acceptable salt, solvate, or hydrate thereof, wherein the dose comprises about 600 mg to about 1200 mg, or about 600 mg to about 1800 mg of Compound 1 three times weekly, wherein the patient was previously treated with an erythropoietin stimulating agent (ESA), and wherein the hemoglobin levels are increased to about at least 10 g/dL from a baseline hemoglobin level.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

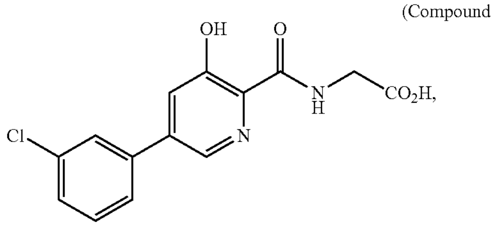

or a pharmaceutically acceptable salt, solvate, or hydrate thereof, wherein the dose comprises about 600 mg to about 1200 mg, or about 600 mg to about 1800 mg of Compound 1 three times weekly, wherein anemia is anemia associated with or secondary to dialysis-dependent chronic kidney disease (DD-CKD), and wherein the hemoglobin levels are increased to about at least 10 g/dL from a baseline hemoglobin level.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

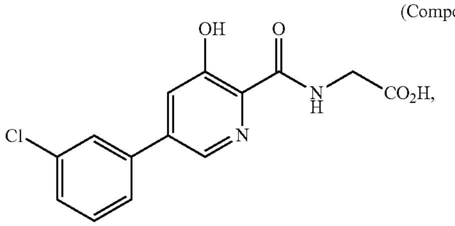

or a pharmaceutically acceptable salt, solvate, or hydrate thereof, wherein the dose comprises about 600 mg to about 1200 mg, or about 600 mg to about 1800 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

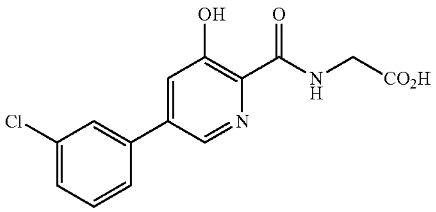

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, and wherein the hemoglobin levels are increased to about at least 10 g/dL from a baseline hemoglobin level.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300

U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

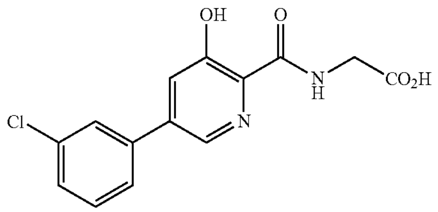

or a pharmaceutically acceptable salt, solvate, or hydrate thereof, for at least about 12 weeks, wherein the dose comprises about 150 mg to about 1200 mg, or about 150 mg to about 1800 mg of the Compound 1 three times weekly, wherein the patient was previously administered a daily dose of Compound 1, and wherein the hemoglobin levels are increased to about at least 10 g/dL from a baseline hemoglobin level.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

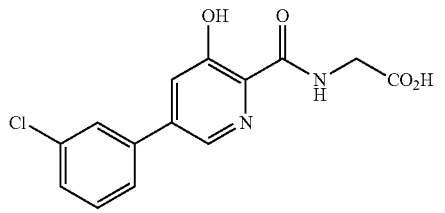

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein the patient was previously treated with an erythropoietin stimulating agent (ESA), and wherein the hemoglobin levels are increased to about at least 10 g/dL from a baseline hemoglobin level.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

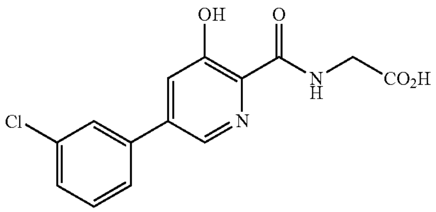

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein anemia is anemia associated with or secondary to dialysis-dependent chronic kidney disease (DD-CKD), and wherein the hemoglobin levels are increased to about at least 10 g/dL from a baseline hemoglobin level.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

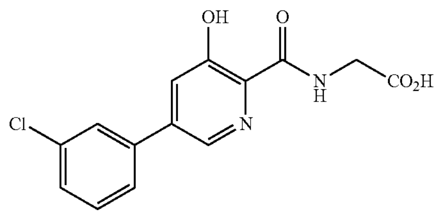

or a pharmaceutically acceptable salt, solvate, or hydrate thereof, wherein the dose comprises about 150-1200 mg, or about 150-1800 mg of the Compound 1 three times weekly, wherein the patient was previously administered a daily dose of Compound 1, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient's hemoglobin levels are increased to about 10.0-13.0 g/dL from a baseline hemoglobin level. In embodiments, the patient's hemoglobin levels are increased to about 10.0-12.0 g/dL from a baseline hemoglobin level. In embodiments, the patient's hemoglobin levels are increased to about 10.0-11.0 g/dL from a baseline hemoglobin level.

In embodiments, the patient's baseline hemoglobin level is about <10 g/dL. In embodiments, the patient's baseline hemoglobin level is about <9.5 g/dL. In embodiments, the patient's baseline hemoglobin level is about <9 g/dL. In embodiments, the patient's baseline hemoglobin level is about <8.5 g/dL.

In embodiments, the patient's baseline hemoglobin level is about <10 g/dL and the patient's hemoglobin levels are increased to about 10.0-12.0 g/dL from a baseline hemoglobin level. In embodiments, the patient's baseline hemoglobin level is about <10 g/dL and the patient's hemoglobin levels are increased to about 10.0-11.0 g/dL.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

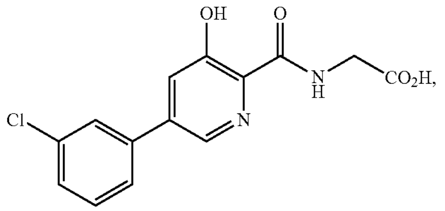

or a pharmaceutically acceptable salt, solvate, or hydrate thereof, wherein the dose comprises about 750 mg to about 1200 mg, or about 750 mg to about 1800 mg of Compound 1 once daily, and wherein the hemoglobin levels are maintained at about 10.0 g/dL to about 13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

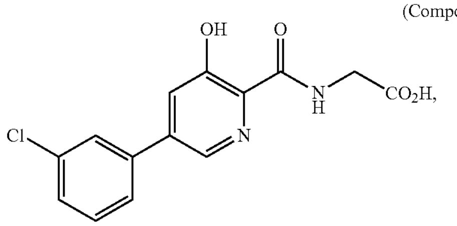

or a pharmaceutically acceptable salt, solvate, or hydrate thereof, for at least about 12 to about 260 weeks, wherein the dose comprises about 750 mg to about 1200 mg, or about 750 mg to about 1800 mg of Compound 1 once daily, and wherein the hemoglobin levels are maintained at about 10.0-13.0 g/dL.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily In embodiments, the dose comprises about 1650 mg of Compound 1 once daily In embodiments, the dose comprises about 1800 mg of Compound 1 once daily In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

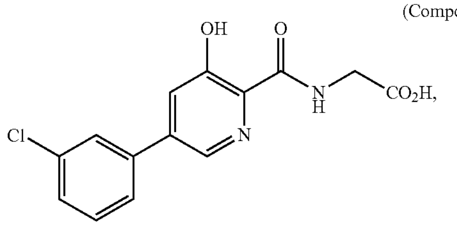

or a pharmaceutically acceptable salt, solvate, or hydrate thereof, wherein the dose comprises about 750 mg to about 1200 mg, or about 750 mg to about 1800 mg of Compound 1 once daily, wherein the patient was previously treated with an erythropoietin stimulating agent (ESA), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

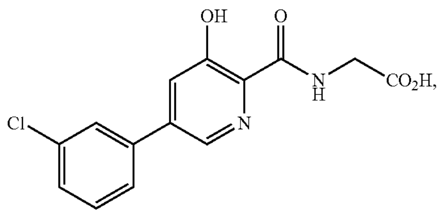

or a pharmaceutically acceptable salt, solvate, or hydrate thereof, wherein the dose comprises about 750 mg to about 1200 mg, or about 750 mg to about 1800 mg of Compound 1 once daily, wherein anemia is anemia associated with or secondary to dialysis-dependent chronic kidney disease (DD-CKD), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

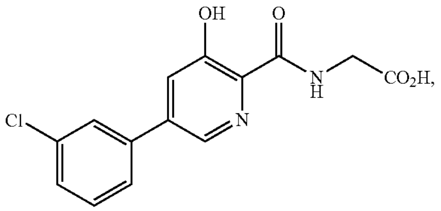

or a pharmaceutically acceptable salt, solvate, or hydrate thereof, wherein the dose comprises about 750 mg to about 1200 mg, or about 750 mg to about 1800 mg of Compound 1 once daily, wherein the patient was previously treated with an erythropoietin stimulating agent (ESA), wherein anemia is anemia associated with or secondary to dialysis-dependent chronic kidney disease (DD-CKD), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 750 mg to about 900 mg of Compound 1 once daily. In embodiments, the dose comprises about 750 mg of Compound 1 once daily. In embodiments, the dose comprises about 900 mg of Compound 1 once daily. In embodiments, the dose comprises about 1200 mg of Compound 1 once daily. In embodiments, the dose comprises about 1350 mg of Compound 1 once daily. In embodiments, the dose comprises about 1500 mg of Compound 1 once daily. In embodiments, the dose comprises about 1650 mg of Compound 1 once daily. In embodiments, the dose comprises about 1800 mg of Compound 1 once daily.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

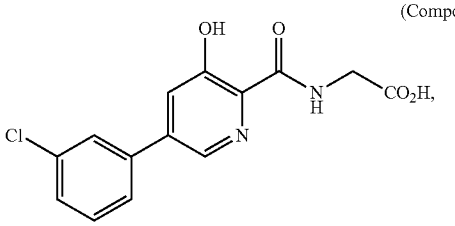

or a pharmaceutically acceptable salt, solvate, or hydrate thereof, wherein the dose comprises about 600 mg to about 1200 mg, or about 600 mg to about 1800 mg of Compound 1 three times weekly, and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

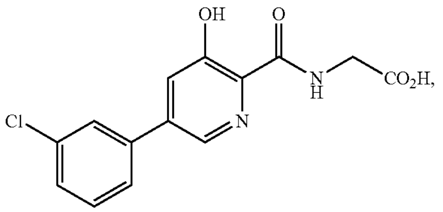

or a pharmaceutically acceptable salt, solvate, or hydrate thereof, for at least about 12 weeks, wherein the dose comprises about 600 mg to about 1200 mg, or about 600 mg to about 1800 mg of Compound 1 three times weekly, and wherein the hemoglobin levels are maintained at about 10.0-13.0 g/dL.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

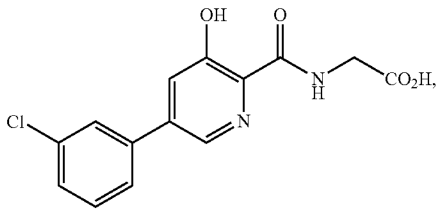

or a pharmaceutically acceptable salt, solvate, or hydrate thereof, wherein the dose comprises about 600 mg to about 1200 mg, or about 600 mg to about 1800 mg of Compound 1 three times weekly, wherein the patient was previously treated with an erythropoietin stimulating agent (ESA), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

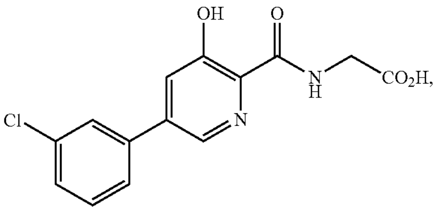

or a pharmaceutically acceptable salt, solvate, or hydrate thereof, wherein the dose comprises about 600 mg to about 1200 mg, or about 600 mg to about 1800 mg of Compound 1 three times weekly, wherein anemia is anemia associated with or secondary to dialysis-dependent chronic kidney disease (DD-CKD), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

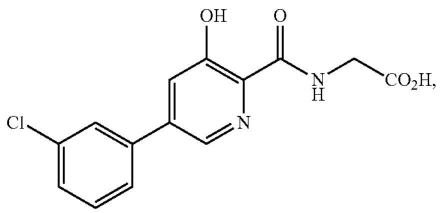

or a pharmaceutically acceptable salt, solvate, or hydrate thereof, wherein the dose comprises about 600 mg to about 1200 mg, or about 600 mg to about 1800 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 600 mg to about 900 mg of Compound 1 three times weekly. In embodiments, the dose comprises about 750 mg to about 1200 mg of Compound 1 three times weekly. In embodiments, the dose comprises about 600 mg of Compound 1 three times weekly. In embodiments, the dose comprises about 750 mg of Compound 1 three times weekly. In embodiments, the dose comprises about 900 mg of Compound 1 three times weekly. In embodiments, the dose comprises about 1200 mg of Compound 1 three times weekly. In embodiments, the dose comprises about 1350 mg of Compound 1 three times weekly. In embodiments, the dose comprises about 1500 mg of Compound 1 three times weekly. In embodiments, the dose comprises about 1650 mg of Compound 1 three times weekly. In embodiments, the dose comprises about 1800 mg of Compound 1 three times weekly.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

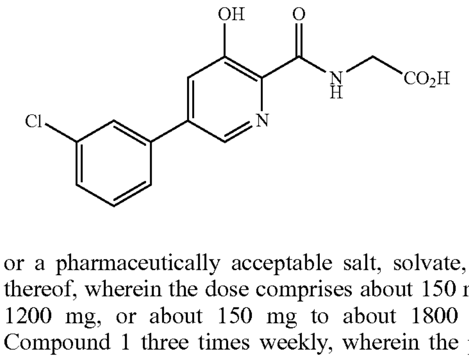

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

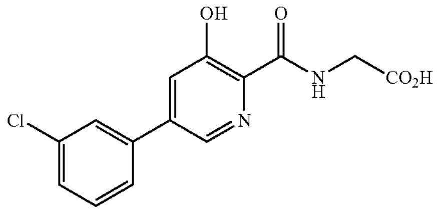

or a pharmaceutically acceptable salt, solvate, or hydrate thereof, for at least about 12 weeks, wherein the dose comprises about 150 mg to about 1200 mg, or about 150 mg to about 1800 mg of the Compound 1 three times weekly, wherein the patient was previously administered a daily dose of Compound 1, and wherein the hemoglobin levels are maintained at about 10.0-13.0 g/dL.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

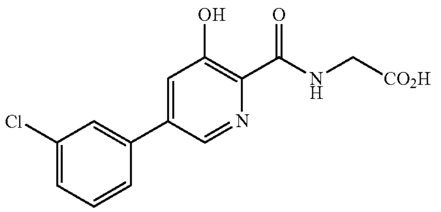

or a pharmaceutically acceptable salt, solvate, or hydrate thereof, wherein the dose comprises about 150-1200 mg, or about 150-1800 mg of the Compound 1 three times weekly, wherein the patient was previously administered a daily dose of Compound 1, wherein the patient was previously treated with an erythropoietin stimulating agent (ESA), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient has anemia associated with or secondary to chronic kidney disease (CKD). In embodiments, the chronic kidney disease is dialysis-dependent chronic kidney disease (DD-CKD). In embodiments, the chronic kidney disease is non-dialysis dependent chronic kidney disease (NDD-CKD).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

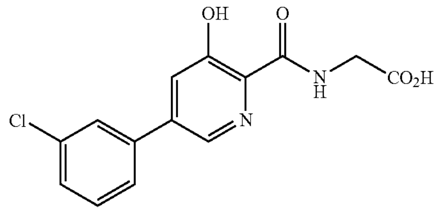

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein anemia is anemia associated with or secondary to dialysis-dependent chronic kidney disease (DD-CKD), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiments, the patient previously has been treated with an erythropoiesis stimulating agent (ESA). In embodiments, the patient previously has not been treated with an erythropoiesis stimulating agent (ESA).

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In one aspect, the invention relates to a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

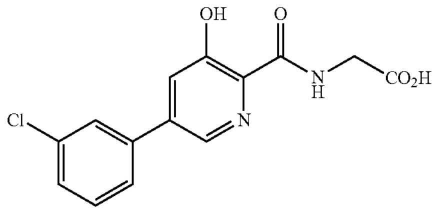

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein the patient was previously treated with an erythropoietin stimulating agent (ESA), wherein anemia is anemia associated with or secondary to dialysis-dependent chronic kidney disease (DD-CKD), and wherein the hemoglobin levels are maintained at about 10.0-13.0 g/dL.

In embodiments, the patient's hemoglobin levels are maintained at about 10.0 g/dL to about 12.0 g/dL. In embodiments, the patient's hemoglobin levels are maintained at about 10.0 g/dL to about 11.0 g/dL. In embodiments, the patient's hemoglobin levels are maintained at about 11.0 g/dL to about 13.0 g/dL. In embodiments, the patient's hemoglobin levels are maintained at about 11.0 g/dL to about 12.0 g/dL.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprises about 150 mg of Compound 1. In embodiments, the patient was previously administered a daily dose comprises about 300 mg of Compound 1. In embodiments, the patient was previously administered a daily dose comprises about 450 mg of Compound 1. In embodiments, the patient was previously administered a daily dose comprises about 600 mg of Compound 1.

In embodiment, the ESA is epoetin, darbepoetin alfa (DA), or methoxy polyethylene glycol-epoetin beta (epoetin beta pegol). In embodiments, the ESA is epoetin. In embodiments, the epoetin is epoetin alfa, epoetin beta, epoetin gamma, epoetin kappa, or a combination thereof. In embodiments, the epoetin is epoetin alfa.

In embodiments, the patient previously has been treated with epoetin alfa at a dose of about 10 U/kg of body weight to about 500 U/kg of body weight three times weekly. In embodiments, the patient previously has been treated with epoetin alfa at a dose of about 25 U/kg of body weight to about 300 U/kg of body weight three times weekly. In embodiments, the patient previously has been treated with epoetin alfa at a dose of about 50 U/kg of body weight to 200 U/kg of body weight three times weekly. In embodiments, the patient previously has been treated with epoetin alfa at a dose of about 50 U/kg of body weight to 200 U/kg of body weight three times weekly. In embodiments, the patient previously has been treated with about ≤90 U/kg/week epoetin alfa. In embodiments, the patient previously has been treated with about >90 U/kg/week to about <300 U/kg/week epoetin alfa. In embodiments, the patient previously has been treated with about ≥300 U/kg/week epoetin alfa. In embodiments, the patient previously has been treated with epoetin alfa at an amount of about 1,500 U/week to about 90,000 U/week. In embodiments, the patient previously has been treated with epoetin alfa at an amount of about 4,500 U/week.

In embodiments, the patient previously has been treated with DA at a dose of about 0.25 mcg/kg of body weight to 0.75 μg/kg of body weight once weekly or once every two weeks. In embodiments, the patient previously has been treated with DA at a dose of about 0.45 μg/kg of body weight once weekly. In embodiments, the patient previously has been treated with DA at a dose of about 0.75 μg/kg of body weight once every two weeks. In embodiments, the patient previously has been treated with DA at an amount of about 6.25-200 μg/week. In embodiments, the patient previously has been treated with ≤0.45 μg/kg/week DA. In embodiments, the patient previously has been treated with >0.45 μg/kg/week and ≤1.5 μg/kg/week DA.

In embodiments, the patient previously has been treated with epoetin beta pegol at a dose of about 0.3 mcg/kg of body weight to about 1.2 μg/kg of body weight once every two weeks or about 0.6 μg/kg of body weight to about 2.4 μg/kg of body weight once a month. In embodiments, the patient previously has been treated with epoetin beta pegol at a dose of about 0.6 μg/kg of body weight once every two weeks or about 1.2 μg/kg of body weight once a month. In embodiments, the patient previously has been treated with ≤250 μg/month epoetin beta pegol.

In embodiments, the patient previously has been treated with any of the ESA described herein for about ≥4 weeks. In embodiments, the patient previously has been treated with any of the ESA described herein for about ≥6 weeks. In embodiments, the patient previously has been treated with any of the ESA described herein for about ≥8 weeks. In embodiments, the patient previously has been treated with any of the ESA described herein for about ≥12 weeks.

In embodiments, the dose is administered to the patient for at least about 12 to at least about 260 weeks. In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

BRIEF DESCRIPTION OF DRAWINGS

FIGS. 15*a*-15*d* illustrate mean (+SD) vadadustat concentration (μg/mL) versus nominal time in the Low Epoetin Stratum (Linear Scale) (Pharmacokinetic Population, Main Study) on week 1, week 1+1 day, week 11, and week 13, respectively.

DETAILED DESCRIPTION OF THE INVENTION

Figure 1:
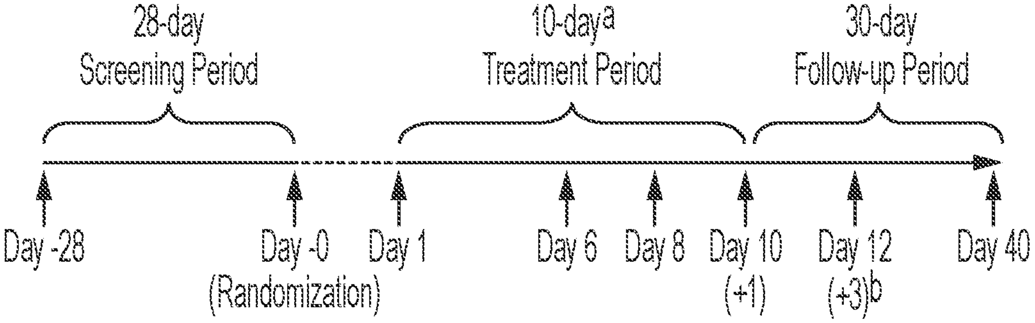
FIG. 1 illustrates the study design for the ESA group of the Phase 1b, Randomized, Open-Label Study that Evaluate the Pharmacokinetics, Pharmacodynamics, and Safety of Vadadustat in Hemodialysis Subjects with Anemia Associated with Chronic Kidney Disease.

Described herein are new therapeutic methods comprising administration of vadadustat ({[5-(3-chlorophenyl)-3-hydroxypyridine-2-carbonyl]amino}acetic acid; (Compound 1 or VDT or MT-6548). In particular, methods comprising administration of increased doses of Compound 1 can result in unexpected, durable therapeutic benefits to patients, including patient populations described herein. For example, administration of Compound 1 at doses are at or greater than about 600 mg can achieve therapeutic efficacy according to a daily schedule (e.g., about 750-1200 mg, or about 750-1800 mg of Compound 1 daily) or dosing about three times per week (e.g., about 600-1200 mg, or about 600-1800 mg of Compound 1 administered three times per week). Such increased doses can be administered to patients who have previously received a daily dose of Compound 1 and/or an erythropoietin stimulating agent (ESA). For example, methods described herein can be effective in increasing, achieving and/or maintaining a target hemoglobin (Hb) level in patients, including within a target range such as a Hb range that is about 11.0-13.0 g/dL.

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference for all purposes.

Approximately or about: As used herein, the term "approximately" or "about," as applied to one or more values of interest, refers to a value that is similar to a stated reference value. In embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Dose(s): As used herein, the term "dose(s)" means a quantity of the compound or a pharmaceutically acceptable salt, solvate, or hydrate thereof to be administered at one time. A dose may comprise a single unit dosage form, or alternatively may comprise more than a single unit dosage form (e.g., a single dose may comprise two tablets), or even less than a single unit dosage form (e.g., a single dose may comprise half of a tablet). A dose described herein may be administered at various intervals. For example, a patient can receive a dose as described herein daily or weekly (e.g., once weekly or three times per week).

Daily dose: As used herein, the term "daily dose" means a quantity of the compound, or a pharmaceutically acceptable salt, solvate, or hydrate thereof that is administered in a 24-hour period. Accordingly, a daily dose may be administered all at once (i.e., once daily dosing) or alternatively the daily dosing may be divided such that administration of the compound is twice daily, three times daily, or even four times daily.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control subject" is a subject afflicted with the same form of disease as the subject being treated, who is about the same age as the subject being treated.

Initial dose: As used herein, the term "initial dose" means a starting quantity or the resumed quantity after dose interruption of the compound or a pharmaceutically acceptable salt, solvate, or hydrate thereof, to be administered at one time.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable", as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid, or with organic acids such as acetic acid, trifluoroacetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{-alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate, and aryl sulfonate. Further pharmaceutically acceptable salts include salts formed from the quaternization of an amine using an appropriate electrophile, e.g., an alkyl halide, to form a quarternized alkylated amino salt.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one-unit dose.

Treating: As used herein, the term "treat," "treatment," or "treating" refers to any method used to partially or completely alleviate, ameliorate, relieve, inhibit, delay onset of reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

As used herein, the term "HIF prolyl hydroxylase" is art-recognized and may be abbreviated as "PHD". HIF prolyl hydroxylase is also known as "prolyl hydroxylase domain-containing protein" which may be abbreviated as "PHD". In this regard, there are three different PHD isoforms, PHD1, PHD2, and PHD3, also referred to as EGLN2, EGLN1, and EGLN3, or HPH3, HPH2, and HPH1, respectively.

As used herein, the term "unit dosage form(s)" includes tablets; caplets; capsules, such as soft elastic gelatin capsules; sachets; cachets; troches; lozenges; dispersions; powders; solutions; gels; liquid dosage forms suitable for oral or mucosal administration to a patient, including suspensions (e.g., aqueous or non-aqueous liquid suspensions), emulsions (e.g., oil-in-water emulsions, or a water-in-oil liquid emulsion), solutions, and elixirs; and sterile solids (e.g., crystalline or amorphous solids) that can be reconstituted to provide liquid dosage forms suitable for oral or parenteral administration to a patient. The unit dosage form does not necessarily have to be administered as a single dose nor does a single unit dosage form necessarily constitute an entire dose.

Further abbreviations and acronyms are provided below.

ACTH adrenocorticotropic hormone
AE adverse event
ALT alanine aminotransferase (SGPT)
ANOVA analysis of variance
AST aspartate aminotransferase (SGOT)
BUN blood urea nitrogen
C Celsius
CBC complete blood count
CHF congestive heart failure
CKD chronic kidney disease CKD-EPI Chronic Kidney Disease Epidemiology Collaboration
CMH Cochran-Mantel-Haenszel
CPK creatine phosphokinase
CRF case report form
CRO contract research organization
CS clinically significant
CV cardiovascular
CVD cardiovascular disease
dL deciliter
DVT deep venous thrombosis
EAC Endpoint Adjudication Committee
ECG electrocardiogram
EDC electronic data capture
eGFR estimated glomerular filtration rate
EOT end of treatment
EPO erythropoietin
ESA erythropoiesis-stimulating agent
ESRD end-stage renal disease
EU European Union
F Fahrenheit
FDA Food and Drug Administration
g gram
GCP Good Clinical Practice
GFR glomerular filtration rate
GMP Good Manufacturing Practice
HA health authority
HDL high-density lipoprotein
Hb hemoglobin
HIF hypoxia-inducible factor
HIFPH hypoxia-inducible factor prolyl-hydroxylase
HIF-PHI hypoxia-inducible factor prolyl-hydroxylase inhibitor
$IC_{50}$ 50% inhibitory concentration
ICH International Conference on Harmonization
IDMC Independent Data Monitoring Committee
IDMS isotope dilution mass spectrometry
IEC independent ethics committee
INR international normalized ratio
IRB institutional review board
IV intravenous(ly)
IWR interactive web response
JSDT Japanese Society for Dialysis Therapy
JSN Japanese Society of Nephrology
KDIGO Kidney Disease: Improving Global Outcomes
kg kilogram
LDH lactate dehydrogenase
LDL low-density lipoprotein
LLN lower limit of normal
MACE major adverse cardiovascular events
MCH mean corpuscular (cell) hemoglobin
MCHC mean corpuscular (cell) hemoglobin concentration
MCV mean corpuscular (cell) volume
MedDRA Medical Dictionary for Regulatory Activities
μM micromolar
mg milligram
mL milliliter
mRNA messenger ribonucleic acid
MTD maximum tolerated dose
NDD-CKD non-dialysis dependent chronic kidney disease
ng nanogram
PD pharmacodynamics(s)
PE pulmonary embolism
PEP primary evaluation period
PHD prolyl 4-hydroxylase domain
PK pharmacokinetic(s)
PP per protocol
PT prothrombin time
PTT partial thromboplastin time
QA quality assurance
QC quality control
QD once daily
RBC red blood cell
RDW red cell distribution width
ROW rest of world
rh-Epo or recombinant human epoetin
rHuEPO
SAE serious adverse event
SAP Statistical Analysis Plan
SC subcutaneous(ly)
SEP secondary evaluation period
SGOT serum glutamic oxaloacetic transaminase (AST)
SGPT serum glutamic pyruvic transaminase (ALT)
SmPC summary of product characteristics
SV Screening visit
TIBC total iron binding capacity
TIW three times weekly
TREAT Trial to Reduce Cardiovascular Events with Aranesp Therapy
TSAT transferrin saturation
uACR urine albumin-to-creatinine ratio
ULN upper limit of normal
US United States
VEGF vascular endothelial growth factor
WBC white blood cell
WHO World Health Organization Vadadustat Vadadustat ({[5-(3-chlorophenyl)-3-hydroxypyridine-2-carbonyl]amino}acetic acid; (Compound 1 or VDT or MT-6548) is a Hypoxia Inducible Factor Prolyl Hydroxylase inhibitor (HIF-PH inhibitor).

Compound 1

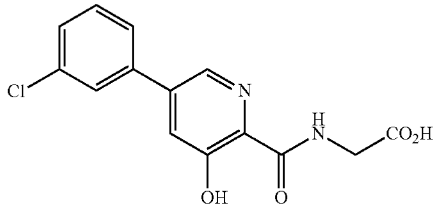

Compound 1 has emerged as a new drug that is highly useful for treating or preventing anemia secondary to or associated with chronic kidney disease, without prolonged, supraphysiologic erythropoietin (EPO) levels.

Anemia Associated with Chronic Kidney Disease (CKD)

Anemia commonly occurs in people with CKD—the permanent, partial loss of kidney function. Anemia might begin to develop in the early stages of CKD, when someone has 20 to 50 percent of normal kidney function. Anemia tends to worsen as CKD progresses. Most people who have total loss of kidney function, or kidney failure, have anemia. A person has kidney failure when he or she needs a kidney transplant or dialysis (e.g., hemodialysis or peritoneal dialysis) in order to live. When kidneys are diseased or damaged, they do not make enough EPO. As a result, the bone marrow makes fewer red blood cells, causing anemia. When blood has fewer red blood cells, it deprives the body of the oxygen it needs. Causes of anemia in people with kidney disease include blood loss from hemodialysis and low levels of the following nutrients found in food, such as iron, vitamin B12, and folic acid. Other causes of anemia in CKD patients include problems with bone marrow; inflammatory problems—such as arthritis, lupus, or inflammatory bowel disease—in which the body's immune system attacks the body's own cells and organs; chronic infections such as diabetic ulcers; and malnutrition.

Methods of Treatment

As described herein, Compound 1 can result in effective and durable treatment of anemia in patients with CKD. For example, methods described herein can be effective in increasing and/or maintaining a target hemoglobin (Hb) level in patients receiving therapy with Compound 1. In embodiments, methods described herein are suitable for increasing, achieving, and/or maintaining hemoglobin (Hb) levels within a target range. In embodiments, the Hb range is about 11.0-13.0 g/dL.

In one aspect, methods described herein include a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

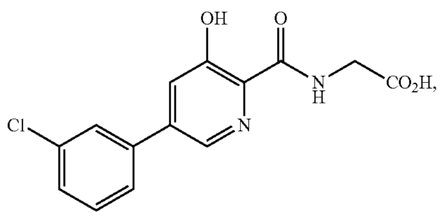

or a pharmaceutically acceptable salt, solvate, or hydrate thereof, wherein the dose can be any doses described herein (e.g., about 750 mg to about 1200 mg or about 750 mg to about 1800 mg once daily, or about 600 mg to about 1200 mg or about 600 mg to about 1800 mg three times weekly).

In embodiments, the patient is administered a dose of about 750-1800 mg of Compound 1 once daily. In embodiments, the patient is administered a dose of about 750-1200 mg of Compound 1 once daily. In embodiments, Compound 1 is administered orally to the patient. In embodiments, Compound 1 is in a unit dosage form (e.g., a unit dosage form formulated for oral administration such as tablets or capsules). In embodiments, the unit dosage form comprises about 150 mg, about 300 mg, or about 450 mg of Compound 1. In embodiments, the dose is about 750 mg of Compound 1 once daily. In embodiments, the dose is about 900 mg of Compound 1 once daily. In embodiments, the dose is about 1050 mg of Compound 1 once daily. In embodiments, the dose is about 1200 mg Compound 1 once daily. In embodiments, the dose is about 1350 mg Compound 1 once daily. In embodiments, the dose is about 1500 mg Compound 1 once daily. In embodiments, the dose is about 1650 mg Compound 1 once daily. In embodiments, the dose is about 1800 mg Compound 1 once daily.

In embodiments, the patient is administered a dose of about 600-1800 mg of Compound 1 three times weekly. In embodiments, the patient is administered a dose of about 600-1200 mg of Compound 1 three times weekly. In embodiments, Compound 1 is administered orally to the patient. In embodiments, Compound 1 is in a unit dosage form (e.g., a unit dosage form formulated for oral administration such as tablets or capsules). In embodiments, the unit dosage form comprises about 150 mg, about 300 mg, or about 450 mg of Compound 1. In embodiments, the dose is about 600 mg of Compound 1 three times weekly. In embodiments, the dose is about 750 mg of Compound 1 three times weekly. In embodiments, the dose is about 900 mg of Compound 1 three times weekly. In embodiments, the dose is about 1050 mg Compound 1 three times weekly. In embodiments, the dose is about 900 mg of Compound 1 three times weekly. In embodiments, the dose is about 1200 mg Compound 1 three times weekly. In embodiments, the dose is about 1350 mg Compound 1 three times weekly. In embodiments, the dose is about 1500 mg Compound 1 three times weekly. In embodiments, the dose is about 1650 mg Compound 1 three times weekly. In embodiments, the dose is about 1800 mg Compound 1 three times weekly.

In embodiments, a daily dose of Compound 1 is at least about 300 mg (e.g., about 300-1200 mg or about 300-1800 mg). In embodiments, an initial daily dose of Compound 1 is at least about 300 mg (e.g., about 300-1200 mg or about 300-1800 mg). In embodiments, a daily dose of Compound 1 is about 300 mg. In embodiments, an initial daily dose of Compound 1 is about 300 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the daily dose did not exceed 600 mg prior to administration of the TIW dose. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 450 mg (e.g., about 450-1200 mg or about 450-1800 mg). In embodiments, an initial daily dose of Compound 1 is at least about 450 mg (e.g., about 450-1200 mg or about 450-1800 mg). In embodiments, a daily dose of Compound 1 is about 450 mg. In embodiments, an initial daily dose of Compound 1 is about 450 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the daily dose did not exceed 600 mg prior to administration of the TIW dose. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 600 mg (e.g., about 600-1200 mg or about 600-1800 mg). In embodiments, an initial daily dose of Compound 1 is at least about 600 mg (e.g., about 600-1200 mg or about 600-1800 mg). In embodiments, a daily dose of Compound 1 is about 600 mg. In embodiments, an initial daily dose of Compound 1 is about 600 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the daily dose did not exceed 600 mg prior to administration of the TIW dose. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 750 mg (e.g., about 750-1200 mg or about 750-1200 mg). In embodiments, an initial daily dose of Compound 1 is at least about 750 mg (e.g., about 750-1200 mg or about 750-1200 mg). In embodiments, a daily dose of Compound 1 is about 750 mg. In embodiments, an initial daily dose of Compound 1 is about 750 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 900 mg (e.g., about 900-1200 mg or about 900-1800 mg). In embodiments, an initial daily dose of Compound 1 is at least about 900 mg (e.g., about 900-1200 mg or about 900-1800 mg). In embodiments, a daily dose of Compound 1 is about 900 mg. In embodiments, an initial daily dose of Compound 1 is about 900 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 1050 mg (e.g., about 1050-1200 mg or about 1050-1800 mg). In embodiments, an initial daily dose of Compound 1 is at least about 1050 mg (e.g., about 1050-1200 mg or about 1050-1800 mg). In embodiments, a daily dose of Compound 1 is about 1050 mg. In embodiments, an initial daily dose of Compound 1 is about 1050 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 1200 mg (e.g., about 1200-1800 mg). In embodiments, an initial daily dose of Compound 1 is at least about 1200 mg (e.g., about 1200-1800 mg). In embodiments, a daily dose of Compound 1 is about 1200 mg. In embodiments, an initial daily dose of Compound 1 is about 1200 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 1350 mg (e.g., about 1350-1800 mg). In embodiments, an initial daily dose of Compound 1 is at least about 1350 mg (e.g., about 1350-1800 mg). In embodiments, a daily dose of Compound 1 is about 1350 mg. In embodiments, an initial daily dose of Compound 1 is about 1350 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 1500 mg (e.g., about 1500-1800 mg). In embodiments, an initial daily dose of Compound 1 is at least about 1500 mg (e.g., about 1500-1800 mg). In embodiments, a daily dose of Compound 1 is about 1500 mg. In embodiments, an initial daily dose of Compound 1 is about 1500 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 1650 mg (e.g., about 1650-1800 mg). In embodiments, an initial daily dose of Compound 1 is at least about 1650 mg (e.g., about 1650-1800 mg). In embodiments, a daily dose of Compound 1 is about 1650 mg. In embodiments, an initial daily dose of Compound 1 is about 1650 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the TIW dose of Compound 1 is about 150 mg greater than the last daily dose of Compound 1. In embodiments, the patient continues to receive a daily dose of Compound 1.

In embodiments, a daily dose of Compound 1 is at least about 1800 mg. In embodiments, an initial daily dose of Compound 1 is at least about 1800 mg. In embodiments, a daily dose of Compound 1 is about 1800 mg. In embodiments, an initial daily dose of Compound 1 is about 1800 mg. In embodiments, the patient is then administered a dose comprising about 600 mg-1200 mg of Compound 1 three times weekly (TIW) after receiving an initial daily dose. In embodiments, the patient is then administered a dose comprising about 600 mg-1800 mg of Compound 1 three times weekly (TIW) after receiving an initial daily dose. In embodiments, the patient receives the administration of the TIW dose follows an initial period of daily dosing that is at least about 2, 3, 4, 5, 6, 7, 8, 9, 10, 11, 12, 13, 14, 15, or 16 weeks. In embodiments, the patient receives the administration of the TIW dose follows an initial period of daily dosing that is at least about 12 weeks. In embodiments, the TIW dose of Compound 1 is about 150 mg greater than the last daily dose of Compound 1. In embodiments, the patient continues to receive a daily dose of Compound 1.

In embodiments, the patient previously has not been treated with an erythropoiesis stimulating agent (ESA).

In embodiments, the patient previously has been treated with an erythropoiesis stimulating agent (ESA). In embodiments, the ESA is epoetin, darbepoetin alfa (DA), or methoxy polyethylene glycol-epoetin beta (epoetin beta pegol). In embodiments, the ESA is epoetin. In embodiments, the epoetin comprises epoetin alfa, epoetin beta, epoetin gamma, epoetin kappa, or a combination thereof. In embodiments, the epoetin is epoetin alfa. In embodiments, the ESA is darbepoetin alfa (DA). In embodiments, the ESA is methoxy polyethylene glycol-epoetin beta (epoetin beta pegol).

In embodiments, the patient previously has been treated with epoetin alfa at any of the doses described herein. In embodiments, the patient previously has been treated with epoetin alfa at a dose of about 50 U/kg to 100 Units/kg of body weight three times weekly. In embodiments, the patient has been previously treated with epoetin alfa at a dose of about 10 U/kg of body weight to about 500 U/kg of body weight 3 times weekly. In embodiments, the patient has been previously treated with epoetin alfa at a dose of about 10 U/kg of body weight to about 300 U/kg of body weight 3 times weekly. In embodiments, the patient has been previously treated with epoetin alfa at a dose of about 25 U/kg of body weight to about 300 U/kg of body weight 3 times weekly. In embodiments, the patient has been previously treated with epoetin alfa at a dose of about 50 U/kg of body weight to about 300 U/kg of body weight 3 times weekly. In embodiments, the patient has been previously treated with epoetin alfa at a dose of about 50 U/kg of body weight to about 200 U/kg of body weight 3 times weekly. In embodiments, the patient has been previously treated with epoetin alfa at a dose of about 50 U/kg of body weight to about 100 U/kg of body weight 3 times weekly. In embodiments, the patient has been previously treated with epoetin alfa in an amount of about ≤90 U/kg/week. In embodiments, a patient has been previously treated with epoetin alfa in an amount of about >90 U/kg/week to about <300 U/kg/week. In embodiments, the patient has been previously treated with epoetin alfa in an amount of about ≥300 U/kg/week. In embodiments, the patient has been previously treated with epoetin alfa in an amount of about 1,500 U/week to about 90,000 U/week. In embodiments, the patient has been previously treated with epoetin alfa in an amount of about ≥4500 U/week. In embodiments, the patient has been previously treated with epoetin alfa in an amount of about <4500 U/week.

In embodiments, the patient previously has been treated with darbepoetin alfa (DA) at a dose of about 0.45 mcg/kg of body weight weekly. In other embodiments, the patient previously has been treated with DA at a dose of about 0.75 mcg/kg of body weight every 2 weeks. In embodiments, the patient has been previously treated with DA at a dose of about 0.25 mcg/kg of body weight to about 0.75 mcg/kg of body weight once every four weeks. In embodiments, the patient has been previously treated with DA at a dose of about 0.25 mcg/kg of body weight to about 0.75 mcg/kg of body weight once every two weeks. In embodiments, the patient has been previously treated with DA at a dose of about 0.25 mcg/kg of body weight to about 0.75 mcg/kg of body weight once a week. In some embodiments, the patient previously has been treated with 0.45 mcg/kg of body weight of darbepoetin alfa weekly. In embodiments, the patient previously has been treated with at least 0.75 mcg/kg of body weight of darbepoetin alfa every 2 weeks. In embodiments, the patient has been previously treated with darbepoetin alfa in a dosage amount of about ≥15 μg weekly. In embodiments, the patient has been previously treated with darbepoetin alfa in a dosage amount of about <15 μg weekly. In embodiments, the patient has been previously treated with darbepoetin alfa in a dosage amount of about 6.25-200 mcg/week. In embodiments, the patient has been previously treated with darbepoetin alfa in a dosage amount of about ≤0.45 μg/kg/week. In embodiments, the patient has been previously treated with darbepoetin alfa in a dosage amount of about >0.45 μg/kg/week. In embodiments, the patient has been previously treated with darbepoetin alfa in a dosage amount of about >0.45 μg/kg/week and ≤1.50 μg/kg/week.

In embodiments, the patient previously has been treated with epoetin beta pegol at a dose of about 0.6 mcg/kg of body weight once every two weeks. In embodiments, the patient has been previously treated with epoetin beta pegol at a dose of about 0.3 mcg/kg of body weight to about 1.20 mcg/kg of body weight once every two weeks. In embodiments, the patient has been previously treated with epoetin beta pegol at a dose of about 0.6 mcg/kg of body weight to about 2.4 mcg/kg of body weight once monthly. In embodiments, the patient has been previously treated with epoetin beta pegol at a dose of about 0.6 mcg/kg once every two weeks. In embodiments, the patient has been previously treated with epoetin beta pegol at a dose of about 1.2 mcg/kg once every two weeks. In embodiments, the patient has been previously treated with epoetin beta pegol at an amount of about ≤250 μg/month.

In embodiments, the patient has anemia associated with or secondary to chronic kidney disease (CKD). In embodiments, the chronic kidney disease is non-dialysis dependent chronic kidney disease (NDD-CKD). In embodiments, the chronic kidney disease is dialysis-dependent chronic kidney disease (DD-CKD). In embodiments, the patient with CKD receives dialysis or previously has received dialysis. In embodiments, dialysis is hemodialysis (e.g., a patient with HD-CKD). In embodiments, dialysis is peritoneal dialysis (e.g., a patient with PD-CKD). In embodiments, the patient with CKD receives dialysis (e.g., hemodialysis or peritoneal dialysis). In embodiments, the patient with CKD previously received dialysis (e.g., hemodialysis or peritoneal dialysis).

In embodiments, the dose of Compound 1 is administered to the patient over a period of treatment that is at least about 12-260 weeks (e.g., at least about 12 weeks, at least about 24 weeks, at least about 28 weeks, at least about 32 weeks, at least about 36 weeks, at least about 40 weeks, at least about 44 weeks, at least about 48 weeks, at least about 52 weeks, at least about 64 weeks, at least about 76 weeks, at least about 88 weeks, at least about 104 weeks, at least about 116 weeks, at least about 128 weeks, at least about 140 weeks, at least about 156 weeks, at least about 168 weeks, at least about 180 weeks, at least about 192 weeks, at least about 208 weeks, or at least about 260 weeks). In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In another aspect, methods described herein include a method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

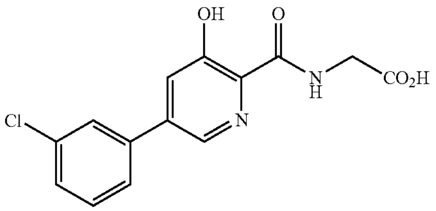

or a pharmaceutically acceptable salt, solvate, or hydrate thereof, wherein the dose comprises about 150 mg to about 1200 mg or about 150 mg to about 1800 mg of the Compound 1 three times weekly, and wherein the patient was previously administered a daily dose of Compound 1.

In embodiments, the dose comprises about 150 mg to about 600 mg three times weekly. In embodiments, the dose comprises about 600 mg to about 1200 mg three times weekly. In embodiments, the dose comprises about 750 mg to about 1200 mg three times weekly. In embodiments, the dose comprises about 600 mg to about 1800 mg three times weekly. In embodiments, the dose comprises about 750 mg to about 1800 mg three times weekly. In embodiments, the dose comprises about 150 mg three times weekly. In embodiments, the dose comprises about 300 mg three times weekly. In embodiments, the dose comprises about 450 mg three times weekly. In embodiments, the dose comprises about 600 mg three times weekly. In embodiments, the dose comprises about 750 mg three times weekly. In embodiments, the dose comprises about 900 mg three times weekly. In embodiments, the dose comprises about 1050 mg three times weekly. In embodiments, the dose comprises about 1200 mg three times weekly. In embodiments, the dose comprises about 1350 mg three times weekly. In embodiments, the dose comprises about 1500 mg three times weekly. In embodiments, the dose comprises about 1650 mg three times weekly. In embodiments, the dose comprises about 1800 mg three times weekly.

In embodiments, the patient was previously administered a daily dose comprising about 150 mg of Compound 1. In embodiments, the patient was previously administered a daily dose comprising about 300 mg of Compound 1. In embodiments, the patient was previously administered a daily dose comprising about 450 mg of Compound 1. In embodiments, the patient was previously administered a daily dose comprising about 600 mg of Compound 1.

In embodiments, the patient previously has not been treated with an erythropoiesis stimulating agent (ESA).

In embodiments, the patient previously has been treated with an erythropoiesis stimulating agent (ESA). In embodiments, the ESA is epoetin, darbepoetin alfa (DA), or methoxy polyethylene glycol-epoetin beta (epoetin beta pegol). In embodiments, the ESA is epoetin. In embodiments, the epoetin comprises epoetin alfa, epoetin beta, epoetin gamma, epoetin kappa, or a combination thereof. In embodiments, the epoetin is epoetin alfa. In embodiments, the ESA is darbepoetin alfa (DA). In embodiments, the ESA is methoxy polyethylene glycol-epoetin beta (epoetin beta pegol).

In embodiments, the patient previously has been treated with epoetin alfa at any of the doses described herein. In embodiments, the patient previously has been treated with epoetin alfa at a dose of about 50 U/kg to 100 Units/kg of body weight three times weekly. In embodiments, the patient has been previously treated with epoetin alfa at a dose of about 10 U/kg of body weight to about 500 U/kg of body weight 3 times weekly. In embodiments, the patient has been previously treated with epoetin alfa at a dose of about 10 U/kg of body weight to about 300 U/kg of body weight 3 times weekly. In embodiments, the patient has been previously treated with epoetin alfa at a dose of about 25 U/kg of body weight to about 300 U/kg of body weight 3 times weekly. In embodiments, the patient has been previously treated with epoetin alfa at a dose of about 50 U/kg of body weight to about 300 U/kg of body weight 3 times weekly. In embodiments, the patient has been previously treated with epoetin alfa at a dose of about 50 U/kg of body weight to about 200 U/kg of body weight 3 times weekly. In embodiments, the patient has been previously treated with epoetin alfa at a dose of about 50 U/kg of body weight to about 100 U/kg of body weight 3 times weekly. In embodiments, the patient has been previously treated with epoetin alfa in an amount of about ≤90 U/kg/week. In embodiments, a patient has been previously treated with epoetin alfa in an amount of about >90 U/kg/week to about <300 U/kg/week. In embodiments, the patient has been previously treated with epoetin alfa in an amount of about ≥300 U/kg/week. In embodiments, the patient has been previously treated with epoetin alfa in an amount of about 1,500 U/week to about 90,000 U/week. In embodiments, the patient has been previously treated with epoetin alfa in an amount of about ≥4500 U/week. In embodiments, the patient has been previously treated with epoetin alfa in an amount of about <4500 U/week.

In embodiments, the patient previously has been treated with darbepoetin alfa (DA) at a dose of about 0.45 mcg/kg of body weight weekly. In other embodiments, the patient previously has been treated with DA at a dose of about 0.75 mcg/kg of body weight every 2 weeks. In embodiments, the patient has been previously treated with DA at a dose of about 0.25 mcg/kg of body weight to about 0.75 mcg/kg of body weight once every four weeks. In embodiments, the patient has been previously treated with DA at a dose of about 0.25 mcg/kg of body weight to about 0.75 mcg/kg of body weight once every two weeks. In embodiments, the patient has been previously treated with DA at a dose of about 0.25 mcg/kg of body weight to about 0.75 mcg/kg of body weight once a week. In some embodiments, the patient previously has been treated with 0.45 mcg/kg of body weight of darbepoetin alfa weekly. In embodiments, the patient previously has been treated with at least 0.75 mcg/kg of body weight of darbepoetin alfa every 2 weeks. In embodiments, the patient has been previously treated with darbepoetin alfa in a dosage amount of about ≥15 μg weekly. In embodiments, the patient has been previously treated with darbepoetin alfa in a dosage amount of about <15 μg weekly. In embodiments, the patient has been previously treated with darbepoetin alfa in a dosage amount of about 6.25-200 mcg/week. In embodiments, the patient has been previously treated with darbepoetin alfa in a dosage amount of about ≤0.45 μg/kg/week. In embodiments, the patient has been previously treated with darbepoetin alfa in a dosage amount of about >0.45 μg/kg/week. In embodiments, the patient has been previously treated with darbepoetin alfa in a dosage amount of about >0.45 μg/kg/week and ≤1.50 μg/kg/week.

In embodiments, the patient previously has been treated with epoetin beta pegol at a dose of about 0.6 mcg/kg of body weight once every two weeks. In embodiments, the patient has been previously treated with epoetin beta pegol at a dose of about 0.3 mcg/kg of body weight to about 1.20 mcg/kg of body weight once every two weeks. In embodiments, the patient has been previously treated with epoetin beta pegol at a dose of about 0.6 mcg/kg of body weight to about 2.4 mcg/kg of body weight once monthly. In embodiments, the patient has been previously treated with epoetin beta pegol at a dose of about 0.6 mcg/kg once every two weeks. In embodiments, the patient has been previously treated with epoetin beta pegol at a dose of about 1.2 mcg/kg once every two weeks. In embodiments, the patient has been previously treated with epoetin beta pegol at an amount of about ≤250 μg/month.

In embodiments, the patient has anemia associated with or secondary to chronic kidney disease (CKD). In embodiments, the chronic kidney disease is non-dialysis dependent chronic kidney disease (NDD-CKD). In embodiments, the chronic kidney disease is dialysis-dependent chronic kidney disease (DD-CKD). In embodiments, the patient with CKD receives dialysis or previously has received dialysis. In embodiments, dialysis is hemodialysis (e.g., a patient with HD-CKD). In embodiments, dialysis is peritoneal dialysis (e.g., a patient with PD-CKD). In embodiments, the patient with CKD receives dialysis (e.g., hemodialysis or peritoneal dialysis). In embodiments, the patient with CKD previously received dialysis (e.g., hemodialysis or peritoneal dialysis).

In embodiments, the dose of Compound 1 is administered to the patient over a period of treatment that is at least about 12-260 weeks (e.g., at least about 12 weeks, at least about 24 weeks, at least about 28 weeks, at least about 32 weeks, at least about 36 weeks, at least about 40 weeks, at least about 44 weeks, at least about 48 weeks, at least about 52 weeks, at least about 64 weeks, at least about 76 weeks, at least about 88 weeks, at least about 104 weeks, at least about 116 weeks, at least about 128 weeks, at least about 140 weeks, at least about 156 weeks, at least about 168 weeks, at least about 180 weeks, at least about 192 weeks, at least about 208 weeks, or at least about 260 weeks). In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In another aspect, methods described herein include a method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

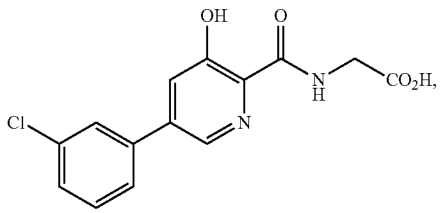

or a pharmaceutically acceptable salt, solvate, or hydrate thereof, wherein the dose can be any doses described herein (e.g., about 750 mg to about 1200 mg once daily or about 600 mg to about 1200 mg three times weekly, or about 750 mg to about 1800 mg once daily or about 600 mg to about 1800 mg three times weekly).

In embodiments, the patient is administered a dose of about 750-1200 mg of Compound 1 once daily. In embodiments, the patient is administered a dose of about 750-1800 mg of Compound 1 once daily. In embodiments, Compound 1 is administered orally to the patient. In embodiments, Compound 1 is in a unit dosage form (e.g., a unit dosage form formulated for oral administration such as tablets or capsules). In embodiments, the unit dosage form comprises about 150 mg, about 300 mg, or about 450 mg of Compound 1. In embodiments, the dose is about 750 mg of Compound 1 once daily. In embodiments, the dose is about 900 mg of Compound 1 once daily. In embodiments, the dose is about 1050 mg of Compound 1 once daily. In embodiments, the dose is about 1200 mg Compound 1 once daily. In embodiments, the dose is about 1350 mg Compound 1 once daily. In embodiments, the dose is about 1500 mg Compound 1 once daily. In embodiments, the dose is about 1650 mg Compound 1 once daily. In embodiments, the dose is about 1800 mg Compound 1 once daily.

In embodiments, the patient is administered a dose of about 600-1200 mg of Compound 1 three times weekly. In embodiments, the patient is administered a dose of about 600-1800 mg of Compound 1 three times weekly. In embodiments, Compound 1 is administered orally to the patient. In embodiments, Compound 1 is in a unit dosage form (e.g., a unit dosage form formulated for oral administration such as tablets or capsules). In embodiments, the unit dosage form comprises about 150 mg, about 300 mg, or about 450 mg of Compound 1. In embodiments, the dose is about 600 mg of Compound 1 three times weekly. In embodiments, the dose is about 750 mg of Compound 1 three times weekly. In embodiments, the dose is about 900 mg of Compound 1 three times weekly. In embodiments, the dose is about 1050 mg Compound 1 three times weekly. In embodiments, the dose is about 900 mg of Compound 1 three times weekly. In embodiments, the dose is about 1200 mg Compound 1 three times weekly. In embodiments, the dose is about 1350 mg Compound 1 three times weekly. In embodiments, the dose is about 1500 mg Compound 1 three times weekly. In embodiments, the dose is about 1650 mg Compound 1 three times weekly. In embodiments, the dose is about 1800 mg Compound 1 three times weekly.

In embodiments, the hemoglobin levels are increased to about at least 10.0 g/dL from a baseline hemoglobin level. In embodiments, the hemoglobin levels are increased to about at least 10.0 g/dL to 13.0 g/dL from a baseline hemoglobin level. In embodiments, the hemoglobin levels are increased to about at least 10.0 g/dL to about 12.0 g/dL from a baseline hemoglobin level. In embodiments, the hemoglobin levels are increased to about at least 10.0 g/dL to about 11.0 g/dL from a baseline hemoglobin level. In embodiments, the hemoglobin levels are increased to about at least ≥9.0 g/dL from a baseline hemoglobin level.

In embodiments, the patient has a baseline hemoglobin level of <10.0 g/dL. In embodiments, the patient has a baseline hemoglobin level of <9.0 g/dL. In embodiments, the patient has a baseline hemoglobin level of <8.0 g/dL.

In embodiments, the patient previously has not been treated with an erythropoiesis stimulating agent (ESA).

In embodiments, the patient previously has been treated with an erythropoiesis stimulating agent (ESA). In embodiments, the ESA is epoetin, darbepoetin alfa (DA), or methoxy polyethylene glycol-epoetin beta (epoetin beta pegol). In embodiments, the ESA is epoetin. In embodiments, the epoetin comprises epoetin alfa, epoetin beta, epoetin gamma, epoetin kappa, or a combination thereof. In embodiments, the epoetin is epoetin alfa. In embodiments, the ESA is darbepoetin alfa (DA). In embodiments, the ESA is methoxy polyethylene glycol-epoetin beta (epoetin beta pegol).

In embodiments, the patient previously has been treated with epoetin alfa at any of the doses described herein. In embodiments, the patient previously has been treated with epoetin alfa at a dose of about 50 U/kg to 100 Units/kg of body weight three times weekly. In embodiments, the patient has been previously treated with epoetin alfa at a dose of about 10 U/kg of body weight to about 500 U/kg of body weight 3 times weekly. In embodiments, the patient has been previously treated with epoetin alfa at a dose of about 10 U/kg of body weight to about 300 U/kg of body weight 3 times weekly. In embodiments, the patient has been previously treated with epoetin alfa at a dose of about 25 U/kg of body weight to about 300 U/kg of body weight 3 times weekly. In embodiments, the patient has been previously treated with epoetin alfa at a dose of about 50 U/kg of body weight to about 300 U/kg of body weight 3 times weekly. In embodiments, the patient has been previously treated with epoetin alfa at a dose of about 50 U/kg of body weight to about 200 U/kg of body weight 3 times weekly. In embodiments, the patient has been previously treated with epoetin alfa at a dose of about 50 U/kg of body weight to about 100 U/kg of body weight 3 times weekly. In embodiments, the patient has been previously treated with epoetin alfa in an amount of about ≤90 U/kg/week. In embodiments, a patient has been previously treated with epoetin alfa in an amount of about >90 U/kg/week to about <300 U/kg/week. In embodiments, the patient has been previously treated with epoetin alfa in an amount of about ≥300 U/kg/week. In embodiments, the patient has been previously treated with epoetin alfa in an amount of about 1,500 U/week to about 90,000 U/week. In embodiments, the patient has been previously treated with epoetin alfa in an amount of about ≥4500 U/week. In embodiments, the patient has been previously treated with epoetin alfa in an amount of about <4500 U/week.

In embodiments, the patient previously has been treated with darbepoetin alfa (DA) at a dose of about 0.45 mcg/kg of body weight weekly. In other embodiments, the patient previously has been treated with DA at a dose of about 0.75 mcg/kg of body weight every 2 weeks. In embodiments, the patient has been previously treated with DA at a dose of about 0.25 mcg/kg of body weight to about 0.75 mcg/kg of body weight once every four weeks. In embodiments, the patient has been previously treated with DA at a dose of about 0.25 mcg/kg of body weight to about 0.75 mcg/kg of body weight once every two weeks. In embodiments, the patient has been previously treated with DA at a dose of about 0.25 mcg/kg of body weight to about 0.75 mcg/kg of body weight once a week. In some embodiments, the patient previously has been treated with 0.45 mcg/kg of body weight of darbepoetin alfa weekly. In embodiments, the patient previously has been treated with at least 0.75 mcg/kg of body weight of darbepoetin alfa every 2 weeks. In embodiments, the patient has been previously treated with darbepoetin alfa in a dosage amount of about ≥15 μg weekly. In embodiments, the patient has been previously treated with darbepoetin alfa in a dosage amount of about <15 μg weekly. In embodiments, the patient has been previously treated with darbepoetin alfa in a dosage amount of about 6.25-200 mcg/week. In embodiments, the patient has been previously treated with darbepoetin alfa in a dosage amount of about ≤0.45 μg/kg/week. In embodiments, the patient has been previously treated with darbepoetin alfa in a dosage amount of about >0.45 μg/kg/week. In embodiments, the patient has been previously treated with darbepoetin alfa in a dosage amount of about >0.45 μg/kg/week and ≤1.50 μg/kg/week.

In embodiments, the patient previously has been treated with epoetin beta pegol at a dose of about 0.6 mcg/kg of body weight once every two weeks. In embodiments, the patient has been previously treated with epoetin beta pegol at a dose of about 0.3 mcg/kg of body weight to about 1.20 mcg/kg of body weight once every two weeks. In embodiments, the patient has been previously treated with epoetin beta pegol at a dose of about 0.6 mcg/kg of body weight to about 2.4 mcg/kg of body weight once monthly. In embodiments, the patient has been previously treated with epoetin beta pegol at a dose of about 0.6 mcg/kg once every two weeks. In embodiments, the patient has been previously treated with epoetin beta pegol at a dose of about 1.2 mcg/kg once every two weeks. In embodiments, the patient has been previously treated with epoetin beta pegol at an amount of about ≤250 μg/month.

In embodiments, the patient has anemia associated with or secondary to chronic kidney disease (CKD). In embodiments, the chronic kidney disease is non-dialysis dependent chronic kidney disease (NDD-CKD). In embodiments, the chronic kidney disease is dialysis-dependent chronic kidney disease (DD-CKD). In embodiments, the patient with CKD receives dialysis or previously has received dialysis. In embodiments, dialysis is hemodialysis (e.g., a patient with HD-CKD). In embodiments, dialysis is peritoneal dialysis (e.g., a patient with PD-CKD). In embodiments, the patient with CKD receives dialysis (e.g., hemodialysis or peritoneal dialysis). In embodiments, the patient with CKD previously received dialysis (e.g., hemodialysis or peritoneal dialysis).

In embodiments, the dose of Compound 1 is administered to the patient over a period of treatment that is at least about 12-260 weeks (e.g., at least about 12 weeks, at least about 24 weeks, at least about 28 weeks, at least about 32 weeks, at least about 36 weeks, at least about 40 weeks, at least about 44 weeks, at least about 48 weeks, at least about 52 weeks, at least about 64 weeks, at least about 76 weeks, at least about 88 weeks, at least about 104 weeks, at least about 116 weeks, at least about 128 weeks, at least about 140 weeks, at least about 156 weeks, at least about 168 weeks, at least about 180 weeks, at least about 192 weeks, at least about 208 weeks, or at least about 260 weeks). In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In another aspect, methods described herein include a method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

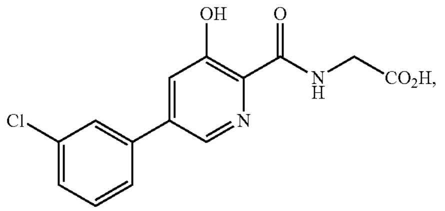

or a pharmaceutically acceptable salt, solvate, or hydrate thereof, wherein the dose can be any doses described herein (e.g., about 750 mg to about 1200 mg once daily or about 600 mg to about 1200 mg three times weekly, or about 750 mg to about 1800 mg once daily or about 600 mg to about 1800 mg three times weekly).

In embodiments, the patient is administered a dose of about 750-1200 mg of Compound 1 once daily. In embodiments, the patient is administered a dose of about 750-1800 mg of Compound 1 once daily. In embodiments, Compound 1 is administered orally to the patient. In embodiments, Compound 1 is in a unit dosage form (e.g., a unit dosage form formulated for oral administration such as tablets or capsules). In embodiments, the unit dosage form comprises about 150 mg, about 300 mg, or about 450 mg of Compound 1. In embodiments, the dose is about 750 mg of Compound 1 once daily. In embodiments, the dose is about 900 mg of Compound 1 once daily. In embodiments, the dose is about 1050 mg of Compound 1 once daily. In embodiments, the dose is about 1200 mg Compound 1 once daily. In embodiments, the dose is about 1350 mg Compound 1 once daily. In embodiments, the dose is about 1500 mg Compound 1 once daily. In embodiments, the dose is about 1650 mg Compound 1 once daily. In embodiments, the dose is about 1800 mg Compound 1 once daily.

In embodiments, the patient is administered a dose of about 600-1200 mg of Compound 1 three times weekly. In embodiments, the patient is administered a dose of about 600-1800 mg of Compound 1 three times weekly. In embodiments, Compound 1 is administered orally to the patient. In embodiments, Compound 1 is in a unit dosage form (e.g., a unit dosage form formulated for oral administration such as tablets or capsules). In embodiments, the unit dosage form comprises about 150 mg, about 300 mg, or about 450 mg of Compound 1. In embodiments, the dose is about 600 mg of Compound 1 three times weekly. In embodiments, the dose is about 750 mg of Compound 1 three times weekly. In embodiments, the dose is about 900 mg of Compound 1 three times weekly. In embodiments, the dose is about 1050 mg Compound 1 three times weekly. In embodiments, the dose is about 900 mg of Compound 1 three times weekly. In embodiments, the dose is about 1200 mg Compound 1 three times weekly. In embodiments, the dose is about 1350 mg Compound 1 three times weekly. In embodiments, the dose is about 1500 mg Compound 1 three times weekly. In embodiments, the dose is about 1650 mg Compound 1 three times weekly. In embodiments, the dose is about 1800 mg Compound 1 three times weekly.

In embodiments, the hemoglobin levels are maintained at about 10.0 g/dL to about 13.0 g/dL. In embodiments, the hemoglobin levels are maintained at about 10.0 g/dL to about 12.0 g/dL. In embodiments, the hemoglobin levels are maintained at about 10.0 g/dL to about 11.0 g/dL.

In embodiments, the patient previously has not been treated with an erythropoiesis stimulating agent (ESA).

In embodiments, the patient previously has been treated with an erythropoiesis stimulating agent (ESA). In embodiments, the ESA is epoetin, darbepoetin alfa (DA), or methoxy polyethylene glycol-epoetin beta (epoetin beta pegol). In embodiments, the ESA is epoetin. In embodiments, the epoetin comprises epoetin alfa, epoetin beta, epoetin gamma, epoetin kappa, or a combination thereof. In embodiments, the epoetin is epoetin alfa. In embodiments, the ESA is darbepoetin alfa (DA). In embodiments, the ESA is methoxy polyethylene glycol-epoetin beta (epoetin beta pegol).

In embodiments, the patient previously has been treated with epoetin alfa at any of the doses described herein. In embodiments, the patient previously has been treated with epoetin alfa at a dose of about 50 U/kg to 100 Units/kg of body weight three times weekly. In embodiments, the patient has been previously treated with epoetin alfa at a dose of about 10 U/kg of body weight to about 500 U/kg of body weight 3 times weekly. In embodiments, the patient has been previously treated with epoetin alfa at a dose of about 10 U/kg of body weight to about 300 U/kg of body weight 3 times weekly. In embodiments, the patient has been previously treated with epoetin alfa at a dose of about 25 U/kg of body weight to about 300 U/kg of body weight 3 times weekly. In embodiments, the patient has been previously treated with epoetin alfa at a dose of about 50 U/kg of body weight to about 300 U/kg of body weight 3 times weekly. In embodiments, the patient has been previously treated with epoetin alfa at a dose of about 50 U/kg of body weight to about 200 U/kg of body weight 3 times weekly. In embodiments, the patient has been previously treated with epoetin alfa at a dose of about 50 U/kg of body weight to about 100 U/kg of body weight 3 times weekly. In embodiments, the patient has been previously treated with epoetin alfa in an amount of about ≤90 U/kg/week. In embodiments, a patient has been previously treated with epoetin alfa in an amount of about >90 U/kg/week to about <300 U/kg/week. In embodiments, the patient has been previously treated with epoetin alfa in an amount of about ≥300 U/kg/week. In embodiments, the patient has been previously treated with epoetin alfa in an amount of about 1,500 U/week to about 90,000 U/week. In embodiments, the patient has been previously treated with epoetin alfa in an amount of about ≥4500 U/week. In embodiments, the patient has been previously treated with epoetin alfa in an amount of about <4500 U/week.

In embodiments, the patient previously has been treated with darbepoetin alfa (DA) at a dose of about 0.45 mcg/kg of body weight weekly. In other embodiments, the patient previously has been treated with DA at a dose of about 0.75 mcg/kg of body weight every 2 weeks. In embodiments, the patient has been previously treated with DA at a dose of about 0.25 mcg/kg of body weight to about 0.75 mcg/kg of body weight once every four weeks. In embodiments, the patient has been previously treated with DA at a dose of about 0.25 mcg/kg of body weight to about 0.75 mcg/kg of body weight once every two weeks. In embodiments, the patient has been previously treated with DA at a dose of about 0.25 mcg/kg of body weight to about 0.75 mcg/kg of body weight once a week. In some embodiments, the patient previously has been treated with 0.45 mcg/kg of body weight of darbepoetin alfa weekly. In embodiments, the patient previously has been treated with at least 0.75 mcg/kg of body weight of darbepoetin alfa every 2 weeks. In embodiments, the patient has been previously treated with darbepoetin alfa in a dosage amount of about ≥15 μg weekly. In embodiments, the patient has been previously treated with darbepoetin alfa in a dosage amount of about <15 μg weekly. In embodiments, the patient has been previously treated with darbepoetin alfa in a dosage amount of about 6.25-200 mcg/week. In embodiments, the patient has been previously treated with darbepoetin alfa in a dosage amount of about ≤0.45 μg/kg/week. In embodiments, the patient has been previously treated with darbepoetin alfa in a dosage amount of about >0.45 μg/kg/week. In embodiments, the patient has been previously treated with darbepoetin alfa in a dosage amount of about >0.45 μg/kg/week and ≤1.50 μg/kg/week.

In embodiments, the patient previously has been treated with epoetin beta pegol at a dose of about 0.6 mcg/kg of body weight once every two weeks. In embodiments, the patient has been previously treated with epoetin beta pegol at a dose of about 0.3 mcg/kg of body weight to about 1.20 mcg/kg of body weight once every two weeks. In embodiments, the patient has been previously treated with epoetin beta pegol at a dose of about 0.6 mcg/kg of body weight to about 2.4 mcg/kg of body weight once monthly. In embodiments, the patient has been previously treated with epoetin beta pegol at a dose of about 0.6 mcg/kg once every two weeks. In embodiments, the patient has been previously treated with epoetin beta pegol at a dose of about 1.2 mcg/kg once every two weeks. In embodiments, the patient has been previously treated with epoetin beta pegol at an amount of about ≤250 μg/month.

In embodiments, the patient has anemia associated with or secondary to chronic kidney disease (CKD). In embodiments, the chronic kidney disease is non-dialysis dependent chronic kidney disease (NDD-CKD). In embodiments, the chronic kidney disease is dialysis-dependent chronic kidney disease (DD-CKD). In embodiments, the patient with CKD receives dialysis or previously has received dialysis. In embodiments, dialysis is hemodialysis (e.g., a patient with HD-CKD). In embodiments, dialysis is peritoneal dialysis (e.g., a patient with PD-CKD). In embodiments, the patient with CKD receives dialysis (e.g., hemodialysis or peritoneal dialysis). In embodiments, the patient with CKD previously received dialysis (e.g., hemodialysis or peritoneal dialysis).

In embodiments, the dose of Compound 1 is administered to the patient over a period of treatment that is at least about 12-260 weeks (e.g., at least about 12 weeks, at least about 24 weeks, at least about 28 weeks, at least about 32 weeks, at least about 36 weeks, at least about 40 weeks, at least about 44 weeks, at least about 48 weeks, at least about 52 weeks, at least about 64 weeks, at least about 76 weeks, at least about 88 weeks, at least about 104 weeks, at least about 116 weeks, at least about 128 weeks, at least about 140 weeks, at least about 156 weeks, at least about 168 weeks, at least about 180 weeks, at least about 192 weeks, at least about 208 weeks, or at least about 260 weeks). In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

Erythropoietin Stimulating Agents (ESA)

In embodiments, a patient has not been previously treated with an erythropoiesis stimulating agent (ESA).

Methods described herein also can be beneficial to patients who have previously been treated with an erythropoiesis-stimulating agent (ESA). Methods described herein can be particularly beneficial in achieving the desired therapeutic outcome while avoiding or reducing adverse effects associated with ESA therapy. Exemplary adverse effects may include cardiovascular events, rapid deterioration of kidney function, earlier requirement for dialysis, and vascular access failure.

Darbepoetin alfa. In embodiments, a patient previously has been treated with darbepoetin alfa (DA) in accordance to the US package insert (PI), European Union (EU) Summary of Product Characteristics (SmPC), local prescribing information, or physician's clinical discretion (e.g., as described herein). In some embodiments, the NDD-CKD patient or the DD-CKD patient was previously treated with about 0.45 mcg/kg of body weight of darbepoetin alfa intravenously or subcutaneously weekly. In other embodiments the NDD-CKD patient or the DD-CKD patient was previously treated with about 0.75 mcg/kg of body weight of darbepoetin alfa intravenously or subcutaneously every 2 weeks. In some embodiments the NDD-CKD or the DD-CKD patient was previously treated with at least 0.45 mcg/kg of body weight of darbepoetin alfa intravenously or subcutaneously at 4 week intervals.

Darbepoetin alfa is available in single dose vials as 25, 40, 60, 100, 200, 300, and 500 mcg/1 mL, and 150 mcg/0.75 mL. Darbepoetin alfa is also available as single-dose prefilled syringes as 25 mcg/0.42 mL, 40 mcg/0.4 mL, 60 mcg/0.3 mL, 100 mcg/0.5 mL, 150 mcg/0.3 mL, 200 mcg/0.4 mL, 300 mcg/0.6 mL, and 500 mcg/1 mL. Darbepoetin alfa can be administered intravenously or subcutaneously. In embodiments, a patient has been previously treated with darbepoetin alfa (DA) in a dosage amount of about 0.25 mcg/kg of body weight to about 0.75 mcg/kg of body weight once every four weeks. In embodiments, a patient has been previously treated with darbepoetin alfa (DA) in a dosage amount of about 0.25 mcg/kg of body weight to about 0.75 mcg/kg of body weight once every two weeks. In embodiments, a patient has been previously treated with darbepoetin alfa (DA) in a dosage amount of about 0.25 mcg/kg of body weight to about 0.75 mcg/kg of body weight once a week. In some embodiments, the patient was previously treated with 0.45 mcg/kg of body weight of darbepoetin alfa intravenously or subcutaneously weekly. In other embodiments the patient was previously treated with at least 0.75 mcg/kg of body weight of darbepoetin alfa intravenously or subcutaneously every 2 weeks. In embodiments, a patient has been previously treated with darbepoetin alfa in a dosage amount of about ≥15 μg weekly. In embodiments, a patient has been previously treated with darbepoetin alfa in a dosage amount of about <15 μg weekly. In embodiments, a patient has been previously treated with darbepoetin alfa in a dosage amount of about 6.25-200 mcg/week. In embodiments, a patient has been previously treated with darbepoetin alfa in a dosage amount of about ≤0.45 μg/kg/week. In embodiments, a patient has been previously treated with darbepoetin alfa in a dosage amount of about >0.45 μg/kg/week. In embodiments, a patient has been previously treated with darbepoetin alfa in a dosage amount of about >0.45 μg/kg/week and ≤1.50 μg/kg/week. In embodiments, the patient has DD-CKD. In embodiments, the patient has NDD-CKD.

Epoetin alfa. In embodiments, a patient previously received treatment with epoetin alfa in accordance to the US package insert (PI), European Union (EU) Summary of Product Characteristics (SmPC), local prescribing information, or physician's clinical discretion (e.g., as described herein). In some embodiments, the DD-CKD patient or the NDD-CKD patient was previously treated with epoetin alfa at a dose of at least 50 to 100 Units/kg of body weight three times weekly. Epoetin alfa can be administered intravenously or subcutaneously. Preferably, intravenous route is recommended for patients on hemodialysis. Epoetin alfa is available as an injectable form as 2,000 Units/mL, 3,000 Units/mL, 4,000 Units/mL, and 10,000 Units/mL in single-dose vials; and as 20,000 Units/2 mL (10,000 Units/mL) and 20,000 Units/mL in multiple-dose vials containing benzyl alcohol. In embodiments, a patient has been previously treated with epoetin alfa in an amount of about 10 U/kg of body weight to about 500 U/kg of body weight 3 times weekly. In embodiments, a patient has been previously treated with epoetin alfa in an amount of about 10 U/kg of body weight to about 300 U/kg of body weight 3 times weekly. In embodiments, a patient has been previously treated with epoetin alfa in an amount of about 25 U/kg of body weight to about 300 U/kg of body weight 3 times weekly. In embodiments, a patient has been previously treated with epoetin alfa in an amount of about 50 U/kg of body weight to about 300 U/kg of body weight 3 times weekly. In embodiments, a patient has been previously treated with epoetin alfa in an amount of about 50 U/kg of body weight to about 200 U/kg of body weight 3 times weekly. In embodiments, a patient has been previously treated with epoetin alfa in an amount of about 50 U/kg of body weight to about 100 U/kg of body weight 3 times weekly. In embodiments, a patient has been previously treated with epoetin alfa in an amount of about ≤90 U/kg/week. In embodiments, a patient has been previously treated with epoetin alfa in an amount of about >90 U/kg/week to about <300 U/kg/week. In embodiments, a patient has been previously treated with epoetin alfa in an amount of about ≥300 U/kg/week. In embodiments, a patient has been previously treated with epoetin alfa in an amount of about 1,500 U/week to about 90,000 U/week. In embodiments, a patient has been previously treated with epoetin alfa in an amount of about ≥4500 U/week. In embodiments, a patient has been previously treated with epoetin alfa in an amount of about <4500 U/week.

Epoetin beta. In embodiments, a patient previously received treatment with epoetin beta (e.g., as described herein). In some embodiments, the DD-CKD patient or the NDD-CKD patient was previously treated with 20 IU/kg of epoetin beta three times weekly. In some embodiments, the DD-CKD patient or the NDD-CKD patient is at least 80 IU/kg of epoetin beta three times weekly. The preferable route for administration is intravenously. Epoetin beta is available as 500 IU, 2000 IU, 3000 IU, 4000 IU, 5000 IU, 6000 IU, 10,000 IU, 20,000 IU, and 30,000 IU solutions for injection as single-dose prefilled syringes.

Epoetin beta pegol. In embodiments, a patient previously received treatment with epoetin beta pegol (e.g., as described herein). In some embodiments, the DD-CKD patient or the NDD-CKD patient was previously treated with epoetin beta pegol at a dose of about 0.6 mcg/kg of body weight administered once every two weeks. Epoetin beta pegol can be administered intravenously or subcutaneously. The preferable route for administration is intravenously. Epoetin beta pegol is available for injection as prefilled syringes in 50, 75, 100, 150, 200, or 250 mcg in 0.3 mL solutions of epoetin beta pegol. In embodiments, a patient has been previously treated with epoetin beta pegol in a dosage amount of about 0.3 mcg/kg of body weight to about 1.20 mcg/kg of body weight once every two weeks. In embodiments, a patient has been previously treated with epoetin beta pegol in a dosage amount of about 0.6 mcg/kg of body weight to about 2.4 mcg/kg of body weight once monthly. In embodiments, a patient has been previously treated with epoetin beta pegol in a dosage amount of about 0.6 mcg/kg once every two weeks. In embodiments, a patient has been previously treated with epoetin beta pegol in a dosage amount of about 1.2 mcg/kg once every two weeks. In embodiments, a patient has been previously treated with epoetin beta pegol at an amount of about ≤250 μg/month.

Dialysis Status

The methods described herein can be beneficial to patients of different dialysis status.

In embodiments, the patient's dialysis status can be used to select an initial dose of Compound 1. In embodiments, the patient's dialysis status can be used to modify the dose of Compound 1 (e.g., a dose increase within about six or eight weeks of commencing treatment with Compound 1).

In embodiments, the patient is non-dialysis dependent. For example, in some embodiments, the patient has non-dialysis chronic kidney disease (a NDD-CKD patient).

In embodiments, the patient is dialysis-dependent. For example, in embodiments, the patient has dialysis dependent chronic kidney disease (a DD-CKD patient).

In embodiments, the patient receives or previously has received dialysis. In embodiments, the patient receives dialysis. In embodiments, the patient previously received dialysis.

In embodiments, dialysis is hemodialysis (HD). In embodiments, the patient with chronic kidney disease receives or previously received hemodialysis. In embodiments, the patient with chronic kidney disease receives hemodialysis. In embodiments, the patient with chronic kidney disease previously received hemodialysis.

In embodiments, dialysis is peritoneal dialysis (PD). In embodiments, the patient with chronic kidney disease receives or previously received peritoneal dialysis. In embodiments, the patient with chronic kidney disease receives peritoneal dialysis. In embodiments, the patient with chronic kidney disease previously received peritoneal dialysis.

Tune and Length of Administration

The methods described herein are suitable for treating anemia, increasing hemoglobin levels, and maintaining hemoglobin levels in a patient over an extended period of time. In embodiments, anemia is anemia secondary to or associated with chronic kidney disease (CKD). In embodiments, the CKD non-dialysis dependent CKD (NDD-CKD). In embodiments, the CKD is dialysis-dependent CKD (DD-CKD), e.g., hemodialysis or peritoneal dialysis.

In embodiments, a dose of Compound 1 is administered to the patient over a period of treatment that is at least about 12-260 weeks (e.g., at least about 12 weeks, at least about 24 weeks, at least about 28 weeks, at least about 32 weeks, at least about 36 weeks, at least about 40 weeks, at least about 44 weeks, at least about 48 weeks, at least about 52 weeks, at least about 64 weeks, at least about 76 weeks, at least about 88 weeks, at least about 104 weeks, at least about 116 weeks, at least about 128 weeks, at least about 140 weeks, at least about 156 weeks, at least about 168 weeks, at least about 180 weeks, at least about 192 weeks, at least about 208 weeks, or at least about 260 weeks). In embodiments, the dose is administered to the patient for at least about 12 weeks. In embodiments, the dose is administered to the patient for at least about 24 weeks. In embodiments, the dose is administered to the patient for at least about 28 weeks. In embodiments, the dose is administered to the patient for at least about 32 weeks. In embodiments, the dose is administered to the patient for at least about 36 weeks. In embodiments, the dose is administered to the patient for at least about 40 weeks. In embodiments, the dose is administered to the patient for at least about 44 weeks. In embodiments, the dose is administered to the patient for at least about 48 weeks. In embodiments, the dose is administered to the patient for at least about 52 weeks. In embodiments, the dose is administered to the patient for at least about 64 weeks. In embodiments, the dose is administered to the patient for at least about 76 weeks. In embodiments, the dose is administered to the patient for at least about 88 weeks. In embodiments, the dose is administered to the patient for at least about 104 weeks. In embodiments, the dose is administered to the patient for at least about 116 weeks. In embodiments, the dose is administered to the patient for at least about 128 weeks. In embodiments, the dose is administered to the patient for at least about 140 weeks. In embodiments, the dose is administered to the patient for at least about 156 weeks. In embodiments, the dose is administered to the patient for at least about 168 weeks. In embodiments, the dose is administered to the patient for at least about 180 weeks. In embodiments, the dose is administered to the patient for at least about 192 weeks. In embodiments, the dose is administered to the patient for at least about 208 weeks. In embodiments, the dose is administered to the patient for at least about 260 weeks.

In the methods described herein, Compound 1 is suitable to be administered at various times of the day. In certain embodiments, the patient does not have endogenous EPO circadian circulation expression patterns. In certain embodiments, the Compound 1 is administered to mimic the normal and endogenous circadian pattern of the EPO (i.e., of a healthy person), such that the peak of the EPO expression occurs between 6 p.m. and midnight. In certain embodiments, the compound is administered at a time such that the EPO peak is earlier than the cortisol peak, specifically, such that the EPO peak precedes the cortisol peak by about 1 hour, by about 2 hours, by about 3 hours, by about 4 hours, by about 5 hours, by about 6 hours, by about 7 hours, or by about 8 hours. In certain embodiments, the cortisol peak is in the morning. In certain embodiments, the compound is administered at 8 a.m., 9 a.m., 10 a.m., 11 a.m., 12 p.m., 1 p.m., or 2 p.m. In certain embodiments, Compound 1 is administered after breakfast. In certain embodiments, compound 1 is administered between breakfast and 8 a.m., 9 a.m., 10 a.m., 11 a.m., 12 p.m., 1 p.m., or 2 p.m. In certain embodiments, compound 1 is administered before lunch. In certain embodiments, Compound 1 is administered between breakfast and lunch. In certain embodiments Compound 1 is administered after lunch. In certain embodiments, Compound 1 is administered between lunch and 2 p.m. In certain embodiments, Compound 1 is administered every day at the or at about the same time.

Safety Assessment

Methods described herein can also avoid or reduce adverse events and/or adverse drug reactions, including those typically associated with ESA therapy. For example, methods described herein can avoid or reduce adverse events related to cardiovascular events, retinal disorders, and/or malignancy.

In embodiments, the methods described herein avoid or reduce the risk of thrombosis. In some such embodiments, the thrombosis is thromboembolism. The term "thromboembolism" refers to the formation in a blood vessel of a clot (thrombus) that breaks loose and is carried by the blood stream to plug another vessel. The clot may plug a vessel in the lungs, brain, gastrointestinal tract, kidneys, or leg. Thromboembolism can be fatal. Such thromboembolic conditions include, but are not limited to, as cerebral infarctions, myocardial infarctions, and pulmonary embolisms. Accordingly, the methods described herein can avoid or reduce adverse events related to thromboembolism such as cerebral infarction, myocardial infarction, and/or pulmonary embolism.

Iron-Related Parameters and Red Blood Cell Indices

Methods described herein can also achieve favorable results in iron-related parameters (e.g., serum ferritin, transferrin saturation (TSAT), total iron-binding capacity (TIBC), hepcidin, serum iron, and/or monthly dose of iron by any route of administration) and/or red blood cell indices (e.g., mean corpuscular volume (MCV), mean corpuscular hemoglobin (MCH), mean corpuscular hemoglobin concentration (MCHC), and/or red cell distribution width (RDW)). For examples, methods described herein can achieve favorable results in these parameters and indices as compared to other methods of treating anemia, including ESA therapy.

Total Iron Binding Capacity (TIBC). Total iron binding capacity (TIBC) is a measure of the blood's capacity to bind iron with transferrin and is performed by drawing blood and measuring the maximum amount of iron that the blood can carry. Accordingly, the TIBC is representative of the amount of circulating transferrin, which contains two binding sites for transporting iron from iron storage sites to erythroid progenitor cells.

Phase 2a clinical trials showed that, in stage 3, 4, or 5 CKD patients, Compound 1 was able to increase total iron binding capacity (TIBC) levels, at 6 weeks post administration as compared to placebo treated patients. Unexpectedly, the increase in TIBC levels was not associated with an increase in serum iron levels. Further, it was also discovered that Compound 1 resulted in a dose-related increase in TIBC and a decrease in transferrin saturation (TSAT), suggesting administration of Compound 1 results in enhanced iron mobilization.

In embodiments, a patient has an increase in total iron binding capacity (TIBC) relative to a baseline level. In some embodiments, methods described herein raise the TIBC relative to a baseline TIBC in a patient, without significantly increasing the serum iron level relative to a baseline.

In certain embodiments, the TIBC increases by about 10 μg/dL, about 20 μg/dL, about 30 μg/dL, about 40 μg/dL, about 50 μg/dL about 60 μg/dL, about 70 μg/dL, about 80 μg/dL, about 90 μg/dL or about 100 μg/dL relative to a baseline TIBC. In certain embodiments, the TIBC increases by at least about 10 μg/dL, at least about 20 μg/dL, at least about 30 μg/dL, at least about 40 μg/dL, at least about 50 μg/dL, at least about 60 μg/dL, at least about 70 μg/dL, at least about 80 μg/dL, at least about 90 μg/dL or at least about 100 μg/dL. In certain embodiments, the TIBC increases by between about 10 μg/dL and about 60 μg/dL, between about 10 μg/dL and about 50 μg/dL, between about 10 μg/dL and about 40 μg/dL, between about 10 μg/dL and about 30 μg/dL, or between about 10 μg/dL and about 20 μg/dL. In certain embodiments, the TIBC increases by between 20 μg/dL and about 60 μg/dL, between about 30 μg/dL and about 60 μg/dL, between 40 μg/dL and about 60 μg/dL, or between about 50 μg/dL and about 60 μg/dL.

In certain such embodiments, the TIBC increase occurs over about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 24 weeks relative to a baseline TIBC.

In certain embodiments, administration of Compound 1 is suitable to increase the total iron binding capacity in the patient by at least 5%, 10%, 15%, 20%, 25%, 30%, 35%, 40%, 45%, or at least 50%. In more specific embodiments, the pharmaceutically effective amount is suitable to increase the total iron binding capacity in the patient by at least 5%, 10%, 15%, 20%, 25%, 30%, 35%, 40%, 45%, or at least 50% while the total serum iron levels are not increased, or are increased by at most 1%, 2%, 3%, 4%, 5%, 6%, 7%, 8%, 9%, 10%, 15%, 20%, or at most 25%.

In certain embodiments, unsaturated iron binding capacity (UIBC) may be determined by adding serum to an alkaline buffer/reductant solution containing a known concentration of iron to saturate the available binding sites on transferrin. The Ferrozine chromogen reacts only with the $Fe^{2+}$; therefore, an iron reductant is added to insure that all iron is present in the ferrous state. The excess unbound divalent iron reacts with Ferrozine chromogen to form a magenta complex, which is measure spectrophotometerically. The unsaturated iron binding capacity (UIBC) is equal to the difference measured in the concentrations of the added iron solution and the excess unbound iron. Serum TIBC is equal to total serum iron plus UIBC and may therefore be calculated using the results of the UIBC and serum iron determinations.

Serum Iron. In certain embodiments, serum iron may be determined using a test based on the FerroZine method without deproteinization. Specimens are analyzed on the Roche Modular Instrument utilizing Roche Diagnostics Reagents. Under acidic conditions, iron is liberated from transferrin. The detergent clarifies lipemic samples. Ascorbate reduces the released Fe3+ ions to Fe2+ ions, which then react with FerroZine to form a colored complex. The color intensity is directly proportional to the iron concentration and can be measured photometrically.

Serum iron level measurements determine how much iron is in the plasma. The amount of iron that is found in serum is dependent on the ability to mobilize the iron that is stored in cells. This process of iron mobilization is controlled by ferroportin and hepcidin which work in concert to regulate the amount of iron that is exported to the plasma. Ferroportin moves iron in and out of cells, while hepcidin regulates the action of ferroportin, thereby determining whether iron is released into the plasma or retained in the cell. Accordingly, it is possible to have large amounts of iron stored in cells, but relatively low levels of serum iron depending on the activity of ferroportin and hepcidin.

In certain embodiments, the serum iron level increases by less than about 20 μg/dL, less than about 15 μg/dL, less than about 10 μg/dL, or less than about 5 μg/dL relative to a baseline serum iron level. In certain embodiments, the serum iron level increases by between about 0 μg/dL and about 20 μg/dL, between about 0 μg/dL and about 15 μg/dL, between about 0 μg/dL and about 10 μg/dL, or between about 0 μg/dL and about 5 μg/dL.

Hepcidin Levels. In embodiments, a patient has a decrease in hepcidin level relative to a baseline level.

In certain embodiments, hepcidin level decreases less than about 20%, less than about 15%, less than about 10%, less than about 5%, less than about 4%, less than about 3%, less than about 2%, or less than about 1% relative to the baseline hepcidin level. In certain embodiments, hepcidin level decreases by between about 0% and about 20%, between about 0% and about 15%, between about 0% and about 10%, or between about 0% and about 5%, between about 0% and about 4%, between about 0% and about 3%, between about 0% and about 2%, or between about 0% and about 1% relative to the baseline hepcidin expression level. In certain embodiments, hepcidin level decreases by about 20%, about 15%, about 10%, about 5%, about 4%, about 3%, about 2%, or about 1% relative to the baseline hepcidin level.

In embodiments, methods described herein can increase the peak levels of serum hepcidin during the circadian cycle by at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, or at least 150% relative to the trough levels of serum hepcidin without decreasing the serum levels of hepcidin by more than 1%, 2%, 3%, 4%, 5%, 6%, 7%, 8%, 9%, 10%, 11%, 12%, 13%, 14%, 15%, 16%, 17%, 18%, 19%, or by more than 20% relative to hepcidin levels prior to administration of Compound 1.

In embodiments, methods described herein can be suitable to increase the peak levels of hepcidin levels by at least 2%, 3%, 4%, 5%, 6%, 7%, 8%, 9%, 10%, 11%, 12%, 13%, 14%, 15%, 16%, 17%, 18%, or at least 20%, relative to hepcidin levels prior to the treatment without decreasing the serum levels of hepcidin by more than 1%, 2%, 3%, 4%, 5%, 6%, 7%, 8%, 9%, 10%, 11%, 12%, 13%, 14%, 15%, 16%, 17%, 18%, 19%, or by more than 20% relative to hepcidin levels prior to administration of Compound 1.

In certain embodiments, hepcidin level may be determined, as described in Ganz, T. et al., "Immunoassay for human serum hepcidin" *Blood* 112: 4292-97 (2008). Briefly, the antibody to human hepcidin was purified on staphylococcal protein A columns according to the manufacturer's protocol; 96-well plates were coated with the antibody and incubated with 100 μL (standard samples) or 200 μL (samples with very low concentration of hepcidin) of 1:20 dilution of serum or 1:10 dilution of urine in Tris-buffered saline containing 0.05% Tween-20 (TBS-Tween 20), with 10 ng/mL of biotinylated hepcidin-25 added as the tracer. Standard curves were prepared by serial 2-fold dilution of synthetic hepcidin 4000 ng/mL in TBS-Tween 20 buffer containing the tracer. The integrity and bioactivity of synthetic hepcidin and biotinylated hepcidin were verified by mass spectrometry and by bioassay with ferroportin-green fluorescent protein expressing HEK-293 cells. After washing, the assay was developed with streptavidin-peroxidase and tetramethyl benzidine. The enzymatic reaction was stopped by sulfuric acid, and the plate was read at 450 nm on a DTX 880 microplate reader. Standard curves were fitted with 12-point fit using GraphPad Prism software. The fitted curve was then used to convert sample absorbance readings to hepcidin concentrations.

Hemoglobin Levels. In certain embodiments, hemoglobin values are adjusted for altitude, gender, and age of the patient.

In embodiments, a patient has a baseline hemoglobin level of about <10 g/dL. In embodiments, a patient has a baseline hemoglobin level of about ≤9 g/dL. In embodiments, a patient has a baseline hemoglobin level of about ≤8 g/dL.

In embodiments, methods described herein increase and/or maintain the level of hemoglobin to/within a target range or level.

In embodiments, the target hemoglobin range is about 11.0-13.0 g/dL. In embodiments, the target hemoglobin range is about 10.0-12.0 g/dL. In embodiments, the target hemoglobin range is about 10.0-11.0 g/dL. In embodiments, the target hemoglobin level is ≥10.0 g/dL.

In embodiments, the hemoglobin levels of the patient are maintained at a level of 8.0 g/dL and at or below about 13.0 g/dL, at least about 8.5 g/dL and at or below 13.0 g/dL, at least about 9.0 g/dL and at or below 13.0 g/dL, at least about 9.5 g/dL and at or below 13.0 g/dL, or at least about 10.0 g/dL and at or below about 13.0 g/dL. In certain such embodiments, hemoglobin levels are maintained at a level of at least about 11.0 g/dL and at or below about 13.0 g/dL. In certain such embodiments, hemoglobin levels are maintained at a level of at least about 11.0 g/dL and at or below about 12.0 g/dL. In embodiments, hemoglobin levels are maintained at about 10.0-13.0 g/dL. In embodiments, hemoglobin levels are maintained at about 10.0-12.0 g/dL. In embodiments, hemoglobin levels are maintained at about 11.0-13.0 g/dL. In embodiments, hemoglobin levels are maintained at about 11.0-12.0 g/dL.

In embodiments, a patient has a hemoglobin level of about 8.0 g/dL to about 13.0 g/dL. In embodiments, a patient has a hemoglobin level of about 8.0 g/dL to about 12.0 g/dL. In embodiments, a patient has a hemoglobin level of about 8.0 g/dL to about 11.0 g/dL. In embodiments, a patient has a hemoglobin level of about 9.0 g/dL to about 12.0 g/dL. In embodiments, a patient has a hemoglobin level of about 9.5 g/dL to about 12.0 g/dL. In embodiments, a patient has a hemoglobin level of about 9.0 g/dL to about 12.5 g/dL. In embodiments, a patient has a hemoglobin level of about <11.0 g/dL. In embodiments, a patient has a hemoglobin level of about >11.5 g/dL. In embodiments, a patient has a hemoglobin level of about ≥9.5 g/dL to about <11.0 g/dL. In embodiments, a patient has a hemoglobin level of about ≥8.0 g/dL to about <11.0 g/dL. In embodiments, a patient has a hemoglobin level of about ≥12.0 g/dL. In embodiments, a patient has a hemoglobin level of about ≥13.0 g/dL.

In embodiments, methods describe herein increase the level of hemoglobin by at least about 0.2 g/dL, by at least about 0.3 g/dL, by at least about 0.4 g/dL, by at least about 0.5 g/dL, by at least about 0.6 g/dL, by at least about 0.7 g/dL, by at least about 0.8 g/dL, by at least about 0.9 g/dL, by at least about 1.0 g/dL, by at least about 1.2 g/dL, or by at least about 1.5 g/dL relative to a baseline hemoglobin level in the patient.

In embodiments, hemoglobin levels are increased to about 10.0-12.0 g/dL. In embodiments, hemoglobin levels are increased to about 10.0-11.0 g/dL. In embodiments, hemoglobin levels are increased to about 11.0-13.0 g/dL. In embodiments, hemoglobin levels are increased to about ≥10.0 g/dL.

In certain embodiments, the level of serum hemoglobin is raised by between about 0.1 and about 1.0 g/dL, between about 0.1 and about 0.9 g/dL, about 0.1 and about 0.8 g/dL, about 0.1 and about 0.7 g/dL, about 0.1 and about 0.6 g/dL, or about 0.1 and about 0.5 g/dL over a period of time, such as about one week, about two weeks, about three weeks, about four weeks, about five weeks, or about six weeks relative to the baseline hemoglobin level. In certain embodiments, the level of hemoglobin is raised by at least about 0.1 g/dL, about 0.2 g/dL, about 0.3 g/dL, about 0.4 g/dL, about 0.5 g/dL, about 0.6 g/dL, about 0.7 g/dL, about 0.8 g/dL, about 0.9, or about 1.0 g/dL over a period of time, such as about one week, about two weeks, about three weeks, about four weeks, about five weeks, or about six weeks relative to the baseline hemoglobin level.

In certain embodiments, the level of hemoglobin is raised by about 0.1 g/dL over a period of one week relative to the baseline hemoglobin level. In certain embodiments, the level of hemoglobin is raised by about 0.1 g/dL over a period of two weeks relative to the baseline hemoglobin level. In certain embodiments, the level of hemoglobin is raised by about 0.5 g/dL over a period of three weeks relative to the baseline hemoglobin level. In certain embodiments, the level of hemoglobin is raised by about 0.6 g/dL over a period of four weeks relative to the baseline hemoglobin level. In certain embodiments, the level of hemoglobin is raised by about 0.6 g/dL over a period of five weeks relative to the baseline hemoglobin level. In certain embodiments, the level of hemoglobin is raised by about 0.6 g/dL over a period of six weeks relative to the baseline hemoglobin level.

Serum hemoglobin levels may be determined, for example using standard approach CBC where red cells are lysed and potassium ferricyanide oxidizes hemoglobin to methemoglobin, which combines with potassium cyanide forming cyanmethemoglobin. The brown color is measured spectrophotometrically and the corresponding hemoglobin reported.

Serum Ferritin and Transferrin Saturation (TSAT). In embodiments, a patient has a decrease in serum ferritin level relative to a baseline level.

In embodiments, a patient has a ferritin level of at least about 50 ng/mL or even at least about 100 ng/mL. In embodiments, serum ferritin is maintained at a level of between about 50 ng/mL and about 300 ng/mL. In embodiments, a patient has a serum ferritin level of about >100 ng/mL.

In embodiments, transferrin saturation (TSAT) decreases relative to a baseline TSAT. In embodiments, a patient has a transferrin saturation (TSAT) of at least about 15%, at least about 18%, or even at least about 20%. In embodiments, a patient has a serum ferritin level of about ≥100 ng/mL and/or a transferrin saturation (TSAT) of ≥20%.

In embodiments, a patient has a serum ferritin level of about ≥100 ng/mL and/or a transferrin saturation (TSAT) of ≥20%. In embodiments, a patient has a serum ferritin level of about ≥100 ng/mL and a transferrin saturation (TSAT) of about ≥20%.

Patient Populations

The dose and dosage regimens described herein may be used in methods for treating anemia secondary to or associated with CKD, comprising administering to a patient having anemia an effective amount of Compound 1, or a pharmaceutically acceptable salt thereof.

As described herein, methods can be useful for the treatment of patients of having various dialysis statuses (e.g., a dialysis status as described herein).

In certain embodiments, the patient has non-dialysis-dependent chronic kidney disease (NDD-CKD). The NDD-CKD patients include those CKD patients who do not yet require the life-supporting treatments for kidney failure, such as kidney replacement therapy (RRT, including maintenance dialysis or kidney transplantation).

In other embodiments, the patient is a dialysis dependent CKD patient (DD-CKD). DD-CKD patients are in end-stage kidney disease. ESKD is typically the irreversible conclusion of the NDD-CKD. Even though the NDD-CKD status refers to the status of persons with earlier stages of CKD (stages 1 to 4), people with advanced stage of CKD (stage 5), who have not yet started kidney replacement therapy, are also referred to as NDD-CKD. Therefore, in some embodiments, the NDD-CKD patient will need or begin dialysis during the administration of Compound 1. In embodiments, dialysis is hemodialysis (HD). In embodiments, dialysis is peritoneal dialysis (PD).

In some embodiments, the patient had been previously treated with an ESA, such as an erythropoietin mimetic. In certain embodiments the ESA is an rhEPO product, including, but not limited to, epoetin alfa, epoetin beta, darbepoetin, or peginesatide. (e.g., epoetin alfa, epoetin beta, darbepoetin, or peginesatide). In some embodiments, at least eight (8) weeks prior to being administered Compound 1, the patient discontinued use of the ESA. In certain embodiments, the patient is refractory or resistant to treatment with an ESA.

In some embodiments, the patient has a ferritin level of at least about 100 ng/mL. In other embodiments, the patient has a transferritin saturation of at least about 20%.

In some embodiments, the patient has a body mass index (BMI) of less than about 30 kg/m$^2$.

In embodiments, a patient is an adult. In embodiments, a patient is ≥18 years old. In embodiments, a patient is ≥20 years old. In certain embodiments, the patient is between the ages of about 20 years old and about 90 years old, for example between the ages of about 25 years old and about 90 years old, between the ages of about 30 years old and about 90 years old, between the ages of about 35 years old and about 90 years old, between the ages of about 40 years old and about 90 years old, between the ages of about 45 years old and about 90 years old, between the ages of about 50 years old and about 90 years old, between the ages of about 55 years old and about 90 years old, between the ages of about 60 years old and about 90 years old, between the ages of about 60 years old and about 85 years old, or between the ages of about 60 years old and about 80 years old. In certain embodiments, the patient is between the ages of about 60 years old and about 80 years old. In certain embodiments, the patient is about 70 years old.

In some embodiments, the patient is at least 20 years old, at least 25 years old, at least 30 years old, at least 35 years old, at least 40 years old, at least 45 years old, at least 50 years old, at least 55 years old, at least 60 years old, at least 65 years old, at least 70 years old, at least 75 years old, at least 80 years old, at least 85 years old, or at least 90 years old. In some embodiments, the patient is about 20 years old, about 21 years old, about 22 years old, about 23 years old, about 24 years old, about 25 years old, about 26 years old, about 27 years old, about 28 years old, about 29 years old, about 30 years old, about 31 years old, about 32 years old, about 33 years old, about 34 years old, about 35 years old, about 36 years old, about 37 years old, about 38 years old, about 39 years old, about 40 years old, about 41 years old, about 42 years old, about 43 years old, about 44 years old, about 45 years old, about 46 years old, about 47 years old, about 48 years old, about 49 years old, about 50 years old, about 51 years old, 52 years old, about 53 years old, about 54 years old, about 55 years old, about 56 years old, about 57 years old, about 58 years old, about 59 years old, about 60 years old, about 61 years old, about 62 years old, about 63 years old, about 64 years old, about 65 years old, about 66 years old, about 67 years old, about 68 years old, about 69 years old, about 70 years old, about 71 years old, about 72 years old, about 73 years old, about 74 years old, about 75 years old, about 76 years old, about 77 years old, about 78 years old, about 79 years old, about 80 years old, about 81 years old, about 82 years old, about 83 years old, about 84 years old, about 85 years old, about 86 years old, about 87 years old, about 88 years old, about 89 years old, or about 90 years old.

The patient may be a member of any racial or ethnic subpopulation, including White, Black, Hispanic, and Asian. The patient may also be male or female.

Hyporesponders

In some embodiments, the patient is an ESA hyporesponder, i.e., the patient does not respond adequately to ESA or is resistant to ESA treatment. In embodiments, an ESA hyporesponder comprises acute hyporesponder and/or chronic hyporesponder.

ESA resistance, or ESA hyporesponsiveness, is a state in which hemoglobin response is less than typically anticipated for a given dose of ESA, and a higher dose of ESA is typically administered to hyporesponders. ESA hyporesponsiveness can be chronic (persistent) or acute (transient). Hyporesponsiveness can be determined by a method demonstrated in Sibbel, S. P., Koro, C. E., Brunelli, S. M. et al. Characterization of chronic and acute ESA hyporesponse: a retrospective cohort study of hemodialysis patients. *BMC Nephrol* 16, 144 (2015). https://doi.org/10.1186/s12882-015-0138-x. Other definitions of hyporesponsive can be found in Luo et al., Spectrum and Burden of Erythropoiesis Stimulating Agent Hyporesponsiveness Among Contemporary Hemodialysis Patients. *Am J Kidney Dis* 2016; 68:763-771 and Locatelli et al., Revised European best practice guidelines for the management of anaemia in patients with chronic renal failure. *Nephrol Dial Transplant.* 2004; 19(Suppl2):1-47.

Additional embodiments for hyporesponder and/or hyporesponsive patient populations include those described in Karaboyas A, Morgenstern H, Fleischer N L, et al. Inflammation and Erythropoiesis-Stimulating Agent Response in Hemodialysis Patients: A Self-matched Longitudinal Study of Anemia Management in the Dialysis Outcomes and Practice Patterns Study (DOPPS). *Kidney Medicine.* 2020; 2(3):286-96; Kimachi M, Fukuma S, Yamazaki S, et al. Minor Elevation in C-Reactive Protein Levels Predicts Incidence of Erythropoiesis-Stimulating Agent Hyporesponsiveness among Hemodialysis Patients. *Nephron.* 2015; 131 (2):123-30; Mohammadpour A-H, Nazemian F, Khaiat M, et al. Evaluation of the effect of pentoxifylline on erythropoietin-resistant anemia in hemodialysis patients. *Saudi Journal of Kidney Diseases and Transplantation.* 2014; 25(1): 73-8; Suttorp M M, Hoekstra T, Rotmans J I, et al. Erythropoiesis-stimulating agent resistance and mortality in hemodialysis and peritoneal dialysis patients. *BMC Nephrology.* 2013; 14(1):200; and Tsuruya K, Hayashi T, Yamamoto H, et al. Renal prognoses by different target hemoglobin levels achieved by epoetin beta pegol dosing to chronic kidney disease patients with hyporesponsive anemia to erythropoiesis-stimulating agent: a multicenter open-label randomized controlled study. *Clinical and Experimental Nephrology.* 2021; 25(5):456-66, including as described herein.

In embodiments, acute ESA hyporesponse can be defined as hyporesponse lasting <4 months. In embodiments, the patient is an ESA hyporesponder. In embodiments, the patient is an acute ESA hyporesponder.

In embodiments, chronic ESA hyporesponse can be defined as hyporesponse lasting ≥4 months. In embodiments, the patient is an ESA hyporesponder. In embodiments, the patient is a chronic ESA hyporesponder.

ESA hyporesponsiveness can be determined by ESA hemoglobin levels, iron indices, and/or ESA dose. In embodiments, ESA hyporesponsiveness is determined by ESA dose and hemoglobin levels. In embodiments, a hyporesponder receives an ESA dose of >7700/treatment of epoetin alfa three times a week (or equivalent units of other ESAs, e.g., darbepoetin alfa or epoetin beta pegol, based on manufacturers' recommendation) and has hemoglobin level of <10 g/dL on each of 2 successive bimonthly measurements. In embodiments, a hyporesponder receives an ESA dose of ≥300 U/kg/week of epoetin alfa (or equivalent units of other ESAs, e.g., darbepoetin alfa or epoetin beta pegol, based on manufacturers' recommendation) and has a hemoglobin level below a target range, e.g., <10 g/dL.

In embodiments, a hyporesponder receives an ESA dose (e.g., >8,000 units/week for HD, or >4,000 units/week for PD patients) and has a hemoglobin level below a target range (e.g., <11 g/dL). In embodiments, a hyporesponder (e.g., a HD patient) receives an ESA dose of >8,000 units/week. In embodiments, a hyporesponder (e.g., a PD patient) receives an ESA dose of >4,000 units/week.

In embodiments, a hyporesponder receives an ESA dose of ≥9,000 U/week (e.g., ≥9,000 U/week of recombinant human epoetin [rHuEPO]-α or rHuEPO-β) and has a hemoglobin level below a target range (e.g., <10 g/dL). In embodiments, a hyporesponder receives an ESA dose of ≥60 μg/week (e.g., ≥60 μg/week of darbepoetin-α), and has a hemoglobin level below a target range (e.g., <10 g/dL).

In embodiments, a hyporesponder receives an ESA dose of ≥12,000 IU/week (e.g., ≥12,000 IU/week of rh-Epo), and has a hemoglobin level below a target range (e.g., <10.7 g/dL).

In embodiments, a hyporesponder receives an ESA dose of >6,000 U/week, and has a hemoglobin level below a target range (e.g., <10 g/dL). In embodiments, a hyporesponder receives an ESA dose of >8,000 U/week, and has a hemoglobin level below a target range (e.g., <10 g/dL).

In embodiments, a hyporesponder receives an above median ESA dose. In embodiments, a hyporesponder receives an ESA dose of ≥12,000 IU/week. In embodiments, a hyporesponder receives an ESA dose of ≥9,000 U/week. In embodiments, a hyporesponder receives an ESA dose of >8,000 units/week. In embodiments, a hyporesponder receives an ESA dose of >6,000 U/week. In embodiments, a hyporesponder receives an ESA dose of >4,000 U/week.

In embodiments, a hyporesponder has a lower baseline hemoglobin level compared to an ESA responder. In embodiments, a hyporesponder has a baseline hemoglobin level of <11 g/dL. In embodiments, a hyporesponder has a baseline hemoglobin level of <10.7 g/dL. In embodiments, a hyporesponder has a baseline hemoglobin level of <10.0 g/dL. In embodiments, a patient has a baseline hemoglobin level of <9.5 g/dL. In embodiments, a patient has a baseline hemoglobin level of <9.0 g/dL. In embodiments, a patient has a baseline hemoglobin level of about 8.0-10.0 g/dL. In embodiments, a patient has a baseline hemoglobin level of about 8.5-10.0 g/dL.

In embodiments, a hyporesponder has a lower TSAT compared to an ESA responder. In embodiments, a patient has a TSAT of 530%. In embodiments, a patient has a TSAT of ≤25%. In embodiments, a patient has a TSAT of 520%. In embodiments, a patient has a TSAT of ≤15%.

In embodiments, a patient is a hyporesponder. In embodiments, the patient receives an ESA (e.g., darbepoetin alfa, epoetin alfa, epoetin beta, or epoetin beta pegol) dose as described herein. In embodiments, the patient receives an ESA (e.g., darbepoetin alfa, epoetin alfa, epoetin beta, or epoetin beta pegol) dose (e.g., a dose as described herein) for about at least 8 weeks.

In embodiments, a patient is a hyporesponder. In embodiments, the patient receives ≥1 μg/kg/week of DA. In embodiments, the patient receives >100 μg/week of DA. In embodiments, the patient receives >50 μg/week of epoetin beta pegol. In embodiments, the patient receives >23000 IU/week of epoetin alfa or epoetin analogues. In embodiments, the patient receives ≥300 U/kg/week epoetin alfa. In embodiments, the patient receives ≥7700 U of epoetin alfa per dialysis session.

In embodiments, the patient receives ≥1 μg/kg/week of DA for about at least 8 weeks. In embodiments, the patient receives >100 μg/week of DA for about at least 8 weeks. In embodiments, the patient receives >50 μg/week of epoetin beta pegol for about at least 8 weeks. In embodiments, the patient receives >23000 IU/week of epoetin alfa or epoetin analogues for about at least 8 weeks. In embodiments, the patient receives ≥300 U/kg/week epoetin alfa for about at least 8 weeks. In embodiments, the patient receives ≥7700 U of epoetin alfa per dialysis session for about at least 8 weeks.

In embodiments, a patient who is a hyporesponder receives an initial daily dose of Compound 1 that is at least about 600 mg. In embodiments, a patient who is a hyporesponder receives an initial daily dose of Compound 1 that is about 600 mg.

In embodiments, a patient previously received a mean weekly epoetin alfa dose that was ~≥300 U/kg/week prior to commencement of therapy with Compound 1. In embodiments, the mean weekly epoetin alfa dose was received for at least about 2, 3, 4, 5, 6, 7, 8, 9, or 10 weeks prior to treatment with Compound 1.

Glomerular Filtration Rate

A glomerular filtration rate (GFR)≥60 ml/min/1.73 $m^2$ is considered normal without chronic kidney disease if there is no kidney damage present.

Kidney damage is defined signs of damage seen in blood, urine, or imaging studies which includes lab albumin/creatinine ratio (ACR)≥30. All people with a GFR<60 ml/min/1.73 $m^2$ for 3 months are defined as having chronic kidney disease.

Protein in the urine is regarded as an independent marker for worsening of kidney function and cardiovascular disease.

There are five (5) stages for CKD as shown in Table 1.

TABLE 1

Chronic Kidney Disease (CKD) Staging
CKD G1-5 A1-3 glomerular filtration rate
(GFR) and albumin/creatinine ratio (ACR)

| | | | ACR | | |
|---|---|---|---|---|---|
| | | | A1 Normal to mildly increased <30 | A2 Moderately increased 30-300 | A3 Severely increased >300 |
| G1 | Normal | 90+ | 1 if kidney damage present | 1 | 2 |
| G2 | Mildly decreased | 60-89 | 1 if kidney damage present | 1 | 2 |
| G3a | Mildly to moderately decreased | 45-59 | 1 | 2 | 3 |
| G3b | Moderately to severely decreased | 30-44 | 2 | 3 | 3 |
| G4 | Severely decreased | 15-29 | 3 | 4+ | 4+ |
| G5 | Kidney failure | <15 | 4+ | 4+ | 4+ |

Numbers 1-4 indicates risk of progression as well as frequency of monitoring (number of times a year).
Kidney Disease Improving Global Outcomes - KDIGO 2012 Clinical Practice Guideline for the Evaluation and Management of Chronic Kidney Disease Stage 1: Slightly diminished function; kidney damage with normal or relatively high GFR (≥90 mL/min/1.73 $m^2$) and persistent albuminuria. Kidney damage is defined as pathological abnormalities or markers of damage, including abnormalities in blood or urine tests or imaging studies.

Stage 2: Mild reduction in GFR (60-89 mL/min/1.73 $m^2$) with kidney damage. Kidney damage is defined as pathological abnormalities or markers of damage, including abnormalities in blood or urine tests or imaging studies.

Stage 3: Moderate reduction in GFR (30-59 mL/min/1.73 $m^2$). British guidelines distinguish between stage 3A (GFR 45-59) and stage 3B (GFR 30-44) for purposes of screening and referral.

Stage 4: Severe reduction in GFR (15-29 mL/min/1.73 $m^2$). Preparation for kidney replacement therapy.

Stage 5: Established kidney failure (GFR<15 mL/min/1.73 $m^2$), permanent kidney replacement therapy, or end-stage kidney disease.

GFR can be estimated based on a serum creatinine levels. Creatinine is a muscle waste product that is filtered from the blood by the kidneys and released into the urine at a relatively steady rate. When kidney function decreases, less creatinine is eliminated and concentrations increase in the blood. With the creatinine test, a reasonable estimate of the actual GFR can be determined. Different equations may be used to calculate eGFR. In some embodiments, eGFR is calculated based on Chronic Kidney Disease Epidemiology Collaboration (CKD-EPI) creatinine equation (2009). In other embodiments, eGFR is calculated by Equation 1 (Eq. 1):

$$\text{eGFR (mL/min/1.73 m}^2\text{)}=194\times\text{serum creatinine}-1.094\times\text{age}-0.287\text{(females: }\times 0.739\text{)} \quad \text{(Eq. 1)}$$

In some embodiments, the patient has an eGFR of less than about 60 mL/min/1.73 $m^2$, less than about 45 mL/min/1.73 $m^2$, less than about 30 mL/min/1.73 $m^2$, less than about 15 mL/min/1.73 $m^2$, or less than about 15 mL/min/1.73 $m^2$.

In certain embodiments, the CKD is stage 1, 2, 3, 4, or 5 chronic kidney disease. In certain such embodiments, the CKD is stage 3, 4, or 5 chronic kidney disease. In certain embodiments, the CKD is stage 1 chronic kidney disease. In certain embodiments, the CKD is stage 2 chronic kidney disease. In certain embodiments, the CKD is stage 3 chronic kidney disease. In certain embodiments, the CKD is stage 4 chronic kidney disease. In certain embodiments, the CKD is stage 5 chronic kidney disease. In certain embodiments, the chronic kidney disease is pre-dialysis chronic kidney disease. In certain embodiments, the patient is a dialysis patient and these patients may be referred to as having end stage renal disease (ESRD).

Doses and Dosing Regimens

The specific doses of Compound 1 in any of the methods described herein can be administered in any manner known to the skilled artisan. Exemplary doses are provided herein, including in the Examples.

Exemplary doses of Compound 1 include doses of about 150-1800 mg of Compound 1. In embodiments, the dose comprises about 150 mg-1200 mg of Compound 1. In embodiments, the dose comprises about 450 mg-1200 mg of Compound 1. In embodiments, the dose comprises about 600 mg-1200 mg of Compound 1. In embodiments, the dose comprises about 750 mg-1200 mg of Compound 1. In embodiments, the dose comprises about 450 mg-1800 mg of Compound 1. In embodiments, the dose comprises about 600 mg-1800 mg of Compound 1. In embodiments, the dose comprises about 750 mg-1800 mg of Compound 1. In embodiments, a dose of Compound 1 is about 150 mg. In embodiments, a dose of Compound 1 is about 300 mg. In embodiments, a dose of Compound 1 is about 450 mg. In embodiments, a dose of Compound 1 is about 600 mg. In embodiments, a dose of Compound 1 is about 750 mg. In embodiments, a dose of Compound 1 is about 900 mg. In embodiments, a dose of Compound 1 is about 1050 mg. In embodiments, a dose of Compound 1 is about 1200 mg. In embodiments, a dose of Compound 1 is about 1350 mg. In embodiments, a dose of Compound 1 is about 1500 mg. In embodiments, a dose of Compound 1 is about 1650 mg. In embodiments, a dose of Compound 1 is about 1800 mg.

In embodiments, any exemplary dose described herein (e.g., a dose of Compound 1 that is about 150 mg, about 300 mg, about 450 mg, about 600 mg, about 750 mg, about 900 mg, about 1050 mg, about 1200 mg, about 1350 mg, about 1500 mg, about 1650 mg, or about 1800 mg) is administered to a patient about once daily. In embodiments, a dose is about 750 mg-1800 mg of Compound 1 administered once daily. In embodiments, a dose is about 750 mg-1200 mg of Compound 1 administered once daily. In embodiments, a dose is about 750 mg-900 mg of Compound 1 administered once daily. In embodiments, a dose is about 900 mg-1800 mg of Compound 1 administered once daily. In embodiments, a dose is about 900 mg-1200 mg of Compound 1 administered once daily. In embodiments, a dose is about 150 mg Compound 1 administered once daily. In embodiments, a dose is about 300 mg Compound 1 administered once daily. In embodiments, a dose is about 450 mg Compound 1 administered once daily. In embodiments, a dose is about 600 mg Compound 1 administered once daily. In embodiments, a dose is about 750 mg Compound 1 administered once daily. In embodiments, a dose is about 900 mg Compound 1 administered once daily. In embodiments, a dose is about 1050 mg Compound 1 administered once daily. In embodiments, a dose is about 1200 mg Compound 1 administered once daily. In embodiments, a dose is about 1350 mg Compound 1 administered once daily. In embodiments, a dose is about 1500 mg Compound 1 administered once daily. In embodiments, a dose is about 1650 mg Compound 1 administered once daily. In embodiments, a dose is about 1800 mg Compound 1 administered once daily.

In embodiments, any exemplary dose described herein (e.g., a dose of Compound 1 that is about 150 mg, about 300 mg, about 450 mg, about 600 mg, about 750 mg, about 900 mg, about 1050 mg, about 1200 mg, about 1350 mg, about 1500 mg, about 1650 mg, or about 1800 mg) is administered to a patient about once weekly. In embodiments, a dose is about 150 mg Compound 1 administered once weekly. In embodiments, a dose is about 300 mg Compound 1 administered once weekly. In embodiments, a dose is about 450 mg Compound 1 administered once weekly. In embodiments, a dose is about 600 mg Compound 1 administered once weekly. In embodiments, a dose is about 750 mg Compound 1 administered once weekly. In embodiments, a dose is about 900 mg Compound 1 administered once weekly. In embodiments, a dose is about 1050 mg Compound 1 administered once weekly. In embodiments, a dose is about 1200 mg Compound 1 administered once weekly. In embodiments, a dose is about 1350 mg Compound 1 administered once weekly. In embodiments, a dose is about 1500 mg Compound 1 administered once weekly. In embodiments, a dose is about 1650 mg Compound 1 administered once weekly. In embodiments, a dose is about 1800 mg Compound 1 administered once weekly.

In embodiments, any exemplary dose described herein (e.g., a dose of Compound 1 that is about 150 mg, about 300 mg, about 450 mg, about 600 mg, about 750 mg, about 900 mg, about 1050 mg, about 1200 mg, about 1350 mg, about 1500 mg, about 1650 mg, or about 1800 mg) is administered to a patient about three times weekly. In embodiments, a dose is about 600 mg-1800 mg of Compound 1 administered three times weekly. In embodiments, a dose is about 600 mg-1200 mg of Compound 1 administered three times weekly. In embodiments, a dose is about 600 mg-900 mg of Compound 1 administered three times weekly. In embodiments, a dose is about 750 mg-900 mg of Compound 1 administered three times weekly. In embodiments, a dose is about 900 mg-1800 mg of Compound 1 administered three times weekly. In embodiments, a dose is about 900 mg-1200 mg of Compound 1 administered three times weekly. In embodiments, a dose is about 150 mg Compound 1 administered three times weekly. In embodiments, a dose is about 300 mg Compound 1 administered three times weekly. In embodiments, a dose is about 450 mg Compound 1 administered three times weekly. In embodiments, a dose is about 600 mg Compound 1 administered three times weekly. In embodiments, a dose is about 750 mg Compound 1 administered three times weekly. In embodiments, a dose is about 900 mg Compound 1 administered three times weekly. In embodiments, a dose is about 1050 mg Compound 1 administered three times weekly. In embodiments, a dose is about 1200 mg Compound 1 administered three times weekly. In embodiments, a dose is about 1350 mg Compound 1 administered three times weekly. In embodiments, a dose is about 1500 mg Compound 1 administered three times weekly. In embodiments, a dose is about 1650 mg Compound 1 administered three times weekly. In embodiments, a dose is about 1800 mg Compound 1 administered three times weekly.

A patient can receive any exemplary dose according to any exemplary dosing frequency for a certain number of consecutive weeks, e.g., as described herein.

In embodiments of any methods described herein, the patient is administered a dose of Compound 1 (e.g., about 150 mg, about 300 mg, about 450 mg, about 600 mg, about 750 mg, about 900 mg, about 1050 mg, about 1200 mg, about 1350 mg, about 1500 mg, about 1650 mg, or about 1800 mg) for a period that is at least about 12, 24, 28, 32, 36, 40, 44, 48, 52, 64, 76, 88, 104, 116, 128, 140, 156, 168, 180, 192, 208, or 260 weeks. In embodiments, the patient is administered a dose of Compound 1 that is about 450 mg-1800 mg for a period that is at least about 12, 24, 28, 32, 36, 40, 44, 48, 52, 64, 76, 88, 104, 116, 128, 140, 156, 168, 180, 192, 208, or 260 weeks. In embodiments, the patient is administered a dose of Compound 1 that is about 600 mg-1800 mg for a period that is at least about 12, 24, 28, 32, 36, 40, 44, 48, 52, 64, 76, 88, 104, 116, 128, 140, 156, 168, 180, 192, 208, or 260 weeks. In embodiments, the patient is administered a dose of Compound 1 that is about 750 mg-1800 mg for a period that is at least about 12, 24, 28, 32, 36, 40, 44, 48, 52, 64, 76, 88, 104, 116, 128, 140, 156, 168, 180, 192, 208, or 260 weeks. In embodiments, the patient is administered a dose of Compound 1 that is about 450 mg-1200 mg for a period that is at least about 12, 24, 28, 32, 36, 40, 44, 48, 52, 64, 76, 88, 104, 116, 128, 140, 156, 168, 180, 192, 208, or 260 weeks. In embodiments, the patient is administered a dose of Compound 1 that is about 600 mg-1200 mg for a period that is at least about 12, 24, 28, 32, 36, 40, 44, 48, 52, 64, 76, 88, 104, 116, 128, 140, 156, 168, 180, 192, 208, or 260 weeks. In embodiments, the patient is administered a dose of Compound 1 that is about 750 mg-1200 mg for a period that is at least about 12, 24, 28, 32, 36, 40, 44, 48, 52, 64, 76, 88, 104, 116, 128, 140, 156, 168, 180, 192, 208, or 260 weeks. In embodiments, the patient is administered a dose of Compound 1 that is about 600 mg-900 mg for a period that is at least about 12, 24, 28, 32, 36, 40, 44, 48, 52, 64, 76, 88, 104, 116, 128, 140, 156, 168, 180, 192, 208, or 260 weeks. In embodiments, the patient is administered a dose of Compound 1 that is about 750 mg-900 mg for a period that is at least about 12, 24, 28, 32, 36, 40, 44, 48, 52, 64, 76, 88, 104, 116, 128, 140, 156, 168, 180, 192, 208, or 260 weeks. In embodiments, a dose of Compound 1 is administered to the patient for at least about 12 weeks. In embodiments, a dose of Compound 1 is administered to the patient for at least about 24 weeks. In embodiments, a dose of Compound 1 is administered to the patient for at least about 28 weeks. In embodiments, a dose of Compound 1 is administered to the patient for at least about 32 weeks. In embodiments, a dose of Compound 1 is administered to the patient for at least about 36 weeks. In embodiments, a dose of Compound 1 is administered to the patient for at least about 40 weeks. In embodiments, a dose of Compound 1 is administered to the patient for at least about 44 weeks. In embodiments, a dose of Compound 1 is administered to the patient for at least about 48 weeks. In embodiments, a dose of Compound 1 is administered to the patient for at least about 52 weeks. In embodiments, a dose of Compound 1 is administered to the patient for at least about 64 weeks. In embodiments, a dose of Compound 1 is administered to the patient for at least about 76 weeks. In embodiments, a dose of Compound 1 is administered to the patient for at least about 88 weeks. In embodiments, a dose of Compound 1 is administered to the patient for at least about 104 weeks. In embodiments, a dose of Compound 1 is administered to the patient for at least about 116 weeks. In embodiments, a dose of Compound 1 is administered to the patient for at least about 128 weeks. In embodiments, a dose of Compound 1 is administered to the patient for at least about 140 weeks. In embodiments, a dose of Compound 1 is administered to the patient for at least about 156 weeks. In embodiments, a dose of Compound 1 is administered to the patient for at least about 168 weeks. In embodiments, a dose of Compound 1 is administered to the patient for at least about 180 weeks. In embodiments, a dose of Compound 1 is administered to the patient for at least about 192 weeks. In embodiments, a dose of Compound 1 is administered to the patient for at least about 208 weeks. In embodiments, a dose of Compound 1 is administered to the patient for at least about 260 weeks. In embodiments, a dose is about 150 mg-1800 mg (e.g., administered once daily, once a week, or three times per week). In embodiments, a dose is about 450 mg-1800 mg (e.g., administered once daily, once a week, or three times per week). In embodiments, a dose is about 600 mg-1800 mg (e.g., administered once daily, once a week, or three times per week). In embodiments, a dose is about 750 mg-1800 mg (e.g., administered once daily, once a week, or three times per week). In embodiments, a dose is about 150 mg-1200 mg (e.g., administered once daily, once a week, or three times per week). In embodiments, a dose is about 450 mg-1200 mg (e.g., administered once daily, once a week, or three times per week). In embodiments, a dose is about 600 mg-1200 mg (e.g., administered once daily, once a week, or three times per week). In embodiments, a dose is about 750 mg-1200 mg (e.g., administered once daily, once a week, or three times per week). In embodiments, a dose is about 600 mg-900 mg (e.g., administered once daily, once a week, or three times per week). In embodiments, a dose is about 750 mg-900 mg (e.g., administered once daily, once a week, or three times per week). In embodiments, a dose is about 150 mg (e.g., administered once daily, once a week, or three times per week). In embodiments, a dose is about 300 mg (e.g., administered once daily, once a week, or three times per week). In embodiments, a dose is about 450 mg (e.g., administered once daily, once a week, or three times per week). In embodiments, a dose is about 600 mg (e.g., administered once daily, once a week, or three times per week). In embodiments, a dose is about 750 mg (e.g., administered once daily, once a week, or three times per week). In embodiments, a dose is about 900 mg (e.g., administered once daily, once a week, or three times per week). In embodiments, a dose is about 1050 mg (e.g., administered once daily, once a week, or three times per week). In embodiments, a dose is about 1200 mg (e.g., administered once daily, once a week, or three times per week). In embodiments, a dose is about 1350 mg (e.g., administered once daily, once a week, or three times per week). In embodiments, a dose is about 1500 mg (e.g., administered once daily, once a week, or three times per week). In embodiments, a dose is about 1650 mg (e.g., administered once daily, once a week, or three times per week). In embodiments, a dose is about 1800 mg (e.g., administered once daily, once a week, or three times per week).

In embodiments of any methods described herein, a dose comprising about 150 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 150 mg Compound 1 is administered to a patient for at least about 6-52, 6-48, 6-42, 6-36, 6-30, 6-24, 6-18, or 6-12 consecutive weeks. In embodiments, a dose comprising about 150 mg of Compound 1 is administered to a patient for at least about 8, 10, 12, 14, 16, 18, 20, 22, or 24 consecutive weeks. In embodiments, a dose comprising about 150 mg of Compound 1 is administered to a patient for at least about 26, 28, 30, 32, 34, 36, 38, 40, 42, 44, 46, 48, 50, or 52 consecutive weeks. In embodiments, a dose comprising about 150 mg of Compound 1 is administered to a patient once daily for at least about 8 weeks. In embodiments, a dose comprising about 150 mg of Compound 1 is administered to a patient three times weekly for at least about 8 weeks. In embodiments, a dose comprising about 150 mg of Compound 1 is administered to a patient once daily for at least about 12 weeks. In embodiments, a dose comprising about 150 mg of Compound 1 is administered to a patient three times weekly for at least about 12 weeks. In embodiments, a dose comprising about 150 mg of Compound 1 is administered to a patient once daily for at least about 24 weeks. In embodiments, a dose comprising about 150 mg of Compound 1 is administered to a patient three times weekly for at least about 24 weeks. In embodiments, a dose comprising about 150 mg of Compound 1 is administered to a patient once daily for at least about 28 weeks. In embodiments, a dose comprising about 150 mg of Compound 1 is administered to a patient three times weekly for at least about 28 weeks. In embodiments, a dose comprising about 150 mg of Compound 1 is administered to a patient once daily for at least about 32 weeks. In embodiments, a dose comprising about 150 mg of Compound 1 is administered to a patient three times weekly for at least about 32 weeks. In embodiments, a dose comprising about 150 mg of Compound 1 is administered to a patient once daily for at least about 36 weeks. In embodiments, a dose comprising about 150 mg of Compound 1 is administered to a patient three times weekly for at least about 36 weeks. In embodiments, a dose comprising about 150 mg of Compound 1 is administered to a patient once daily for at least about 40 weeks. In embodiments, a dose comprising about 150 mg of Compound 1 is administered to a patient three times weekly for at least about 40 weeks. In embodiments, a dose comprising about 150 mg of Compound 1 is administered to a patient once daily for at least about 44 weeks. In embodiments, a dose comprising about 150 mg of Compound 1 is administered to a patient three times weekly for at least about 44 weeks. In embodiments, a dose comprising about 150 mg of Compound 1 is administered to a patient once daily for at least about 48 weeks. In embodiments, a dose comprising about 150 mg of Compound 1 is administered to a patient three times weekly for at least about 48 weeks. In embodiments, a dose comprising about 150 mg of Compound 1 is administered to a patient once daily for at least about 52 weeks. In embodiments, a dose comprising about 150 mg of Compound 1 is administered to a patient three times weekly for at least about 52 weeks. In embodiments, a dose comprising about 150 mg of Compound 1 is administered to a patient once daily for at least about 64 weeks. In embodiments, a dose comprising about 150 mg of Compound 1 is administered to a patient three times weekly for at least about 64 weeks. In embodiments, a dose comprising about 150 mg of Compound 1 is administered to a patient once daily for at least about 76 weeks. In embodiments, a dose comprising about 150 mg of Compound 1 is administered to a patient three times weekly for at least about 76 weeks. In embodiments, a dose comprising about 150 mg of Compound 1 is administered to a patient once daily for at least about 88 weeks. In embodiments, a dose comprising about 150 mg of Compound 1 is administered to a patient three times weekly for at least about 88 weeks. In embodiments, a dose comprising about 150 mg of Compound 1 is administered to a patient once daily for at least about 104 weeks. In embodiments, a dose comprising about 150 mg of Compound 1 is administered to a patient three times weekly for at least about 104 weeks. In embodiments, a dose comprising about 150 mg of Compound 1 is administered to a patient once daily for at least about 116 weeks. In embodiments, a dose comprising about 150 mg of Compound 1 is administered to a patient three times weekly for at least about 116 weeks. In embodiments, a dose comprising about 150 mg of Compound 1 is administered to a patient once daily for at least about 128 weeks. In embodiments, a dose comprising about 150 mg of Compound 1 is administered to a patient three times weekly for at least about 128 weeks. In embodiments, a dose comprising about 150 mg of Compound 1 is administered to a patient once daily for at least about 140 weeks. In embodiments, a dose comprising about 150 mg of Compound 1 is administered to a patient three times weekly for at least about 140 weeks. In embodiments, a dose comprising about 150 mg of Compound 1 is administered to a patient once daily for at least about 156 weeks. In embodiments, a dose comprising about 150 mg of Compound 1 is administered to a patient three times weekly for at least about 156 weeks. In embodiments, a dose comprising about 150 mg of Compound 1 is administered to a patient once daily for at least about 168 weeks. In embodiments, a dose comprising about 150 mg of Compound 1 is administered to a patient three times weekly for at least about 168 weeks. In embodiments, a dose comprising about 150 mg of Compound 1 is administered to a patient once daily for at least about 180 weeks. In embodiments, a dose comprising about 150 mg of Compound 1 is administered to a patient three times weekly for at least about 180 weeks. In embodiments, a dose comprising about 150 mg of Compound 1 is administered to a patient once daily for at least about 192 weeks. In embodiments, a dose comprising about 150 mg of Compound 1 is administered to a patient three times weekly for at least about 192 weeks. In embodiments, a dose comprising about 150 mg of Compound 1 is administered to a patient once daily for at least about 208 weeks. In embodiments, a dose comprising about 150 mg of Compound 1 is administered to a patient three times weekly for at least about 208 weeks. In embodiments, a dose comprising about 150 mg of Compound 1 is administered to a patient once daily for at least about 260 weeks. In embodiments, a dose comprising about 150 mg of Compound 1 is administered to a patient three times weekly for at least about 260 weeks.

In embodiments of any methods described herein, a dose comprising about 300 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 300 mg Compound 1 is administered to a patient for at least about 6-52, 6-48, 6-42, 6-36, 6-30, 6-24, 6-18, or 6-12 consecutive weeks. In embodiments, a dose comprising about 300 mg of Compound 1 is administered to a patient for at least about 8, 10, 12, 14, 16, 18, 20, 22, or 24 consecutive weeks. In embodiments, a dose comprising about 300 mg of Compound 1 is administered to a patient for at least about 26, 28, 30, 32, 34, 36, 38, 40, 42, 44, 46, 48, 50, or 52 consecutive weeks. In embodiments, a dose comprising about 300 mg of Compound 1 is administered to a patient once daily for at least about 8 weeks. In embodiments, a dose comprising about 300 mg of Compound 1 is administered to a patient three times weekly for at least about 8 weeks. In embodiments, a dose comprising about 300 mg of Compound 1 is administered to a patient once daily for at least about 12 weeks. In embodiments, a dose comprising about 300 mg of Compound 1 is administered to a patient three times weekly for at least about 12 weeks. In embodiments, a dose comprising about 300 mg of Compound 1 is administered to a patient once daily for at least about 24 weeks. In embodiments, a dose comprising about 300 mg of Compound 1 is administered to a patient three times weekly for at least about 24 weeks. In embodiments, a dose comprising about 300 mg of Compound 1 is administered to a patient once daily for at least about 28 weeks. In embodiments, a dose comprising about 300 mg of Compound 1 is administered to a patient three times weekly for at least about 28 weeks. In embodiments, a dose comprising about 300 mg of Compound 1 is administered to a patient once daily for at least about 32 weeks. In embodiments, a dose comprising about 300 mg of Compound 1 is administered to a patient three times weekly for at least about 32 weeks. In embodiments, a dose comprising about 300 mg of Compound 1 is administered to a patient once daily for at least about 36 weeks. In embodiments, a dose comprising about 300 mg of Compound 1 is administered to a patient three times weekly for at least about 36 weeks. In embodiments, a dose comprising about 300 mg of Compound 1 is administered to a patient once daily for at least about 40 weeks. In embodiments, a dose comprising about 300 mg of Compound 1 is administered to a patient three times weekly for at least about 40 weeks. In embodiments, a dose comprising about 300 mg of Compound 1 is administered to a patient once daily for at least about 44 weeks. In embodiments, a dose comprising about 300 mg of Compound 1 is administered to a patient three times weekly for at least about 44 weeks. In embodiments, a dose comprising about 300 mg of Compound 1 is administered to a patient once daily for at least about 48 weeks. In embodiments, a dose comprising about 300 mg of Compound 1 is administered to a patient three times weekly for at least about 48 weeks. In embodiments, a dose comprising about 300 mg of Compound 1 is administered to a patient once daily for at least about 52 weeks. In embodiments, a dose comprising about 300 mg of Compound 1 is administered to a patient three times weekly for at least about 52 weeks. In embodiments, a dose comprising about 300 mg of Compound 1 is administered to a patient once daily for at least about 64 weeks. In embodiments, a dose comprising about 300 mg of Compound 1 is administered to a patient three times weekly for at least about 64 weeks. In embodiments, a dose comprising about 300 mg of Compound 1 is administered to a patient once daily for at least about 76 weeks. In embodiments, a dose comprising about 300 mg of Compound 1 is administered to a patient three times weekly for at least about 76 weeks. In embodiments, a dose comprising about 300 mg of Compound 1 is administered to a patient once daily for at least about 88 weeks. In embodiments, a dose comprising about 300 mg of Compound 1 is administered to a patient three times weekly for at least about 88 weeks. In embodiments, a dose comprising about 300 mg of Compound 1 is administered to a patient once daily for at least about 104 weeks. In embodiments, a dose comprising about 300 mg of Compound 1 is administered to a patient three times weekly for at least about 104 weeks. In embodiments, a dose comprising about 300 mg of Compound 1 is administered to a patient once daily for at least about 116 weeks. In embodiments, a dose comprising about 300 mg of Compound 1 is administered to a patient three times weekly for at least about 116 weeks. In embodiments, a dose comprising about 300 mg of Compound 1 is administered to a patient once daily for at least about 128 weeks. In embodiments, a dose comprising about 300 mg of Compound 1 is administered to a patient three times weekly for at least about 128 weeks. In embodiments, a dose comprising about 300 mg of Compound 1 is administered to a patient once daily for at least about 140 weeks. In embodiments, a dose comprising about 300 mg of Compound 1 is administered to a patient three times weekly for at least about 140 weeks. In embodiments, a dose comprising about 300 mg of Compound 1 is administered to a patient once daily for at least about 156 weeks. In embodiments, a dose comprising about 300 mg of Compound 1 is administered to a patient three times weekly for at least about 156 weeks. In embodiments, a dose comprising about 300 mg of Compound 1 is administered to a patient once daily for at least about 168 weeks. In embodiments, a dose comprising about 300 mg of Compound 1 is administered to a patient three times weekly for at least about 168 weeks. In embodiments, a dose comprising about 300 mg of Compound 1 is administered to a patient once daily for at least about 180 weeks. In embodiments, a dose comprising about 300 mg of Compound 1 is administered to a patient three times weekly for at least about 180 weeks. In embodiments, a dose comprising about 300 mg of Compound 1 is administered to a patient once daily for at least about 192 weeks. In embodiments, a dose comprising about 300 mg of Compound 1 is administered to a patient three times weekly for at least about 192 weeks. In embodiments, a dose comprising about 300 mg of Compound 1 is administered to a patient once daily for at least about 208 weeks. In embodiments, a dose comprising about 300 mg of Compound 1 is administered to a patient three times weekly for at least about 208 weeks. In embodiments, a dose comprising about 300 mg of Compound 1 is administered to a patient once daily for at least about 260 weeks. In embodiments, a dose comprising about 300 mg of Compound 1 is administered to a patient three times weekly for at least about 260 weeks.

In embodiments of any methods described herein, a dose comprising about 450 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 450 mg Compound 1 is administered to a patient for at least about 6-52, 6-48, 6-42, 6-36, 6-30, 6-24, 6-18, or 6-12 consecutive weeks. In embodiments, a dose comprising about 450 mg of Compound 1 is administered to a patient for at least about 8, 10, 12, 14, 16, 18, 20, 22, or 24 consecutive weeks. In embodiments, a dose comprising about 450 mg of Compound 1 is administered to a patient for at least about 26, 28, 30, 32, 34, 36, 38, 40, 42, 44, 46, 48, 50, or 52 consecutive weeks. In embodiments, a dose comprising about 450 mg of Compound 1 is administered to a patient once daily for at least about 8 weeks. In embodiments, a dose comprising about 450 mg of Compound 1 is administered to a patient three times weekly for at least about 8 weeks. In embodiments, a dose comprising about 1% 450 mg of Compound 1 is administered to a patient once daily for at least about 12 weeks. In embodiments, a dose comprising about 450 mg of Compound 1 is administered to a patient three times weekly for at least about 12 weeks. In embodiments, a dose comprising about 450 mg of Compound 1 is administered to a patient once daily for at least about 24 weeks. In embodiments, a dose comprising about 450 mg of Compound 1 is administered to a patient three times weekly for at least about 24 weeks. In embodiments, a dose comprising about 450 mg of Compound 1 is administered to a patient once daily for at least about 28 weeks. In embodiments, a dose comprising about 450 mg of Compound 1 is administered to a patient three times weekly for at least about 28 weeks. In embodiments, a dose comprising about 450 mg of Compound 1 is administered to a patient once daily for at least about 32 weeks. In embodiments, a dose comprising about 450 mg of Compound 1 is administered to a patient three times weekly for at least about 32 weeks. In embodiments, a dose comprising about 450 mg of Compound 1 is administered to a patient once daily for at least about 36 weeks. In embodiments, a dose comprising about 450 mg of Compound 1 is administered to a patient three times weekly for at least about 36 weeks. In embodiments, a dose comprising about 450 mg of Compound 1 is administered to a patient once daily for at least about 40 weeks. In embodiments, a dose comprising about 450 mg of Compound 1 is administered to a patient three times weekly for at least about 40 weeks. In embodiments, a dose comprising about 450 mg of Compound 1 is administered to a patient once daily for at least about 44 weeks. In embodiments, a dose comprising about 450 mg of Compound 1 is administered to a patient three times weekly for at least about 44 weeks. In embodiments, a dose comprising about 450 mg of Compound 1 is administered to a patient once daily for at least about 48 weeks. In embodiments, a dose comprising about 450 mg of Compound 1 is administered to a patient three times weekly for at least about 48 weeks. In embodiments, a dose comprising about 450 mg of Compound 1 is administered to a patient once daily for at least about 52 weeks. In embodiments, a dose comprising about 450 mg of Compound 1 is administered to a patient three times weekly for at least about 52 weeks. In embodiments, a dose comprising about 450 mg of Compound 1 is administered to a patient once daily for at least about 64 weeks. In embodiments, a dose comprising about 450 mg of Compound 1 is administered to a patient three times weekly for at least about 64 weeks. In embodiments, a dose comprising about 450 mg of Compound 1 is administered to a patient once daily for at least about 76 weeks. In embodiments, a dose comprising about 450 mg of Compound 1 is administered to a patient three times weekly for at least about 76 weeks. In embodiments, a dose comprising about 450 mg of Compound 1 is administered to a patient once daily for at least about 88 weeks. In embodiments, a dose comprising about 450 mg of Compound 1 is administered to a patient three times weekly for at least about 88 weeks. In embodiments, a dose comprising about 450 mg of Compound 1 is administered to a patient once daily for at least about 104 weeks. In embodiments, a dose comprising about 450 mg of Compound 1 is administered to a patient three times weekly for at least about 104 weeks. In embodiments, a dose comprising about 450 mg of Compound 1 is administered to a patient once daily for at least about 116 weeks. In embodiments, a dose comprising about 450 mg of Compound 1 is administered to a patient three times weekly for at least about 116 weeks. In embodiments, a dose comprising about 450 mg of Compound 1 is administered to a patient once daily for at least about 128 weeks. In embodiments, a dose comprising about 450 mg of Compound 1 is administered to a patient three times weekly for at least about 128 weeks. In embodiments, a dose comprising about 450 mg of Compound 1 is administered to a patient once daily for at least about 140 weeks. In embodiments, a dose comprising about 450 mg of Compound 1 is administered to a patient three times weekly for at least about 140 weeks. In embodiments, a dose comprising about 450 mg of Compound 1 is administered to a patient once daily for at least about 156 weeks. In embodiments, a dose comprising about 450 mg of Compound 1 is administered to a patient three times weekly for at least about 156 weeks. In embodiments, a dose comprising about 450 mg of Compound 1 is administered to a patient once daily for at least about 168 weeks. In embodiments, a dose comprising about 450 mg of Compound 1 is administered to a patient three times weekly for at least about 168 weeks. In embodiments, a dose comprising about 450 mg of Compound 1 is administered to a patient once daily for at least about 180 weeks. In embodiments, a dose comprising about 450 mg of Compound 1 is administered to a patient three times weekly for at least about 180 weeks. In embodiments, a dose comprising about 450 mg of Compound 1 is administered to a patient once daily for at least about 192 weeks. In embodiments, a dose comprising about 450 mg of Compound 1 is administered to a patient three times weekly for at least about 192 weeks. In embodiments, a dose comprising about 450 mg of Compound 1 is administered to a patient once daily for at least about 208 weeks. In embodiments, a dose comprising about 450 mg of Compound 1 is administered to a patient three times weekly for at least about 208 weeks. In embodiments, a dose comprising about 450 mg of Compound 1 is administered to a patient once daily for at least about 260 weeks. In embodiments, a dose comprising about 450 mg of Compound 1 is administered to a patient three times weekly for at least about 260 weeks.

In embodiments of any methods described herein, a dose comprising about 600 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 600 mg Compound 1 is administered to a patient for at least about 6-52, 6-48, 6-42, 6-36, 6-30, 6-24, 6-18, or 6-12 consecutive weeks. In embodiments, a dose comprising about 600 mg of Compound 1 is administered to a patient for at least about 8, 10, 12, 14, 16, 18, 20, 22, or 24 consecutive weeks. In embodiments, a dose comprising about 600 mg of Compound 1 is administered to a patient for at least about 26, 28, 30, 32, 34, 36, 38, 40, 42, 44, 46, 48, 50, or 52 consecutive weeks. In embodiments, a dose comprising about 600 mg of Compound 1 is administered to a patient once daily for at least about 8 weeks. In embodiments, a dose comprising about 600 mg of Compound 1 is administered to a patient three times weekly for at least about 8 weeks. In embodiments, a dose comprising about 600 mg of Compound 1 is administered to a patient once daily for at least about 12 weeks. In embodiments, a dose comprising about 600 mg of Compound 1 is administered to a patient three times weekly for at least about 12 weeks. In embodiments, a dose comprising about 600 mg of Compound 1 is administered to a patient once daily for at least about 24 weeks. In embodiments, a dose comprising about 600 mg of Compound 1 is administered to a patient three times weekly for at least about 24 weeks. In embodiments, a dose comprising about 600 mg of Compound 1 is administered to a patient once daily for at least about 28 weeks. In embodiments, a dose comprising about 600 mg of Compound 1 is administered to a patient three times weekly for at least about 28 weeks. In embodiments, a dose comprising about 600 mg of Compound 1 is administered to a patient once daily for at least about 32 weeks. In embodiments, a dose comprising about 600 mg of Compound 1 is administered to a patient three times weekly for at least about 32 weeks. In embodiments, a dose comprising about 600 mg of Compound 1 is administered to a patient once daily for at least about 36 weeks. In embodiments, a dose comprising about 600 mg of Compound 1 is administered to a patient three times weekly for at least about 36 weeks. In embodiments, a dose comprising about 600 mg of Compound 1 is administered to a patient once daily for at least about 40 weeks. In embodiments, a dose comprising about 600 mg of Compound 1 is administered to a patient three times weekly for at least about 40 weeks. In embodiments, a dose comprising about 600 mg of Compound 1 is administered to a patient once daily for at least about 44 weeks. In embodiments, a dose comprising about 600 mg of Compound 1 is administered to a patient three times weekly for at least about 44 weeks. In embodiments, a dose comprising about 600 mg of Compound 1 is administered to a patient once daily for at least about 48 weeks. In embodiments, a dose comprising about 600 mg of Compound 1 is administered to a patient three times weekly for at least about 48 weeks. In embodiments, a dose comprising about 600 mg of Compound 1 is administered to a patient once daily for at least about 52 weeks. In embodiments, a dose comprising about 600 mg of Compound 1 is administered to a patient three times weekly for at least about 52 weeks. In embodiments, a dose comprising about 600 mg of Compound 1 is administered to a patient once daily for at least about 64 weeks. In embodiments, a dose comprising about 600 mg of Compound 1 is administered to a patient three times weekly for at least about 64 weeks. In embodiments, a dose comprising about 600 mg of Compound 1 is administered to a patient once daily for at least about 76 weeks. In embodiments, a dose comprising about 600 mg of Compound 1 is administered to a patient three times weekly for at least about 76 weeks. In embodiments, a dose comprising about 600 mg of Compound 1 is administered to a patient once daily for at least about 88 weeks. In embodiments, a dose comprising about 600 mg of Compound 1 is administered to a patient three times weekly for at least about 88 weeks. In embodiments, a dose comprising about 600 mg of Compound 1 is administered to a patient once daily for at least about 104 weeks. In embodiments, a dose comprising about 600 mg of Compound 1 is administered to a patient three times weekly for at least about 104 weeks. In embodiments, a dose comprising about 600 mg of Compound 1 is administered to a patient once daily for at least about 116 weeks. In embodiments, a dose comprising about 600 mg of Compound 1 is administered to a patient three times weekly for at least about 116 weeks. In embodiments, a dose comprising about 600 mg of Compound 1 is administered to a patient once daily for at least about 128 weeks. In embodiments, a dose comprising about 600 mg of Compound 1 is administered to a patient three times weekly for at least about 128 weeks. In embodiments, a dose comprising about 600 mg of Compound 1 is administered to a patient once daily for at least about 140 weeks. In embodiments, a dose comprising about 600 mg of Compound 1 is administered to a patient three times weekly for at least about 140 weeks. In embodiments, a dose comprising about 600 mg of Compound 1 is administered to a patient once daily for at least about 156 weeks. In embodiments, a dose comprising about 600 mg of Compound 1 is administered to a patient three times weekly for at least about 156 weeks. In embodiments, a dose comprising about 600 mg of Compound 1 is administered to a patient once daily for at least about 168 weeks. In embodiments, a dose comprising about 600 mg of Compound 1 is administered to a patient three times weekly for at least about 168 weeks. In embodiments, a dose comprising about 600 mg of Compound 1 is administered to a patient once daily for at least about 180 weeks. In embodiments, a dose comprising about 600 mg of Compound 1 is administered to a patient three times weekly for at least about 180 weeks. In embodiments, a dose comprising about 600 mg of Compound 1 is administered to a patient once daily for at least about 192 weeks. In embodiments, a dose comprising about 600 mg of Compound 1 is administered to a patient three times weekly for at least about 192 weeks. In embodiments, a dose comprising about 600 mg of Compound 1 is administered to a patient once daily for at least about 208 weeks. In embodiments, a dose comprising about 600 mg of Compound 1 is administered to a patient three times weekly for at least about 208 weeks. In embodiments, a dose comprising about 600 mg of Compound 1 is administered to a patient once daily for at least about 260 weeks. In embodiments, a dose comprising about 600 mg of Compound 1 is administered to a patient three times weekly for at least about 260 weeks.

In embodiments of any methods described herein, a dose comprising about 750 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 750 mg Compound 1 is administered to a patient for at least about 6-52, 6-48, 6-42, 6-36, 6-30, 6-24, 6-18, or 6-12 consecutive weeks. In embodiments, a dose comprising about 750 mg of Compound 1 is administered to a patient for at least about 8, 10, 12, 14, 16, 18, 20, 22, or 24 consecutive weeks. In embodiments, a dose comprising about 750 mg of Compound 1 is administered to a patient for at least about 26, 28, 30, 32, 34, 36, 38, 40, 42, 44, 46, 48, 50, or 52 consecutive weeks. In embodiments, a dose comprising about 750 mg of Compound 1 is administered to a patient once daily for at least about 8 weeks. In embodiments, a dose comprising about 750 mg of Compound 1 is administered to a patient three times weekly for at least about 8 weeks. In embodiments, a dose comprising about 750 mg of Compound 1 is administered to a patient once daily for at least about 12 weeks. In embodiments, a dose comprising about 750 mg of Compound 1 is administered to a patient three times weekly for at least about 12 weeks. In embodiments, a dose comprising about 750 mg of Compound 1 is administered to a patient once daily for at least about 24 weeks. In embodiments, a dose comprising about 750 mg of Compound 1 is administered to a patient three times weekly for at least about 24 weeks. In embodiments, a dose comprising about 750 mg of Compound 1 is administered to a patient once daily for at least about 28 weeks. In embodiments, a dose comprising about 750 mg of Compound 1 is administered to a patient three times weekly for at least about 28 weeks. In embodiments, a dose comprising about 750 mg of Compound 1 is administered to a patient once daily for at least about 32 weeks. In embodiments, a dose comprising about 750 mg of Compound 1 is administered to a patient three times weekly for at least about 32 weeks. In embodiments, a dose comprising about 750 mg of Compound 1 is administered to a patient once daily for at least about 36 weeks. In embodiments, a dose comprising about 750 mg of Compound 1 is administered to a patient three times weekly for at least about 36 weeks. In embodiments, a dose comprising about 750 mg of Compound 1 is administered to a patient once daily for at least about 40 weeks. In embodiments, a dose comprising about 750 mg of Compound 1 is administered to a patient three times weekly for at least about 40 weeks. In embodiments, a dose comprising about 750 mg of Compound 1 is administered to a patient once daily for at least about 44 weeks. In embodiments, a dose comprising about 750 mg of Compound 1 is administered to a patient three times weekly for at least about 44 weeks. In embodiments, a dose comprising about 750 mg of Compound 1 is administered to a patient once daily for at least about 48 weeks. In embodiments, a dose comprising about 750 mg of Compound 1 is administered to a patient three times weekly for at least about 48 weeks. In embodiments, a dose comprising about 750 mg of Compound 1 is administered to a patient once daily for at least about 52 weeks. In embodiments, a dose comprising about 750 mg of Compound 1 is administered to a patient three times weekly for at least about 52 weeks. In embodiments, a dose comprising about 750 mg of Compound 1 is administered to a patient once daily for at least about 64 weeks. In embodiments, a dose comprising about 750 mg of Compound 1 is administered to a patient three times weekly for at least about 64 weeks. In embodiments, a dose comprising about 750 mg of Compound 1 is administered to a patient once daily for at least about 76 weeks. In embodiments, a dose comprising about 750 mg of Compound 1 is administered to a patient three times weekly for at least about 76 weeks. In embodiments, a dose comprising about 750 mg of Compound 1 is administered to a patient once daily for at least about 88 weeks. In embodiments, a dose comprising about 750 mg of Compound 1 is administered to a patient three times weekly for at least about 88 weeks. In embodiments, a dose comprising about 750 mg of Compound 1 is administered to a patient once daily for at least about 104 weeks. In embodiments, a dose comprising about 750 mg of Compound 1 is administered to a patient three times weekly for at least about 104 weeks. In embodiments, a dose comprising about 750 mg of Compound 1 is administered to a patient once daily for at least about 116 weeks. In embodiments, a dose comprising about 750 mg of Compound 1 is administered to a patient three times weekly for at least about 116 weeks. In embodiments, a dose comprising about 750 mg of Compound 1 is administered to a patient once daily for at least about 128 weeks. In embodiments, a dose comprising about 750 mg of Compound 1 is administered to a patient three times weekly for at least about 128 weeks. In embodiments, a dose comprising about 750 mg of Compound 1 is administered to a patient once daily for at least about 140 weeks. In embodiments, a dose comprising about 750 mg of Compound 1 is administered to a patient three times weekly for at least about 140 weeks. In embodiments, a dose comprising about 750 mg of Compound 1 is administered to a patient once daily for at least about 156 weeks. In embodiments, a dose comprising about 750 mg of Compound 1 is administered to a patient three times weekly for at least about 156 weeks. In embodiments, a dose comprising about 750 mg of Compound 1 is administered to a patient once daily for at least about 168 weeks. In embodiments, a dose comprising about 750 mg of Compound 1 is administered to a patient three times weekly for at least about 168 weeks. In embodiments, a dose comprising about 750 mg of Compound 1 is administered to a patient once daily for at least about 180 weeks. In embodiments, a dose comprising about 750 mg of Compound 1 is administered to a patient three times weekly for at least about 180 weeks. In embodiments, a dose comprising about 750 mg of Compound 1 is administered to a patient once daily for at least about 192 weeks. In embodiments, a dose comprising about 750 mg of Compound 1 is administered to a patient three times weekly for at least about 192 weeks. In embodiments, a dose comprising about 750 mg of Compound 1 is administered to a patient once daily for at least about 208 weeks. In embodiments, a dose comprising about 750 mg of Compound 1 is administered to a patient three times weekly for at least about 208 weeks. In embodiments, a dose comprising about 750 mg of Compound 1 is administered to a patient once daily for at least about 260 weeks. In embodiments, a dose comprising about 750 mg of Compound 1 is administered to a patient three times weekly for at least about 260 weeks.

In embodiments of any methods described herein, a dose comprising about 900 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 900 mg Compound 1 is administered to a patient for at least about 6-52, 6-48, 6-42, 6-36, 6-30, 6-24, 6-18, or 6-12 consecutive weeks. In embodiments, a dose comprising about 900 mg of Compound 1 is administered to a patient for at least about 8, 10, 12, 14, 16, 18, 20, 22, or 24 consecutive weeks. In embodiments, a dose comprising about 900 mg of Compound 1 is administered to a patient for at least about 26, 28, 30, 32, 34, 36, 38, 40, 42, 44, 46, 48, 50, or 52 consecutive weeks. In embodiments, a dose comprising about 900 mg of Compound 1 is administered to a patient once daily for at least about 8 weeks. In embodiments, a dose comprising about 900 mg of Compound 1 is administered to a patient three times weekly for at least about 8 weeks. In embodiments, a dose comprising about 900 mg of Compound 1 is administered to a patient once daily for at least about 12 weeks. In embodiments, a dose comprising about 900 mg of Compound 1 is administered to a patient three times weekly for at least about 12 weeks. In embodiments, a dose comprising about 900 mg of Compound 1 is administered to a patient once daily for at least about 24 weeks. In embodiments, a dose comprising about 900 mg of Compound 1 is administered to a patient three times weekly for at least about 24 weeks. In embodiments, a dose comprising about 900 mg of Compound 1 is administered to a patient once daily for at least about 28 weeks. In embodiments, a dose comprising about 900 mg of Compound 1 is administered to a patient three times weekly for at least about 28 weeks. In embodiments, a dose comprising about 900 mg of Compound 1 is administered to a patient once daily for at least about 32 weeks. In embodiments, a dose comprising about 900 mg of Compound 1 is administered to a patient three times weekly for at least about 32 weeks. In embodiments, a dose comprising about 900 mg of Compound 1 is administered to a patient once daily for at least about 36 weeks. In embodiments, a dose comprising about 900 mg of Compound 1 is administered to a patient three times weekly for at least about 36 weeks. In embodiments, a dose comprising about 900 mg of Compound 1 is administered to a patient once daily for at least about 40 weeks. In embodiments, a dose comprising about 900 mg of Compound 1 is administered to a patient three times weekly for at least about 40 weeks. In embodiments, a dose comprising about 900 mg of Compound 1 is administered to a patient once daily for at least about 44 weeks. In embodiments, a dose comprising about 900 mg of Compound 1 is administered to a patient three times weekly for at least about 44 weeks. In embodiments, a dose comprising about 900 mg of Compound 1 is administered to a patient once daily for at least about 48 weeks. In embodiments, a dose comprising about 900 mg of Compound 1 is administered to a patient three times weekly for at least about 48 weeks. In embodiments, a dose comprising about 900 mg of Compound 1 is administered to a patient once daily for at least about 52 weeks. In embodiments, a dose comprising about 900 mg of Compound 1 is administered to a patient three times weekly for at least about 52 weeks. In embodiments, a dose comprising about 900 mg of Compound 1 is administered to a patient once daily for at least about 64 weeks. In embodiments, a dose comprising about 900 mg of Compound 1 is administered to a patient three times weekly for at least about 64 weeks. In embodiments, a dose comprising about 900 mg of Compound 1 is administered to a patient once daily for at least about 76 weeks. In embodiments, a dose comprising about 900 mg of Compound 1 is administered to a patient three times weekly for at least about 76 weeks. In embodiments, a dose comprising about 900 mg of Compound 1 is administered to a patient once daily for at least about 88 weeks. In embodiments, a dose comprising about 900 mg of Compound 1 is administered to a patient three times weekly for at least about 88 weeks. In embodiments, a dose comprising about 900 mg of Compound 1 is administered to a patient once daily for at least about 104 weeks. In embodiments, a dose comprising about 900 mg of Compound 1 is administered to a patient three times weekly for at least about 104 weeks. In embodiments, a dose comprising about 900 mg of Compound 1 is administered to a patient once daily for at least about 116 weeks. In embodiments, a dose comprising about 900 mg of Compound 1 is administered to a patient three times weekly for at least about 116 weeks. In embodiments, a dose comprising about 900 mg of Compound 1 is administered to a patient once daily for at least about 128 weeks. In embodiments, a dose comprising about 900 mg of Compound 1 is administered to a patient three times weekly for at least about 128 weeks. In embodiments, a dose comprising about 900 mg of Compound 1 is administered to a patient once daily for at least about 140 weeks. In embodiments, a dose comprising about 900 mg of Compound 1 is administered to a patient three times weekly for at least about 140 weeks. In embodiments, a dose comprising about 900 mg of Compound 1 is administered to a patient once daily for at least about 156 weeks. In embodiments, a dose comprising about 900 mg of Compound 1 is administered to a patient three times weekly for at least about 156 weeks. In embodiments, a dose comprising about 900 mg of Compound 1 is administered to a patient once daily for at least about 168 weeks. In embodiments, a dose comprising about 900 mg of Compound 1 is administered to a patient three times weekly for at least about 168 weeks. In embodiments, a dose comprising about 900 mg of Compound 1 is administered to a patient once daily for at least about 180 weeks. In embodiments, a dose comprising about 900 mg of Compound 1 is administered to a patient three times weekly for at least about 180 weeks. In embodiments, a dose comprising about 900 mg of Compound 1 is administered to a patient once daily for at least about 192 weeks. In embodiments, a dose comprising about 900 mg of Compound 1 is administered to a patient three times weekly for at least about 192 weeks. In embodiments, a dose comprising about 900 mg of Compound 1 is administered to a patient once daily for at least about 208 weeks. In embodiments, a dose comprising about 900 mg of Compound 1 is administered to a patient three times weekly for at least about 208 weeks. In embodiments, a dose comprising about 900 mg of Compound 1 is administered to a patient once daily for at least about 260 weeks. In embodiments, a dose comprising about 900 mg of Compound 1 is administered to a patient three times weekly for at least about 260 weeks.

In embodiments of any methods described herein, a dose comprising about 1050 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 1050 mg Compound 1 is administered to a patient for at least about 6-52, 6-48, 6-42, 6-36, 6-30, 6-24, 6-18, or 6-12 consecutive weeks. In embodiments, a dose comprising about 1050 mg of Compound 1 is administered to a patient for at least about 8, 10, 12, 14, 16, 18, 20, 22, or 24 consecutive weeks. In embodiments, a dose comprising about 1050 mg of Compound 1 is administered to a patient for at least about 26, 28, 30, 32, 34, 36, 38, 40, 42, 44, 46, 48, 50, or 52 consecutive weeks. In embodiments, a dose comprising about 1050 mg of Compound 1 is administered to a patient once daily for at least about 8 weeks. In embodiments, a dose comprising about 1050 mg of Compound 1 is administered to a patient three times weekly for at least about 8 weeks. In embodiments, a dose comprising about 1050 mg of Compound 1 is administered to a patient once daily for at least about 12 weeks. In embodiments, a dose comprising about 1050 mg of Compound 1 is administered to a patient three times weekly for at least about 12 weeks. In embodiments, a dose comprising about 1050 mg of Compound 1 is administered to a patient once daily for at least about 24 weeks. In embodiments, a dose comprising about 1050 mg of Compound 1 is administered to a patient three times weekly for at least about 24 weeks. In embodiments, a dose comprising about 1050 mg of Compound 1 is administered to a patient once daily for at least about 28 weeks. In embodiments, a dose comprising about 1050 mg of Compound 1 is administered to a patient three times weekly for at least about 28 weeks. In embodiments, a dose comprising about 1050 mg of Compound 1 is administered to a patient once daily for at least about 32 weeks. In embodiments, a dose comprising about 1050 mg of Compound 1 is administered to a patient three times weekly for at least about 32 weeks. In embodiments, a dose comprising about 1050 mg of Compound 1 is administered to a patient once daily for at least about 36 weeks. In embodiments, a dose comprising about 1050 mg of Compound 1 is administered to a patient three times weekly for at least about 36 weeks. In embodiments, a dose comprising about 1050 mg of Compound 1 is administered to a patient once daily for at least about 40 weeks. In embodiments, a dose comprising about 1050 mg of Compound 1 is administered to a patient three times weekly for at least about 40 weeks. In embodiments, a dose comprising about 1050 mg of Compound 1 is administered to a patient once daily for at least about 44 weeks. In embodiments, a dose comprising about 1050 mg of Compound 1 is administered to a patient three times weekly for at least about 44 weeks. In embodiments, a dose comprising about 1050 mg of Compound 1 is administered to a patient once daily for at least about 48 weeks. In embodiments, a dose comprising about 1050 mg of Compound 1 is administered to a patient three times weekly for at least about 48 weeks. In embodiments, a dose comprising about 1050 mg of Compound 1 is administered to a patient once daily for at least about 52 weeks. In embodiments, a dose comprising about 1050 mg of Compound 1 is administered to a patient three times weekly for at least about 52 weeks. In embodiments, a dose comprising about 1050 mg of Compound 1 is administered to a patient once daily for at least about 64 weeks. In embodiments, a dose comprising about 1050 mg of Compound 1 is administered to a patient three times weekly for at least about 64 weeks. In embodiments, a dose comprising about 1050 mg of Compound 1 is administered to a patient once daily for at least about 76 weeks. In embodiments, a dose comprising about 1050 mg of Compound 1 is administered to a patient three times weekly for at least about 76 weeks. In embodiments, a dose comprising about 1050 mg of Compound 1 is administered to a patient once daily for at least about 88 weeks. In embodiments, a dose comprising about 1050 mg of Compound 1 is administered to a patient three times weekly for at least about 88 weeks. In embodiments, a dose comprising about 1050 mg of Compound 1 is administered to a patient once daily for at least about 104 weeks. In embodiments, a dose comprising about 1050 mg of Compound 1 is administered to a patient three times weekly for at least about 104 weeks. In embodiments, a dose comprising about 1050 mg of Compound 1 is administered to a patient once daily for at least about 116 weeks. In embodiments, a dose comprising about 1050 mg of Compound 1 is administered to a patient three times weekly for at least about 116 weeks. In embodiments, a dose comprising about 1050 mg of Compound 1 is administered to a patient once daily for at least about 128 weeks. In embodiments, a dose comprising about 1050 mg of Compound 1 is administered to a patient three times weekly for at least about 128 weeks. In embodiments, a dose comprising about 1050 mg of Compound 1 is administered to a patient once daily for at least about 140 weeks. In embodiments, a dose comprising about 1050 mg of Compound 1 is administered to a patient three times weekly for at least about 140 weeks. In embodiments, a dose comprising about 1050 mg of Compound 1 is administered to a patient once daily for at least about 156 weeks. In embodiments, a dose comprising about 1050 mg of Compound 1 is administered to a patient three times weekly for at least about 156 weeks. In embodiments, a dose comprising about 1050 mg of Compound 1 is administered to a patient once daily for at least about 168 weeks. In embodiments, a dose comprising about 1050 mg of Compound 1 is administered to a patient three times weekly for at least about 168 weeks. In embodiments, a dose comprising about 1050 mg of Compound 1 is administered to a patient once daily for at least about 180 weeks. In embodiments, a dose comprising about 1050 mg of Compound 1 is administered to a patient three times weekly for at least about 180 weeks. In embodiments, a dose comprising about 1050 mg of Compound 1 is administered to a patient once daily for at least about 192 weeks. In embodiments, a dose comprising about 1050 mg of Compound 1 is administered to a patient three times weekly for at least about 192 weeks. In embodiments, a dose comprising about 1050 mg of Compound 1 is administered to a patient once daily for at least about 208 weeks. In embodiments, a dose comprising about 1050 mg of Compound 1 is administered to a patient three times weekly for at least about 208 weeks. In embodiments, a dose comprising about 1050 mg of Compound 1 is administered to a patient once daily for at least about 260 weeks. In embodiments, a dose comprising about 1050 mg of Compound 1 is administered to a patient three times weekly for at least about 260 weeks.

In embodiments of any methods described herein, a dose comprising about 1200 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 1200 mg Compound 1 is administered to a patient for at least about 6-52, 6-48, 6-42, 6-36, 6-30, 6-24, 6-18, or 6-12 consecutive weeks. In embodiments, a dose comprising about 1200 mg of Compound 1 is administered to a patient for at least about 8, 10, 12, 14, 16, 18, 20, 22, or 24 consecutive weeks. In embodiments, a dose comprising about 1200 mg of Compound 1 is administered to a patient for at least about 26, 28, 30, 32, 34, 36, 38, 40, 42, 44, 46, 48, 50, or 52 consecutive weeks. In embodiments, a dose comprising about 1200 mg of Compound 1 is administered to a patient once daily for at least about 8 weeks. In embodiments, a dose comprising about 1200 mg of Compound 1 is administered to a patient three times weekly for at least about 8 weeks. In embodiments, a dose comprising about 1200 mg of Compound 1 is administered to a patient once daily for at least about 12 weeks. In embodiments, a dose comprising about 1200 mg of Compound 1 is administered to a patient three times weekly for at least about 12 weeks. In embodiments, a dose comprising about 1200 mg of Compound 1 is administered to a patient once daily for at least about 24 weeks. In embodiments, a dose comprising about 1200 mg of Compound 1 is administered to a patient three times weekly for at least about 24 weeks. In embodiments, a dose comprising about 1200 mg of Compound 1 is administered to a patient once daily for at least about 28 weeks. In embodiments, a dose comprising about 1200 mg of Compound 1 is administered to a patient three times weekly for at least about 28 weeks. In embodiments, a dose comprising about 1200 mg of Compound 1 is administered to a patient once daily for at least about 32 weeks. In embodiments, a dose comprising about 1200 mg of Compound 1 is administered to a patient three times weekly for at least about 32 weeks. In embodiments, a dose comprising about 1200 mg of Compound 1 is administered to a patient once daily for at least about 36 weeks. In embodiments, a dose comprising about 1200 mg of Compound 1 is administered to a patient three times weekly for at least about 36 weeks. In embodiments, a dose comprising about 1200 mg of Compound 1 is administered to a patient once daily for at least about 40 weeks. In embodiments, a dose comprising about 1200 mg of Compound 1 is administered to a patient three times weekly for at least about 40 weeks. In embodiments, a dose comprising about 1200 mg of Compound 1 is administered to a patient once daily for at least about 44 weeks. In embodiments, a dose comprising about 1200 mg of Compound 1 is administered to a patient three times weekly for at least about 44 weeks. In embodiments, a dose comprising about 1200 mg of Compound 1 is administered to a patient once daily for at least about 48 weeks. In embodiments, a dose comprising about 1200 mg of Compound 1 is administered to a patient three times weekly for at least about 48 weeks. In embodiments, a dose comprising about 1200 mg of Compound 1 is administered to a patient once daily for at least about 52 weeks. In embodiments, a dose comprising about 1200 mg of Compound 1 is administered to a patient three times weekly for at least about 52 weeks. In embodiments, a dose comprising about 1200 mg of Compound 1 is administered to a patient once daily for at least about 64 weeks. In embodiments, a dose comprising about 1200 mg of Compound 1 is administered to a patient three times weekly for at least about 64 weeks. In embodiments, a dose comprising about 1200 mg of Compound 1 is administered to a patient once daily for at least about 76 weeks. In embodiments, a dose comprising about 1200 mg of Compound 1 is administered to a patient three times weekly for at least about 76 weeks. In embodiments, a dose comprising about 1200 mg of Compound 1 is administered to a patient once daily for at least about 88 weeks. In embodiments, a dose comprising about 1200 mg of Compound 1 is administered to a patient three times weekly for at least about 88 weeks. In embodiments, a dose comprising about 1200 mg of Compound 1 is administered to a patient once daily for at least about 104 weeks. In embodiments, a dose comprising about 1200 mg of Compound 1 is administered to a patient three times weekly for at least about 104 weeks. In embodiments, a dose comprising about 1200 mg of Compound 1 is administered to a patient once daily for at least about 116 weeks. In embodiments, a dose comprising about 1200 mg of Compound 1 is administered to a patient three times weekly for at least about 116 weeks. In embodiments, a dose comprising about 1200 mg of Compound 1 is administered to a patient once daily for at least about 128 weeks. In embodiments, a dose comprising about 1200 mg of Compound 1 is administered to a patient three times weekly for at least about 128 weeks. In embodiments, a dose comprising about 1200 mg of Compound 1 is administered to a patient once daily for at least about 140 weeks. In embodiments, a dose comprising about 1200 mg of Compound 1 is administered to a patient three times weekly for at least about 140 weeks. In embodiments, a dose comprising about 1200 mg of Compound 1 is administered to a patient once daily for at least about 156 weeks. In embodiments, a dose comprising about 1200 mg of Compound 1 is administered to a patient three times weekly for at least about 156 weeks. In embodiments, a dose comprising about 1200 mg of Compound 1 is administered to a patient once daily for at least about 168 weeks. In embodiments, a dose comprising about 1200 mg of Compound 1 is administered to a patient three times weekly for at least about 168 weeks. In embodiments, a dose comprising about 1200 mg of Compound 1 is administered to a patient once daily for at least about 180 weeks. In embodiments, a dose comprising about 1200 mg of Compound 1 is administered to a patient three times weekly for at least about 180 weeks. In embodiments, a dose comprising about 1200 mg of Compound 1 is administered to a patient once daily for at least about 192 weeks. In embodiments, a dose comprising about 1200 mg of Compound 1 is administered to a patient three times weekly for at least about 192 weeks. In embodiments, a dose comprising about 1200 mg of Compound 1 is administered to a patient once daily for at least about 208 weeks. In embodiments, a dose comprising about 1200 mg of Compound 1 is administered to a patient three times weekly for at least about 208 weeks. In embodiments, a dose comprising about 1200 mg of Compound 1 is administered to a patient once daily for at least about 260 weeks. In embodiments, a dose comprising about 1200 mg of Compound 1 is administered to a patient three times weekly for at least about 260 weeks.

In embodiments of any methods described herein, a dose comprising about 1350 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 1350 mg Compound 1 is administered to a patient for at least about 6-52, 6-48, 6-42, 6-36, 6-30, 6-24, 6-18, or 6-12 consecutive weeks. In embodiments, a dose comprising about 1350 mg of Compound 1 is administered to a patient for at least about 8, 10, 12, 14, 16, 18, 20, 22, or 24 consecutive weeks. In embodiments, a dose comprising about 1350 mg of Compound 1 is administered to a patient for at least about 26, 28, 30, 32, 34, 36, 38, 40, 42, 44, 46, 48, 50, or 52 consecutive weeks. In embodiments, a dose comprising about 1350 mg of Compound 1 is administered to a patient once daily for at least about 8 weeks. In embodiments, a dose comprising about 1350 mg of Compound 1 is administered to a patient three times weekly for at least about 8 weeks. In embodiments, a dose comprising about 1350 mg of Compound 1 is administered to a patient once daily for at least about 12 weeks. In embodiments, a dose comprising about 1350 mg of Compound 1 is administered to a patient three times weekly for at least about 12 weeks. In embodiments, a dose comprising about 1350 mg of Compound 1 is administered to a patient once daily for at least about 24 weeks. In embodiments, a dose comprising about 1350 mg of Compound 1 is administered to a patient three times weekly for at least about 24 weeks. In embodiments, a dose comprising about 1350 mg of Compound 1 is administered to a patient once daily for at least about 28 weeks. In embodiments, a dose comprising about 1350 mg of Compound 1 is administered to a patient three times weekly for at least about 28 weeks. In embodiments, a dose comprising about 1350 mg of Compound 1 is administered to a patient once daily for at least about 32 weeks. In embodiments, a dose comprising about 1350 mg of Compound 1 is administered to a patient three times weekly for at least about 32 weeks. In embodiments, a dose comprising about 1350 mg of Compound 1 is administered to a patient once daily for at least about 36 weeks. In embodiments, a dose comprising about 1350 mg of Compound 1 is administered to a patient three times weekly for at least about 36 weeks. In embodiments, a dose comprising about 1350 mg of Compound 1 is administered to a patient once daily for at least about 40 weeks. In embodiments, a dose comprising about 1350 mg of Compound 1 is administered to a patient three times weekly for at least about 40 weeks. In embodiments, a dose comprising about 1350 mg of Compound 1 is administered to a patient once daily for at least about 44 weeks. In embodiments, a dose comprising about 1350 mg of Compound 1 is administered to a patient three times weekly for at least about 44 weeks. In embodiments, a dose comprising about 1350 mg of Compound 1 is administered to a patient once daily for at least about 48 weeks. In embodiments, a dose comprising about 1350 mg of Compound 1 is administered to a patient three times weekly for at least about 48 weeks. In embodiments, a dose comprising about 1350 mg of Compound 1 is administered to a patient once daily for at least about 52 weeks. In embodiments, a dose comprising about 1350 mg of Compound 1 is administered to a patient three times weekly for at least about 52 weeks. In embodiments, a dose comprising about 1350 mg of Compound 1 is administered to a patient once daily for at least about 64 weeks. In embodiments, a dose comprising about 1350 mg of Compound 1 is administered to a patient three times weekly for at least about 64 weeks. In embodiments, a dose comprising about 1350 mg of Compound 1 is administered to a patient once daily for at least about 76 weeks. In embodiments, a dose comprising about 1350 mg of Compound 1 is administered to a patient three times weekly for at least about 76 weeks. In embodiments, a dose comprising about 1350 mg of Compound 1 is administered to a patient once daily for at least about 88 weeks. In embodiments, a dose comprising about 1350 mg of Compound 1 is administered to a patient three times weekly for at least about 88 weeks. In embodiments, a dose comprising about 1350 mg of Compound 1 is administered to a patient once daily for at least about 104 weeks. In embodiments, a dose comprising about 1350 mg of Compound 1 is administered to a patient three times weekly for at least about 104 weeks. In embodiments, a dose comprising about 1350 mg of Compound 1 is administered to a patient once daily for at least about 116 weeks. In embodiments, a dose comprising about 1350 mg of Compound 1 is administered to a patient three times weekly for at least about 116 weeks. In embodiments, a dose comprising about 1350 mg of Compound 1 is administered to a patient once daily for at least about 128 weeks. In embodiments, a dose comprising about 1350 mg of Compound 1 is administered to a patient three times weekly for at least about 128 weeks. In embodiments, a dose comprising about 1350 mg of Compound 1 is administered to a patient once daily for at least about 140 weeks. In embodiments, a dose comprising about 1350 mg of Compound 1 is administered to a patient three times weekly for at least about 140 weeks. In embodiments, a dose comprising about 1350 mg of Compound 1 is administered to a patient once daily for at least about 156 weeks. In embodiments, a dose comprising about 1350 mg of Compound 1 is administered to a patient three times weekly for at least about 156 weeks. In embodiments, a dose comprising about 1350 mg of Compound 1 is administered to a patient once daily for at least about 168 weeks. In embodiments, a dose comprising about 1350 mg of Compound 1 is administered to a patient three times weekly for at least about 168 weeks. In embodiments, a dose comprising about 1350 mg of Compound 1 is administered to a patient once daily for at least about 180 weeks. In embodiments, a dose comprising about 1350 mg of Compound 1 is administered to a patient three times weekly for at least about 180 weeks. In embodiments, a dose comprising about 1350 mg of Compound 1 is administered to a patient once daily for at least about 192 weeks. In embodiments, a dose comprising about 1350 mg of Compound 1 is administered to a patient three times weekly for at least about 192 weeks. In embodiments, a dose comprising about 1350 mg of Compound 1 is administered to a patient once daily for at least about 208 weeks. In embodiments, a dose comprising about 1350 mg of Compound 1 is administered to a patient three times weekly for at least about 208 weeks. In embodiments, a dose comprising about 1350 mg of Compound 1 is administered to a patient once daily for at least about 260 weeks. In embodiments, a dose comprising about 1350 mg of Compound 1 is administered to a patient three times weekly for at least about 260 weeks.

In embodiments of any methods described herein, a dose comprising about 1500 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 1500 mg Compound 1 is administered to a patient for at least about 6-52, 6-48, 6-42, 6-36, 6-30, 6-24, 6-18, or 6-12 consecutive weeks. In embodiments, a dose comprising about 1500 mg of Compound 1 is administered to a patient for at least about 8, 10, 12, 14, 16, 18, 20, 22, or 24 consecutive weeks. In embodiments, a dose comprising about 1500 mg of Compound 1 is administered to a patient for at least about 26, 28, 30, 32, 34, 36, 38, 40, 42, 44, 46, 48, 50, or 52 consecutive weeks. In embodiments, a dose comprising about 1500 mg of Compound 1 is administered to a patient once daily for at least about 8 weeks. In embodiments, a dose comprising about 1500 mg of Compound 1 is administered to a patient three times weekly for at least about 8 weeks. In embodiments, a dose comprising about 1500 mg of Compound 1 is administered to a patient once daily for at least about 12 weeks. In embodiments, a dose comprising about 1500 mg of Compound 1 is administered to a patient three times weekly for at least about 12 weeks. In embodiments, a dose comprising about 1500 mg of Compound 1 is administered to a patient once daily for at least about 24 weeks. In embodiments, a dose comprising about 1500 mg of Compound 1 is administered to a patient three times weekly for at least about 24 weeks. In embodiments, a dose comprising about 1500 mg of Compound 1 is administered to a patient once daily for at least about 28 weeks. In embodiments, a dose comprising about 1500 mg of Compound 1 is administered to a patient three times weekly for at least about 28 weeks. In embodiments, a dose comprising about 1500 mg of Compound 1 is administered to a patient once daily for at least about 32 weeks. In embodiments, a dose comprising about 1500 mg of Compound 1 is administered to a patient three times weekly for at least about 32 weeks. In embodiments, a dose comprising about 1500 mg of Compound 1 is administered to a patient once daily for at least about 36 weeks. In embodiments, a dose comprising about 1500 mg of Compound 1 is administered to a patient three times weekly for at least about 36 weeks. In embodiments, a dose comprising about 1500 mg of Compound 1 is administered to a patient once daily for at least about 40 weeks. In embodiments, a dose comprising about 1500 mg of Compound 1 is administered to a patient three times weekly for at least about 40 weeks. In embodiments, a dose comprising about 1500 mg of Compound 1 is administered to a patient once daily for at least about 44 weeks. In embodiments, a dose comprising about 1500 mg of Compound 1 is administered to a patient three times weekly for at least about 44 weeks. In embodiments, a dose comprising about 1500 mg of Compound 1 is administered to a patient once daily for at least about 48 weeks. In embodiments, a dose comprising about 1500 mg of Compound 1 is administered to a patient three times weekly for at least about 48 weeks. In embodiments, a dose comprising about 1500 mg of Compound 1 is administered to a patient once daily for at least about 52 weeks. In embodiments, a dose comprising about 1500 mg of Compound 1 is administered to a patient three times weekly for at least about 52 weeks. In embodiments, a dose comprising about 1500 mg of Compound 1 is administered to a patient once daily for at least about 64 weeks. In embodiments, a dose comprising about 1500 mg of Compound 1 is administered to a patient three times weekly for at least about 64 weeks. In embodiments, a dose comprising about 1500 mg of Compound 1 is administered to a patient once daily for at least about 76 weeks. In embodiments, a dose comprising about 1500 mg of Compound 1 is administered to a patient three times weekly for at least about 76 weeks. In embodiments, a dose comprising about 1500 mg of Compound 1 is administered to a patient once daily for at least about 88 weeks. In embodiments, a dose comprising about 1500 mg of Compound 1 is administered to a patient three times weekly for at least about 88 weeks. In embodiments, a dose comprising about 1500 mg of Compound 1 is administered to a patient once daily for at least about 104 weeks. In embodiments, a dose comprising about 1500 mg of Compound 1 is administered to a patient three times weekly for at least about 104 weeks. In embodiments, a dose comprising about 1500 mg of Compound 1 is administered to a patient once daily for at least about 116 weeks. In embodiments, a dose comprising about 1500 mg of Compound 1 is administered to a patient three times weekly for at least about 116 weeks. In embodiments, a dose comprising about 1500 mg of Compound 1 is administered to a patient once daily for at least about 128 weeks. In embodiments, a dose comprising about 1500 mg of Compound 1 is administered to a patient three times weekly for at least about 128 weeks. In embodiments, a dose comprising about 1500 mg of Compound 1 is administered to a patient once daily for at least about 140 weeks. In embodiments, a dose comprising about 1500 mg of Compound 1 is administered to a patient three times weekly for at least about 140 weeks. In embodiments, a dose comprising about 1500 mg of Compound 1 is administered to a patient once daily for at least about 156 weeks. In embodiments, a dose comprising about 1500 mg of Compound 1 is administered to a patient three times weekly for at least about 156 weeks. In embodiments, a dose comprising about 1500 mg of Compound 1 is administered to a patient once daily for at least about 168 weeks. In embodiments, a dose comprising about 1500 mg of Compound 1 is administered to a patient three times weekly for at least about 168 weeks. In embodiments, a dose comprising about 1500 mg of Compound 1 is administered to a patient once daily for at least about 180 weeks. In embodiments, a dose comprising about 1500 mg of Compound 1 is administered to a patient three times weekly for at least about 180 weeks. In embodiments, a dose comprising about 1500 mg of Compound 1 is administered to a patient once daily for at least about 192 weeks. In embodiments, a dose comprising about 1500 mg of Compound 1 is administered to a patient three times weekly for at least about 192 weeks. In embodiments, a dose comprising about 1500 mg of Compound 1 is administered to a patient once daily for at least about 208 weeks. In embodiments, a dose comprising about 1500 mg of Compound 1 is administered to a patient three times weekly for at least about 208 weeks. In embodiments, a dose comprising about 1500 mg of Compound 1 is administered to a patient once daily for at least about 260 weeks. In embodiments, a dose comprising about 1500 mg of Compound 1 is administered to a patient three times weekly for at least about 260 weeks.

In embodiments of any methods described herein, a dose comprising about 1650 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 1650 mg Compound 1 is administered to a patient for at least about 6-52, 6-48, 6-42, 6-36, 6-30, 6-24, 6-18, or 6-12 consecutive weeks. In embodiments, a dose comprising about 1650 mg of Compound 1 is administered to a patient for at least about 8, 10, 12, 14, 16, 18, 20, 22, or 24 consecutive weeks. In embodiments, a dose comprising about 1650 mg of Compound 1 is administered to a patient for at least about 26, 28, 30, 32, 34, 36, 38, 40, 42, 44, 46, 48, 50, or 52 consecutive weeks. In embodiments, a dose comprising about 1650 mg of Compound 1 is administered to a patient once daily for at least about 8 weeks. In embodiments, a dose comprising about 1650 mg of Compound 1 is administered to a patient three times weekly for at least about 8 weeks. In embodiments, a dose comprising about 1650 mg of Compound 1 is administered to a patient once daily for at least about 12 weeks. In embodiments, a dose comprising about 1650 mg of Compound 1 is administered to a patient three times weekly for at least about 12 weeks. In embodiments, a dose comprising about 1650 mg of Compound 1 is administered to a patient once daily for at least about 24 weeks. In embodiments, a dose comprising about 1650 mg of Compound 1 is administered to a patient three times weekly for at least about 24 weeks. In embodiments, a dose comprising about 1650 mg of Compound 1 is administered to a patient once daily for at least about 28 weeks. In embodiments, a dose comprising about 1650 mg of Compound 1 is administered to a patient three times weekly for at least about 28 weeks. In embodiments, a dose comprising about 1650 mg of Compound 1 is administered to a patient once daily for at least about 32 weeks. In embodiments, a dose comprising about 1650 mg of Compound 1 is administered to a patient three times weekly for at least about 32 weeks. In embodiments, a dose comprising about 1650 mg of Compound 1 is administered to a patient once daily for at least about 36 weeks. In embodiments, a dose comprising about 1650 mg of Compound 1 is administered to a patient three times weekly for at least about 36 weeks. In embodiments, a dose comprising about 1650 mg of Compound 1 is administered to a patient once daily for at least about 40 weeks. In embodiments, a dose comprising about 1650 mg of Compound 1 is administered to a patient three times weekly for at least about 40 weeks. In embodiments, a dose comprising about 1650 mg of Compound 1 is administered to a patient once daily for at least about 44 weeks. In embodiments, a dose comprising about 1650 mg of Compound 1 is administered to a patient three times weekly for at least about 44 weeks. In embodiments, a dose comprising about 1650 mg of Compound 1 is administered to a patient once daily for at least about 48 weeks. In embodiments, a dose comprising about 1650 mg of Compound 1 is administered to a patient three times weekly for at least about 48 weeks. In embodiments, a dose comprising about 1650 mg of Compound 1 is administered to a patient once daily for at least about 52 weeks. In embodiments, a dose comprising about 1650 mg of Compound 1 is administered to a patient three times weekly for at least about 52 weeks. In embodiments, a dose comprising about 1650 mg of Compound 1 is administered to a patient once daily for at least about 64 weeks. In embodiments, a dose comprising about 1650 mg of Compound 1 is administered to a patient three times weekly for at least about 64 weeks. In embodiments, a dose comprising about 1650 mg of Compound 1 is administered to a patient once daily for at least about 76 weeks. In embodiments, a dose comprising about 1650 mg of Compound 1 is administered to a patient three times weekly for at least about 76 weeks. In embodiments, a dose comprising about 1650 mg of Compound 1 is administered to a patient once daily for at least about 88 weeks. In embodiments, a dose comprising about 1650 mg of Compound 1 is administered to a patient three times weekly for at least about 88 weeks. In embodiments, a dose comprising about 1650 mg of Compound 1 is administered to a patient once daily for at least about 104 weeks. In embodiments, a dose comprising about 1650 mg of Compound 1 is administered to a patient three times weekly for at least about 104 weeks. In embodiments, a dose comprising about 1650 mg of Compound 1 is administered to a patient once daily for at least about 116 weeks. In embodiments, a dose comprising about 1650 mg of Compound 1 is administered to a patient three times weekly for at least about 116 weeks. In embodiments, a dose comprising about 1650 mg of Compound 1 is administered to a patient once daily for at least about 128 weeks. In embodiments, a dose comprising about 1650 mg of Compound 1 is administered to a patient three times weekly for at least about 128 weeks. In embodiments, a dose comprising about 1650 mg of Compound 1 is administered to a patient once daily for at least about 140 weeks. In embodiments, a dose comprising about 1650 mg of Compound 1 is administered to a patient three times weekly for at least about 140 weeks. In embodiments, a dose comprising about 1650 mg of Compound 1 is administered to a patient once daily for at least about 156 weeks. In embodiments, a dose comprising about 1650 mg of Compound 1 is administered to a patient three times weekly for at least about 156 weeks. In embodiments, a dose comprising about 1650 mg of Compound 1 is administered to a patient once daily for at least about 168 weeks. In embodiments, a dose comprising about 1650 mg of Compound 1 is administered to a patient three times weekly for at least about 168 weeks. In embodiments, a dose comprising about 1650 mg of Compound 1 is administered to a patient once daily for at least about 180 weeks. In embodiments, a dose comprising about 1650 mg of Compound 1 is administered to a patient three times weekly for at least about 180 weeks. In embodiments, a dose comprising about 1650 mg of Compound 1 is administered to a patient once daily for at least about 192 weeks. In embodiments, a dose comprising about 1650 mg of Compound 1 is administered to a patient three times weekly for at least about 192 weeks. In embodiments, a dose comprising about 1650 mg of Compound 1 is administered to a patient once daily for at least about 208 weeks. In embodiments, a dose comprising about 1650 mg of Compound 1 is administered to a patient three times weekly for at least about 208 weeks. In embodiments, a dose comprising about 1650 mg of Compound 1 is administered to a patient once daily for at least about 260 weeks. In embodiments, a dose comprising about 1650 mg of Compound 1 is administered to a patient three times weekly for at least about 260 weeks.

In embodiments of any methods described herein, a dose comprising about 1800 mg of Compound 1 is administered to a patient for at least about 12, 24, 28, 32, 36, 40, 44, 48, 52, 53, 64, 76, 88, 104, 116, 128, 140, 156, 168, 180, 192, 208, or 260 weeks. In embodiments of any methods described herein, a dose of comprising about 1800 mg Compound 1 is administered to a patient for at least about 6-52, 6-48, 6-42, 6-36, 6-30, 6-24, 6-18, or 6-12 consecutive weeks. In embodiments, a dose comprising about 1800 mg of Compound 1 is administered to a patient for at least about 8, 10, 12, 14, 16, 18, 20, 22, or 24 consecutive weeks. In embodiments, a dose comprising about 1800 mg of Compound 1 is administered to a patient for at least about 26, 28, 30, 32, 34, 36, 38, 40, 42, 44, 46, 48, 50, or 52 consecutive weeks. In embodiments, a dose comprising about 1800 mg of Compound 1 is administered to a patient once daily for at least about 8 weeks. In embodiments, a dose comprising about 1800 mg of Compound 1 is administered to a patient three times weekly for at least about 8 weeks. In embodiments, a dose comprising about 1800 mg of Compound 1 is administered to a patient once daily for at least about 12 weeks. In embodiments, a dose comprising about 1800 mg of Compound 1 is administered to a patient three times weekly for at least about 12 weeks. In embodiments, a dose comprising about 1800 mg of Compound 1 is administered to a patient once daily for at least about 24 weeks. In embodiments, a dose comprising about 1800 mg of Compound 1 is administered to a patient three times weekly for at least about 24 weeks. In embodiments, a dose comprising about 1800 mg of Compound 1 is administered to a patient once daily for at least about 28 weeks. In embodiments, a dose comprising about 1800 mg of Compound 1 is administered to a patient three times weekly for at least about 28 weeks. In embodiments, a dose comprising about 1800 mg of Compound 1 is administered to a patient once daily for at least about 32 weeks. In embodiments, a dose comprising about 1800 mg of Compound 1 is administered to a patient three times weekly for at least about 32 weeks. In embodiments, a dose comprising about 1800 mg of Compound 1 is administered to a patient once daily for at least about 36 weeks. In embodiments, a dose comprising about 1800 mg of Compound 1 is administered to a patient three times weekly for at least about 36 weeks. In embodiments, a dose comprising about 1800 mg of Compound 1 is administered to a patient once daily for at least about 40 weeks. In embodiments, a dose comprising about 1800 mg of Compound 1 is administered to a patient three times weekly for at least about 40 weeks. In embodiments, a dose comprising about 1800 mg of Compound 1 is administered to a patient once daily for at least about 44 weeks. In embodiments, a dose comprising about 1800 mg of Compound 1 is administered to a patient three times weekly for at least about 44 weeks. In embodiments, a dose comprising about 1800 mg of Compound 1 is administered to a patient once daily for at least about 48 weeks. In embodiments, a dose comprising about 1800 mg of Compound 1 is administered to a patient three times weekly for at least about 48 weeks. In embodiments, a dose comprising about 1800 mg of Compound 1 is administered to a patient once daily for at least about 52 weeks. In embodiments, a dose comprising about 1800 mg of Compound 1 is administered to a patient three times weekly for at least about 52 weeks. In embodiments, a dose comprising about 1800 mg of Compound 1 is administered to a patient once daily for at least about 64 weeks. In embodiments, a dose comprising about 1800 mg of Compound 1 is administered to a patient three times weekly for at least about 64 weeks. In embodiments, a dose comprising about 1800 mg of Compound 1 is administered to a patient once daily for at least about 76 weeks. In embodiments, a dose comprising about 1800 mg of Compound 1 is administered to a patient three times weekly for at least about 76 weeks. In embodiments, a dose comprising about 1800 mg of Compound 1 is administered to a patient once daily for at least about 88 weeks. In embodiments, a dose comprising about 1800 mg of Compound 1 is administered to a patient three times weekly for at least about 88 weeks. In embodiments, a dose comprising about 1800 mg of Compound 1 is administered to a patient once daily for at least about 104 weeks. In embodiments, a dose comprising about 1800 mg of Compound 1 is administered to a patient three times weekly for at least about 104 weeks. In embodiments, a dose comprising about 1800 mg of Compound 1 is administered to a patient once daily for at least about 116 weeks. In embodiments, a dose comprising about 1800 mg of Compound 1 is administered to a patient three times weekly for at least about 116 weeks. In embodiments, a dose comprising about 1800 mg of Compound 1 is administered to a patient once daily for at least about 128 weeks. In embodiments, a dose comprising about 1800 mg of Compound 1 is administered to a patient three times weekly for at least about 128 weeks. In embodiments, a dose comprising about 1800 mg of Compound 1 is administered to a patient once daily for at least about 140 weeks. In embodiments, a dose comprising about 1800 mg of Compound 1 is administered to a patient three times weekly for at least about 140 weeks. In embodiments, a dose comprising about 1800 mg of Compound 1 is administered to a patient once daily for at least about 156 weeks. In embodiments, a dose comprising about 1800 mg of Compound 1 is administered to a patient three times weekly for at least about 156 weeks. In embodiments, a dose comprising about 1800 mg of Compound 1 is administered to a patient once daily for at least about 168 weeks. In embodiments, a dose comprising about 1800 mg of Compound 1 is administered to a patient three times weekly for at least about 168 weeks. In embodiments, a dose comprising about 1800 mg of Compound 1 is administered to a patient once daily for at least about 180 weeks. In embodiments, a dose comprising about 1800 mg of Compound 1 is administered to a patient three times weekly for at least about 180 weeks. In embodiments, a dose comprising about 1800 mg of Compound 1 is administered to a patient once daily for at least about 192 weeks. In embodiments, a dose comprising about 1800 mg of Compound 1 is administered to a patient three times weekly for at least about 192 weeks. In embodiments, a dose comprising about 1800 mg of Compound 1 is administered to a patient once daily for at least about 208 weeks. In embodiments, a dose comprising about 1800 mg of Compound 1 is administered to a patient three times weekly for at least about 208 weeks. In embodiments, a dose comprising about 1800 mg of Compound 1 is administered to a patient once daily for at least about 260 weeks. In embodiments, a dose comprising about 1800 mg of Compound 1 is administered to a patient three times weekly for at least about 260 weeks.

A patient can receive any exemplary dose according to any exemplary dosing frequency for a threshold treating period. In embodiments, a treating period comprises uninterrupted treatment with Compound 1. In embodiments, a treating period comprises interruption (e.g., a patient does not receive Compound 1 for a period of 1-7 days, about 1 week, or about 2 weeks).

In embodiments of any methods described herein, the patient receives a dose of Compound 1 that is at least about 150 mg up to about any of weeks 1-12, 1-6, 24-32, 24-40, or 24-52 of a treating period. In embodiments of any methods described herein, the patient receives a dose of Compound 1 that is at least about 150 mg up to about week 24, week 28, or week 32 of treatment with Compound 1. In embodiments of any methods described herein, the patient receives a dose of Compound 1 that is at least about 150 mg up to about week 46, week 48, week 50, or week 52 of treatment with Compound 1. In embodiments, the dose is about 150 mg-1800 mg of Compound 1. In embodiments, the dose is about 450 mg-1800 mg of Compound 1. In embodiments, the dose is about 600 mg-1800 mg of Compound 1. In embodiments, the dose is about 750 mg-1800 mg of Compound 1. In embodiments, the dose is about 150 mg-1200 mg of Compound 1. In embodiments, the dose is about 450 mg-1200 mg of Compound 1. In embodiments, the dose is about 600 mg-1200 mg of Compound 1. In embodiments, the dose is about 750 mg-1200 mg of Compound 1. In embodiments, the dose is about 600 mg-900 mg of Compound 1. In embodiments, the dose is about 750 mg-900 mg of Compound 1. In embodiments, the dose is about 150 mg of Compound 1. In embodiments, the dose is about 300 mg of Compound 1. In embodiments, the dose is about 450 mg of Compound 1. In embodiments, the dose is about 600 mg of Compound 1. In embodiments, the dose is about 750 mg of Compound 1. In embodiments, the dose is about 900 mg of Compound 1. In embodiments, the dose is about 1050 mg of Compound 1. In embodiments, the dose is about 1200 mg of Compound 1. In embodiments, the dose is about 1350 mg of Compound 1. In embodiments, the dose is about 1500 mg of Compound 1. In embodiments, the dose is about 1650 mg of Compound 1. In embodiments, the dose is about 1800 mg of Compound 1. In embodiments, the dose is about 150 mg-1200 mg of Compound 1 once daily or three times weekly. In embodiments, the dose is about 450 mg-1200 mg of Compound 1 once daily or three times weekly. In embodiments, the dose is about 600 mg-1200 mg of Compound 1 once daily or three times weekly. In embodiments, the dose is about 750 mg-1200 mg of Compound 1 once daily or three times weekly. In embodiments, the dose is about 150 mg-1800 mg of Compound 1 once daily or three times weekly. In embodiments, the dose is about 450 mg-1800 mg of Compound 1 once daily or three times weekly. In embodiments, the dose is about 600 mg-1800 mg of Compound 1 once daily or three times weekly. In embodiments, the dose is about 750 mg-1800 mg of Compound 1 once daily or three times weekly. In embodiments, the dose is about 750 mg-900 mg of Compound 1 once daily or three times weekly. In embodiments, the dose is about 600 mg-900 mg of Compound 1 once daily or three times weekly. In embodiments, the dose is about 150 mg of Compound 1 once daily or three times weekly. In embodiments, the dose is about 300 mg of Compound 1 once daily or three times weekly. In embodiments, the dose is about 450 mg of Compound 1 once daily or three times weekly. In embodiments, the dose is about 600 mg of Compound 1 once daily or three times weekly. In embodiments, the dose is about 750 mg of Compound 1 once daily or three times weekly. In embodiments, the dose is about 900 mg of Compound 1 once daily or three times weekly. In embodiments, the dose is about 1050 mg of Compound 1 once daily or three times weekly. In embodiments, the dose is about 1200 mg of Compound 1 once daily or three times weekly. In embodiments, the dose is about 1350 mg of Compound 1 once daily or three times weekly. In embodiments, the dose is about 1500 mg of Compound 1 once daily or three times weekly. In embodiments, the dose is about 1650 mg of Compound 1 once daily or three times weekly. In embodiments, the dose is about 1800 mg of Compound 1 once daily or three times weekly.

In embodiments, a suitable dosing regimen is based on the identity of an erythropoietin stimulating agent (ESA) therapy, the dosage amount of the ESA, and/or dialysis (e.g., hemodialysis or peritoneal dialysis) previously received by a subject.

In embodiments, a suitable dosing regimen (e.g., as described herein) is selected based on the identity of an ESA therapy (e.g., darbepoetin alfa, epoetin alfa, or epoetin beta pegol) previously received by a subject.

In embodiments, a suitable dosing regimen (e.g., as described herein) is selected based on the dosage amount of an ESA therapy (e.g., a weekly dose amount of darbepoetin alfa) previously received by a subject.

In embodiments, a suitable dosing regimen (e.g., as described herein) is selected based on the dialysis status of a subject (e.g., a patient who receives or previously receives dialysis such as hemodialysis or peritoneal dialysis). In embodiments, a patient has DD-CKD. In embodiments, a patient has NDD-CKD.

In embodiments, a dosing regimen comprises administering to a patient a dose of Compound 1 that is at least about 150 mg (e.g., a dose that is about 150 mg, about 300 mg, about 450 mg, about 600 mg, about 750 mg, about 900 mg, about 1050 mg, or about 1200 mg) as described herein. In embodiments, the dosing regimen is determined for a patient that has previously treated with darbepoetin alfa (DA) (e.g., received DA within about eight weeks of commencing treatment with Compound 1 or being screened for treatment with Compound 1). In embodiments, the patient has previously been treated with darbepoetin alfa at any of the doses described herein. In embodiments, the dosing regimen is determined for a patient that has previously treated with epoetin alfa (e.g., received epoetin alfa within about eight weeks of commencing treatment with Compound 1 or being screened for treatment with Compound 1). In embodiments, the patient has previously been treated with epoetin alfa at any of the doses described herein. In embodiments, the dosing regimen is determined for a patient that has previously treated with methoxy polyethylene glycol-epoetin beta (epoetin beta pegol) (e.g., received epoetin beta pegol within about eight weeks of commencing treatment with Compound 1 or being screened for treatment with Compound 1). In embodiments, the patient has previously been treated with epoetin beta pegol at any of the doses described herein. In embodiments, the patient has anemia associated with or secondary to chronic kidney disease (CKD). In embodiments, the CKD is dialysis-dependent CKD (DD-CKD). In embodiments, the patient receives dialysis such as hemodialysis (a HD-CKD patient) or peritoneal dialysis (PD-CKD). In embodiments, the CKD is non-dialysis dependent (NDD-CKD). In embodiments, the dose is about 150 mg-1200 mg of Compound 1. In embodiments, the dose is about 450 mg-1200 mg of Compound 1. In embodiments, the dose is about 600 mg-1200 mg of Compound 1. In embodiments, the dose is about 750 mg-1200 mg of Compound 1. In embodiments, the dose is about 150 mg-1800 mg of Compound 1. In embodiments, the dose is about 450 mg-1800 mg of Compound 1. In embodiments, the dose is about 600 mg-1800 mg of Compound 1. In embodiments, the dose is about 750 mg-1800 mg of Compound 1. In embodiments, the dose is about 600 mg-900 mg of Compound 1. In embodiments, the dose is about 750 mg-900 mg of Compound 1. In embodiments, the dose is about 150 mg of Compound 1. In embodiments, the dose is about 300 mg of Compound 1. In embodiments, the dose is about 450 mg of Compound 1. In embodiments, the dose is about 600 mg of Compound 1. In embodiments, the dose is about 750 mg of Compound 1. In embodiments, the dose is about 900 mg of Compound 1. In embodiments, the dose is about 1050 mg of Compound 1. In embodiments, the dose is about 1200 mg of Compound 1. In embodiments, the dose is about 1350 mg of Compound 1. In embodiments, the dose is about 1500 mg of Compound 1. In embodiments, the dose is about 1650 mg of Compound 1. In embodiments, the dose is about 1800 mg of Compound 1. In embodiments, the dose of Compound 1 is administered once daily. In embodiments, the dose of Compound 1 is administered once weekly. In embodiments, the dose of Compound 1 is administered three times weekly. In embodiments, the dose comprises about 750 mg-1800 mg of Compound and is administered once daily. In embodiments, the dose comprises about 750 mg-1200 mg of Compound and is administered once daily. In embodiments, the dose comprises about 750 mg-900 mg of Compound and is administered once daily. In embodiments, the dose comprises about 150 mg-1200 mg of Compound and is administered three times weekly. In embodiments, the dose comprises about 600 mg-1200 mg of Compound and is administered three times weekly. In embodiments, the dose comprises about 150 mg-1800 mg of Compound and is administered three times weekly. In embodiments, the dose comprises about 600 mg-1800 mg of Compound and is administered three times weekly. In embodiments, the dose comprises about 600 mg-900 mg of Compound and is administered three times weekly. In embodiments, the dose comprises about 750 mg-900 mg of Compound and is administered three times weekly. In embodiments, the dose comprises about 150 mg of Compound and is administered once daily or three times weekly. In embodiments, the dose comprises about 300 mg of Compound and is administered once daily or three times weekly. In embodiments, the dose comprises about 450 mg of Compound and is administered once daily or three times weekly. In embodiments, the dose comprises about 600 mg of Compound and is administered once daily or three times weekly. In embodiments, the dose comprises about 750 mg of Compound and is administered once daily or three times weekly. In embodiments, the dose comprises about 900 mg of Compound and is administered once daily or three times weekly. In embodiments, the dose comprises about 1050 mg of Compound and is administered once daily or three times weekly. In embodiments, the dose comprises about 1200 mg of Compound and is administered once daily or three times weekly. In embodiments, the dose comprises about 1350 mg of Compound and is administered once daily or three times weekly. In embodiments, the dose comprises about 1500 mg of Compound and is administered once daily or three times weekly. In embodiments, the dose comprises about 1650 mg of Compound and is administered once daily or three times weekly. In embodiments, the dose comprises about 1800 mg of Compound and is administered once daily or three times weekly.

Doses of Compound 1 are taken orally. Doses of Compound 1 may be taken while fasting, together with fluids, or together with food of any kind. In specific embodiments, doses of Compound 1 may be taken or 1, 2, 3, 4, 5, 6, 7, 8, 9, 10, 11, or 12 hours after a meal, or 1, 2, 3, 4, 5, 6, 7, 8, 9, 10, 11, or 12 hours before a meal. Doses of Compound 1 may be taken at any time of day. In certain embodiments, repeat doses are administered at the same time during the day. In certain embodiments, the dose doses are administered in the morning, around mid-day, or in the evening. In certain embodiments, the doses are administered between 4.00 am and 2.00 pm. In certain embodiments, the doses are administered between 5.00 am and 1.00 pm. In certain embodiments, the doses are administered between 6.00 am and 12.00 noon. In certain embodiments, the doses are administered between 7.00 am and 11.00 am. In certain embodiments, the doses are administered between 8.00 am and 10.00 am. In certain embodiments, the doses are administered before, during, or after breakfast. Administration and dosing regimens may be adjusted as described herein.

In a specific embodiment, the patient is administered a dose comprising about 150 mg to about 1200 mg of Compound 1 three times a week, wherein the patient was previously administered a daily dose of Compound 1. In embodiments, the daily dose of Compound 1 includes about 150, 300, 450, and 600 mg. In embodiments, the patient was previously administered a daily dose of Compound 1 for at least about 4 weeks, at least about 8 weeks, or at least about 12 weeks. In embodiments, the patient has anemia secondary to or associated to chronic kidney disease (CKD). In embodiments, the CKD is dialysis-dependent CKD (DD-CKD). In embodiments, the CKD is non-dialysis dependent CKD (NDD-CKD). In embodiments, the patent previously has been treated with an ESA. In embodiments, the patient previously has not been treated with an ESA. In embodiments, the patient previously has been treated with darbepoetin alfa at any of the doses described herein. In embodiments, the patient previously has been treated with epoetin alfa at any of the doses described herein. In embodiments, the patient previously has been treated with epoetin beta pegol at any of the doses described herein. In embodiments, the patient is administered a dose comprising about 600 mg-1800 mg of Compound 1 three times weekly. In embodiments, the patient is administered a dose comprising about 600 mg-1200 mg of Compound 1 three times weekly. In embodiments, the patient is administered a dose comprising about 150 mg of Compound 1 three times weekly. In embodiments, the patient is administered a dose comprising about 300 mg of Compound 1 three times weekly. In embodiments, the patient is administered a dose comprising about 450 mg of Compound 1 three times weekly. In embodiments, the patient is administered a dose comprising about 600 mg of Compound 1 three times weekly. In embodiments, the patient is administered a dose comprising about 750 mg of Compound 1 three times weekly. In embodiments, the patient is administered a dose comprising about 900 mg of Compound 1 three times weekly. In embodiments, the patient is administered a dose comprising about 1050 mg of Compound 1 three times weekly. In embodiments, the patient is administered a dose comprising about 1200 mg of Compound 1 three times weekly. In embodiments, the patient is administered a dose comprising about 1350 mg of Compound 1 three times weekly. In embodiments, the patient is administered a dose comprising about 1500 mg of Compound 1 three times weekly. In embodiments, the patient is administered a dose comprising about 1650 mg of Compound 1 three times weekly. In embodiments, the patient is administered a dose comprising about 1800 mg of Compound 1 three times weekly.

This section provides several exemplary doses for Compound 1. In certain embodiments, such a dose is the initial dose at the beginning of a treatment. In other embodiments, such a dose is the adjusted dose at a later time during the course of treatment.

In embodiments of any methods described herein, a dose of Compound 1 can be adjusted or maintained based on a patient's hemoglobin (Hb) level. In embodiments, a dose of Compound 1 is adjusted (e.g., by about 150 mg of Compound 1) if a patient's hemoglobin (Hb) level is <11.0 g/dL or >11.5 g/dL. In embodiments, a dose is increased. In embodiments, a dose is decreased. In embodiments, a method comprises adjusting the dose by about 150 mg of Compound 1 if a patient's hemoglobin (Hb) level is <10.0 g/dL or >11.5 g/dL. In embodiments, a method comprises adjusting the dose by about 150 mg of Compound 1 if a patient's hemoglobin (Hb) level is <10.0 g/dL or >12.5 g/dL. In embodiments, a method comprises adjusting the dose by about 150 mg of Compound 1 if a patient's hemoglobin (Hb) level is <10.0 g/dL. In embodiments, a method comprises adjusting the dose comprises increasing the dose by about 150 mg of Compound 1. In embodiments, a method comprises adjusting the dose by about 150 mg of Compound 1 if the patient's hemoglobin (Hb) level is >11.5 g/dL. In methods a method comprises adjusting the dose comprises decreasing the dose by about 150 mg of Compound 1. In embodiments, a method comprises adjusting the dose by about 150 mg of Compound 1 if the patient's hemoglobin (Hb) level is <10.0 g/dL. In embodiments, a method comprises adjusting the dose comprises increasing the dose by about 150 mg of Compound 1. In embodiments, a method comprises adjusting the dose by about 150 mg of Compound 1 if the patient's hemoglobin (Hb) level is >11.5 g/dL. In embodiments, a method comprises adjusting the dose comprises decreasing the dose by about 150 mg of Compound 1.

In embodiments of any methods described herein, a dose of Compound 1 can be adjusted or maintained based on a change in a patient's hemoglobin (Hb) level. In embodiments, a dose is decreased by about 150 mg of Compound 1 if the patient's hemoglobin (Hb) level increases by >1.0 g/dL in a 2-week period or by >2.0 g/dL in about a 4-week period.

In embodiments of any methods described herein, adjusting the dose occurs no more than once in at least every 2 weeks. In embodiments of any methods described herein, adjusting the dose occurs no more than once in at least every 4 weeks. In embodiments of any methods described herein, adjusting the dose occurs no more than once in at least every 6 weeks. In embodiments of any methods described herein, decreasing the dose occurs no more than once in at least every 2 weeks.

Formulations

In certain embodiments, Compound 1 may be provided as a formulation (pharmaceutical composition). In embodiments, a formulation is an oral dosage form (e.g., a tablet or capsule).

Exemplary formulations of Compound 1 are described in WO 2014/200773 and WO/2016/161094, which are incorporated by reference in their entirety. Still further exemplary formulations are described herein.

Also provided are anhydrous pharmaceutical compositions and dosage forms since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers", include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

Excipients. A formulation comprising Compound 1 may comprise one or more excipients.

In certain embodiments, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25 NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Examples of excipients that can be used in formulations described herein include, but are not limited to, insoluble diluents, binders, fillers, disintegrants, glidants, carriers, and lubricants.

In embodiments, formulations of Compound 1 comprise: one or more diluents and/or filler; one or more disintegrants; one or more lubricants; and/or one or more glidants.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methylcellulose, (e.g., Nos. 2208, 2906, 2910), microcrystalline cellulose, and mixtures thereof.

Examples of insoluble diluents and carriers suitable for use in the pharmaceutical compositions and dosage forms provided herein include, but are not limited to, dibasic calcium phosphate and microcrystalline cellulose. Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of diluents/fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, hydroxypropyl methylcellulose (HPMC or hypromellose) (e.g., Methocel E5 Premium LV) and mixtures thereof. In certain embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof. In certain embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate (e.g., Explotab®), potato or tapioca starch, other starches, pre-gelatinized starch, other starches, clays, other algins, other celluloses, gums, and mixtures thereof.

Glidants that can be used in pharmaceutical compositions and dosage forms include, but are not limited to fumed silica, magnesium carbonate, magnesium stearate, colloidal silicon dioxide (e.g., Aerosil, Cab-O-Sil), starch and talc.

Lubricants that can be used in pharmaceutical compositions and dosage forms include, but are not limited to, calcium stearate, magnesium stearate (e.g. Hyqual® 5712), mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, MD), a coagulated aerosol of synthetic silica (marketed by Degussa Co. of Plano, TX), CAB-O-SIL (a pyrogenic colloidal silicon dioxide product sold by Cabot Co. of Boston, MA), and mixtures thereof.

In embodiments, formulations of Compound 1 can comprise intra-granular components, extra-granular components, and film coating components, wherein the intra-granular components comprise Compound 1, an insoluble diluent/carrier or filler, a disintegrant, and a diluent/filler or binder; wherein the extra-granular components comprise a disintegrant, a glidant, and/or a lubricant; and wherein the film coating components comprise a tablet coating.

In certain embodiments, provided herein are formulations of Compound 1 that comprise about 10%, about 15%, about 20%, about 25%, about 30%, about 35%, about 40%, about 45%, about 50%, about 55%, about 60%, about 65%, about 70%, about 75%, about 80%, about 85%, or about 90% by weight of Compound 1, wherein the weight is the total weight of all intra-granular and extra-granular components of a tablet.

In certain embodiments, provided herein are formulations of Compound 1 that comprise about 5%, about 10%, about 15%, about 20%, about 25%, about 30%, about 35%, about 40%, about 45%, or about 50%, by weight of an insoluble diluent/carrier or filler, wherein the weight is the total weight of all intra-granular and extra-granular components of a tablet.

In certain embodiments, provided herein are formulations of Compound 1 that comprise about 1%, about 1.5%, about 2.0%, about 2.5%, about 3%, about 3.5%, about 4%, about 4.5%, about 5.0%, about 5.5%, about 6.0%, about 6.5%, about 7%, about 7.5%, about 8%, about 8.5%, about 9.0%, about 9.5%, or about 10%, by weight of a disintegrant, wherein the weight is the total weight of all intra-granular and extra-granular components of a tablet.

In certain embodiments, provided herein are formulations of Compound 1 that comprise about 1%, about 1.5%, about 2.0%, about 2.5%, about 3%, about 3.5%, about 4%, about 4.5%, about 5.0%, about 5.5%, about 6.0%, about 6.5%, about 7%, about 7.5%, about 8%, about 8.5%, about 9.0%, about 9.5%, or about 10%, by weight of a diluent/filler or binder, wherein the weight is the total weight of all intra-granular and extra-granular components of a tablet.

In certain embodiments, provided herein are formulations of Compound 1 that comprise about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, or about 0.8%, by weight of a glidant, wherein the weight is the total weight of all intra-granular and extra-granular components of a tablet.

In certain embodiments, provided herein are formulations of Compound 1 that comprise about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, or about 0.8%, about 0.85%, about 0.9%, about 0.95%, about 1.0%, about 1.05%, about 1.1%, about 1.15%, about 1.2%, about 1.2%, about 1.25%, about 1.3%, about 1.35%, about 1.4%, about 1.45%, or about 1.5%, by weight of a lubricant, wherein the weight is the total weight of all intra-granular and extra-granular components of a tablet.

In certain embodiments, provided herein are formulations of Compound 1 comprising intra-granular components, extra-granular components, and film coating components, wherein the intra-granular component comprises about 50% to about 80% by weight of Compound 1, about 10% to about 40% by weight of an insoluble diluent/carrier or filler, about 1.5% to about 4.5% by weight of a disintegrant, and about 1% to about 5% by weight of a diluent/filler binder; wherein the extra-granular component comprises about 1.5% to about 4.5% by weight of a disintegrant, about 0.1% to about 0.4% by weight of a glidant, and about 0.15% to about 1.35% by weight of a lubricant; and wherein the film coating component comprises about 1.0% to about 8% by weight of a tablet coating; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 55% to about 75% by weight of Compound 1, about 15% to about 35% by weight of an insoluble diluent/carrier or filler, about 2.0% to about 4.0% by weight of a disintegrant, and about 1.8% to about 3.8% by weight of a diluent/filler or binder; wherein the extra-granular component comprises about 2.0% to about 4.0% by weight of a disintegrant, about 0.15% to about 0.35% by weight of a glidant, and about 0.35% to about 1.15% by weight of a lubricant; and wherein the film coating component comprises about 1.0% to about 8% by weight of a tablet coating; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 60% to about 70% by weight of Compound 1, about 20% to about 30% by weight of an insoluble diluent/carrier or filler, about 2.5% to about 3.5% by weight of a disintegrant, and about 2.3% to about 3.3% by weight of a diluent/filler or binder; wherein the extra-granular component comprises about 2.5% to about 3.5% by weight of a disintegrant, about 0.2% to about 0.3% by weight of a glidant, about 0.55% to about 0.95% by weight of a lubricant; and wherein the film coating component comprises about 1.0% to about 8% by weight of a tablet coating; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 65% by weight of Compound 1, about 25% by weight of an insoluble diluent/carrier or filler, about 3% by weight of a disintegrant, and about 2.8% by weight of a diluent/filler or binder; wherein the extra-granular component comprises about 3% by weight of a disintegrant, about 0.25% by weight of a glidant, about 0.75% by weight of a lubricant; and wherein the film coating component comprises about 2.0% to about 6.0% by weight of a tablet coating; and wherein the weight is the total weight of all intra-granular and extra-granular components.

In embodiments, formulations of Compound 1 comprise one or more diluents/fillers (e.g., microcrystalline cellulose and/or HPMC (hypromellose)) and a disintegrant (e.g., sodium starch glycolate). In embodiments, a formulation further comprises one or more glidants (e.g., colloidal silicon dioxide). In embodiments, a formulation further comprises one or more lubricants (e.g., magnesium stearate).

In embodiments, formulations of Compound 1 comprise one or more diluents/fillers (e.g., microcrystalline cellulose and/or isomalt), one or more disintegrants (e.g., sodium starch glycolate and/or povidone), and one or more lubricants (e.g., sodium lauryl sulfate). In embodiments, a formulation further comprises one or more glidants (e.g., colloidal silicon dioxide and/or magnesium stearate). In embodiments, a formulation comprises one or more excipients selected from the group consisting of microcrystalline cellulose, sodium starch glycolate, and HPMC (hypromellose). In embodiments, a formulation comprises microcrystalline cellulose, sodium starch glycolate, and HPMC (hypromellose).

In embodiments, the formulations of Compound 1 comprise a film-coating components comprising Opadry®. Opadry® is a commercial film-coating that is a formulated powder blend provided by Colorcon. Opadry® combines polymer, plasticizer and pigment in a dry concentrate. Embodiments of Opadry® useful in the present invention include, but are not limited to, Opadry® I (HPC/HPMC), Opadry® 20A 18334, Opadry® II, Opadry® II HP (PVA-PEG), or another suitable Opadry® suspension (such as polyvinyl alcohol, polyethylene glycol, titanium dioxide, and talc, with or without colorants).

In certain embodiments, provided herein are formulations of Compound 1 comprising intra-granular components, extra-granular components, and film coating components, wherein the intra-granular components comprise Compound 1, microcrystalline cellulose, sodium starch glycolate, and hydroxypropyl methylcellulose, wherein the extra-granular components comprise sodium starch glycolate, colloidal silicon dioxide, and magnesium stearate; and wherein the film-coating components comprise Opadry®.

In certain embodiments, provided herein are formulations of Compound 1 comprising intra-granular components, extra-granular components, and film coating components, wherein the intra-granular component comprises about 50% to about 80% by weight of Compound 1, about 10% to about 40% by weight of microcrystalline cellulose, about 1.5% to about 4.5% by weight of sodium starch glycolate, and about 1% to about 5% by weight of a hydroxypropyl methylcellulose; wherein the extra-granular component comprises about 1.5% to about 4.5% by weight of a sodium starch glycolate, about 0.1% to about 0.4% by weight of colloidal silicon dioxide, and about 0.15% to about 1.35% by weight of magnesium stearate; wherein the film coating component comprises about 1.0% to about 8% by weight of Opadry®; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 55% to about 75% by weight of Compound 1, about 15% to about 35% by weight of microcrystalline cellulose, about 2.0% to about 4.0% by weight of sodium starch glycolate, and about 1.8% to about 3.8% by weight of a hydroxypropyl methylcellulose; wherein the extra-granular component comprises about 2.0% to about 4.0% by weight of a sodium starch glycolate, about 0.15% to about 0.35% by weight of colloidal silicon dioxide, and about 0.35% to about 1.15% by weight of magnesium stearate; wherein the film coating component comprises about 1.0% to about 8% by weight of Opadry®; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 60% to about 70% by weight of Compound 1, about 20% to about 30% by weight of microcrystalline cellulose, about 2.5% to about 3.5% by weight of sodium starch glycolate, and about 2.3% to about 3.3% by weight of a hydroxypropyl methylcellulose; wherein the extra-granular component comprises about 2.5% to about 3.5% by weight of a sodium starch glycolate, about 0.2% to about 0.3% by weight of colloidal silicon dioxide, and about 0.55% to about 0.95% by weight of magnesium stearate; wherein the film coating component comprises about 1.0% to about 8% by weight of Opadry®; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 60% by weight of Compound 1, about 30% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 65% by weight of Compound 1, about 25% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 70% by weight of Compound 1, about 20% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 75% by weight of Compound 1, about 15% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

In certain embodiments, provided herein are formulations of Compound 1 comprising intra-granular components, extra-granular components, and film coating components, wherein the intra-granular component comprises about 80% by weight of Compound 1, about 10% by weight of microcrystalline cellulose, about 3% by weight of sodium starch glycolate, and about 2.8% by weight of a hydroxypropyl methylcellulose; wherein the extra-granular component comprises about 3% by weight of a sodium starch glycolate, about 0.25% by weight of colloidal silicon dioxide, and about 0.75% by weight of magnesium stearate; wherein the film coating component comprises about 2.0% to about 6.0% by weight of Opadry®; and wherein the weight is the total weight of all intra-granular and extra-granular components.

Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's The Science and Practice of Pharmacy, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Liquid Dosage Forms. Liquid dosage forms of Compound 1 for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Unit Dosage Forms Comprising Compound 1

In embodiments, a pharmaceutical composition suitable for the methods described herein is a unit dosage form comprising Compound 1, or a pharmaceutically acceptable salt, solvate, or hydrate thereof.

The structure of Compound 1, or a pharmaceutically acceptable salt, solvate, or hydrate thereof are described in WO 2008/002576, WO/2015/073779, and U.S. Ser. No. 17/095,998, which are incorporated by reference in their entirety.

In embodiments, provided herein are unit dosage forms of Compound 1 that comprise between about 75 mg and about 600 mg of a compound having a structure of Compound 1, or a pharmaceutically acceptable salt, solvate, or hydrate thereof.

In certain other embodiments, provided herein are unit dosage forms of Compound 1 that comprise about 75 mg, 150 mg, 200 mg, 250 mg, 300 mg, 350 mg, 400 mg, 450 mg, 500 mg, 550 mg, or even 600 mg of a compound having a structure Compound 1. In certain embodiments, the unit dosage form comprises about 150 mg, about 185 mg, about 200 mg, about 250 mg, about 300 mg, about 315 mg, or about 450 mg of a compound having a structure of Compound 1, or a pharmaceutically acceptable salt, solvate, or hydrate thereof. In certain such embodiments, the unit dosage form is a capsule comprising about 150 mg, 185 mg, about 200 mg, about 200, about 250 mg, or even about 300 mg of the compound.

In embodiments, a unit dosage form comprises about 75 mg of Compound 1. In embodiments, a unit dosage form is a tablet (e.g., a film-coated tablet). In embodiments, a unit dosage form is a capsule. In embodiments, a unit dosage form comprises excipients that are microcrystalline cellulose, sodium starch glycolate, and/or hydroxypropyl methylcellulose. In embodiments, a unit dosage form comprises intra-granular components, which comprise microcrystalline cellulose, sodium starch glycolate, and/or hydroxypropyl methylcellulose. In embodiments, a unit dosage form comprises excipients that are sodium starch glycolate, colloidal silicon dioxide, and/or magnesium stearate. In embodiments, a unit dosage form comprises extra-granular components, which comprise sodium starch glycolate, colloidal silicon dioxide, and/or magnesium stearate.

In embodiments, a unit dosage form comprises about 150 mg of Compound 1. In embodiments, a unit dosage form is a tablet (e.g., a film-coated tablet). In embodiments, a unit dosage form is a capsule. In embodiments, a unit dosage form comprises excipients that are microcrystalline cellulose, sodium starch glycolate, and/or hydroxypropyl methylcellulose. In embodiments, a unit dosage form comprises intra-granular components, which comprise microcrystalline cellulose, sodium starch glycolate, and/or hydroxypropyl methylcellulose. In embodiments, a unit dosage form comprises excipients that are sodium starch glycolate, colloidal silicon dioxide, and/or magnesium stearate. In embodiments, a unit dosage form comprises extra-granular components, which comprise sodium starch glycolate, colloidal silicon dioxide, and/or magnesium stearate.

In embodiments, a unit dosage form comprises about 300 mg of Compound 1. In embodiments, a unit dosage form is a tablet (e.g., a film-coated tablet). In embodiments, a unit dosage form is a capsule. In embodiments, a unit dosage form comprises excipients that are microcrystalline cellulose, sodium starch glycolate, and/or hydroxypropyl methylcellulose. In embodiments, a unit dosage form comprises intra-granular components, which comprise microcrystalline cellulose, sodium starch glycolate, and/or hydroxypropyl methylcellulose. In embodiments, a unit dosage form comprises excipients that are sodium starch glycolate, colloidal silicon dioxide, and/or magnesium stearate. In embodiments, a unit dosage form comprises extra-granular components, which comprise sodium starch glycolate, colloidal silicon dioxide, and/or magnesium stearate.

In embodiments, a unit dosage form comprises about 450 mg of Compound 1. In embodiments, a unit dosage form is a tablet (e.g., a film-coated tablet). In embodiments, a unit dosage form is a capsule. In embodiments, a unit dosage form comprises excipients that are microcrystalline cellulose, sodium starch glycolate, and/or hydroxypropyl methylcellulose. In embodiments, a unit dosage form comprises intra-granular components, which comprise microcrystalline cellulose, sodium starch glycolate, and/or hydroxypropyl methylcellulose. In embodiments, a unit dosage form comprises excipients that are sodium starch glycolate, colloidal silicon dioxide, and/or magnesium stearate. In embodiments, a unit dosage form comprises extra-granular components, which comprise sodium starch glycolate, colloidal silicon dioxide, and/or magnesium stearate.

In embodiments, a unit dosage form comprises about 600 mg of Compound 1. In embodiments, a unit dosage form is a tablet (e.g., a film-coated tablet). In embodiments, a unit dosage form is a capsule. In embodiments, a unit dosage form comprises excipients that are microcrystalline cellulose, sodium starch glycolate, and/or hydroxypropyl methylcellulose. In embodiments, a unit dosage form comprises intra-granular components, which comprise microcrystalline cellulose, sodium starch glycolate, and/or hydroxypropyl methylcellulose. In embodiments, a unit dosage form comprises excipients that are sodium starch glycolate, colloidal silicon dioxide, and/or magnesium stearate. In embodiments, a unit dosage form comprises extra-granular components, which comprise sodium starch glycolate, colloidal silicon dioxide, and/or magnesium stearate.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Example 1. Phase 1b, Randomized Open-Label Study to Evaluate the Pharmacokinetics, Pharmacodynamics, and Safety of Vadadustat (Compound 1) in Hemodialysis Subjects with Anemia Associated with Chronic Kidney Disease The primary objective of the study was to assess the pharmacokinetics (PK) of vadadustat 600, 750, and 900 mg daily, and IV ESA (darbepoetin alfa or epoetin alfa) in hemodialysis subjects with anemia associated with CKD. Additional objectives included to evaluate the pharmacodynamics (PD) of vadadustat 600, 750, and 900 mg daily, and IV ESA (darbepoetin alfa or epoetin alfa) in hemodialysis subjects with anemia associated with CKD and to assess the safety and tolerability of vadadustat 600, 750, and 900 mg daily and IV ESA (darbepoetin alfa or epoetin alfa) in hemodialysis subjects with anemia associated with CKD.

Study Design. This was a Phase 1b, randomized, open-label study to evaluate the PK, PD, safety, and tolerability of vadadustat 600, 750, or 900 mg daily, or ESA (darbepoetin alfa or epoetin alfa) in hemodialysis subjects with anemia associated with CKD. The study included a 28-day Screening and Randomization period, a 10-day Treatment Period, and a 30-day Safety Follow up Period after the last dose of study drug (vadadustat or ESA). For subjects randomized to vadadustat, study duration also included an ESA washout period of a minimum of 5 days for epoetin alfa or 9 days for darbepoetin alfa or 9-day ESA Washout period prior to dosing on Day 1.

A total of 46 subjects were enrolled in the study. Written informed consent were obtained before any screening procedures were performed. Subjects were screened within 28 days prior to randomization. Eligible subjects were randomized in a 2:2:2:1 ratio to 1 of 4 treatment groups (600, 750, or 900 mg vadadustat QD, or ESA. Randomized subjects began their 10-day Treatment Period within 36 days of initiating screening.

In the ESA group (FIG. 1), subjects began their 10-day Treatment Period within 36 days of initiating screening. Day 1 occurred after a short interdialytic period at the earliest in clinic visit following randomization. Subjects who completed the 10-day Treatment Period had a follow-up visit 2 days (+3) after Day 10. Subjects who discontinued treatment early had a follow-up visit 2 days (+3) after their end-of-treatment (EOT) visit.

Figure 2:
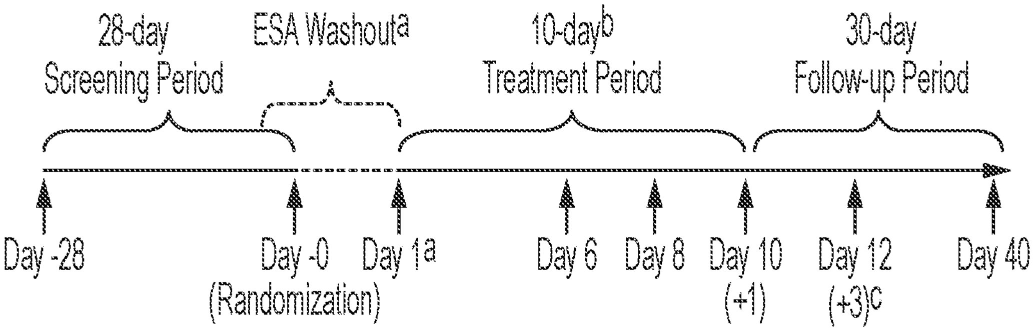
FIG. 2 illustrates the study design for the vadadustat group of the Phase 1b, Randomized, Open-Label Study that Evaluate the Pharmacokinetics, Pharmacodynamics, and Safety of Vadadustat in Hemodialysis Subjects with Anemia Associated with Chronic Kidney Disease.
Figure 3:
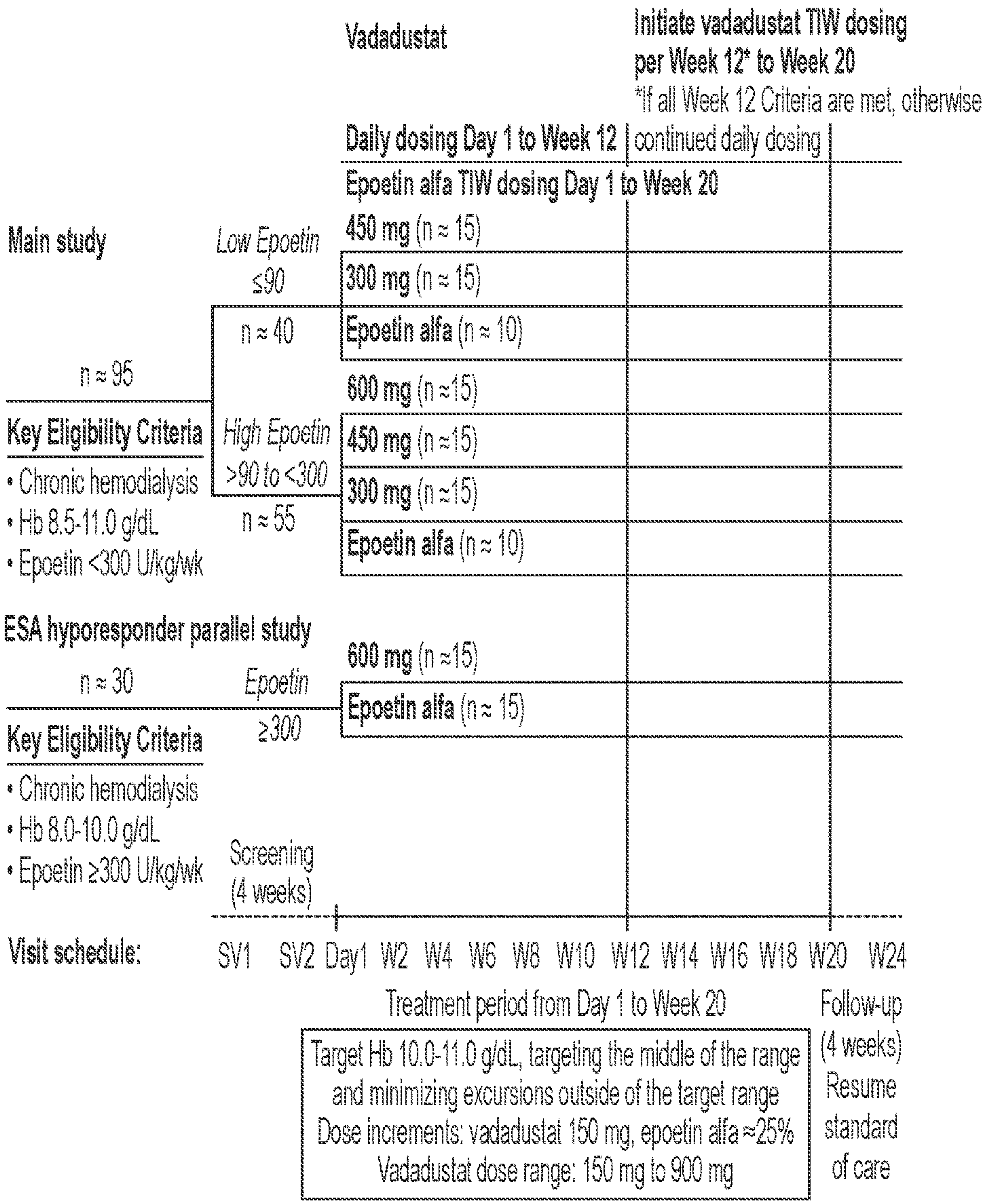
FIG. 3 illustrates the overview of the study design for the phase 2, randomized, open-label, active-controlled, efficacy, safety, pharmacokinetics, and study of oral vadadustat for the treatment of anemia in hemodialysis subjects converting from epoetin alfa.
Figure 4:
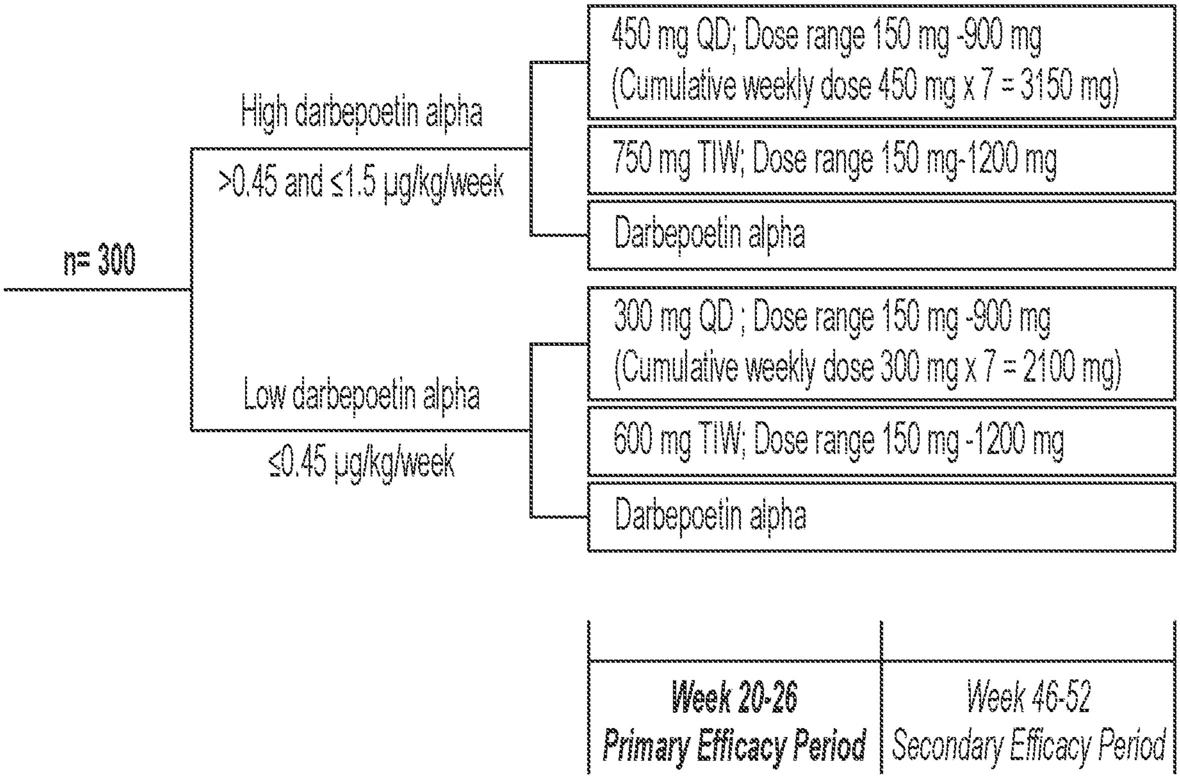
FIG. 4 illustrates the study scheme for the phase 3b, randomized, open-label, active-controlled trial that evaluates the efficacy and safety of oral vadadustat once daily (QD) and three times weekly (TIW) for the maintenance treatment of anemia in hemodialysis subjects converting from erythropoiesis-stimulating agents (ESAs).
Figure 5:
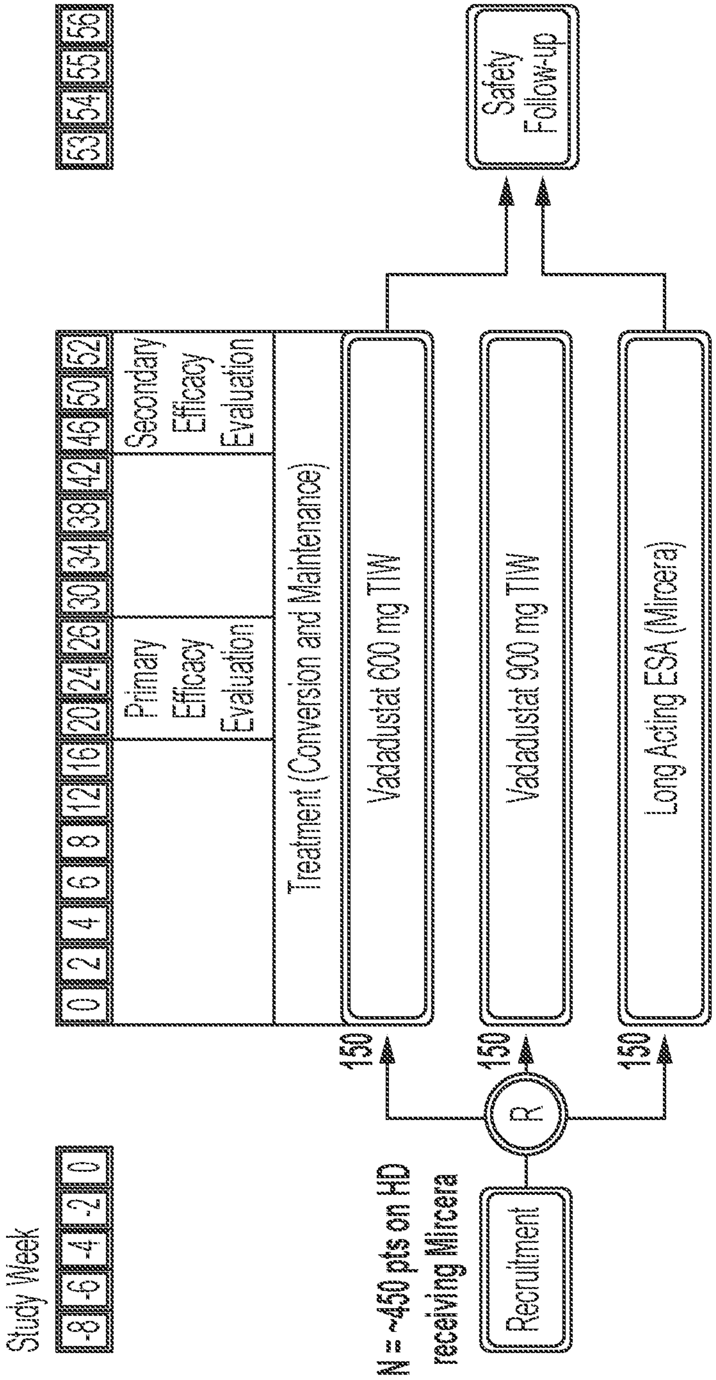
FIG. 5 illustrates the study design for the randomized, open-label, active-controlled study that evaluates the efficacy and safety of dose conversion from a long-acting erythropoiesis-stimulating agent (Mircera®) to three times weekly oral vadadustat (Compound 1) for the maintenance treatment of anemia in hemodialysis subjects.
Figure 6A:
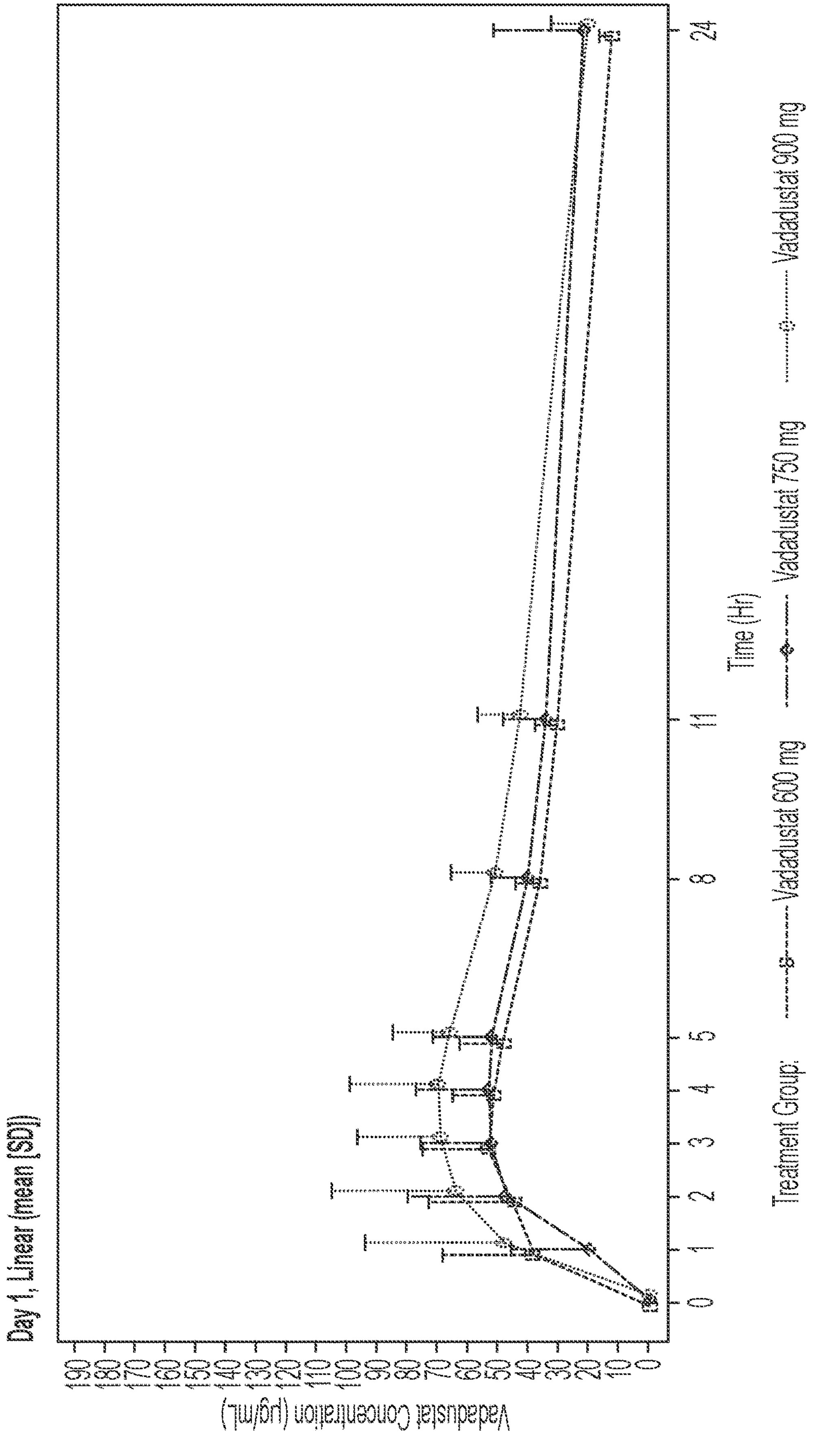
FIGS. 6*a*-6*b* illustrate the vadadustat concentration (μg/ml) versus nominal time on Day 1 (Pharmacokinetic Population).
Figure 6B:
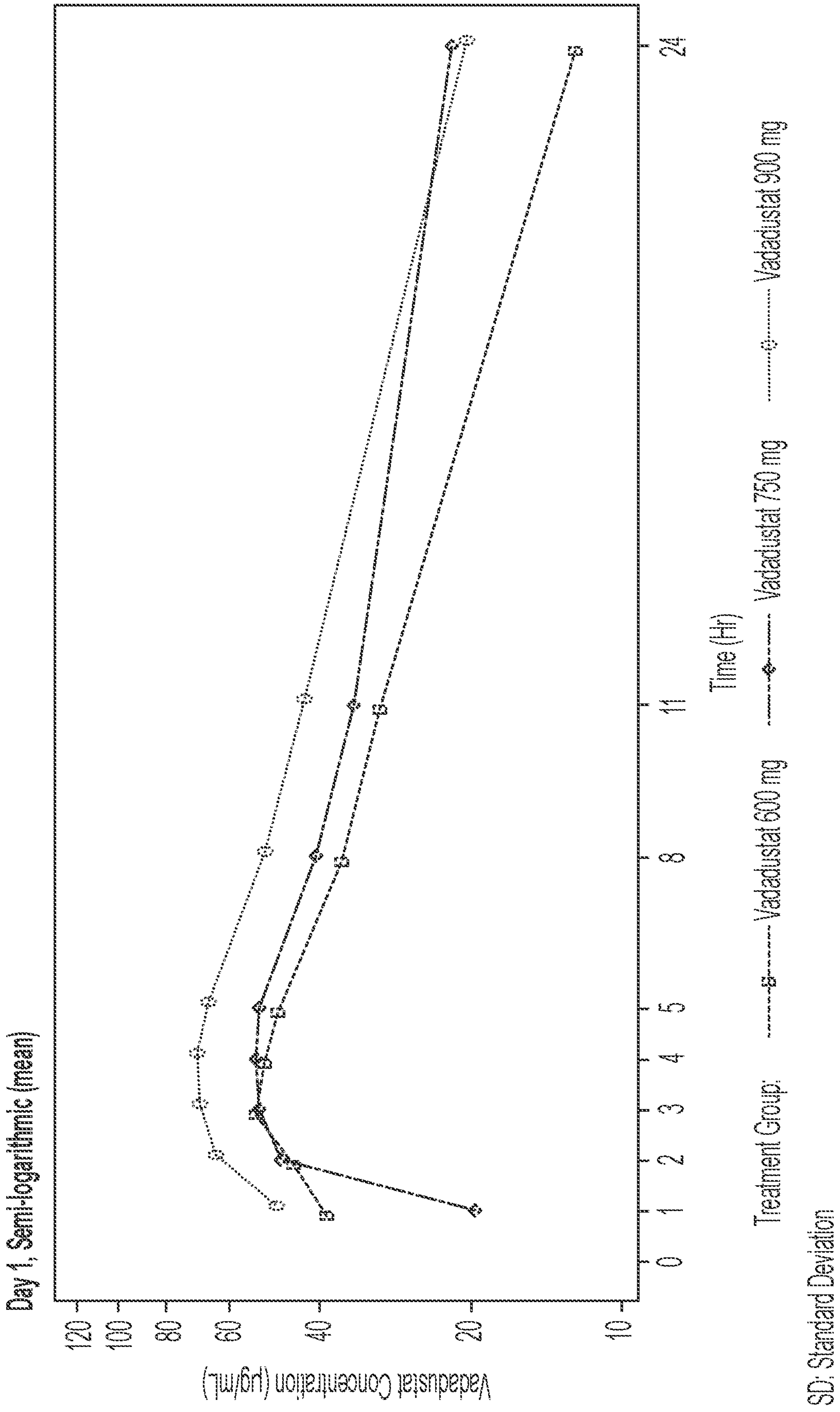
Figure 7A:
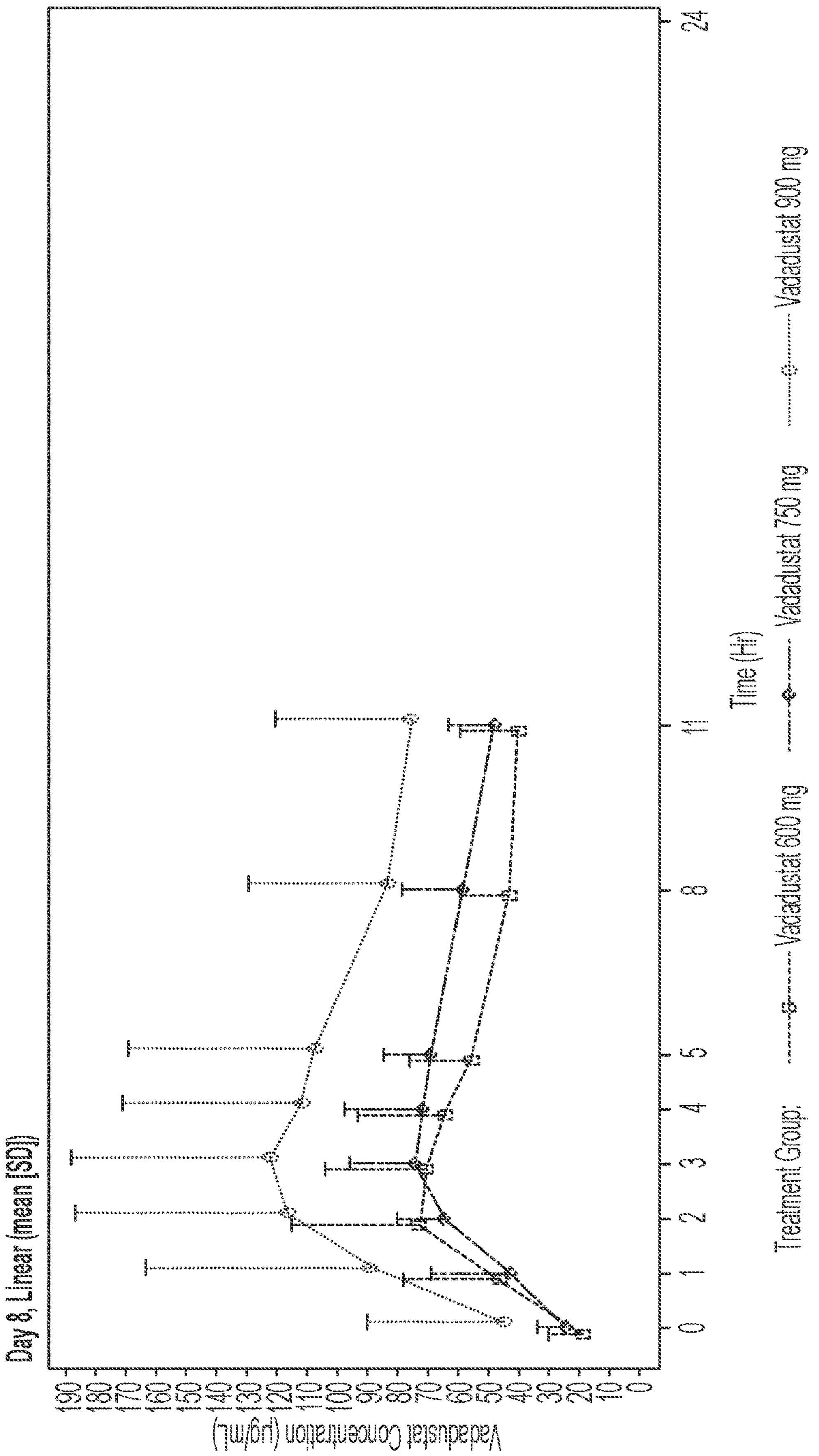
FIGS. 7*a*-7*b* illustrate the vadadustat concentration (μg/ml) versus nominal time on Day 8 (Pharmacokinetic Population).
Figure 7B:
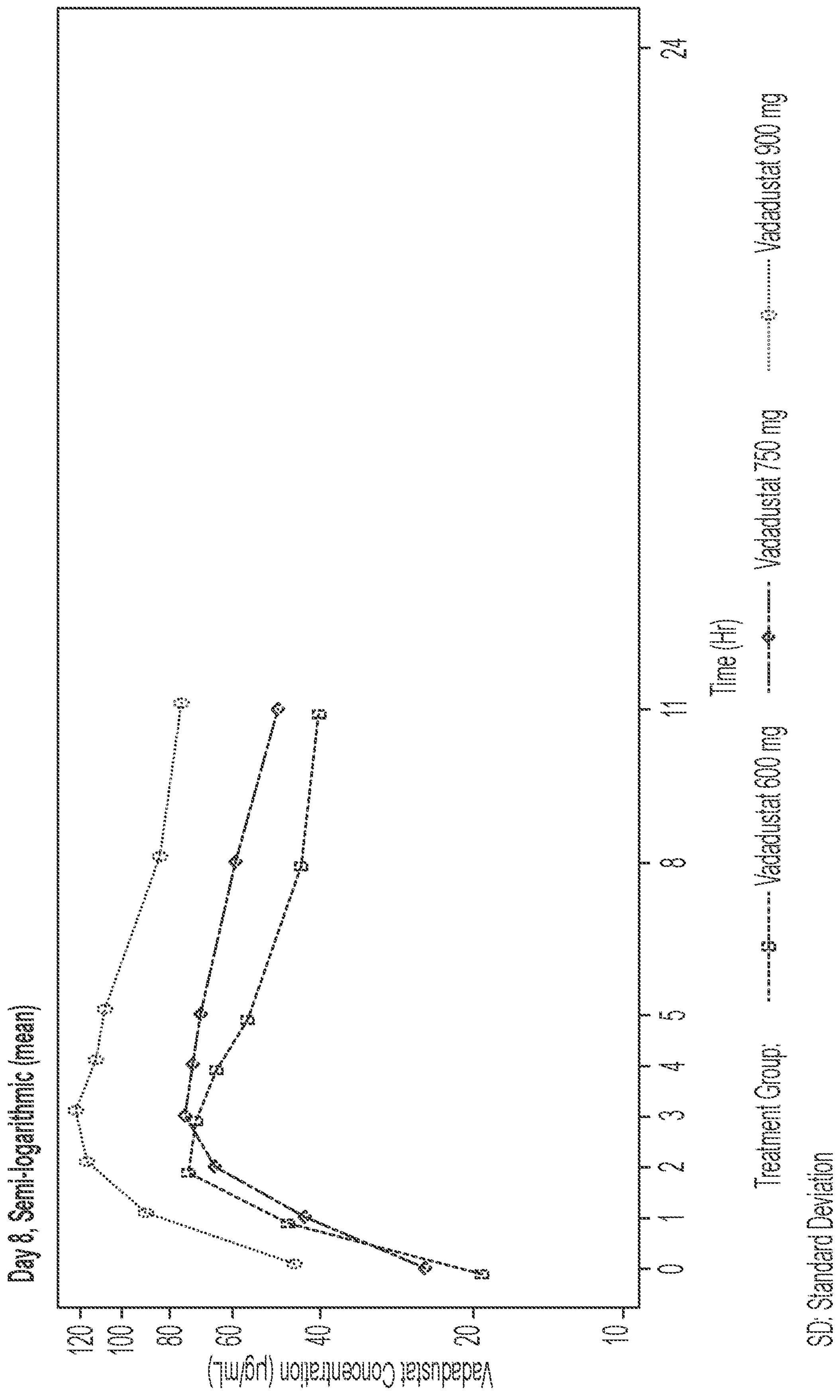

In the vadadustat groups (FIG. 2), subjects did not receive a dose of ESA following randomization and for the duration of the 10-day Treatment Period. The ESA washout period could start from the time of the last dose of ESA prior to randomization, which could include day of randomization. Subjects began their 10-day Treatment Period within 36 days of initiating screening. Day 1 occurred after a short interdialytic period at the earliest in clinic visit following randomization. Subjects who completed the 10-day Treatment Period had a follow-up visit 2 days (+3) after Day 10. Subjects who discontinued treatment early had a follow-up visit 2 days (+3) after their end-of-treatment (EOT) visit.

Eligible subjects were randomly assigned in a 2:2:2:1 ratio to 1 of 4 treatment groups: Group 1—vadadustat 600 mg once daily (QD); Group 2—vadadustat 750 mg QD; Group 3—vadadustat 900 QD; and Group 4—IV ESA. Randomization was stratified by the mean weekly ESA dose calculated over a period of 8 weeks prior to the randomization visit. For darbepoetin, the groups were divided into low dose darbepoetin alfa group (<0.5 μg/kg/week) and high dose darbepoetin alfa group (>0.5 to <1.5 μg/kg/week). For epoetin, the groups were divided into low dose epoetin alfa group (≤90 U/kg/week) and high dose epoetin alfa group (>90 to <300 U/kg/week).

Subjects randomized to the vadadustat treatment groups were required to washout their ESA therapy for 5 half-lives prior to dosing with vadadustat (a minimum of 5 days for epoetin alfa, and a minimum of 9 days for darbepoetin alfa). Subjects did not receive a dose of ESA following randomization and for the duration of the 10-day Treatment Period. The ESA washout period started from the time of the last dose of ESA prior to randomization, which could occur day of randomization.

The subject's 10-day Treatment Period began at the earliest in-clinic hemodialysis visit following completion of their ESA washout. Subjects resumed dosing with ESA in accordance with standard of care after all Day 10 procedures were completed or all EOT (End of Treatment) procedures were completed for subjects who discontinued the 10-Day Treatment Period early.

Subjects began dosing on Day 1 and took vadadustat at approximately the same time each day for a total of 10 days. On Day 1 and Day 8, subjects took vadadustat after all predose procedures are completed and within 30 minutes prior to the start of dialysis so that the 1-hour post dose blood sample for PK and PD was collected during dialysis. Vadadustat could be taken with or without food. Subjects were instructed to make every effort to take the drug consistently, either with or without food. Subjects were instructed to swallow the tablets whole with water.

Subjects randomized to the ESA treatment group continued their current treatment during the study and begin their 10-day Treatment Period at the earliest in-clinic hemodialysis visit following randomization on a day they were scheduled to receive a dose of ESA. IV ESA was administered at the hemodialysis clinic. Within a 30 minute time period, samples were collected for predose time points, dialysis was started and ESA was administered (Time 0). The dose administered was based on the subject's Hb value, dry weight/target weight, and the approved ESA PI for adult patients with CKD on dialysis. The investigator used his/her clinical judgment regarding dosing and adjusts the dose of ESA as clinically indicated in accordance with the approved PI for adult patients with CKD on dialysis.

All subjects were followed for safety for 30 days after the Day 10 visitor 30 days after their last dose of study drug (vadadustat or ESA) if they discontinued study drug treatment early. Subjects returned to the clinic for safety assessments 2-5 days after completing Day 10/EOT and concluded the study with a follow-up telephone call to assess for AEs and concomitant medications 30 days after their last dose of study drug.

PK and EPO Sample. For each vadadustat treatment group, blood samples for vadadustat PK (and its metabolites) and EPO were collected at the following time points: Day 1: predose, and at 1, 2, 3, 4, 5, 8, and 11 hours post dose; Day 2: 24 hours (−2 hours) post Day 1 dose; Day 6: blood sample for EPO analysis only was collected predose on Day 6; Day 8: predose, and at 1, 2, 3, 4, 5, 8, 11 hours post dose, Day 10 or EOT: predose. For the ESA treatment group, blood samples for analysis of EPO were collected at the following time points: Day 1: predose, and at 0.25, 1, 2, 3, 4, 5, 8, and 11 hours post dose; Day 2: 24 hours (−2 hours) post Day 1 dose.

PD Sampling. For all vadadustat and ESA treatment groups, in addition to EPO, blood samples for Hb, reticulocytes and iron indices for PD analyses were collected on Day 1, Day 6 and Day 10. Hepcidin were collected predose on Day 1, Day 6, and Day 10 for PD analysis.

Iron Supplementation. Subjects could receive oral or IV iron supplementation as clinically indicated during the study. Because of the potential for oral iron to reduce the bioavailability of vadadustat, vadadustat was not to be administered concurrently with an oral iron supplement (including multivitamins containing iron), iron-containing phosphate binders, or any oral medications containing iron. The subject could be instructed to take any oral iron supplements (including multivitamins containing iron), iron containing phosphate binders, or any medications containing iron at least 2 hours before or 2 hours after the dose of vadadustat.

Study Duration. Each subject was on study for up to 74 days (~10 weeks), including a 28-day Screening and Randomization period, a 10-day Treatment Period and a 30-day Safety Follow-up period. For subjects randomized to vadadustat, study duration also included a minimum 5 or 9-day ESA Washout period prior to dosing on Day 1.

Inclusion Criteria. Subjects were provided written informed consent before any study procedures were performed. Subjects who met the following inclusion criteria were eligible for randomization. In addition, subjects must continue to meet these criteria following randomization to proceed with dosing on Day 1: (1) Male or female ≥18 years of age at the time of informed consent; (2) Receiving chronic, outpatient in-center hemodialysis TIW for end-stage renal disease for at least 12 weeks prior to Screening; (3) Maintained on IV ESA therapy (mean dose of <1.5 μg/kg/week for darbepoetin alfa, or mean dose of <300 U/kg/week for epoetin alfa) for 8 weeks prior to randomization; (4) Two Hb values between 8.5 and 10.5 g/dL, inclusive, measured at least 4 days apart within 28 days prior to randomization; (5) Investigator determines the subject is not likely to need rescue therapy (ESA administration or RBC transfusion) or require interruption or discontinuation of study drug within the next 30 days; (6) Serum ferritin ≥100 ng/mL and transferrin saturation (TSAT)≥20% within the 28-day Screening Period prior to randomization; (7) Folate and vitamin B12 measurements 2 lower limit of normal within the 28-day Screening Period prior to randomization; (8) Hemodialysis adequacy (Kt/Vurea) as indicated by single-pool Kt/Vurea ≥1.2 using the most recent historical measurement within 12 weeks prior to randomization; (9) Female subjects of childbearing potential who are non-lactating, not pregnant as confirmed by a negative serum pregnancy test at Screening within 9 days prior to dosing on Day 1, and using, and agree to continue using, an acceptable method of contraception for at least 4 weeks prior to first dose of study drug until 30 days after the last dose of study drug; (10) Female subjects of non-childbearing potential who are either surgically sterile (e.g., hysterectomy, bilateral tubal ligation, bilateral oophorectomy) or post-menopausal (>12 months of spontaneous and continuous amenorrhea in a female >55 years old, or >12 months of spontaneous and continuous amenorrhea with a follicle stimulating hormone (FSH) level >40 IU/L in a female <55 years old); (11) Female subjects of childbearing potential who agree not to donate ova during the study and for at least 30 days after the last dose of study drug; (12) Male subjects who have not had a vasectomy must agree to use an acceptable method of contraception from time of first dose of study drug until 30 days after the last dose of the study drug, and to not donate sperm during the study and for at least 30 days after the last dose of study drug; and (13) Understands the procedures and requirements of the study and provides written informed consent and authorization for protected health information disclosure.

Exclusion Criteria. Subjects meeting any of the following exclusion criteria were not eligible for randomization: (1) Treated with any HMG-CoA reductase inhibitor (statin) other than atorvastatin, pravastatin, simvastatin, or rosuvastatin within the 28-day Screening Period prior to randomization. Within the 28-day Screening Period prior to randomization, the maximum allowable dose of simvastatin is 20 mg daily, and the maximum allowable dose of rosuvastatin is 10 mg daily. These restrictions also apply to the dosing period; (2) Treated with clinically relevant substrates of the breast cancer resistant protein (BCRP) transporter (e.g., sulfasalazine, methotrexate, tenofovir, glecaprevir, pibrentasvir, sofosbuvir, letermovir, paritaprevir, voxilaprevir, topotecan, or venetoclax) within 30 days prior to randomization; (3) Anemia with a cause other than CKD (e.g., sickle cell disease, myelodysplastic syndromes, bone marrow fibrosis, hematologic malignancy, myeloma, hemolytic anemia, thalassemia, or pure red cell aplasia); (4) Active bleeding or blood loss within 8 weeks prior to randomization; (5) Red blood cell transfusion within 8 weeks prior to randomization; (6) Anticipated to discontinue hemodialysis or change dialysis modality during the study; (7) History of chronic liver disease (e.g., chronic infectious hepatitis, chronic autoimmune liver disease, cirrhosis or fibrosis of the liver); (8) Aspartate aminotransferase (AST)/serum glutamic oxaloacetic transaminase (SGOT), alanine aminotransferase (ALT)/serum glutamic pyruvic transaminase (SGPT), or total bilirubin >1.5× upper limit of normal (ULN) within the 28-day Screening Period prior to randomization. Subjects with a history of Gilbert's syndrome may participate in the study if they are not jaundiced, have a total bilirubin <3×ULN and AST and ALT are not >1.5×ULN; (9) Current uncontrolled hypertension that would contraindicate the use of darbepoetin alfa or epoetin alfa as determined by the investigator; (10) Acute coronary syndrome (hospitalization for unstable angina or myocardial infarction), surgical or percutaneous intervention for coronary, cerebrovascular, or peripheral artery disease (aortic or lower extremity), surgical or percutaneous valvular replacement or repair, sustained ventricular tachycardia, hospitalization for heart failure (HF) or New York Heart Association Class IV HF, or stroke within 12 weeks prior to randomization; (11) History of new or recurrent malignancy within 2 years prior to Screening or currently receiving treatment or suppressive therapy for cancer. Subjects with treated basal cell carcinoma of skin, curatively resected squamous cell carcinoma of skin, or cervical carcinoma in situ may participate on the study; (12) History of deep vein thrombosis or pulmonary embolism within 12 weeks prior to randomization; (13) History of hemosiderosis or hemochromatosis; (14) History of bilateral native nephrectomy; (15) History of functioning organ transplantation other than corneal transplant; (16) Scheduled organ transplant from a living donor or on the kidney transplant wait list or expected to receive a transplant during the study; (17) History of a prior hematopoietic stem cell or bone marrow transplant (stem cell therapy for knee arthritis is not excluded); (18) Known hypersensitivity to vadadustat excipients, or to darbepoetin alfa or epoetin alfa; (19) Use of an investigational drug within 30 days or 5 half-lives of the investigational drug (whichever is longer) prior to randomization; (20) Prior administration of an HIF-PH inhibitor, including vadadustat; (21) Any other reason, which in the opinion of the investigator, would make the subject not suitable for participation in the study; and (22) Treated with probenecid within the 28-day Screening Period prior to randomization or during the study treatment duration.

Primary Endpoints. For each treatment group, PK parameters included, but were not limited to: area under concentration-time curve from time 0 to the last quantifiable concentration (AUClast), area under concentration-time curve from time 0 to infinity (AUCinf), maximum observed concentration (Cmax), time to maximum observed concentration (Tmax), terminal half-life (t½), apparent clearance (CL/F) or clearance (CL), apparent volume of distribution (Vd/F) or volume of distribution (Vd), vadadustat metabolite(s) Tmax, AUClast, AUCinf, Cmax (vadadustat group only), and erythropoietin (ESA group only).

Secondary Endpoints. For each treatment group, PD parameters included, but were not limited to, as deemed appropriate: hepcidin, erythropoietin (EPO), iron indices (iron, ferritin, total iron-binding capacity [TIBC], TSAT), Hb, and reticulocytes.

Safety Endpoints. Safety could be evaluated by: adverse events (AE), electrocardiogram (ECG), vital signs measurements, and clinical laboratory values.

Statistical Considerations. Data collected throughout the study were summarized using descriptive statistics and listed in the by-subject listings. Continuous variables were summarized using number of subjects with mean, standard deviation (SD), median, minimum, and maximum. For PK related continuous variables, geometric mean and CV were added too. For categorical variables, the number and percentage of subjects in each category were tabulated. Summaries were provided by treatment group within appropriate analysis populations and by time point/time period, as appropriate.

Data Analysis

In embodiment, the analysis populations were defined as follows:

Randomized population was defined as all randomized subjects. Analyses of this population was based on the randomized treatment group.

Safety Population was defined as all subjects who received at least one dose of study drug. This population was analyzed based upon the actual treatment received.

PK Population included all subjects completing the study without any protocol deviation(s) that would impact the study results and for whom the PK profile can be adequately characterized.

The plasma concentration of vadadustat by time for the vadadustat groups in the PK population is presented in FIGS. 6a-6b and FIGS. 7a-7b.

Following Day 1 dosing, exposure for vadadustat, as measured by AUC0-24, increased with increasing dose. Similar dose-dependent increases in vadadustat exposure ($C_{max}$ and AUC) was observed on Day 1 and Day 8 as dose levels increased from 600 to 750 to 900 mg. Mean apparent total body clearance (CL/F) values for each dose on Day 8 were similar indicating dose proportional PK following multiple doses. The median $T_{max}$ of vadadustat was between 2.0 to 3.0 hours and appeared to be similar across all three 600, 750, and 900 mg vadadustat treatment groups, when measured on Day 1 and Day 8 during the dialysis. Mean values of $C_{max}$ and $AUC_{0-24}$ were higher on Day 8 compared to Day 1, indicating accumulation of concentrations; ratios for Day 8/Day 1 of mean $C_{max}$ values ranged from 1.27 to 1.45 and ratios of mean $AUC_{0-24}$ values ranged from 1.39 to 1.84 with the 900 mg dose having the highest ratios.

The summary of plasma concentration of vadadustat-O-glucuronide by time for the vadadustat treatment groups in the PK population is presented in FIGS. 8a-8b and FIGS. 9a-9b.

Figure 8A:
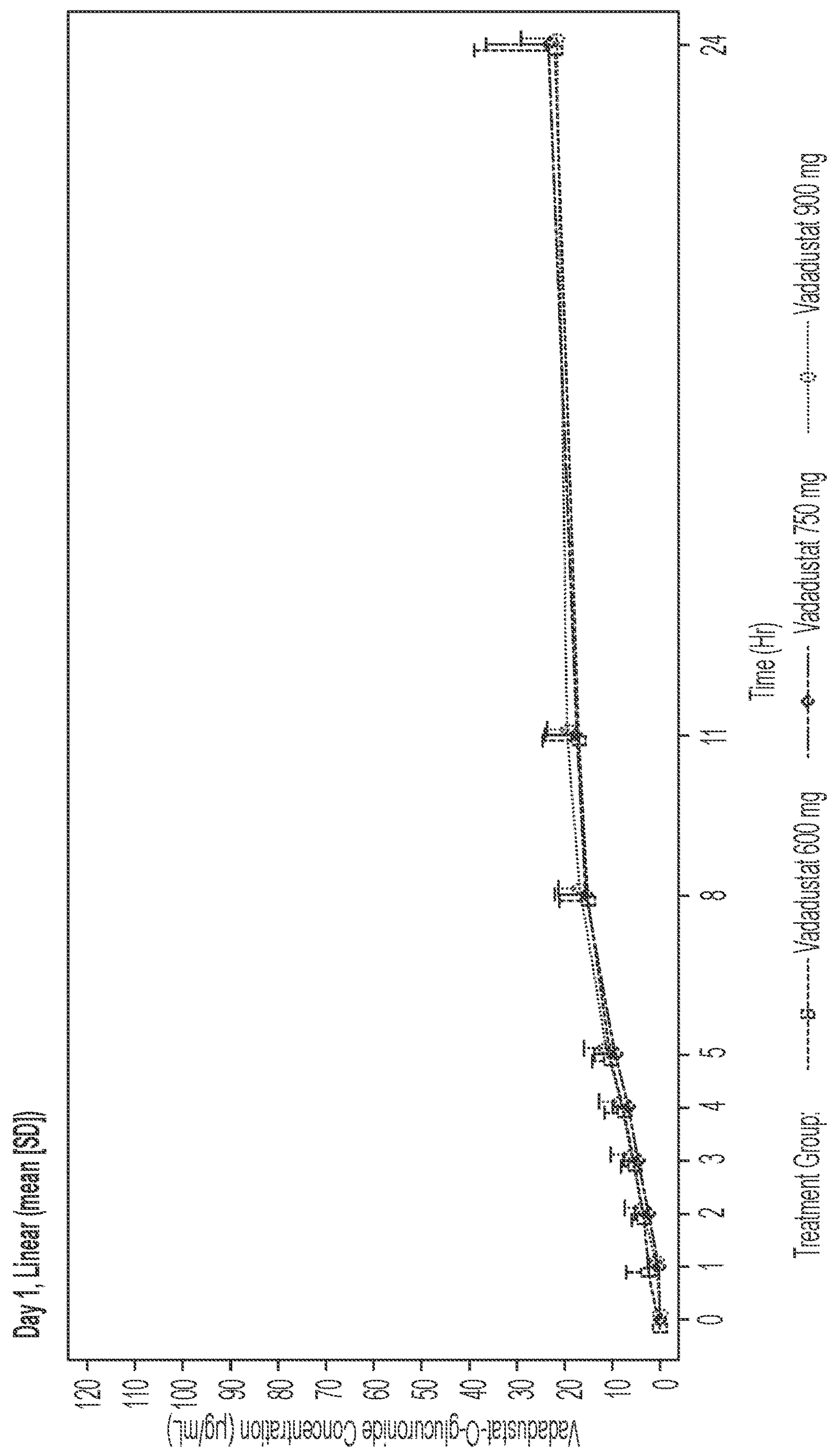
FIGS. 8*a*-8*b* illustrate the vadadustat-o-glucuronide metabolite concentration (μg/mL) versus nominal time on Day 1 (Pharmacokinetic Population).
Figure 8B:
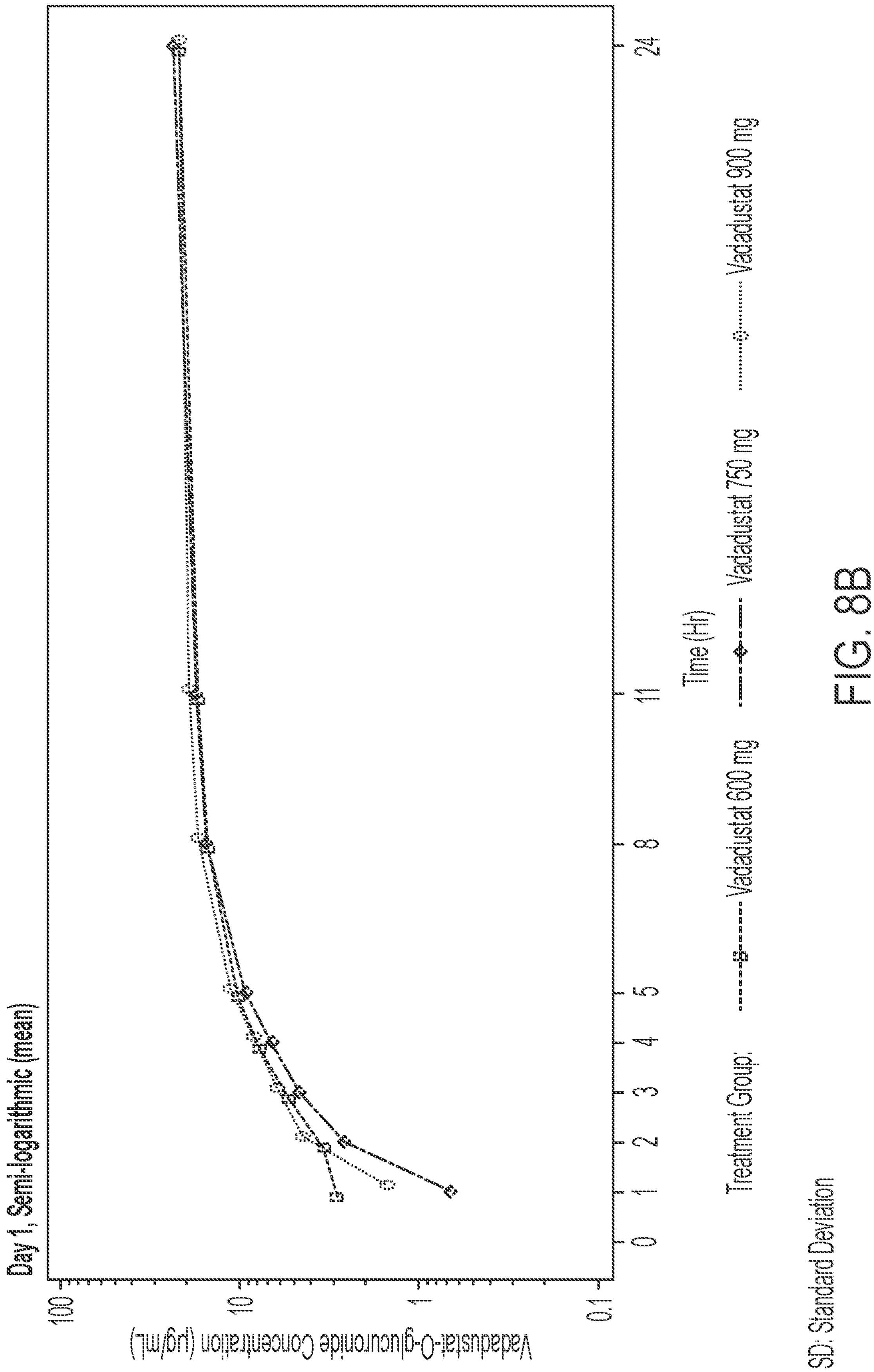
Figure 9A:
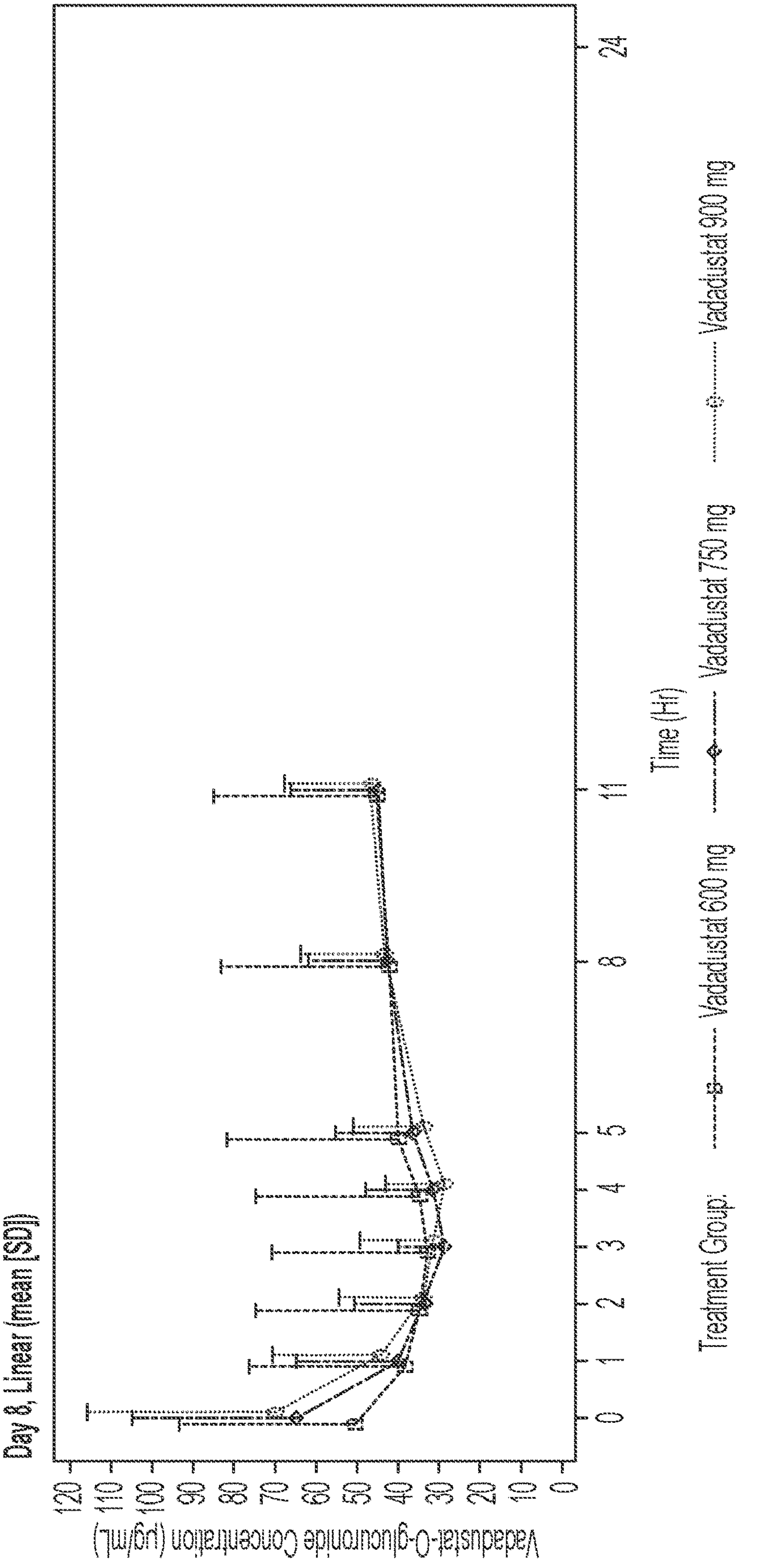
FIGS. 9*a*-9*b* illustrate the vadadustat-o-glucuronide metabolite concentration (μg/mL) versus nominal time on Day 8 (Pharmacokinetic Population).
Figure 9B:
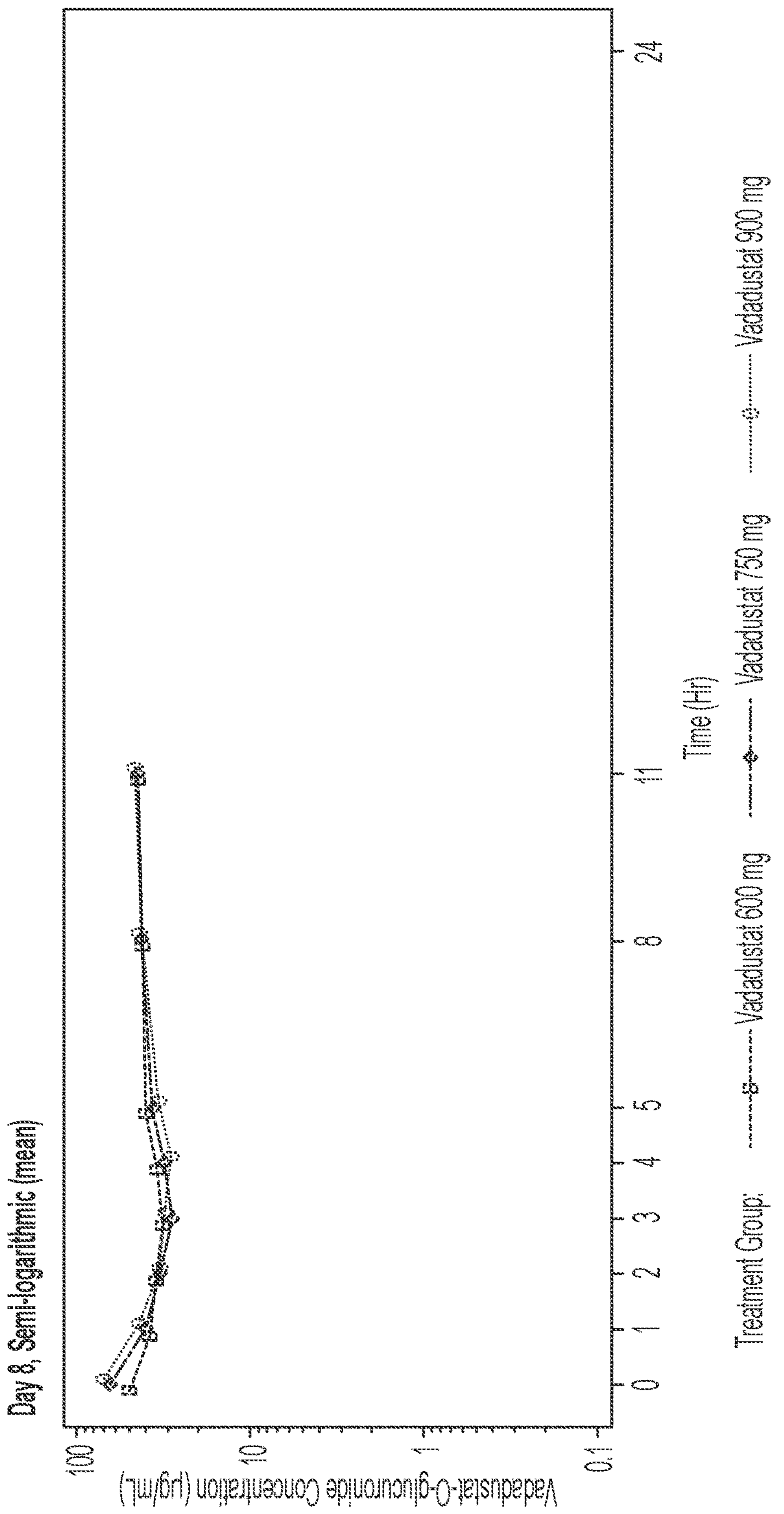

A decrease in vadadustat-O-glucuronide profiles was observed on Day 8 which may be explained by higher trough concentrations from previous dose and delayed metabolite formation following subsequent dose (FIGS. 9a-9b). The delay in metabolite formation was evident and consistent on Day 1 profiles across all dose levels (FIGS. 8a-8b). Based on a comparison of mean Day 2 predose concentrations to predose on Day 8, vadadustat-O-glucuronide concentrations appear to increase 2.5- to 3.5-fold with multiple dosing in a DD population.

Figure 10A:
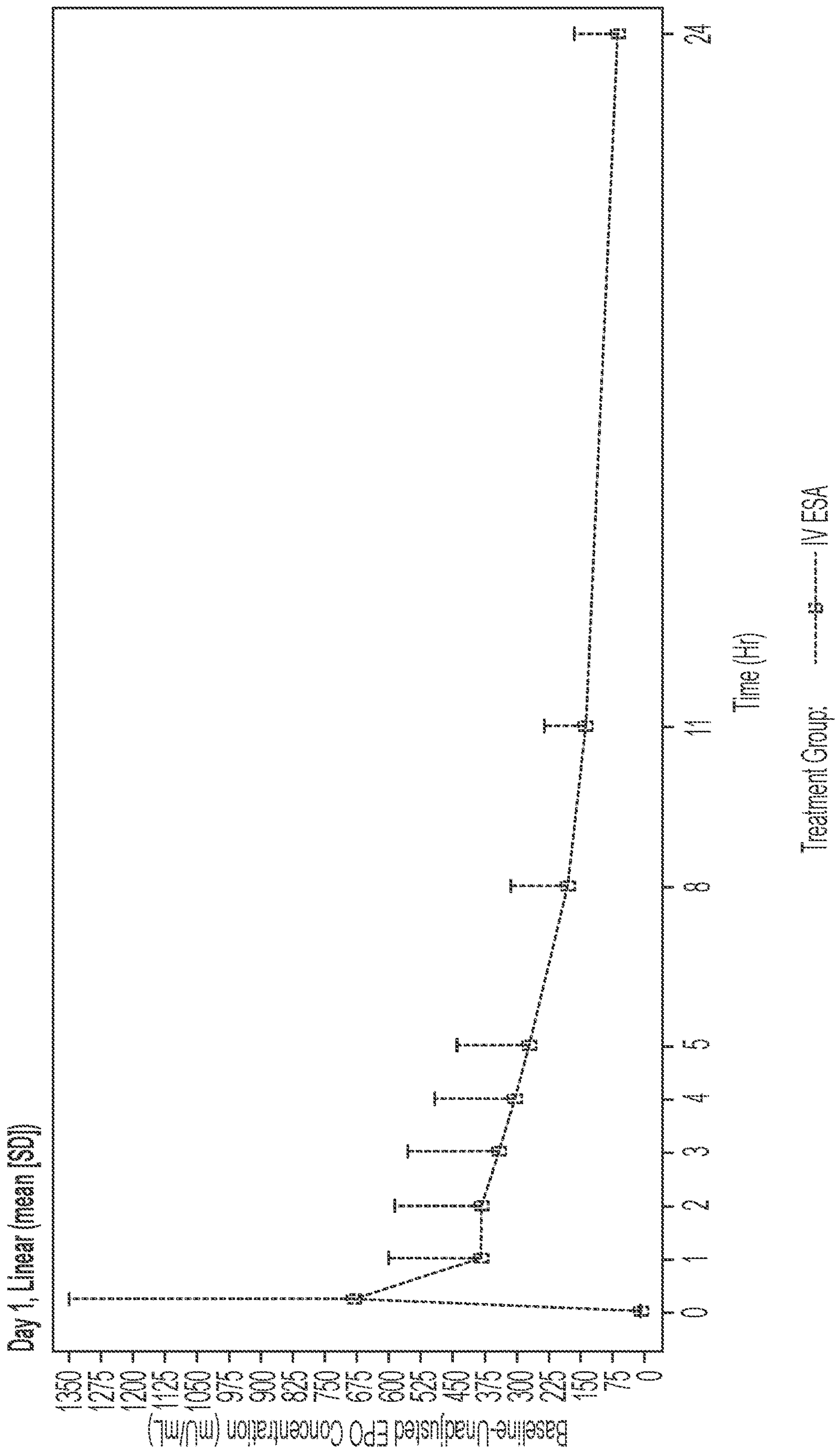
FIGS. 10*a*-10*b* illustrate the baseline-unadjusted erythropoietin concentration (mU/ml) versus nominal time for IV ESA Treatment Group on Day 1 (Pharmacokinetic Population).
Figure 10B:
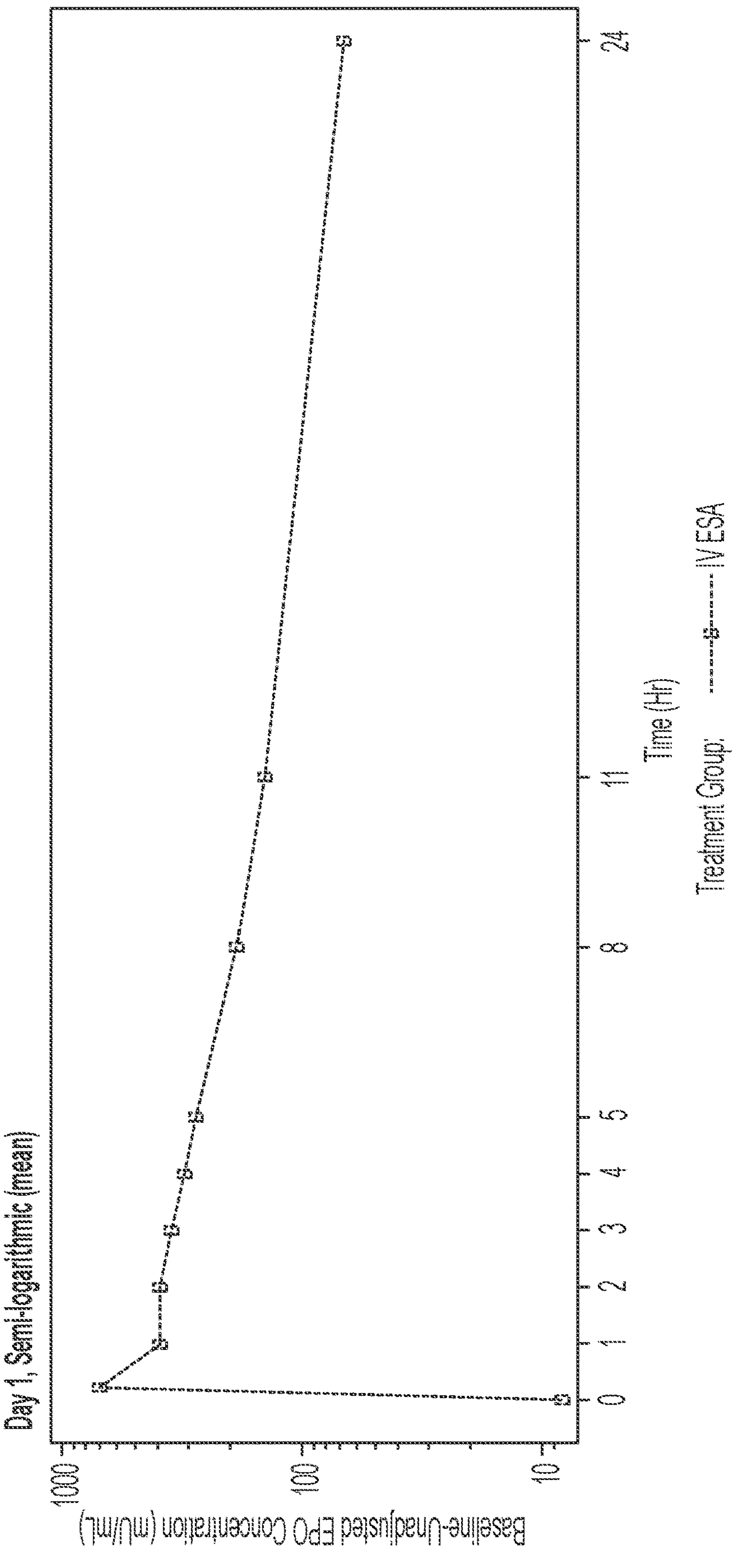
Figure 11A:
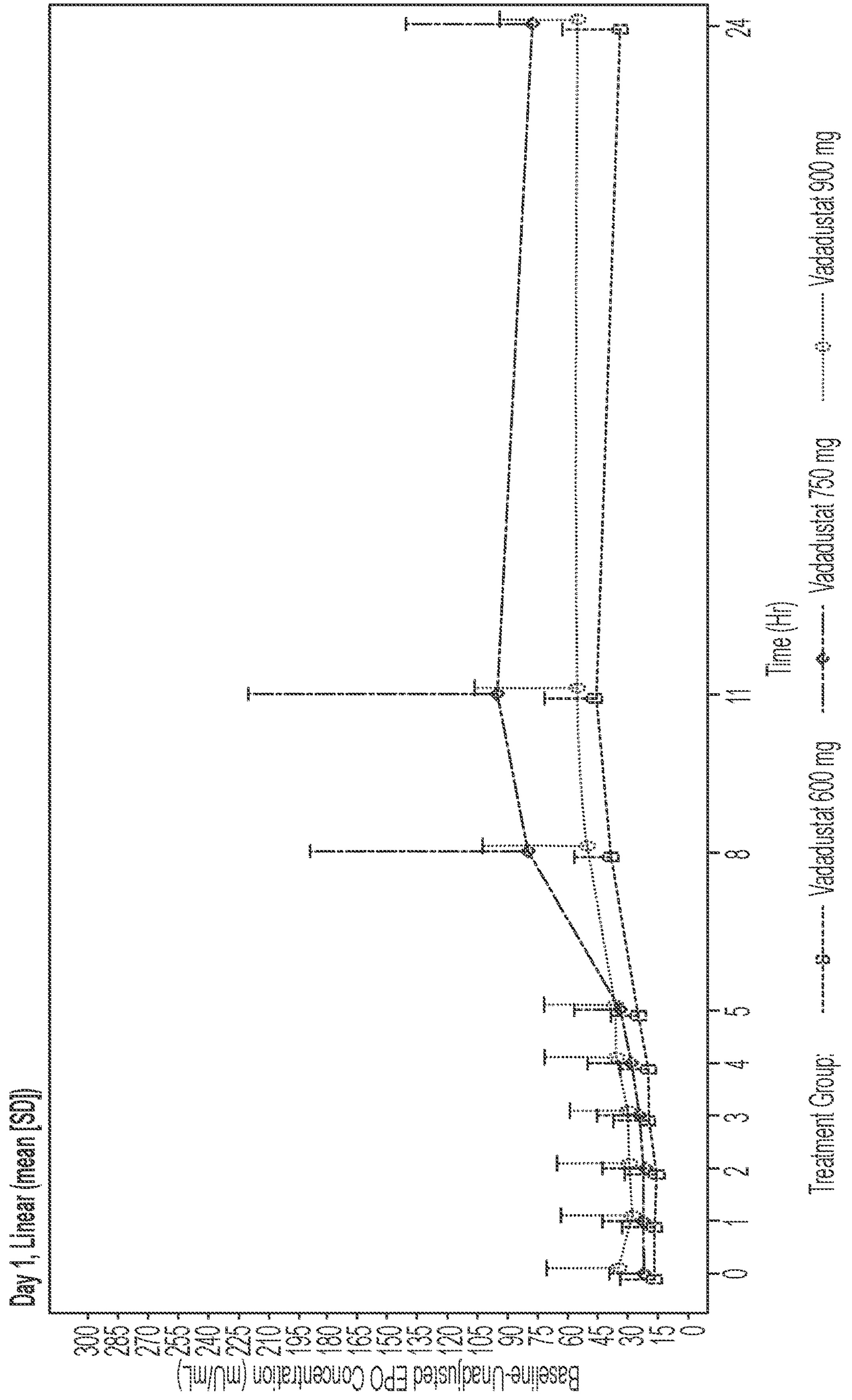
FIGS. 11*a*-11*b* illustrate the baseline-unadjusted erythropoietin concentration (mU/ml) versus nominal time for Vadadustat Treatment Group on Day 1 (Pharmacokinetic Population).
Figure 11B:
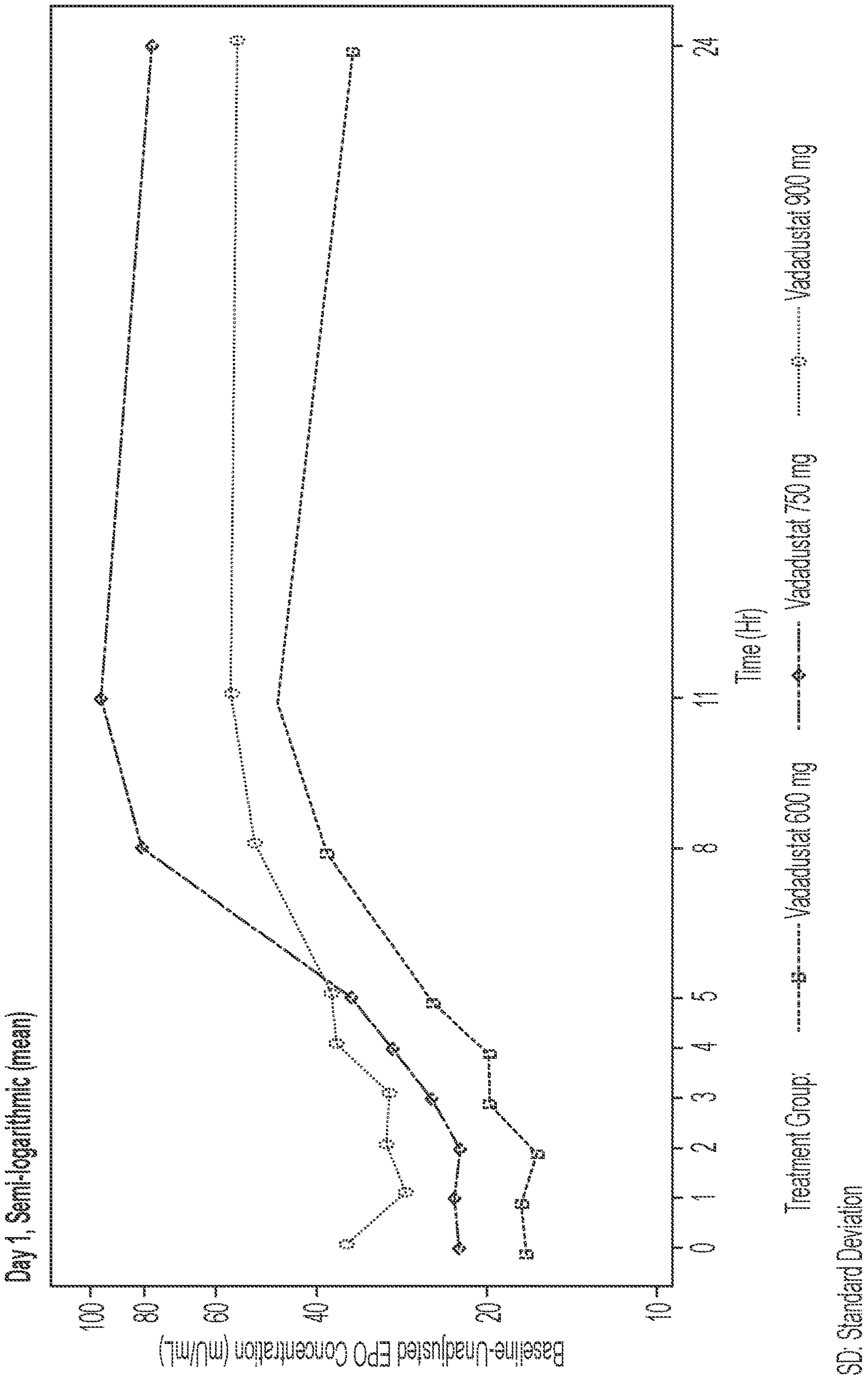
Figure 12A:
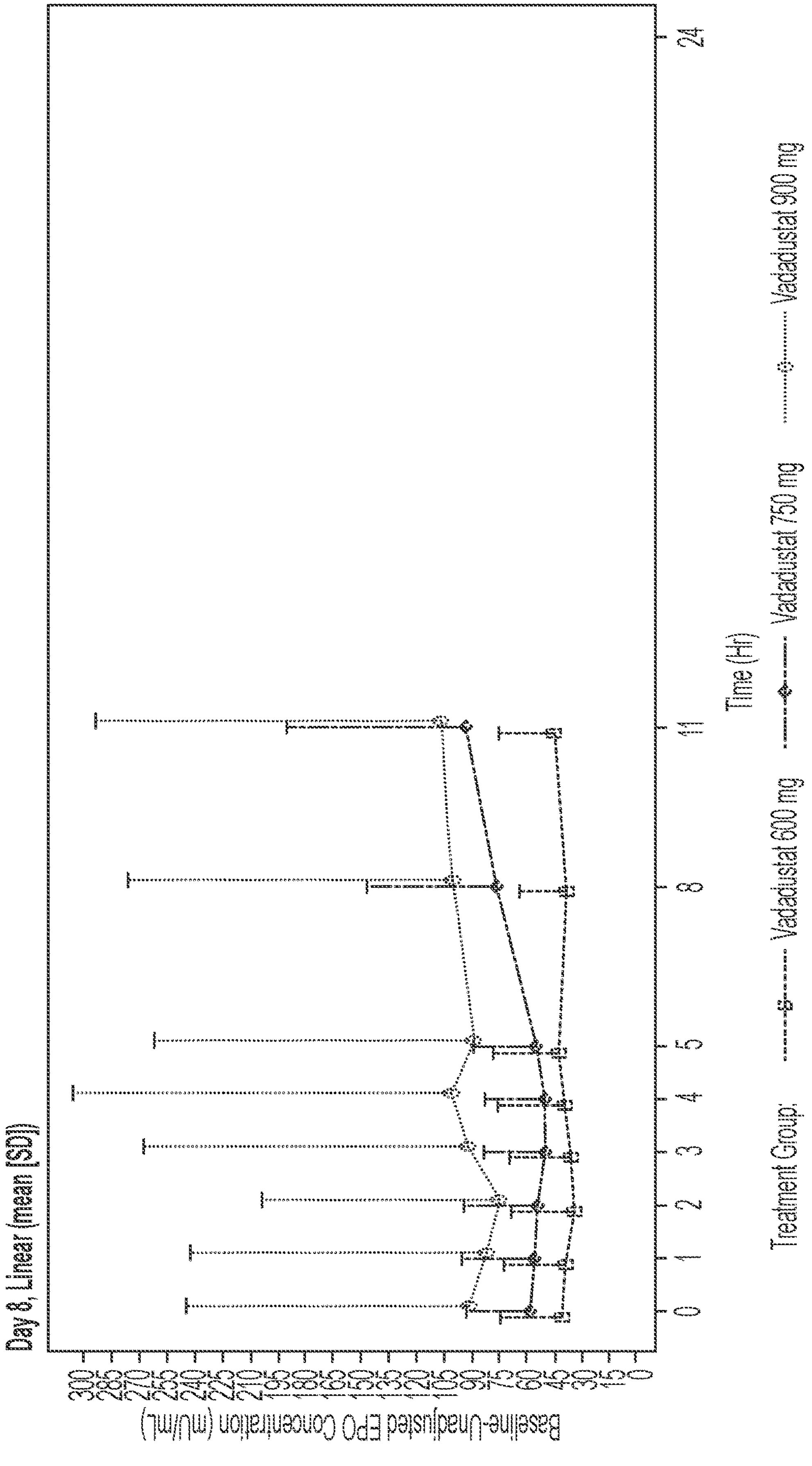
FIGS. 12*a*-12*b* illustrate the baseline-unadjusted erythropoietin concentration (mU/ml) versus nominal time for Vadadustat Treatment Group on Day 8 (Pharmacokinetic Population).
Figure 12B:
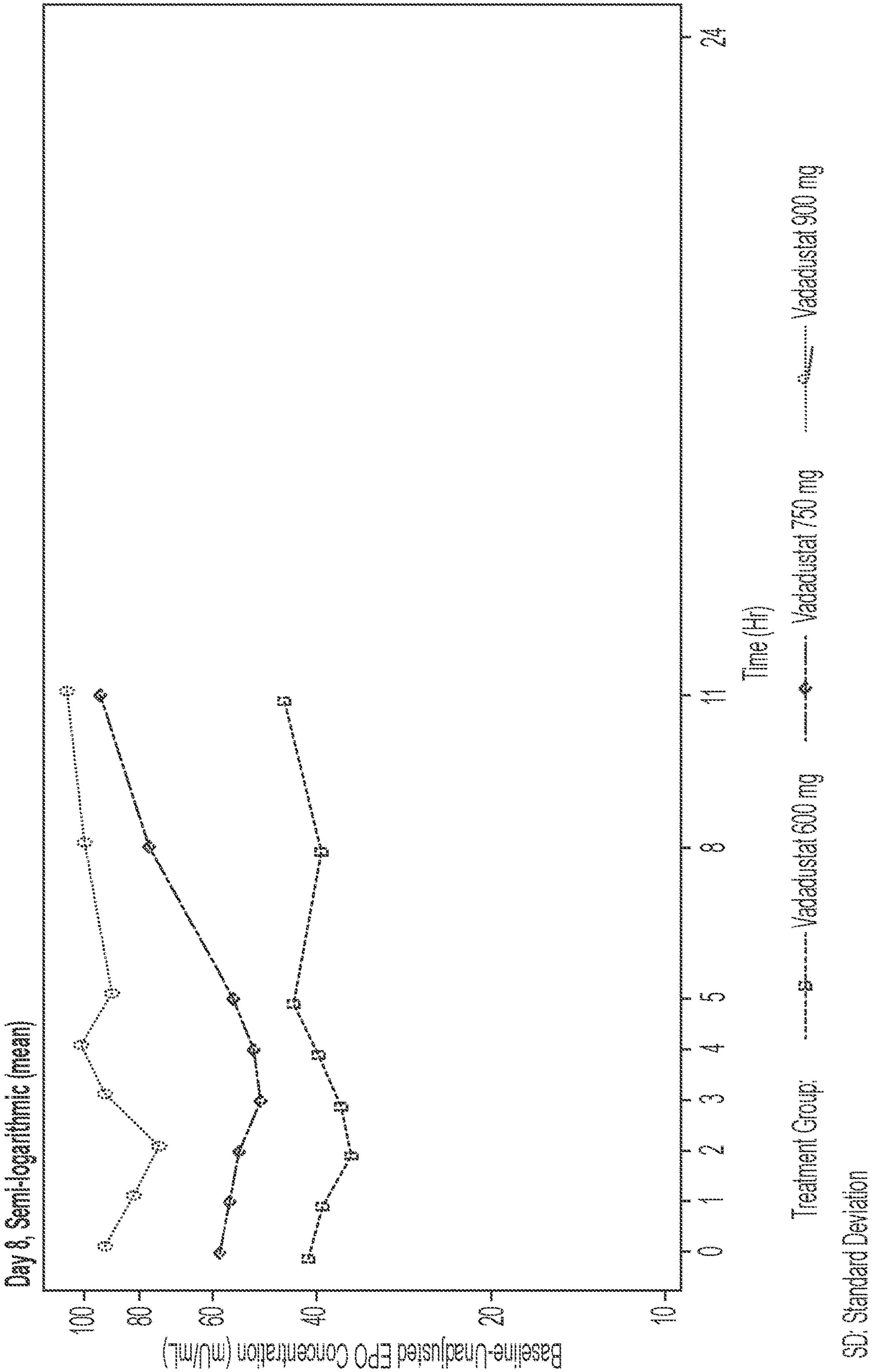

The summary of serum concentration of Baseline-unadjusted EPO by time for the IV ESA treatment group in the PK population is presented in FIGS. 10a-10b.

The summary of serum concentration of Baseline-unadjusted EPO by time for the vadadustat treatment groups in the PK population are presented in FIGS. 1a-11b and FIGS. 12a-12b. The summary of PD parameters for Baseline-unadjusted serum EPO concentration for vadadustat treatment groups by dosing days for the PK population are summarized in Table 2.

TABLE 2

Summary of Pharmacodynamics Parameters for Baseline-unadjusted Serum EPO Concentration for Vadadustat Treatment Groups by Dosing Day (Pharmacokinetic Population)

| | Parameter Statistic (Unit) | | | | | |
|---|---|---|---|---|---|---|
| | Vada 600 mg N = 12 | | Vada 750 mg N = 10 | | Vada 900 mg N = 13 | |
| | Day 1 | Day 8 | Day 1 | Day 8 | Day 1 | Day 8 |
| | $C_{max}$ (μg/mL) | | | | | |
| n | 12 | 12 | 10 | 10 | 13 | 13 |
| Mean (SD) | 53.3 (25.0) | 58.9 (36.9) | 115 (123) | 103 (91.9) | 72.3 (52.6) | 122 (200) |
| | $AUC_{0-11}$ (h · mU/mL)[a] | | | | | |
| n | 12 | 12 | 10 | 10 | 13 | 13 |
| Mean (SD) | 319 (150) | 410 (286) | 569 (623) | 677 (533) | 455 (438) | 981 (1854) |
| | $T_{max}$ (h) | | | | | |
| n | 12 | 12 | 10 | 10 | 13 | 13 |
| Median | 10.09 | 4.50 | 10.94 | 5.01 | 10.00 | 10.00 |
| (min, max) | (3.08, 23.73) | (0.00, 10.27) | (5.00, 23.77) | (0.00, 11.00) | (4.00, 23.92) | (0.00, 11.08) |

$AUC_{0-11}$: area under concentration-time curve from time 0 to 11 h;
$AUC_{last}$: area under concentration-time curve from time 0 to the last quantifiable concentration;
Cmax: maximum observed plasma concentration;
EPO: erythropoietin;
SD: Standard Deviation;
Tmax: time to maximal observed plasma concentration;
Vada: vadadustat
Day 1 included the entire 24-hour sampling period up to Day 2 predose.
Day 8 included samples collected from predose to 11 hours postdose of Day 8.
[a]$AUC_{0-11}$ for Day 1, $AUC_{last}$ for Day 8 ($AUC_{last}$ corresponded to $AUC_{0-11}$ on Day 8).

Following Day 1 dosing, administration of vadadustat 750 mg resulted in higher EPO exposure based on $AUC_{0-11}$. After dosing on Day 1, Cmax of Baseline-unadjusted EPO was highest in the 750 mg treatment group. These concentrations were similar at Day 8, although highest in the 900 mg vadadustat treatment group. Vadadustat showed variable EPO response.

Pharmacokinetic and Pharmacodynamic Analysis: There is a dose-dependent increase in vadadustat exposure ($AUC_{0-24}$ and $C_{max}$) on Day 1 and Day 8. Vadadustat-O-glucuronide on Day 8 also increased in a dose-dependent manner. Vadadustat-O-glucuronide exposure on Day 1 were similar across all dose levels. There is a dose-dependent increase in accumulation of both vadadustat and vadadustat-O-glucuronide observed, most pronounced in the 900 mg vadadustat treatment group. There is a dose-dependent increase of EPO after vadadustat administration that is observed on Day 8. On Day 1, the highest EPO increase was observed in the 750 mg vadadustat treatment group, primarily due to single subject excursion of EPO. There is a much larger increase in EPO after IV ESA administration due to exogenous administration of ESA therapy. There was not a dose-dependent increase in mean Hb levels with vadadustat treatment in this 10-day Treatment period.

Safety: Further, vadadustat oral administration was generally well tolerated. No major safety concerns were observed, and the incidence of drug-related Treatment Emergent Adverse Events (TEAEs) was infrequent and similar across all 3 treatment arms within the vadadustat treatment group.

Example 2. Phase 2, Randomized, Open-Label, Active-Controlled, Efficacy, Safety, Pharmacokinetics, and Pharmacodynamics Study of Oral Vadadustat for the Treatment of Anemia in Hemodialysis Subjects Converting from Epoetin Alfa The primary objective was to assess the efficacy and safety of daily dosing of vadadustat compared to epoetin alfa for 12 weeks in hemodialysis subjects. Additional objectives included to assess the efficacy and safety of three times weekly (TIW) dosing of vadadustat in selected hemodialysis subjects who have been successfully managed with daily dosing of vadadustat through Week 12, to evaluate the PK/PD of daily and TIW dosing of vadadustat in hemodialysis subjects compared to epoetin alfa, and to assess the efficacy and safety of several dosing strategies of vadadustat compared to epoetin alfa during a 20-week Treatment Period in hemodialysis subjects.

The Main study population consisted of adult subjects receiving chronic, outpatient in-center hemodialysis three times weekly (TIW), with 2 screening hemoglobin (Hb) values between 8.5 and 11.0 g/dL (inclusive) and on maintenance treatment with epoetin alfa <300 U/kg/week.

The erythropoiesis-stimulating agent (ESA) hyporesponder parallel study consisted of adult subjects receiving chronic, outpatient in-center hemodialysis TIW, with screening Hb values between 8.0 and 10.0 g/dL (inclusive) and on maintenance treatment with epoetin alfa ≥300 U/kg/week.

Efficacy Endpoints. The primary endpoint was the mean change in Hb between Baseline (average pretreatment Hb) and the primary evaluation period (average Hb from Weeks 10 to 12). Secondary endpoints included proportion of subjects with Hb values within the target range (10.0 to 11.0 g/dL, inclusive) at the primary evaluation period (Weeks 10-12) and for subjects who transitioned to TIW vadadustat dosing, mean change in Hb from primary evaluation period (average Hb from Weeks 10-12) to the secondary period (average Hb from Weeks 18-20). Other secondary endpoints included mean change in Hb from Baseline (average pre-treatment Hb) and the secondary evaluation period (average Hb from Weeks 18-20), proportion of subjects with Hb values within the target range (10.0 to 11.0 g/dL, inclusive) at the secondary evaluation period (Weeks 18 to 20), for subjects who transitioned to TIW vadadustat dosing, proportion of subjects with Hb values within the target range (10.0 to 11.0 g/dL, inclusive) at the secondary evaluation period (Weeks 18-20), proportion of subjects with a mean increase in Hb from Baseline to the primary evaluation period ≥0.5 g/dL (average Hb from Weeks 10-12) or with Hb values within the target range (10.0 to 11.0 g/dL, inclusive) at the primary evaluation period (Weeks 10-12), proportion of subject with a mean increase in Hb from Baseline to the secondary evaluation period ≥0.5 g/dL (average Hb from Weeks 18-20) or with Hb values within the target range (10.0 to 11.0 g/dL, inclusive) at the secondary evaluation period (Weeks 18-20), intravenous (IV) iron supplementation, ESA rescue, and RBC transfusion.

PK/PD Endpoints. An exposure-response analysis of vadadustat and PD measures were conducted as deemed appropriate. The PK parameters included (but were not limited to) the following: area under concentration-time curve from dosing to last measurable concentration ($AUC_{last}$), area under concentration-time curve from dosing to infinity ($AUC_{inf}$), $C_{max}$, apparent total body clearance (CL/F), apparent volume of distribution ($V_d$/F), and terminal half-life ($t_{1/2}$). The PD parameters included (but were not limited to) the following: EPO, reticulocytes, iron, ferritin, TIBC, and hepcidin.

Safety Endpoints. Safety endpoints in this study included the following: AEs, vital sign measurements and clinical laboratory values, Hb>12.0 g/dL, >13.0 g/dL, or >14.0 g/dL; Hb<8.0 g/dL and decline in Hb≥0.5 g/dL from Baseline Hb (Main Study); Hb<7.5 g/dL and decline in Hb≥0.5 g/dL from Baseline Hb (ESA hyporesponder parallel study); Hb increase >1.0 g/dL within any 2-week interval.

Study Design. This was a Phase 2, randomized, open-label study to evaluate vadadustat for the treatment of anemia in hemodialysis subjects converting from epoetin alfa therapy. For all subjects (Main study and ESA hyporesponder parallel study), the study included a Screening Period, a study Treatment Period, and a Safety Follow-Up Period as described below. PK and PD sampling were done throughout the study. The aim was to achieve and maintain Hb levels within the target range of 10.0 to 11.0 g/dL, inclusive, while targeting the middle of the range and minimizing excursions outside the target range.

Randomization. Subjects were randomized to either a vadadustat treatment arm or epoetin alfa treatment arm. Randomization was stratified by mean weekly epoetin alfa dose calculated over a period of 8 weeks prior to SV2: low epoetin alfa dose group (≤90 U/kg/week) or high epoetin alfa dose group (>90 to <300 U/kg/week). In the low epoetin alfa dose group, subjects were randomized in a 3:3:2 ratio to receive either an initial vadadustat daily dose of 450 mg (3 tablets) or 300 mg (2 tablets), or epoetin alfa. In the high epoetin alfa dose group, subjects were randomized in a 3:3:3:2 ratio to receive either an initial vadadustat daily dose of 600 mg (4 tablets), 450 mg (3 tablets) or 300 mg (2 tablets), or epoetin alfa.

In the ESA hyporesponder parallel study, subjects were randomized in a 1:1 ratio to receive either an initial vadadustat daily dose of 600 mg (4 tablets) or epoetin alfa. A subject could enter the washout period only after all eligibility criteria have been met. During the washout period, no epoetin alfa was administered for 5 days in the Main study and 2 days in the ESA hyporesponder parallel study.

Screening Period (up to 28 days; Day −28 to Baseline/Day 1). For all subjects (Main study and ESA hyporesponder parallel study), the Screening Period started at the time the informed consent was signed and was a maximum of 28 days in duration. Baseline/Day 1 was performed within 28 days of the start of Screening. Subjects who meet all eligibility criteria were randomized to a vadadustat treatment arm or an epoetin alfa treatment arm. Subjects were required to stop epoetin alfa treatment for a minimum duration of 5 days before Baseline/Day 1 in the Main study and for a minimum of 2 days before Baseline/Day 1 in the ESA hyporesponder parallel study. In the Main study, randomization was stratified by the mean weekly epoetin dose calculated over a period of 8 weeks prior to Screening Visit 2 (SV2): low epoetin alfa dose group (≤90 U/kg/week) or high epoetin alfa dose group (>90 to <300 U/kg/week).

Study Treatment Period (Baseline/Day 1 to Week 20). For all subjects (Main study and ESA hyporesponder parallel study), the Treatment Period ran from Baseline/Day 1 to Week 20. Dose was adjusted to achieve and maintain Hb levels within the target range of 10.0 to 11.0 g/dL, inclusive, while targeting the middle of the range and minimizing excursions outside of the target range.

Vadadustat Treatment. Subjects in the Main Study randomized to vadadustat: subjects in the low epoetin alfa dose group started vadadustat at an initial, randomly allocated dose of 300 or 450 mg daily; subjects in the high epoetin alfa dose group started vadadustat at an initial, randomly allocated dose of 300, 450, or 600 mg daily. Subjects in the ESA hyporesponder parallel study randomized to vadadustat: subjects received a starting dose of vadadustat 600 mg daily. Transition to TIW for all subjects randomized to vadadustat: all subjects randomized to vadadustat (Main study and ESA hyporesponder parallel study), who completed the 12-week once daily dosing regimen and who met all the Week 12 transition criteria for switching from daily to TIW dosing, initiated TIW dosing at a starting dose one tablet greater (+150 mg) than the final dose in the daily dosing period. Week 12 transition criteria included: Vadadustat daily dose of 600 mg or lower at Week 12; Hb within target range of 10.0 to 11.0 g/dL, inclusive, at Week 12 confirmed by central laboratory Hb value from Week 11 (11 weeks of treatment completed); No receipt of rescue therapy (ESA or RBC transfusion) for worsening of anemia due to CKD from Baseline/Day 1 to Week 12. ESA or RBC transfusion prior to Week 12 for reasons unrelated to worsening of anemia due to CKD (e.g., surgery, gastrointestinal bleed, or inadvertent administration) is not considered rescue therapy; and No other reason, based on the investigator's clinical discretion that would make the subject not suitable for TIW dosing.

Selected subjects who met Week 12 transition criteria could transition to the TIW vadadustat dosing regimen at the Week 12 visit. Subjects on 150, 300, 450, or 600 mg of vadadustat daily at the Week 12 visit could transition to an initial vadadustat TIW dose one tablet greater (+150 mg), i.e., 300, 450, 600, or 750 mg vadadustat TIW, respectively. Subjects were instructed to take vadadustat on dialysis days. After 2 weeks of treatment in the TIW vadadustat dosing regimen (at Week 14), subjects in any vadadustat TIW dosing arms who had a decline in Hb≥0.5 g/dL were eligible for a dose increase by 1 tablet, based on the investigator's clinical discretion.

Subjects who were not eligible to switch from daily vadadustat to TIW dosing at Week 12 could remain on for the remainder of the study. Subjects on TIW dosing could be converted back to vadadustat once daily dosing at the discretion of the investigator in the setting of inadequate Hb response. The starting daily dose after the switch from TIW to daily dosing was based on the investigator's discretion after review of the subject's clinical status and dosing history, in particular, the daily dose previously administered to the subject prior to the transition to TIW dosing (Week 12). Subjects who switched from vadadustat TIW to daily dosing could continue once daily vadadustat until the end of the Treatment Period.

Epoetin Alfa Treatment. Subjects in both the Main study and ESA hyporesponder parallel study randomized to epoetin alfa: all subjects randomized to epoetin alfa received TIW dosing for the entire Treatment Period based on the subject's central laboratory Hb value and the approved epoetin alfa US Package Insert (PI) for adult patients with CKD on dialysis. Initial dosing regimen was approximately the same weekly dose that they were receiving prior to randomization. Dose was adjusted to achieve and maintain Hb levels within the target range of 10.0 to 11.0 g/dL, inclusive, while targeting the middle of the range and minimizing excursions outside of the target range.

Dose Adjustments. Dose adjustments were guided by Hb concentrations and the Guidelines for Dose Adjustment. Hb was monitored via central laboratory throughout the study to determine if the dose of study drug (vadadustat or epoetin alfa) would be adjusted, interrupted, or maintained as follows: (1) Dose adjustments were based on the investigator's clinical discretion, incorporating the protocol guidance below as well as the subject's current Hb level, trajectory, and variability; symptoms; cardiovascular risk; and other features of his/her clinical condition(s); (2) If a dose increase or decrease was required to achieve and maintain Hb levels within the target range of 10.0 to 11.0 g/dL, inclusive, dose was adjusted by 1 dose level (for vadadustat 1 tablet [150 mg], for epoetin alfa approximately 25%); (3) In general, the dose was not increased more frequently than once every 4 weeks. A one-time dose increase after 2 weeks was allowed on only two occasions. subject's dose could be increased by 1 dose level if the subject had a decline in Hb≥0.5 g/dL from Baseline/Day 1 in the first 2-week period (the initial period from Baseline/Day 1 to Week 2 following conversion from prior epoetin alfa therapy). A subject's dose could also be increased by 1 dose level in the first 2-week period after initiation of TIW dosing (from Week 12 to Week 14) for subjects that met criteria for transitioning from daily to TIW dosing; (4) Reduced or interrupted the dose in the setting of a rapid rise in Hb (defined as >1.0 g/dL in any 2-week period); (5) Reduced or interrupted the dose in the setting of Hb>11.0 g/dL; and (6) Interrupted the dose in the setting of a Hb>12.0 g/dL until Hb value fell below 11.0 g/dL. After Hb fell below 11.0 g/dL, restarted study drug and considered restarting at a lower dose. The minimum dose of vadadustat could be 150 mg daily or TIW (one 150 mg tablet daily/TIW) and the maximum dose could be 900 mg daily or TIW (six 150 mg tablets daily/TIW).

Safety Follow-Up Period (Weeks 20-24). For all subjects (Main study and ESA hyporesponder parallel study), the 4-week Safety Follow-Up Period starting at Week 20 could be followed by a post-treatment safety assessment conducted at the beginning of Week 24.

This study design mitigated the risk of vadadustat doses of 750 or 900 mg. Intensive Hb monitoring, a strict dose adjustment algorithm, and phlebotomy were implemented to mitigate the potential risk of a rapid Hb rise, as follows: Hb measurements were scheduled at least every 2 weeks to Week 20; the dose adjustment algorithm would target a narrow Hb range, 10.0 to 11.0 g/dL, inclusive; and the protocol specifies that phlebotomy could be considered in the setting of high Hb levels (>14.0 g/dL) or a high Hb rate of rise, based on the investigator's judgment. Importantly, the Phase 2 studies demonstrated that cessation of treatment resulted in prompt reduction in mean Hb within 2 to 4 weeks.

Iron Supplementation. IV iron could be administered based on ferritin and TSAT levels measured by the central laboratory according to the standardized, low-intensity, iron supplementation protocol in Table 3.

TABLE 3

Iron Supplementation Protocol

| | Ferritin <200 ng/mL | Ferritin 200-500 ng/mL | Ferritin >500 ng/mL |
|---|---|---|---|
| TSAT <20% | IV iron 100 mg every treatment (max 400 mg/month) | IV iron 50 mg weekly | Hold |
| TSAT 20-50% | IV iron 100 mg every week | IV iron 50 mg weekly | Hold |
| TSAT >50% | Hold | Hold | Hold |

Subjects already receiving oral iron supplementation as part of their treatment plan could continue their current treatment regimen. Because of the potential for oral iron to reduce the bioavailability of vadadustat, the study medication was not to be administered concurrently with an oral iron supplement (including multivitamins containing iron), iron containing phosphate binders, or any oral medications containing iron. Subjects were instructed to take any oral medications containing iron at least 2 hours after the dose of vadadustat.

Inclusion Criteria. Subjects who met the following inclusion criteria were considered eligible: (1) ≥18 years of age; (2) Receiving chronic, outpatient in-center hemodialysis (TIW) for ESRD for at least 12 weeks prior to Screening; (3) Maintained on IV epoetin alfa therapy for 8 weeks prior to and including Screening through SV2; (4) Eligibility in the Main study and ESA hyporesponder parallel study is based on the following mean weekly epoetin alfa doses: Main study—mean weekly epoetin alfa dose <300 U/kg/week for 8 weeks prior to SV2, and ESA hyporesponder parallel study—mean weekly epoetin alfa dose >300 U/kg/week for 8 weeks prior to SV2; (5) Two Hb values measured by the central laboratory at least 4 days apart between SV1 and SV2: Main study—2 Hb values between 8.5 and 11.0 g/dL, inclusive, and ESA hyporesponder parallel study—2 Hb values between 8.0 and 10.0 g/dL, inclusive; (6) Serum ferritin ≥100 ng/mL and transferrin saturation (TSAT)≥20% during Screening; (7) Folate and vitamin B12 measurements ≥lower limit of normal during Screening; (8) Hemodialysis adequacy as indicated by single-pool $Kt/V_{urea}$≥1.2 using the most recent historical measurement within 8 weeks prior to or during Screening; and (9) Understands the procedures and requirements of the study and provides written informed consent and authorization for protected health information disclosure.

Exclusion Criteria. Subjects meeting any of the following exclusion criteria were not eligible for randomization: (1) Anemia due to a cause other than CKD (e.g., sickle cell disease, myelodysplastic syndromes, bone marrow fibrosis, hematologic malignancy, myeloma, hemolytic anemia, thalassemia, or pure red cell aplasia); (2) Active bleeding or recent blood loss within 8 weeks prior to randomization; (3) RBC transfusion within 8 weeks prior to randomization; (4) Anticipated to discontinue hemodialysis during the study; (5) Judged by the investigator that the subject is likely to need rescue therapy (ESA administration or RBC transfusion) immediately after enrollment in the study; (6) History of chronic liver disease (e.g., chronic infectious hepatitis, chronic autoimmune liver disease, cirrhosis or fibrosis of the liver); (7) Aspartate aminotransferase (AST)/serum glutamic oxaloacetic transaminase (SGOT), alanine aminotransferase (ALT)/serum glutamic pyruvic transaminase (SGPT), or total bilirubin >1.5× upper limit of normal (ULN) during Screening. Subjects with a history of Gilbert's syndrome are not excluded; (8) Current uncontrolled hypertension as determined by the investigator that would contraindicate the use of epoetin alfa; (9) Acute coronary syndrome (hospitalization for unstable angina or myocardial infarction), surgical or percutaneous intervention for coronary, cerebrovascular or peripheral artery disease (aortic or lower extremity), surgical or percutaneous valvular replacement or repair, sustained ventricular tachycardia, hospitalization for heart failure (HF) or New York Heart Association Class IV HF, or stroke within 12 weeks prior to or during Screening; (10) History of new or recurrent malignancy within 2 years prior to and during Screening or currently receiving treatment or suppressive therapy for cancer. Subjects with treated basal cell carcinoma of skin, curatively resected squamous cell carcinoma of skin, or cervical carcinoma in situ are not excluded; (11) History of deep vein thrombosis or pulmonary embolism within 12 weeks prior to or during Screening; (12) History of hemosiderosis or hemochromatosis; (13) History of prior organ transplantation (subjects with a history of failed kidney transplant or corneal transplants are not excluded); (14) Scheduled organ transplant from a living donor and subjects on the kidney transplant waitlist who are expected to receive a transplant within 6 months; (15) History of a prior hematopoietic stem cell or bone marrow transplant (stem cell therapy for knee arthritis is not excluded); (16) Known hypersensitivity to vadadustat, epoetin alfa, or any of their excipients; (17) Any prior use of a HIF-PH inhibitor or any use of an investigational medication within 30 days or 5 half-lives of the investigational medication (whichever is longer), prior to randomization; (18) For female subjects or non-childbearing potential, inability to confirm surgical sterility (e.g., hysterectomy, bilateral tubal ligation, bilateral oophorectomy) at least 1 month prior to Screening, or not considered post-menopausal (no menses for >1 year with follicle stimulating hormone [FSH]>40 U/L at Screening). For female subjects of childbearing potential, lack of confirmation of the use of acceptable forms of contraception for a minimum of one complete menstrual cycle prior to Screening, positive serum pregnancy test at SV2, or unwilling to use two acceptable forms of contraception (at least one of which must be a barrier method) starting Baseline/Day 1, throughout the Treatment Period and for 30 days after the final study drug administration; (19) Breastfeeding during Screening or throughout the Treatment Period and for 30 days after the final study drug administration; (20) Donation of ova starting at Screening, throughout the Treatment Period, and for 30 days after the final study drug administration; (21) Male subjects who have not had a vasectomy and do not agree to the following: use of an acceptable form of contraception during the study and for 30 days after the last dose of the study drug; to not donate semen during the study and for at least 30 days after the last dose of vadadustat; (22) Subjects with bilateral native nephrectomy; and (23) Any other reason, which in the opinion of the investigator, would make the subject not suitable for participation in the study.

Data Analysis

In embodiment, the analysis populations were defined as follows:

Randomized population: all randomized subjects. Analyses of this population was based on the randomized treatment.

FAS: all subjects in the randomized population who received at least 1 dose of study drug and had at least 1 Hb assessment during the PEP (defined as Weeks 10 to 12 of the study period) and the SEP (defined as Weeks 18 to 20). Analyses of this population was based on the randomized treatment.

Safety population: all subjects in the randomized population who received at least 1 dose of study drug. Analysis of this population was based on the actual treatment received. Subjects who received in error some vadadustat and some epoetin alfa were classified by the more frequently received drug.

PP population: all randomized subjects who received study drug during the primary efficacy period, had at least 1 Hb assessment during the primary efficacy period, received no rescue therapy (with ESA or transfusion) prior to the efficacy period, and had no major protocol deviation affecting the primary endpoint analysis. Analyses of this population was based on actual treatment received.

PK population: included all randomized subjects who received study drug (vadadustat or epoetin alfa) and had enough drug concentrations to estimate AUC and Cmax. Analysis of this population was based on the dose amount taken at the date of PK sampling for the vadadustat group.

The primary efficacy endpoint was analyzed and presented using the Randomized population, FAS, and PP population. Key secondary efficacy endpoints were analyzed for the Randomized and PP populations. All other efficacy endpoints were analyzed using the Randomized population.

Analysis of Efficacy

Summary statistics for the absolute and change from baseline in Hb for the Main Study and data to support the primary endpoint, mean change in Hb between baseline and the PEP (Weeks 10 to 12) for the Randomized population, are presented in Table 4.

TABLE 4

Summary Statistics for Absolute and Change from Baseline in Hemoglobin (Hb, g/dL) (Randomized Population, Main Study)

| Visit Statistics | Low Epoetin Alfa (<90 U/kg/week) | | | High Epoetin Alfa (>90 to <300 U/kg/week) | | | |
|---|---|---|---|---|---|---|---|
| | Vada 300 mg N = 28 | Vada 450 mg N = 26 | Epoetin Alfa N = 23 | Vada 300 mg N = 11 | Vada 450 mg N = 15 | Vada 600 mg N = 15 | Epoetin Alfa N = 13 |
| **Baseline[a]** | | | | | | | |
| n | 28 | 26 | 23 | 11 | 15 | 15 | 13 |
| Mean (SD) | 10.23 (0.570) | 10.15 (0.617) | 10.17 (0.681) | 10.04 (0.605) | 10.13 (0.568) | 10.05 (0.714) | 9.95 (0.795) |
| Median | 10.300 | 10.175 | 10.200 | 10.300 | 10.300 | 10.400 | 10.200 |
| Min, Max | 8.55, 11.1 | 8.8, 11.15 | 8.65, 11.35 | 9.05, 10.8 | 8.9, 10.85 | 8.75, 11.1 | 8.6, 11.2 |
| **Primary Evaluation Period (Average of Weeks 10 to 12)[b]** | | | | | | | |
| n | 25 | 24 | 23 | 8 | 14 | 11 | 12 |
| Mean (SD) | 9.78 (0.742) | 10.08 (1.226) | 10.33 (0.752) | 8.82 (0.761) | 9.96 (1.121) | 9.62 (1.026) | 10.26 (1.056) |
| Median | 9.767 | 10.550 | 10.400 | 8.750 | 9.750 | 9.233 | 10.475 |
| Min, Max | 8.43, 11.13 | 7, 11.87 | 8.9, 11.87 | 7.9, 9.77 | 8.27, 11.5 | 18.5, 11.13 | 8.33, 11.95 |
| **Change from Baseline at Primary Evaluation Period** | | | | | | | |
| n | 25 | 24 | 23 | 8 | 14 | 11 | 12 |
| Mean (SD) | −0.421 (0.732) | −0.074 (1.085) | 0.160 (0.752) | −1.048 (0.730) | −0.130 (1.033) | −0.541 (1.124) | 0.268 (1.009) |
| Median | −0.450 | 0.017 | 0.150 | −0.967 | −0.250 | −0.133 | 0.292 |
| Min, Max | −1.65, 0.68 | −2.25, 1.97 | −1.25, 2.27 | −2.43, −0.13 | −1.63, 1.67 | −2.6, 0.7 | −0.95, 2.22 |
| **Secondary Evaluation Period (Average of Weeks 18 to 20)[c]** | | | | | | | |
| n | 22 | 20 | 23 | 6 | 12 | 9 | 12 |
| Mean (SD) | 9.86 (0.932) | 9.91 (0.909) | 10.24 (0.754) | 9.88 (1.027) | 9.63 (0.954) | 9.57 (0.871) | 10.34 (0.799) |
| Median | 9.775 | 9.917 | 10.050 | 9.575 | 9.475 | 9.450 | 10.400 |
| Min, Max | 8.45, 12.8 | 7.9, 11.35 | 9.17, 11.6 | 8.45, 11.2 | 7.97, 11.4 | 8.1, 11.05 | 8.8, 12 |
| **Change from Baseline at Secondary Evaluation Period** | | | | | | | |
| n | 22 | 20 | 23 | 6 | 12 | 9 | 12 |
| Mean (SD) | −0.327 (1.086) | −0.273 (0.827) | 0.070 (0.954) | 0.017 (1.086) | −0.458 (0.895) | −0.500 (1.025) | 0.343 (0.890) |
| Median | −0.300 | −0.300 | −0.100 | −0.325 | −0.575 | −0.300 | 0.250 |
| Min, Max | −1.8, 3.45 | −1.65, 1.45 | −2, 1.75 | −1, 1.9 | −2.38, 0.85 | −2.4, 0.55 | −0.75, 2.25 |

Hb: hemoglobin; N: number of subjects; SD: standard deviation; Vada: vadadustat Summary statistics are from the observed Hb values; no model was used.

For summary of Baseline, the records with non-missing Baseline values were considered. For summary of post-baseline and change from Baseline, the records with non-missing Baseline and post-baseline values were considered.

[a]Baseline value of Hb is defined as the average of the final two Hb values prior to start of dosing on Day 1.

[b]Primary evaluation period is defined as the average Hb for Weeks 10 to 12.

[c]Secondary evaluation period is defined as the average Hb for Weeks 18 to 20.

As shown in Table 4, mean (standard deviation [SD]) Hb at the PEP (Weeks 10 to 12) was 9.78 (1.048) g/dL in the vadadustat treatment group compared to 10.30 (0.853) g/dL in the epoetin alfa treatment group, and mean (SD) changes from baseline at the PEP were −0.35 (0.976) and 0.20 (0.835) g/dL in the vadadustat and epoetin alfa treatment groups, respectively. In the low epoetin alfa stratum, vadadustat 300 mg subjects had the greatest magnitude of mean (SD) change from baseline at the PEP (−0.42 [0.732] g/dL) followed by epoetin alfa (0.16 [0.752]g/dL) and vadadustat 450 mg (−0.07 [1.085] g/dL). In the high epoetin alfa stratum, vadadustat 300 mg subjects had the greatest magnitude of mean (SD) change from baseline at the PEP (−1.05 [0.730] g/dL), followed by vadadustat 600 mg (−0.54 [1.124] g/dL), epoetin alfa (0.27 [1.009] g/dL), and vadadustat 450 mg (−0.13 [1.034] g/dL).

Figure 13:
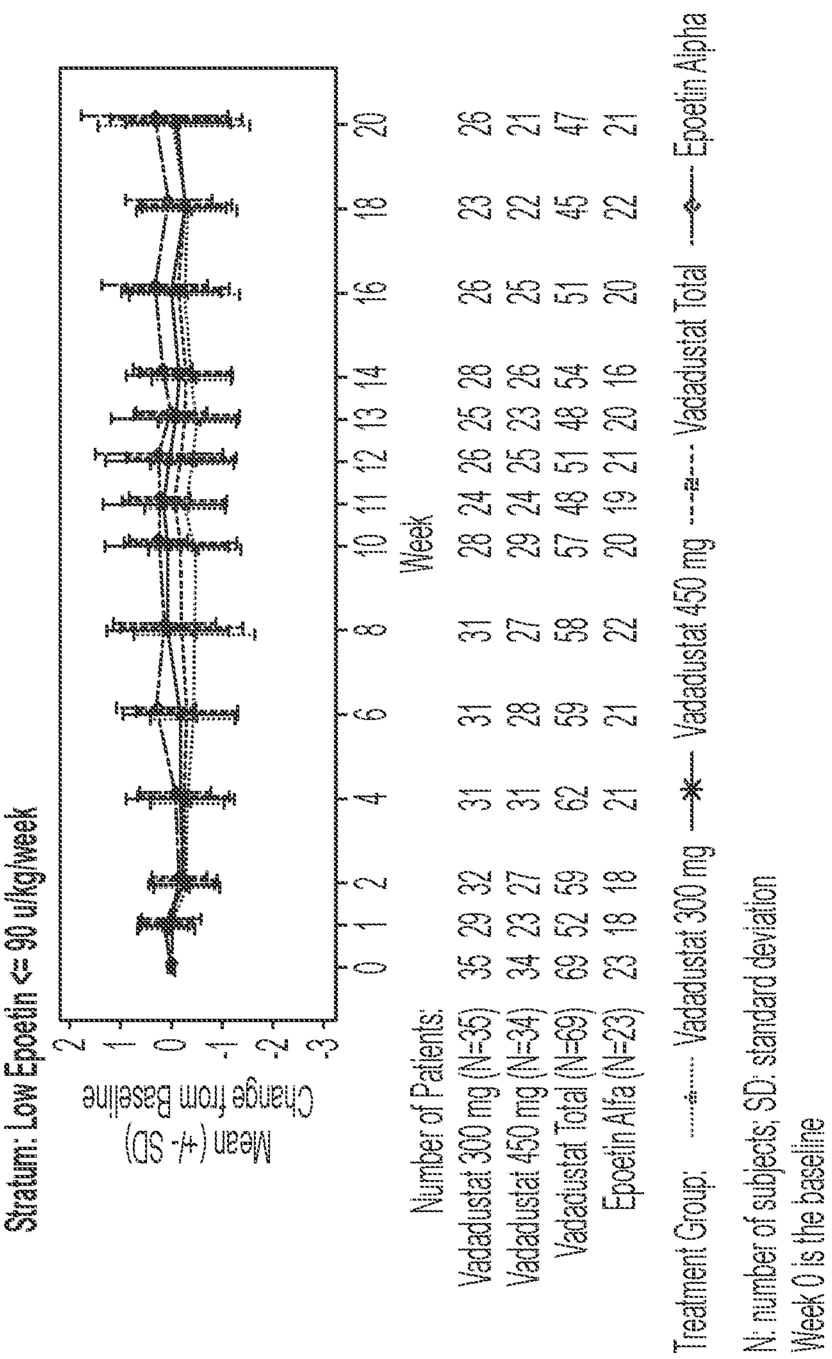
FIG. 13 illustrates the mean change from baseline in hemoglobin (Hb, g/dL) in the Low Epoetin ≤590 U/kg/week Stratum (Randomized Population, Main Study).
Figure 14:
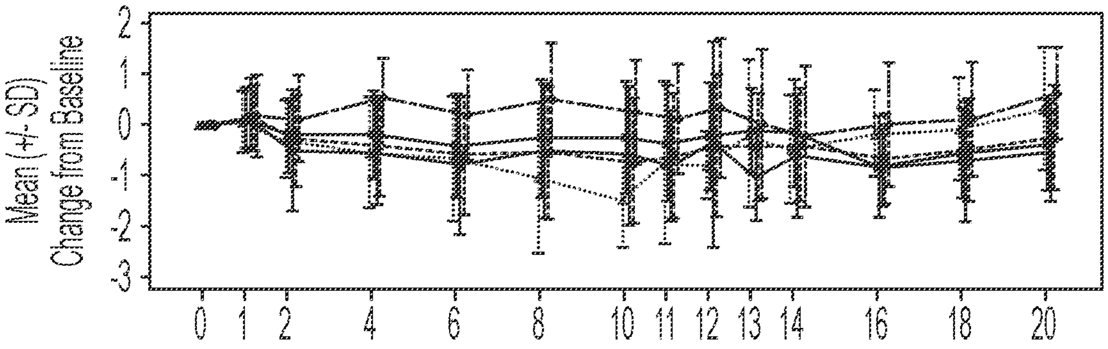
FIG. 14 illustrates the mean change from baseline in hemoglobin (Hb, g/dL) in the High Epoetin >90 to <300 U/kg/week Stratum (Randomized Population, Main Study).
Figure 15A:
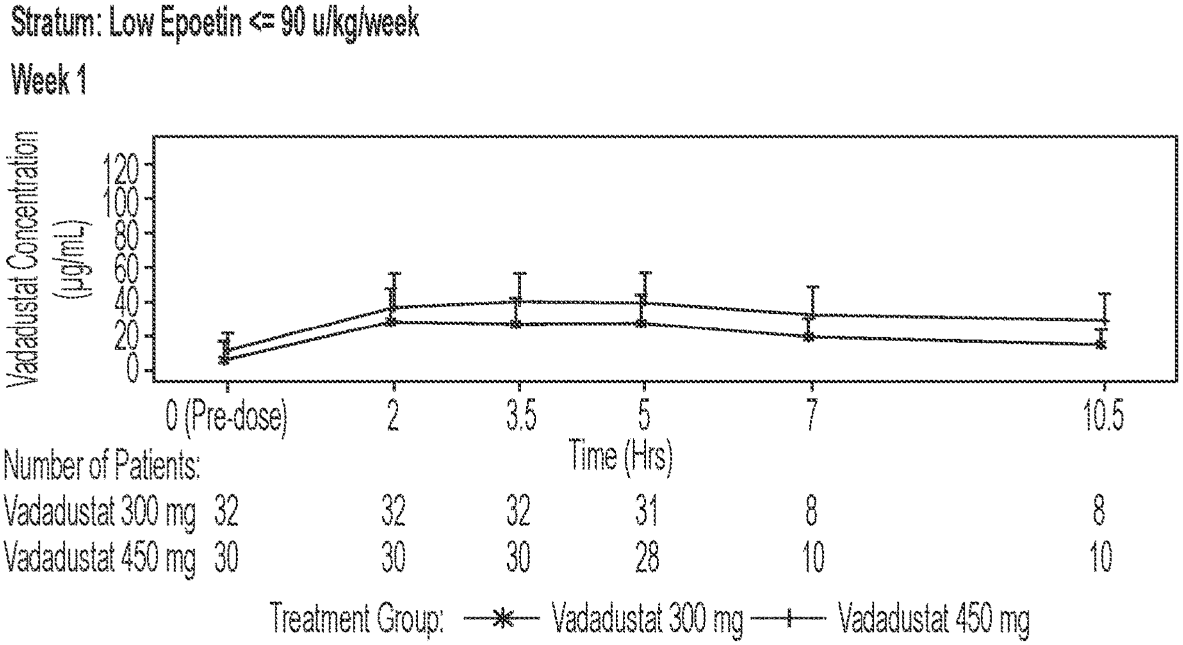
Figure 15B:
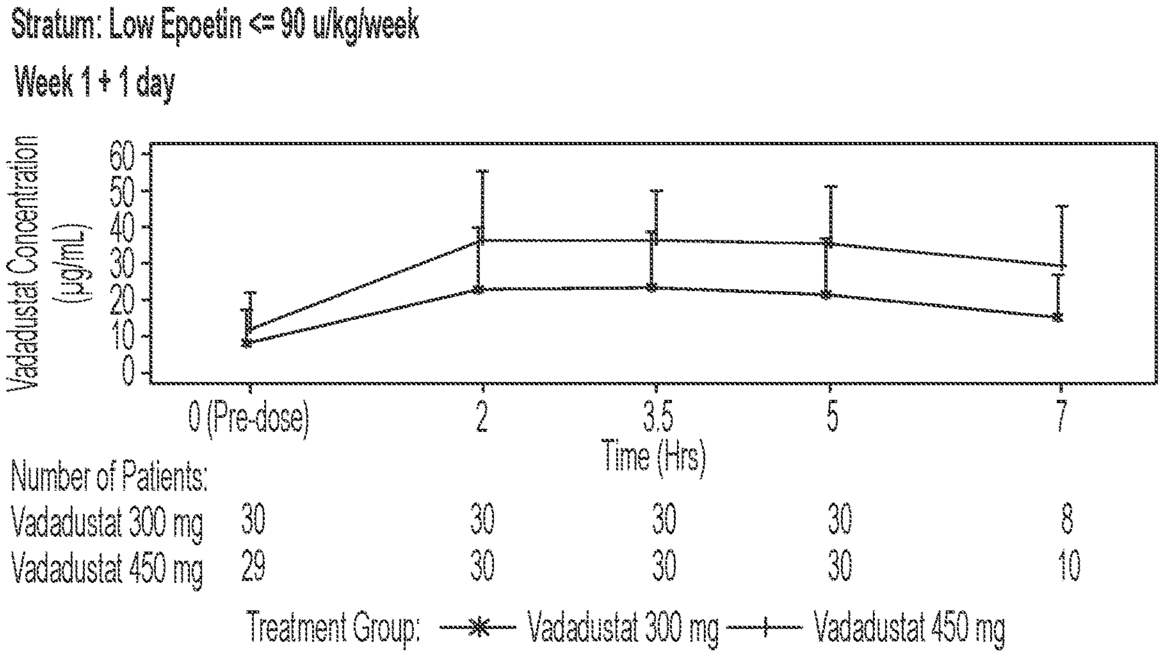
Figure 16A:
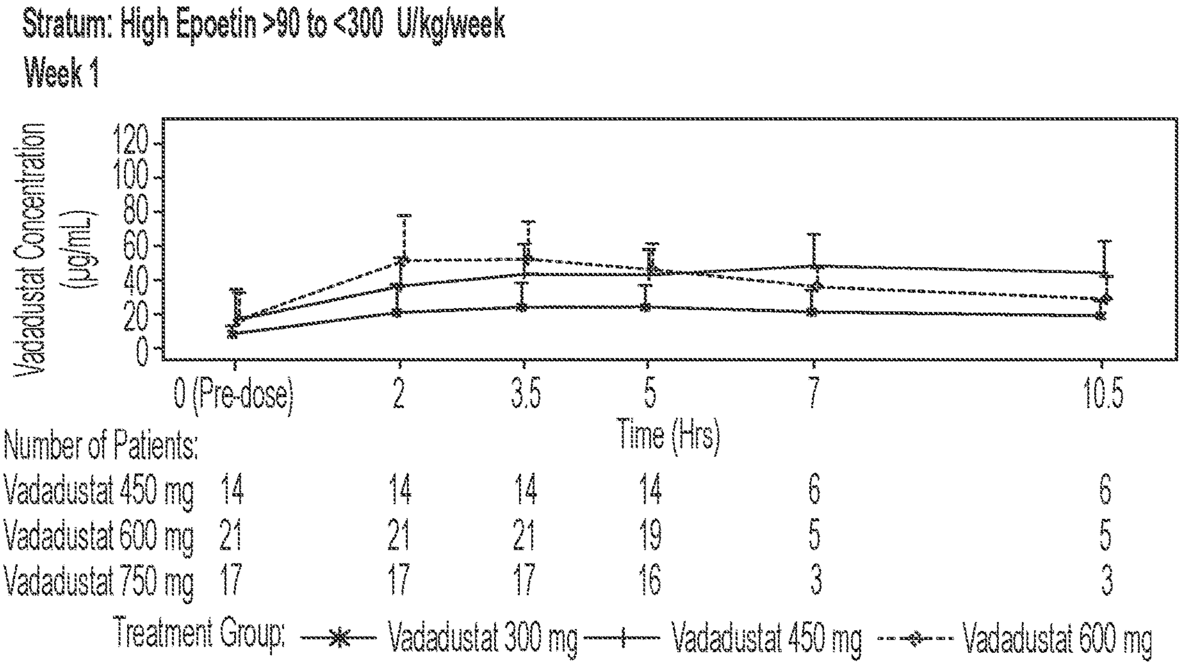
FIGS. 16*a*-16*d* illustrate mean (+SD) vadadustat concentration (μg/mL) versus nominal time in the High Epoetin Stratum (Linear Scale) (Pharmacokinetic Population, Main Study) on week 1, week 1+1 day, week 11, and week 13, respectively.
Figure 16B:
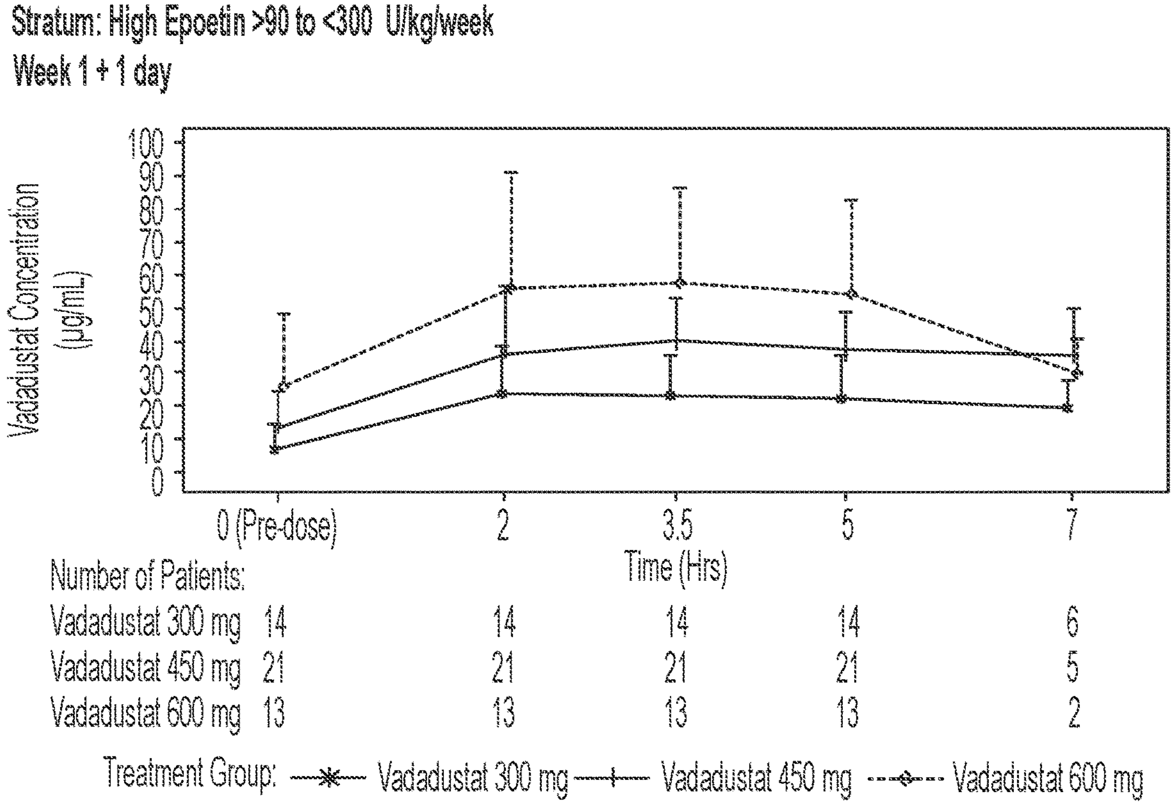
Figure 16C:
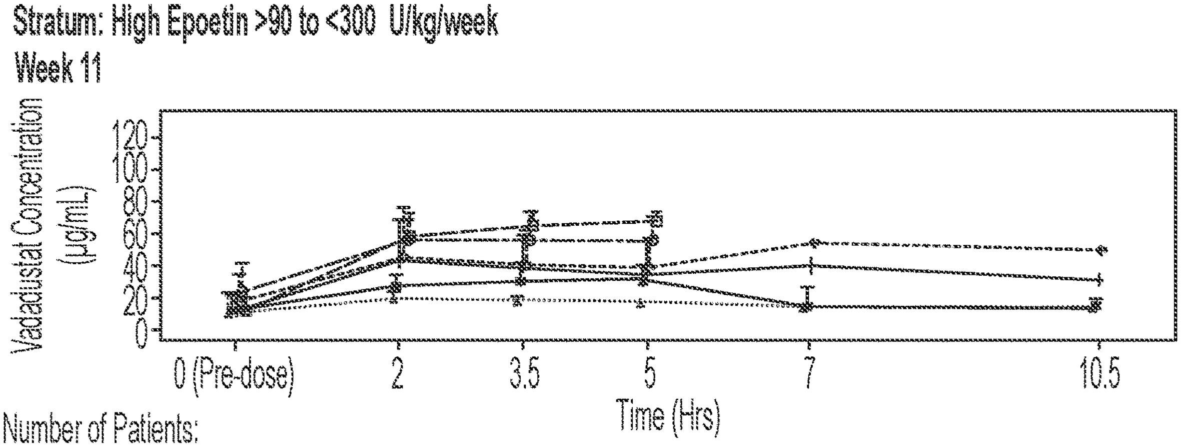
Figure 16D:
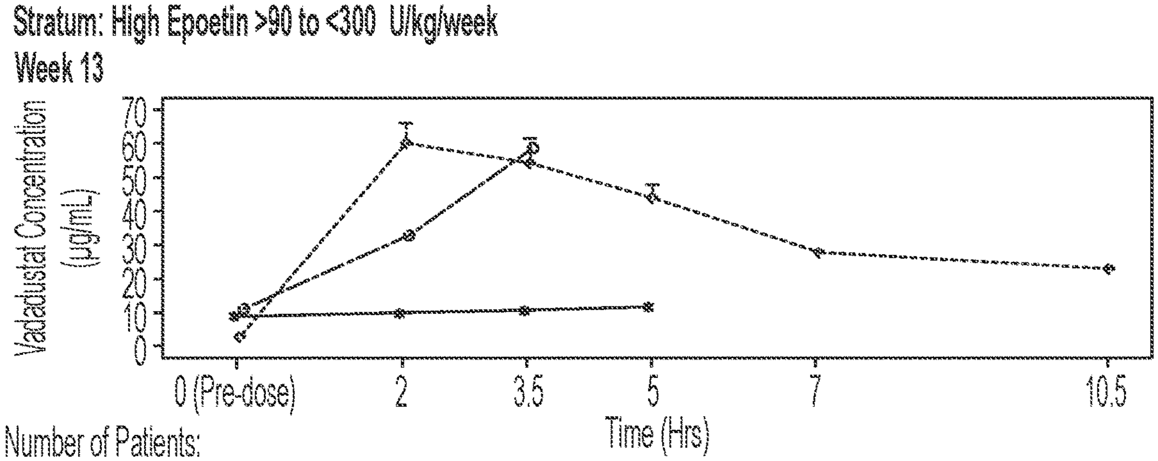
Figure 17A:
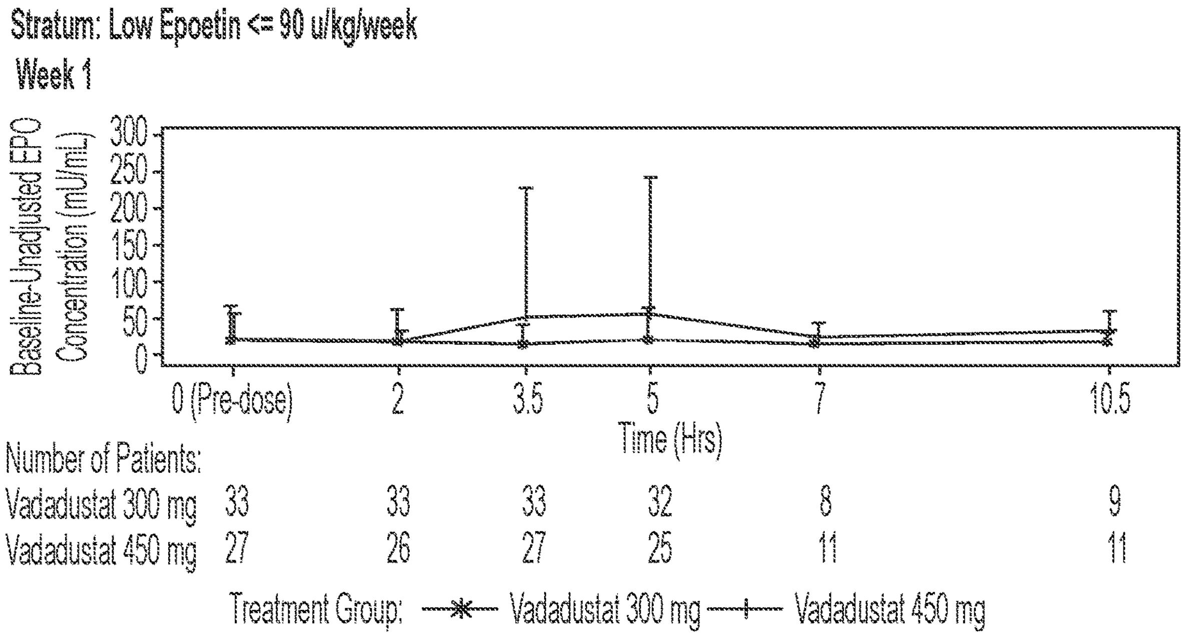
FIGS. 17*a*-17*d* illustrate mean (+SD) Baseline-Unadjusted Erythropoietin Concentration (mU/mL) versus Nominal Time (Linear Scale) for vadadustat treatment groups in the Low Epoetin Stratum (Pharmacokinetic Population, Main Study) on week 1, week 1+1 day, week 11, and week 13, respectively.
Figure 17B:
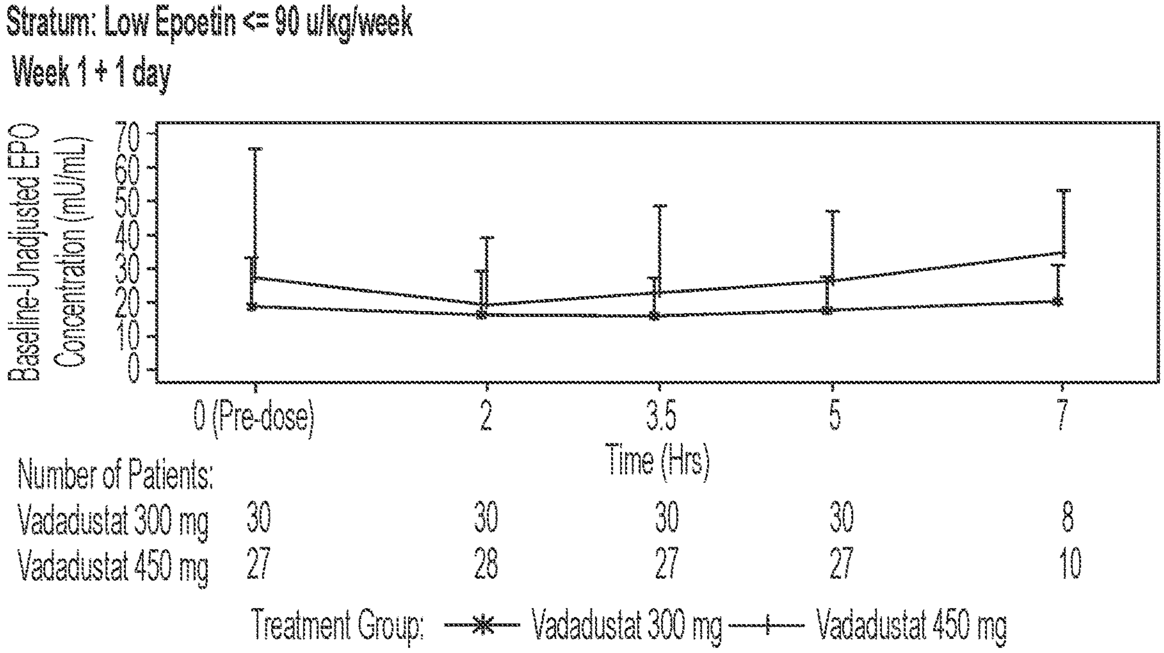
Figure 17C:
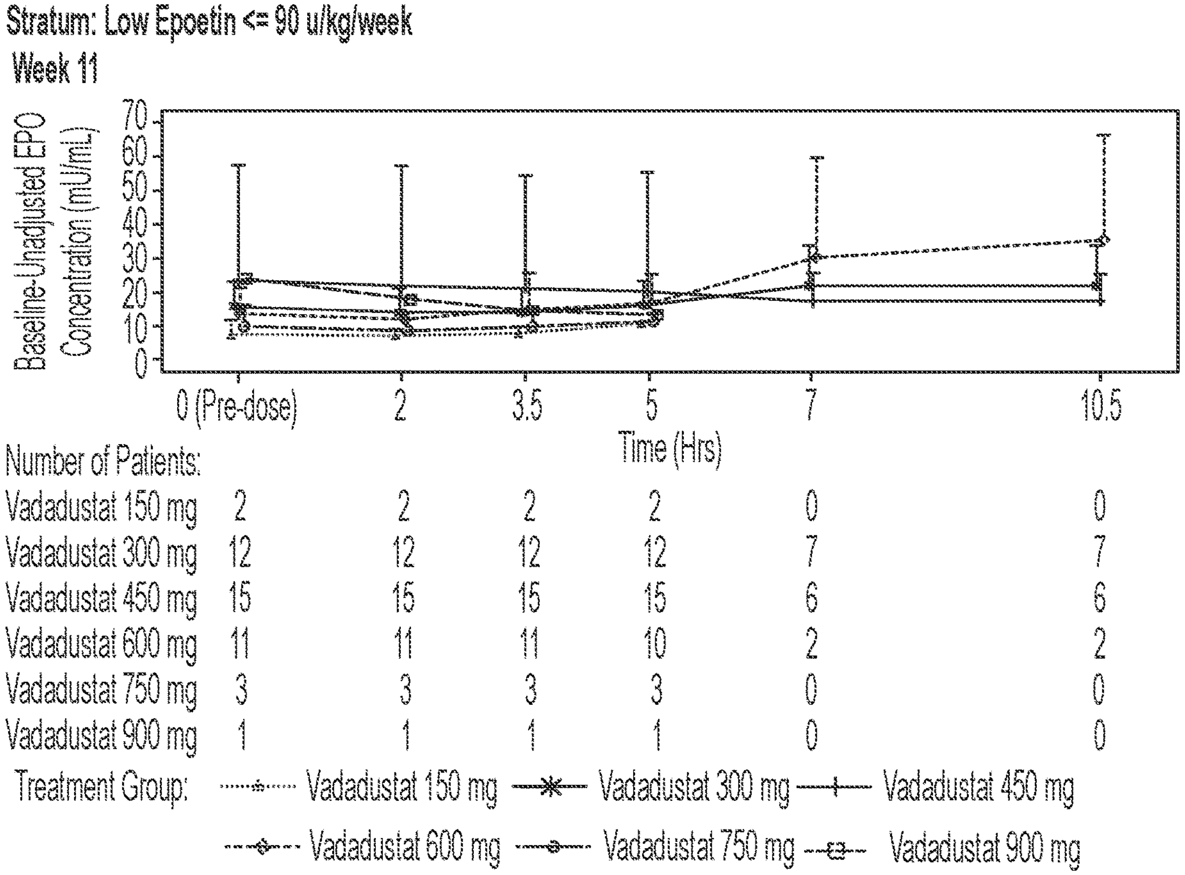
Figure 17D:
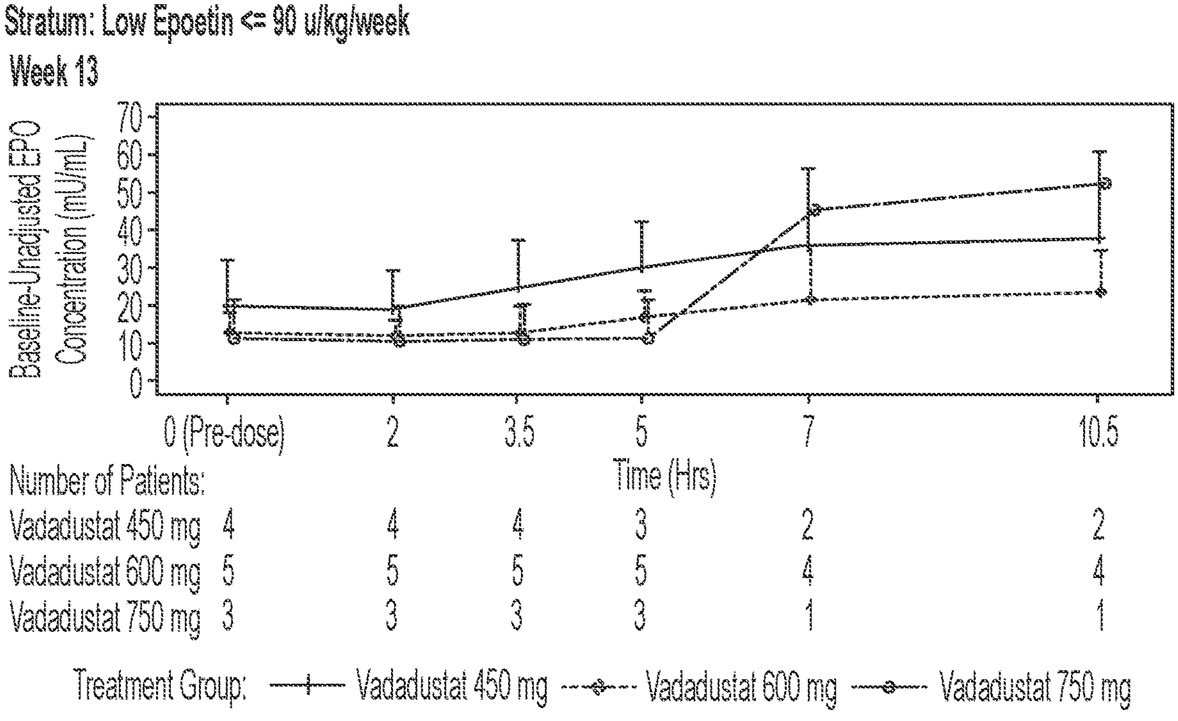
Figure 18A:
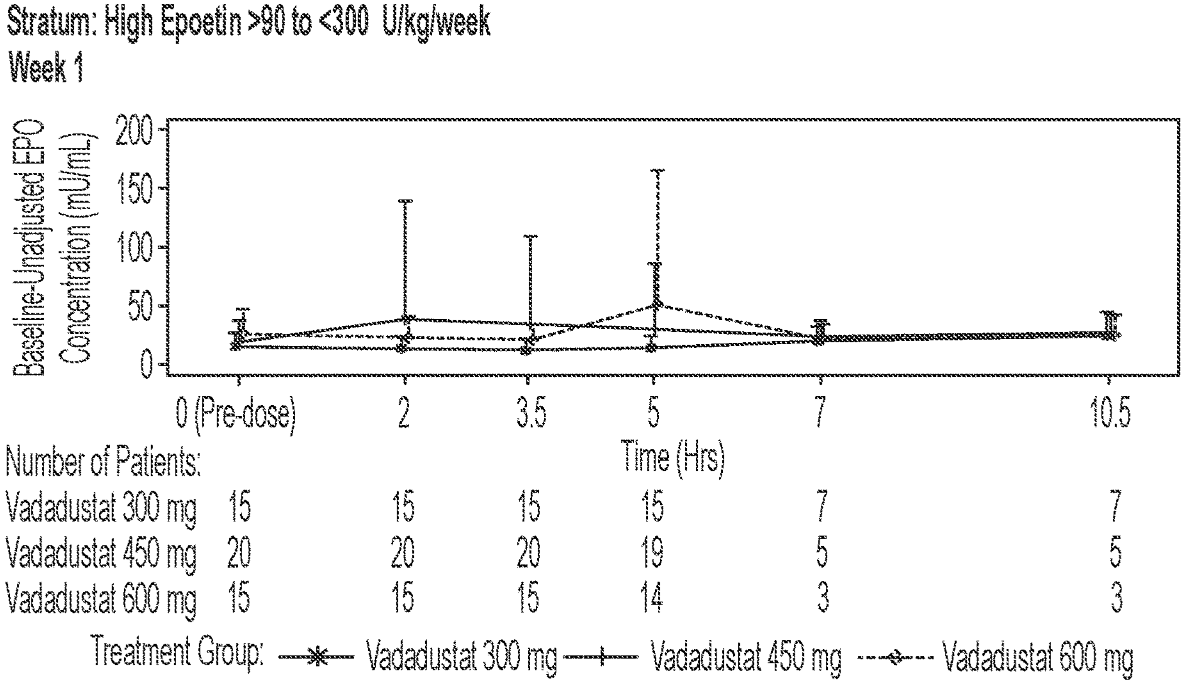
FIGS. 18*a*-18*d* illustrate mean (+SD) Baseline-Unadjusted Erythropoietin Concentration (mU/mL) versus Nominal Time (Linear Scale) for vadadustat treatment groups in the High Epoetin Stratum (Pharmacokinetic Population, Main Study) on week 1, week 1+1 day, week 11, and week 13, respectively.
Figure 18B:
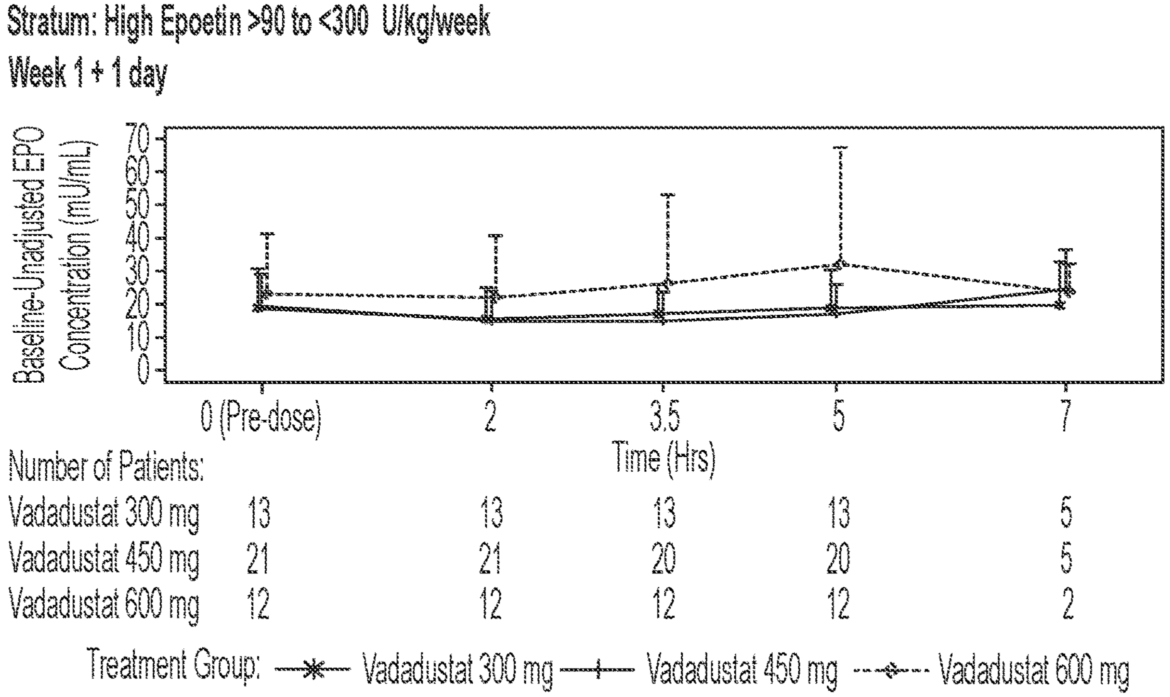
Figure 18C:
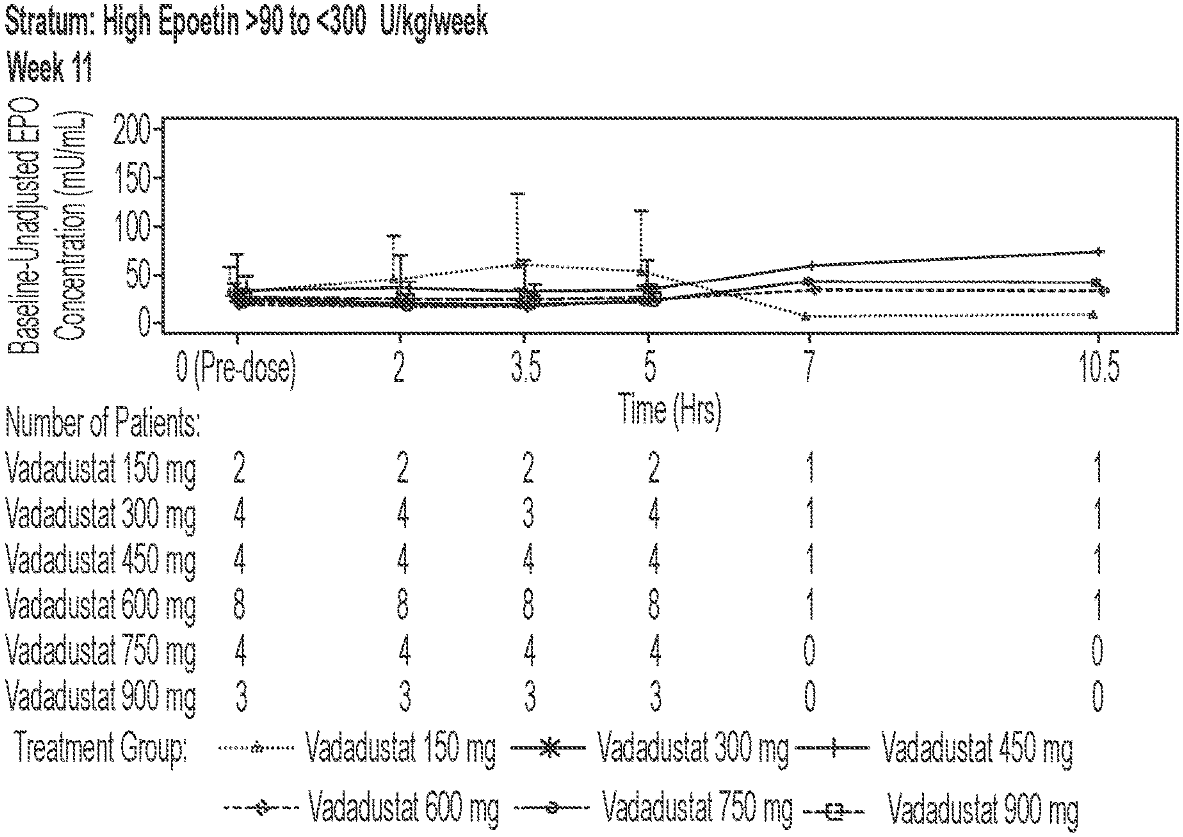
Figure 18D:
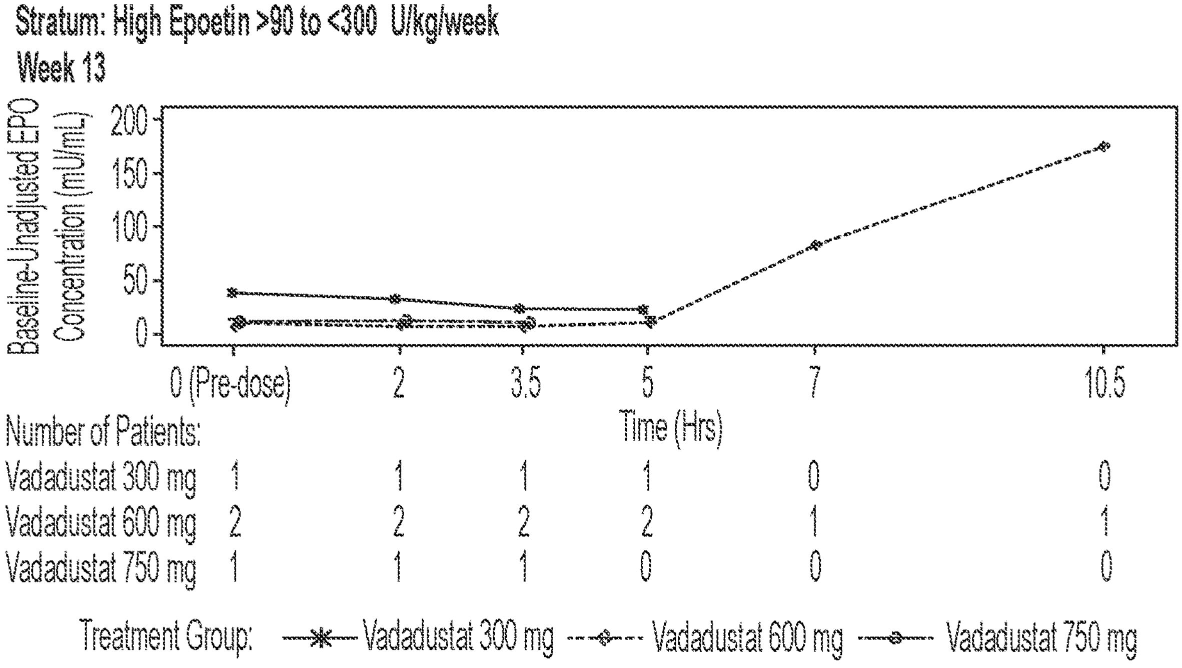

Mean change from baseline in Hb in the low and high epoetin strata are shown for the Randomized population in FIG. 13 and FIG. 14, respectively. Mean change from baseline in Hb in the vadadustat treatment group was lower than the epoetin alfa treatment group throughout. In the low epoetin alfa stratum, no decrease from baseline in Hb was observed (except for the vadadustat 300 mg group throughout treatment). In the high epoetin alfa stratum, vadadustat 300 mg subjects had a decrease from baseline in Hb up to Week 10, after which Hb began to return towards baseline.

Results were similar in the Randomized and PP populations.

The first key secondary endpoint for the Main Study was the proportion of subjects with Hb values within the target range (10.0 to 11.0 g/dL, inclusive) at the PEP (Weeks 10 to 12). The data are summarized in Table 5.

TABLE 5

Proportion of Subjects with Hemoglobin Values within the Target Range (10.0 to 11.0 g/dL) (Randomized Population, Main Study)

| Visit Meet Hb Target | Low Epoetin Alfa (<90 U/kg/week) Vada 300 mg N = 35 | Vada 450 mg N = 34 | Epoetin Alfa N = 23 | High Epoetin Alfa (>90 to <300 U/kg/week) Vada 300 mg N = 18 | Vada 450 mg N = 21 | Vada 600 mg N = 21 | Epoetin Alfa N = 13 |
|---|---|---|---|---|---|---|---|
| Primary Evaluation Period (Average of Weeks 10 to 12) | | | | | | | |
| N2 | 30 | 30 | 23 | 12 | 18 | 14 | 12 |
| Within Target | 12 (40.0) | 13 (43.3) | 15 (65.2) | 1 (8.3) | 4 (22.2) | 4 (28.6) | 6 (50.0) |
| Lower than Target | 16 (53.3) | 11 (36.7) | 5 (21.7) | 11 (91.7) | 10 (55.6) | 8 (57.1) | 4 (33.3) |
| Higher than Target | 2 (6.7) | 6 (20.0) | 3 (13.0) | 0 | 4 (22.2) | 2 (14.3) | 2 (16.7) |
| Secondary Evaluation Period (Average of Weeks 18 to 20) | | | | | | | |
| N2 | 26 | 24 | 23 | 7 | 14 | 10 | 12 |
| Within Target | 6 (23.1) | 7 (29.2) | 9 (39.1) | 2 (28.6) | 3 (21.4) | 2 (20.0) | 6 (50.0) |
| Lower than Target | 16 (61.5) | 14 (58.3) | 10 (43.5) | 4 (57.1) | 9 (64.3) | 7 (70.0) | 5 (41.7) |
| Higher than Target | 4 (15.4) | 3 (12.5) | 4 (17.4) | 1 (14.3) | 2 (14.3) | 1 (10.0) | 1 (8.3) |

N: number of subjects; Vada: vadadustat.
N2 = number of subjects with non-missing values. The percentage was calculated based on N2.

As shown in Table 5, the proportion of subjects having Hb values within target range at the PEP (Weeks 10 to 12) were 32.7% and 60.0% for the vadadustat and epoetin alfa treatment groups, respectively. The proportion of subjects having Hb values within target range at Weeks 10 to 12 was similar between the low and high epoetin alfa stratum, however, the lowest proportion was observed in the vadadustat 300 mg group of the high epoetin alfa stratum (8.3%; Table 2). In the high epoetin alfa strata, the number of subjects within target in the vadadustat treatment groups (particularly vadadustat 300 mg) were numerically lower compared to the epoetin alfa treatment group.

Results for the first key secondary endpoint were similar in the PP population.

The second key secondary endpoint for the Main Study was the mean change in Hb from PEP (average Hb from Weeks 10 to 12) to the SEP (average Hb from Weeks 18 to 20) for subjects who transitioned to TIW vadadustat dosing.

TABLE 6

Summary Statistics for Absolute and Change from Primary Evaluation Period to Secondary Evaluation Period in Hemoglobin (g/dL) for Subjects who Completed 12 Weeks of Treatment (Randomized Population, Main Study)

| Visit Statistics | Vadadustat Total: Subjects switched from QD to TIW N1 = 17 | Subjects did not switch N1 = 90 | Overall N1 = 107 | Epoetin Alfa Total N1 = 35 |
|---|---|---|---|---|
| Primary Evaluation Period (Average of Weeks 10 to 12) | | | | |
| n | 17 | 84 | 101 | 35 |
| Mean (SD) | 10.376 (0.3754) | 9.694 (1.2248) | 9.809 (1.1548) | 10.303 (0.8533) |
| Median | 10.433 | 9.483 | 9.900 | 10.400 |
| Q1, Q3 | 10.067, 10.700 | 8.775, 10.817 | 9.067, 10.767 | 9.600, 10.933 |
| Min, Max | 9.7, 10.9 | 6.6, 12.2 | 6.6, 12.2 | 8.33, 11.95 |
| Secondary Evaluation Period (Average of Weeks 18 to 20) | | | | |
| n | 17 | 62 | 79 | 35 |
| Mean (SD) | 9.955 (1.0716) | 9.854 (0.8378) | 9.876 (0.8867) | 10.269 (0.7596) |
| Q1, Q3 | 9.750, 10.100 | 9.300, 10.400 | 9.350, 10.400 | 9.650, 10.850 |
| Median | 9.900 | 9.800 | 9.800 | 10.350 |
| Min, Max | 7.9, 12.8 | 7.97, 11.4 | 7.9, 12.8 | 8.8, 12 |
| Change from Primary Evaluation Period to Secondary Evaluation Period | | | | |
| n | 17 | 59 | 76 | 35 |
| Mean (SD) | −0.422 (1.1708) | 0.039 (1.2286) | −0.064 (1.2236) | −0.034 (0.7156) |
| Q1, Q3 | −0.733, −0.017 | −0.700, 0.650 | −0.717, 0.433 | −0.617, 0.500 |
| Median | −0.350 | 0.067 | −0.033 | −0.017 |
| Min, Max | −2.57, 2.77 | −2.72, 4.15 | −2.72, 4.15 | −1.05, 1.83 |

Q1: first quartile; Q3: third quartile; SD: standard deviation; TIW: three times per week.
N1 = number of subjects who completed 12 weeks of treatment.

As shown in Table 6, the change in Hb from PEP (Weeks 10 to 12) to SEP (Weeks 18 to 20) in the 17 subjects who switched from QD to TIW was −0.422 g/dL compared to no change (0.039 g/dL) in the 59 subjects who did not switch.

Results for the second key secondary endpoint were similar for the PP population.

Pharmacokinetic and Pharmacodynamic Results

Mean vadadustat concentration in the low and high epoetin alfa strata is shown in FIGS. 15*a*-15*d* and FIGS. 16*a*-16*d*, respectively.

The mean concentration versus time profiles for vadadustat and vadadustat-O-glucuronide exhibited dose dependencies as concentrations increased with dose levels at Week 1, Week 1+1 day, and Week 11. Variability in concentrations was evident across these dose levels.

The mean concentrations-time profiles were similar on dialysis and non-dialysis days on Week 1.

No dose dependent increases in concentrations were observed in the TIW group.

For vadadustat treatment groups in the low epoetin alfa stratum, a dose dependent increase in EPO concentration was observed on Week 1 and Week 1+1 day in the vadadustat 300 and 450 mg dosing groups, and on Week 11 in the vadadustat 150, 300, 450, and 600 mg dosing groups (FIGS. 17*a-d*). In the high epoetin alfa stratum, no particular trend was evident for EPO concentration (FIGS. 18*a-d*).

PD parameters for serum EPO concentration are presented by epoetin alfa stratification for vadadustat treatment groups in Table 7, Table 8a and Table 8b (baseline-unadjusted) and Table 9, Table 10a and Table 10b (baseline-adjusted).

In the vadadustat low epoetin alfa stratum, EPO $C_{max}$ and AUC were dose proportional in Week 1 and Week 1+1 day and were lower compared to the epoetin alfa treatment group. In the vadadustat high epoetin alfa stratum, EPO $C_{max}$ was dose dependent in Week 1, however, the AUC was similar for the 450 and 600 mg vadadustat dose groups. EPO $C_{max}$ was similar for the 300 and 450 mg vadadustat dose groups and higher for the 600 mg dose group, and AUC was dose dependent on Week 1+1 day. As the available data set was limited, a similar trend was not observed on Week 11 and Week 13.

TABLE 7

Summary of Pharmacodynamics Parameters for Baseline-Unadjusted Serum EPO Concentration for Vadadustat Treatment Groups by Epoetin Alfa Stratification at Weeks 1 and 1 + 1 (Pharmacokinetic Population, Main Study)

| Parameter | Vada 300 mg | | Vada 450 mg | | Vada 600 mg | |
|---|---|---|---|---|---|---|
| Statistics | Week 1 | Week 1 + 1 | Week 1 | Week 1 + 1 | Week 1 | Week 1 + 1 |
| Low Epoetin Alfa Stratum ≤90 U/kg/week | | | | | | |
| $AUC_{0-5}$ (h*μg/mL) | | | | | | |
| n | 33 | 30 | 27 | 27 | 0 | 0 |
| Geometric Mean (SD) | 58.5 (193.0) | 65.7 (57.81) | 76.4 (411.9) | 80.2 (123.1) | — | — |
| $C_{max}$ (μg/mL) | | | | | | |
| n | 33 | 30 | 27 | 28 | 0 | 0 |
| Geometric Mean (SD) | 17.6 (47.85) | 19.3 (14.71) | 25.5 (179.80) | 23.9 (37.64) | — | — |
| $T_{max}$ (h) | | | | | | |
| n | 33 | 30 | 27 | 28 | 0 | 0 |
| Median (min, max) | 4.50 (0, 9.50) | 2.75 (0, 6.92) | 4.50 (0, 10.50) | 4.51 (0, 7.43) | — | — |
| High Epoetin Alfa Stratum >90 to <300 U/kg/week | | | | | | |
| $AUC_{0-5}$ (h*μg/mL) | | | | | | |
| n | 15 | 13 | 20 | 21 | 15 | 12 |
| Geometric Mean (SD) | 56.0 (44.74) | 74.9 (41.84) | 79.9 (320.5) | 61.6 (43.15) | 102.0 (103.60) | 89.9 (102.80) |
| $C_{max}$ (μg/mL) | | | | | | |
| n | 15 | 13 | 20 | 21 | 15 | 12 |
| Geometric Mean (SD) | 17.5 (15.64) | 20.5 (12.78) | 23.4 (99.19) | 18.1 (10.86) | 33.2 (108.20) | 27.2 (34.35) |
| $T_{max}$ (h) | | | | | | |
| n | 15 | 13 | 20 | 21 | 15 | 12 |
| Median (min, max) | 2.00 (0, 11.98) | 2.02 (0, 6.78) | 4.53 (0, 9.62) | 0 (0, 6.95) | 0 (0, 9.03) | 2.47 (0, 7.00) |

'—': not applicable;
$AUC_{0-5}$: area under the concentration-time curve from time 0 to 5 hours;
Cmax: maximum observed plasma concentration;
max: maximum;
min: minimum;
SD: standard deviation;
Tmax: time to maximal observed plasma concentration;
Vada: vadadustat;
Geometric Mean = exp(mean of log(value)).

TABLE 8a

Summary of Pharmacodynamics Parameters for Baseline-Unadjusted Serum EPO Concentration for Vadadustat Treatment Groups by Epoetin Alfa Stratification at Weeks 11 and 13 (Pharmacokinetic Population, Main Study, vada 150, 300 and 450 mg)

| | Vada 150 mg | | Vada 300 mg | | Vada 450 mg | |
|---|---|---|---|---|---|---|
| Parameter Statistics | Week 11[a] | Week 13 | Week 11[a] | Week 13 | Week 11[a] | Week 13 |
| Low Epoetin Alfa Stratum ≤90 U/kg/week | | | | | | |
| $AUC_{0-5}$ (h*µg/mL) | | | | | | |
| n | 2 | 0 | 12 | 0 | 15 | 4 |
| Geometric Mean (SD) | 37.6 (11.52) | — | 65.2 (32.67) | — | 65.1 (172.0) | 88.4 (60.49) |
| $C_{max}$ (µg/mL) | | | | | | |
| n | 2 | 0 | 12 | 0 | 15 | 4 |
| Geometric Mean (SD) | 10.7 (0.35) | — | 20.0 (10.06) | — | 17.7 (35.18) | 28.8 (15.51) |
| $T_{max}$ (h) | | | | | | |
| n | 2 | 0 | 12 | 0 | 15 | 4 |
| Median (min, max) | 4.78 (4.50, 5.07) | — | 3.29 (0, 10.00) | — | 2.08 (0, 9.13) | 3.94 (0, 10.50) |
| High Epoetin Alfa Stratum >90 to <300 U/kg/week | | | | | | |
| $AUC_{0-5}$ (h*µg/mL) | | | | | | |
| n | 2 | 0 | 4 | 1 | 4 | 0 |
| Geometric Mean (SD) | 143.0 (233.9) | — | 84.4 (71.75) | 125 (—) | 97.5 (169.3) | — |
| $C_{max}$ (µg/mL) | | | | | | |
| n | 2 | 0 | 4 | 1 | 4 | 0 |
| Geometric Mean (SD) | 39.0 (69.58) | — | 23.5 (19.83) | 39.2 (—) | 24.9 (37.65) | — |
| $T_{max}$ (h) | | | | | | |
| n | 2 | 0 | 4 | 1 | 4 | 0 |
| Median (min, max) | 1.63 (0, 3.25) | — | 0.97 (0, 7.00) | 0 (0, 0) | 0.88 (0, 5.02) | — |

'—': not applicable;
$AUC_{0-5}$: area under the concentration-time curve from time 0 to 5 hours;
Cmax: maximum observed plasma concentration;
max: maximum;
min: minimum;
SD: standard deviation;
Tmax: time to maximal observed plasma concentration;
Vada: vadadustat;
Geometric Mean = exp(mean of log(value)).

TABLE 8b

Summary of Pharmacodynamics Parameters for Baseline-Unadjusted Serum EPO Concentration for Vadadustat Treatment Groups by Epoetin Alfa Stratification at Weeks 11 and 13 (Pharmacokinetic Population, Main Study, vada 600, 750 and 900 mg)

| | Vada 600 mg | | Vada 750 mg | | Vada 900 mg | |
|---|---|---|---|---|---|---|
| Parameter Statistics | Week 11[a] | Week 13 | Week 11[a] | Week 13 | Week 11[a] | Week 13 |
| Low Epoetin Alfa Stratum ≤90 U/kg/week | | | | | | |
| $AUC_{0-5}$ (h*µg/mL) | | | | | | |
| n | 11 | 5 | 3 | 3 | 1 | 0 |
| Geometric Mean (SD) | 53.8 (33.57) | 59.4 (29.51) | 41.3 (18.51) | 40.8 (49.16) | 81.0 (—) | — |
| $C_{max}$ (µg/mL) | | | | | | |
| n | 11 | 5 | 3 | 3 | 1 | 0 |
| Geometric Mean (SD) | 18.5 (15.59) | 20.7 (11.87) | 12.5 (3.48) | 13.2 (26.27) | 24.4 (—) | — |

TABLE 8b-continued

Summary of Pharmacodynamics Parameters for Baseline-Unadjusted Serum EPO Concentration for Vadadustat Treatment Groups by Epoetin Alfa Stratification at Weeks 11 and 13 (Pharmacokinetic Population, Main Study, vada 600, 750 and 900 mg)

| Parameter Statistics | Vada 600 mg Week 11[a] | Vada 600 mg Week 13 | Vada 750 mg Week 11[a] | Vada 750 mg Week 13 | Vada 900 mg Week 11[a] | Vada 900 mg Week 13 |
|---|---|---|---|---|---|---|
| $T_{max}$ (h) | | | | | | |
| n | 11 | 5 | 3 | 3 | 1 | 0 |
| Median | 4.50 | 7.08 | 4.50 | 4.50 | 0 | — |
| (min, max) | (0, 9.25) | (0, 9.17) | (0, 4.75) | (0, 9.25) | (0, 0) | |
| High Epoetin Alfa Stratum >90 to <300 U/kg/week | | | | | | |
| $AUC_{0-5}$ (h*μg/mL) | | | | | | |
| n | 8 | 2 | 4 | 1 | 3 | 0 |
| Geometric Mean (SD) | 83.2 (38.08) | 44.0 (2.93) | 84.6 (51.60) | 42.9 (—) | 96.5 (76.69) | — |
| $C_{max}$ (μg/mL) | | | | | | |
| n | 8 | 2 | 4 | 1 | 3 | 0 |
| Geometric Mean (SD) | 23.4 (14.76) | 49.9 (112.1) | 21.9 (10.35) | 14.1 (—) | 30.2 (15.54) | — |
| $T_{max}$ (h) | | | | | | |
| n | 8 | 2 | 4 | 1 | 3 | 0 |
| Median | 0.92 | 4.63 | 4.06 | 0 | 0 | — |
| (min, max) | (0, 6.98) | (0, 9.25) | (0, 5.00) | (0, 0) | (0, 4.50) | |

'—': not applicable;
$AUC_{0-5}$: area under the concentration-time curve from time 0 to 5 hours;
Cmax: maximum observed plasma concentration;
max: maximum;
min: minimum;
SD: standard deviation;
Tmax: time to maximal observed plasma concentration;
Vada: vadadustat;
Geometric Mean = exp(mean of log(value)).

TABLE 9

Summary of Pharmacodynamics Parameters for Baseline-Adjusted Serum EPO Concentration for Vadadustat Treatment Groups by Epoetin Alfa Stratification at Weeks 1 and 1 + 1 (Pharmacokinetic Population, Main Study)

| Parameter Statistics | Vada 300 mg Week 1 | Vada 300 mg Week 1 + 1 | Vada 450 mg Week 1 | Vada 450 mg Week 1 + 1 | Vada 600 mg Week 1 | Vada 600 mg Week 1 + 1 |
|---|---|---|---|---|---|---|
| Low Epoetin Alfa Stratum ≤90 U/kg/week | | | | | | |
| $AUC_{0-5}$ (h*μg/mL) | | | | | | |
| n | 29 | 25 | 21 | 23 | 0 | 0 |
| Geometric Mean (SD) | 19.6 (206.5) | 30.1 (53.50) | 32.9 (465.1) | 28.3 (128.4) | — | — |
| $C_{max}$ (μg/mL) | | | | | | |
| n | 32 | 29 | 26 | 27 | 0 | 0 |
| Geometric Mean (SD) | 9.1 (49.02) | 10.1 (14.63) | 18.1 (184.1) | 11.8 (38.51) | — | — |
| $T_{max}$ (h) | | | | | | |
| n | 32 | 29 | 26 | 27 | 0 | 0 |
| Median | 4.50 | 2.00 | 1.75 | 4.50 | — | — |
| (min, max) | (0 to 9.50) | (0 to 6.92) | (0 to 10.50) | (0 to 7.43) | | |
| High Epoetin Alfa Stratum >90 to <300 U/kg/week | | | | | | |
| $AUC_{0-5}$ (h*μg/mL) | | | | | | |
| n | 7 | 7 | 16 | 16 | 12 | 10 |
| Geometric Mean (SD) | 18.1 (44.37) | 21.8 (34.45) | 32.5 (357.3) | 23.9 (37.56) | 59.1 (118.50) | 27.0 (110.10) |

TABLE 9-continued

Summary of Pharmacodynamics Parameters for Baseline-Adjusted Serum EPO Concentration for Vadadustat Treatment Groups by Epoetin Alfa Stratification at Weeks 1 and 1 + 1 (Pharmacokinetic Population, Main Study)

| Parameter | Vada 300 mg | | Vada 450 mg | | Vada 600 mg | |
|---|---|---|---|---|---|---|
| Statistics | Week 1 | Week 1 + 1 | Week 1 | Week 1 + 1 | Week 1 | Week 1 + 1 |
| | | | $C_{max}$ (μg/mL) | | | |
| n | 12 | 10 | 17 | 18 | 13 | 10 |
| Geometric | 9.1 | 7.2 | 14.0 | 10.0 | 26.0 | 18.9 |
| Mean (SD) | (17.56) | (10.84) | (107.8) | (9.54) | (117.0) | (36.70) |
| | | | $T_{max}$ (h) | | | |
| n | 12 | 10 | 17 | 18 | 13 | 10 |
| Median | 0 | 0 | 4.50 | 0 | 0 | 2.47 |
| (min, max) | (0 to 11.98)\| | (0 to 6.75) | (0 to 9.62) | (0 to 6.95) | (0, 9.03) | (0, 7.00) |

'—': not applicable;
AUC0-5: area under the concentration-time curve from time 0 to 5 hours;
Cmax: maximum observed plasma concentration;
max: maximum;
min: minimum;
SD: standard deviation;
Tmax: time to maximal observed plasma concentration;
Vada: vadadustat;
Geometric Mean = exp(mean of log(value)).

TABLE 10a

Summary of Pharmacodynamics Parameters for Baseline-Adjusted Serum EPO Concentration for Vadadustat Treatment Groups by Epoetin Alfa Stratification at Weeks 11 and 13 (Pharmacokinetic Population, Main Study, vada 150, 300 and 450 mg)

| | Vada 150 mg | | Vada 300 mg | | Vada 450 mg | |
|---|---|---|---|---|---|---|
| Parameter Statistics | Week 11 | Week 13 | Week 11 | Week 13 | Week 11 | Week 13 |
| | | | Low Epoetin Alfa Stratum ≤90 U/kg/week AUC0-5 (h*μg/mL) | | | |
| n | 2 | 0 | 9 | 0 | 14 | 4 |
| Geometric | 6.81 | — | 31.0 | — | 22.4 | 19.7 |
| Mean (SD) | (8.16) | | (28.86) | | (180.2) | (33.11) |
| | | | $C_{max}$ (μg/mL) | | | |
| n | 2 | 0 | 12 | 0 | 15 | 4 |
| Geometric | 4.32 | — | 14.5 | — | 8.00 | 11.4 |
| Mean (SD) | (0.26) | | (11.84) | | (35.75) | (12.58) |
| | | | $T_{max}$ (h) | | | |
| n | 2 | 0 | 12 | 0 | 15 | 4 |
| Median | 4.78 | — | 1.00 | — | 2.08 | 3.94 |
| (min, max) | (4.50, 5.07) | | (0, 10.00) | | (0, 9.13) | (0, 10.50) |
| | | | High Epoetin Alfa Stratum >90 to <300 U/kg/week AUC0-5 (h*μg/mL) | | | |
| n | 1 | 0 | 2 | 0 | 4 | 0 |
| Geometric | 7.09 | — | 83.0 | — | 49.7 | — |
| Mean (SD) | (—) | | (58.39) | | (181.1) | |
| | | | $C_{max}$ (μg/mL) | | | |
| n | 1 | 0 | 4 | 0 | 4 | 0 |
| Geometric | 4.29 | — | 33.8 | — | 15.5 | — |
| Mean (SD) | (—) | | (19.54) | | (39.32) | |

TABLE 10a-continued

Summary of Pharmacodynamics Parameters for Baseline-Adjusted Serum EPO Concentration for Vadadustat Treatment Groups by Epoetin Alfa Stratification at Weeks 11 and 13 (Pharmacokinetic Population, Main Study, vada 150, 300 and 450 mg)

| Parameter Statistics | Vada 150 mg Week 11 | Vada 150 mg Week 13 | Vada 300 mg Week 11 | Vada 300 mg Week 13 | Vada 450 mg Week 11 | Vada 450 mg Week 13 |
|---|---|---|---|---|---|---|
| $T_{max}$ (h) | | | | | | |
| n | 1 | 0 | 4 | 0 | 4 | 0 |
| Median | 0 | — | 0 | — | 0.88 | — |
| (min, max) | (0, 0) | | (0 to 7.00) | | (0 to 5.02) | |

'—': not applicable;
AUC0-5: area under the concentration-time curve from time 0 to 5 hours;
Cmax: maximum observed plasma concentration;
max: maximum;
min: minimum;
SD: standard deviation;
Tmax: time to maximal observed plasma concentration;
Vada: vadadustat;
Geometric Mean = exp(mean of log(value)).

TABLE 10b

Summary of Pharmacodynamics Parameters for Baseline-Adjusted Serum EPO Concentration for Vadadustat Treatment Groups by Epoetin Alfa Stratification at Weeks 11 and 13 (Pharmacokinetic Population, Main Study, vada 600, 750 and 900 mg)

| Parameter Statistics | Vada 600 mg Week 11 | Vada 600 mg Week 13 | Vada 750 mg Week 11 | Vada 750 mg Week 13 | Vada 900 mg Week 11 | Vada 900 mg Week 13 |
|---|---|---|---|---|---|---|
| Low Epoetin Alfa Stratum ≤90 U/kg/week | | | | | | |
| $AUC_{0-5}$ (h*μg/mL) | | | | | | |
| n | 9 | 5 | 3 | 2 | 1 | 0 |
| Geometric Mean (SD) | 29.8 (24.64) | 7.00 (3.35) | 6.3 (8.26) | 11.7 (52.29) | 17.9 (—) | — |
| $C_{max}$ (μg/mL) | | | | | | |
| n | 10 | 5 | 3 | 3 | 1 | 0 |
| Geometric Mean (SD) | 13.7 (15.29) | 8.1 (5.96) | 3.91 (2.11) | 7.7 (25.81) | 10.8 (—) | — |
| $T_{max}$ (h) | | | | | | |
| n | 10 | 5 | 3 | 3 | 1 | 0 |
| Median (min, max) | 4.00 (0, 9.25) | 7.08 (0, 9.17) | 4.50 (0, 4.75) | 4.50 (0, 9.25) | 0 (0, 0) | — |
| High Epoetin Alfa Stratum >90 to <300 U/kg/week | | | | | | |
| $AUC_{0-5}$ (h*μg/mL) | | | | | | |
| n | 7 | 1 | 3 | 1 | 3 | 0 |
| Geometric Mean (SD) | 41.1 (33.97) | 42.0 (—) | 48.5 (34.81) | 19.0 (—) | 48.3 (88.65) | — |
| Cmax (μg/mL) | | | | | | |
| n | 8 | 2 | 3 | 1 | 3 | 0 |
| Geometric Mean (SD) | 14.6 (16.94) | 173.0 (122.30) | 14.8 (8.75) | 6.8 (—) | 21.4 (18.78) | — |

TABLE 10b-continued

Summary of Pharmacodynamics Parameters for Baseline-Adjusted Serum EPO Concentration for Vadadustat Treatment Groups by Epoetin Alfa Stratification at Weeks 11 and 13 (Pharmacokinetic Population, Main Study, vada 600, 750 and 900 mg)

| | Vada 600 mg | | Vada 750 mg | | Vada 900 mg | |
|---|---|---|---|---|---|---|
| Parameter Statistics | Week 11 | Week 13 | Week 11 | Week 13 | Week 11 | Week 13 |
| Tmax (h) | | | | | | |
| n | 8 | 2 | 3 | 1 | 3 | 0 |
| Median | 0.92 | 4.63 | 4.75 | 0 | 0 | — |
| (min, max) | (0, 6.98) | (0, 9.25) | (0, 5.00) | (0, 0) | (0, 4.50) | |

'—': not applicable;
AUC0-5: area under the concentration-time curve from time 0 to 5 hours;
Cmax: maximum observed plasma concentration;
max: maximum;
min: minimum;
SD: standard deviation;
Tmax: time to maximal observed plasma concentration;
Vada: vadadustat;
Geometric Mean = exp(mean of log(value)).

Pharmacokinetic and Pharmacodynamic Summary and Discussion.

Results were drawn from the Main Study.

Vadadustat PK was similar on dialysis day and non-dialysis day. The mean concentration versus time profiles for vadadustat and vadadustat-O-glucuronide metabolite exhibited dose dependencies as concentrations increased with dose levels at Week 1, Week 1+1 day, and Week 11. However, a single patient in the low epoetin stratification group at vadadustat 900 mg dose on Week 11 exhibited a low concentration profile compared to the rest of the PK population.

Dose dependent increases in EPO concentrations were observed on Week 1 and Week 1+1 day in the vadadustat 300 and 450 mg dosing groups in the low epoetin alfa stratum. No particular trend was observed in the high epoetin alfa stratification group.

A higher EPO Cmax and AUC were observed in the epoetin alfa treatment group compared to the vadadustat treatment group due to exogenous administration of ESA.

Efficacy Summary and Discussion

Conclusions drawn from the Main Study included: treatment with vadadustat resulted in lower mean (SD) Hb overall at Weeks 10 to 12 compared to epoetin alfa.

The primary efficacy endpoint was to assess the mean change in Hb between baseline and the PEP (Weeks 10 to 12) in hemodialysis subjects. In the Main Study, the mean change from baseline in Hb in the vadadustat treatment group was numerically lower than the epoetin alfa treatment group throughout. In the low epoetin alfa stratum, no decrease from baseline in Hb was observed (except for the vadadustat 300 mg group throughout treatment). In the high epoetin alfa stratum, vadadustat 300 mg subjects had a decrease from baseline in Hb up to Week 10, after which Hb began to return towards baseline.

The first key secondary efficacy endpoint was the proportion of subjects with Hb values within the target range (10.0 to 11.0 g/dL, inclusive) at the PEP (Weeks 10 to 12). The proportion of subjects having Hb values within target range at Weeks 10 to 12 was similar between the low and high epoetin alfa strata, however, the lowest proportion was observed in the vadadustat 300 mg group of the high epoetin alfa stratum (8.3%; Table 11). In the high epoetin alfa stratum, the number of subjects within target in the vadadustat treatment groups (particularly vadadustat 300 mg) were numerically lower compared to the epoetin alfa treatment group.

The second key secondary endpoint was the mean change in Hb from PEP (average Hb from Weeks 10 to 12) to the SEP (average Hb from Weeks 18 to 20) for subjects who transitioned to TIW vadadustat dosing. In the Main Study, the change in Hb from PEP to SEP for the 17 subjects who switched from QD to TIW was −0.4 g/dL.

The mean change in Hb between baseline and the SEP was lower in the vadadustat treatment group compared to the epoetin alfa treatment group in the Main Study. Results were similar in mean change in Hb between Baseline and the SEP compared to the primary efficacy endpoint of mean change in Hb between Baseline and the PEP. The mean Hb in the SEP was lower than in the PEP.

In subjects who received any ESA administration, there were more vadadustat treated subjects receiving ESA than epoetin alfa treated subjects from Baseline (inclusive) to Week 20 (inclusive). In subjects who received ESA administration as rescue, there were more vadadustat treated subjects receiving ESA than epoetin alfa treated subjects from Baseline (inclusive) to Week 12 (inclusive).

The proportion of subjects with RBC transfusion and RBC transfusion as rescue were similar for vadadustat treatment groups across all study periods, and there were no RBC transfusions for the epoetin alfa treatment groups.

Dose-dependent increase in EPO levels in Week 1 and Week 1+1 day occurred in the low epoetin stratum. The increase in EPO levels were within what was considered to be physiological range. There was no particular change in the EPO levels in the high epoetin stratum.

Example 3. Phase 3b, Randomized Open-Label, Active-Controlled Trial Evaluating the Efficacy and Safety of Oral Vadadustat (Compound 1) Once Daily (QD) and Three Times Weekly (TIW) for the Maintenance Treatment of Anemia in Hemodialysis Subjects Converting from Erythropoiesis-Stimulating Agents (ESAs)

The primary objective of the trial is to demonstrate the efficacy and safety of vadadustat compared to darbepoetin alfa for the maintenance treatment of anemia in hemodialysis subjects after conversion from current ESA therapy.

Efficacy Endpoints. Primary endpoints of the trial include the following efficacy parameters for change in hemoglobin (Hb) between Baseline (average pretreatment Hb) and the primary evaluation period (average Hb from Weeks 20 to 26, inclusive). Key secondary endpoints of the trial include the following efficacy parameters for change in Hb value between Baseline and the secondary evaluation period (average Hb from Weeks 46 to 52), the proportion of subjects having average Hb values within the target range during the primary evaluation period (Weeks 20 to 26), and the proportion of subjects having average Hb values within the target range during the secondary evaluation period (Weeks 46 to 52). Other secondary endpoints of the trial include the following efficacy parameters: proportion of time with Hb values within the target range during the primary evaluation period (Weeks 20 to 26); proportion of time with Hb values within the target range during the secondary evaluation period (Weeks 46 to 52); proportion of subjects receiving intravenous (IV) iron therapy from Baseline to Week 52; average monthly dose of IV elemental iron administered from Baseline to Week 52 in subjects who have received IV elemental iron; receipt of ESA rescue; proportion of subjects receiving red blood cell (RBC) transfusions from Baseline to Week 26; proportion of subjects receiving RBC transfusions from Baseline to Week 52; change from Screening Visit 2p 36-Item Short Form (SF-36v2) Health-related Quality of Life (HRQOL) scores; change from Screening Visit 2 to the average value in Anemia Subscale ("Additional Concerns") of Functional Assessment of Cancer Therapy-Anemia (FACT-An) Score; change from Screening Visit 2 to the average value in Total FACT-An Score; change from Screening Visit 2 in score of patient global impression of severity (PGI-S); and score of patient global impression of change (PGI-C).

Safety Endpoints. Safety variables of the trial include adverse events (AEs) and serious adverse events (SAEs), vital sign measurements, electrocardiograms (ECGs) and clinical laboratory values including complete blood count (CBC), reticulocyte count, folate, $B_{12}$, C-reactive protein (CRP), serum chemistry, liver function tests (LFTs), iron indices, and lipid profile, episodes of Hb>12.0 g/dL, >13.0 g/dL, or >14.0 g/dL, and the number of episodes of Hb increase >1.0 g/dL within any 2-week interval or >2.0 g/dL within any 4-week interval.

PK/PD Endpoints. Pharmacokinetic endpoints of the trial include the parameters maximum observed plasma concentration ($C_{max}$) and pre-dose trough plasma concentration ($C_{tau}$) for vadadustat. Pharmacodynamic endpoints of the trial include parameters erythropoietin (EPO), reticulocytes, and markers of iron metabolism (iron, ferritin, hepcidin, total iron binding capacity [TIBC], etc.). Exposure-response analysis will be conducted as deemed appropriate.

Trial Design of a Phase 3b, randomized, open-label, sponsor-blind, active-controlled trial of vadadustat versus darbepoetin alfa for the maintenance treatment of anemia in hemodialysis subjects, after conversion from ESA therapy. Following a Screening period of up to 8 weeks (56 days), subjects who meet all eligibility criteria are randomized 1:1:1 to vadadustat QD, vadadustat TIW, or darbepoetin alfa. Subjects are randomized at the Baseline visit using an Interactive Web Response (IWR) system to receive either vadadustat QD, vadadustat TIW, or darbepoetin alfa. Randomization will be stratified with respect to: geographic region (US versus Europe, at least 90 subjects in Europe) and mean weekly darbepoetin alfa dose (or ESA equivalent) calculated over a period of 8 weeks prior to Screening Visit 2: low darbepoetin alfa dose group (≤0.45 μg/kg/week) and high darbepoetin alfa dose group (>0.45 and ≤1.5 μg/kg/week). In each stratum, there will be 3 arms: vadadustat QD, vadadustat TIW, and darbepoetin alfa.

Following screening and randomization, there are 2 periods during the trial: (1) Conversion and Maintenance Treatment Period (Weeks 0 to 52)—conversion to trial medication for maintaining Hb (Weeks 0 to 20), primary efficacy evaluation (Weeks 20 to 26), and secondary efficacy evaluation (Weeks 46 to 52); and (2) Safety Follow-up Period (Early Termination [ET] and Follow-up)—post-treatment safety follow up visit (ET/End of Treatment [EOT]+4 weeks) (in person). Individual subjects participate in total trial duration of approximately 64 weeks.

Dosing Regimen. Vadadustat is provided as 150 and 450 mg tablets, to be taken orally. Darbepoetin alfa, as a solution, is given by IV injection or subcutaneously (SC). Subjects are randomized 1:1:1 to vadadustat QD or vadadustat TIW or darbepoetin alfa. Randomization is stratified by mean weekly darbepoetin alfa dose (or equivalent) calculated over a period of 8 weeks prior to Screening Visit 2: low darbepoetin alfa dose group (≤0.45 μg/kg/week) or high darbepoetin alfa dose group (>0.45 and ≤1.5 μg/kg/week).

In the low darbepoetin alfa dose group, subjects are randomized in a 1:1:1 ratio to receive either an initial vadadustat daily dose of 300 mg daily or 600 mg TIW, or darbepoetin alfa. In the high darbepoetin alfa dose group, subjects are randomized in a 1:1:1 ratio to receive either an initial vadadustat daily dose of 450 mg daily, 750 mg TIW, or darbepoetin alfa. To convert methoxy polyethylene glycol-epoetin beta dose to an equivalent darbepoetin dose, first calculate the total amount of drug administered the previous 8 weeks (in the format of μg/week), divide by the subject's weight, then divide by 225. To convert epoetin analogues to an equivalent darbepoetin dose, first calculate the total amount of drug administered the previous 8 weeks (in the format of U/week), divide by the subject's weight (kg), then divide by 200.

Dosing is initiated at Baseline/Day 1 and the first dose of vadadustat is administered at the trial site after other Baseline/Day 1 procedures have been completed. Thereafter, vadadustat is taken QD or TIW on an outpatient basis. Subjects may take vadadustat with or without food and should be instructed to swallow the tablet(s) whole, without chewing. Subjects are instructed to take vadadustat at roughly the same time each day.

Dose Adjustment. Vadadustat dose adjustments are guided by Hb concentrations and the Guidelines for Dose Adjustment.

Darbepoetin alfa dose adjustments are based on the US package insert (PI), European Union (EU) Summary of Product Characteristics (SmPC), local prescribing information, or investigator's clinical discretion, incorporating the Guidelines for Dose Adjustment as well as the subject's current Hb level, trajectory, and variability; symptoms; cardiovascular risk; and other features of his/her clinical condition(s).

Hemoglobin is monitored via central laboratory throughout the trial to determine if the dose of trial medication (vadadustat or darbepoetin alfa) would be adjusted, interrupted, or maintained as per the Guidelines for Dose Adjustment.

Guidelines for Dose Adjustment. If a dose increase or decrease is required to achieve and maintain Hb levels within the target range of 10.0 to 11.0 g/dL (US) or 10.0 to 12.0 g/dL (Europe), inclusive, dose is adjusted by 1 dose level (for vadadustat 1 tablet [150 mg], for darbepoetin alfa approximately 25%). In general, do not increase the dose more frequently than once every 4 weeks. A one-time dose increase after 2 weeks is allowed on only one occasion: A subject's dose may be increased by 1 dose level if the subject has a decline in Hb≥0.5 g/dL from Baseline/Day 1 in the first 2-week period (the initial period from Baseline/Day 1 to Week 2 following conversion from prior ESA) and if Hb is <10.0 g/dL.

Reduce or interrupt the dose in the setting of a rapid rise in Hb (defined as >1.0 g/dL in any 2-week period or >2.0 g/dL in any 4-week period). Reduce or interrupt the dose in the setting of Hb>11.0 g/dL (US) or >12.0 g/dL (Europe). In the US, interrupt the dose in the setting of a Hb>11.0 g/dL until Hb value falls below 11.0 g/dL. After Hb falls below 11.0 g/dL, restart trial medication and consider restarting at a lower dose. In Europe, interrupt the dose in the setting of a Hb>12.0 g/dL until Hb value falls below 12.0 g/dL. After Hb falls below 12.0 g/dL, restart trial medication and consider restarting at a lower dose.

The minimum dose of vadadustat is 150 mg daily and the maximum dose is 900 mg QD or 1200 mg TIW.

Inclusion Criteria. Subjects are required to meet the following inclusion criteria: (1) ≥18 years of age; receiving chronic, outpatient TIW in-center hemodialysis for end-stage renal disease for at least 12 weeks prior to Screening; (3) hemodialysis adequacy as indicated by single-pool $K_t/V_{urea}$≥1.2 using the most recent historical measurement within 8 weeks prior to or during Screening; (4) Use of any approved ESA for at least the 8 weeks prior to Screening Visit 2; (5) Mean screening Hb as determined by the average of 2 Hb values, at least 4 days apart, measured by the central laboratory during Screening: a) Hb values between 8.0 and 11.0 g/dL (inclusive) in the US, and b) Hb values between 9.0 and 12.0 g/dL (inclusive) in Europe; (6) serum ferritin ≥100 ng/mL and transferrin saturation (TSAT)≥20% during Screening; and (7) folate and vitamin $B_{12}$ measurements ≥lower limit of normal during Screening.

Exclusion Criteria. Subjects will be excluded if they meet any of the following exclusion criteria: (1) women of childbearing potential (WOCBP) who do not agree to practice 2 different methods of birth control or remain abstinent during the trail and for 30 days after the last dose of investigational medicinal product (IMP). If employing birth control, 2 of the following precautions must be used: bilateral orchidectomy of partner, tubal ligation, vaginal diaphragm, intrauterine device, or birth control; (2) women who are breast feeding and/or who have a positive pregnancy test result prior to receiving IMP; (3) subjects with contraindication to required trial assessment; (4) subjects who, is in opinion of the investigator or medical monitor, have a medical history or medical findings inconsistent with safety or trial compliance; (5) anemia due to a cause other than chronic kidney disease (CKD) (eg, sickle cell disease, myelodysplastic syndromes, bone marrow fibrosis, hematologic malignancy, myeloma, hemolytic anemia, thalassemia, or pure red cell aplasia); (6) subjects meeting cut-off of the following equivalent mean weekly doses calculated over 8 weeks prior to Screening Visit 2: a) methoxy polyethylene glycol-epoetin beta >50 μg/week, b) darbepoetin alfa >100 μg/week, and c) epoetin analogues >23000 IU/week; (7) active bleeding or recent blood loss within 8 weeks prior to randomization; (8) RBC transfusion within 8 weeks prior to randomization; (9) anticipated to discontinue hemodialysis during the trial; (10) judged by the investigator that the subject is likely to need rescue therapy (ESA administration or RBC transfusion) immediately after enrollment in the trial; (11) history of chronic liver disease (eg, chronic infectious hepatitis, chronic autoimmune liver disease, cirrhosis or fibrosis of the liver); (12) aspartate aminotransferase (AST)/serum glutamic oxaloacetic transaminase (SGOT), alanine aminotransferase (ALT)/serum glutamic pyruvic transaminase (SGPT), or total bilirubin >1.5× upper limit of normal (ULN) during Screening. Subjects with a history of Gilbert's syndrome are not excluded; (13) current uncontrolled hypertension as determined by the investigator that would contraindicate the use of an ESA; (14) acute coronary syndrome (hospitalization for unstable angina or myocardial infarction), surgical or percutaneous intervention for coronary, cerebrovascular or peripheral artery disease (aortic or lower extremity), surgical or percutaneous valvular replacement or repair, sustained ventricular tachycardia, hospitalization for heart failure (HF) or New York Heart Association Class IV HF, or stroke within 12 weeks prior to or during Screening; (15) history of new or recurrent malignancy within 2 years prior to and during Screening or currently receiving treatment or suppressive therapy for cancer. Subjects with treated basal cell carcinoma of skin, curatively resected squamous cell carcinoma of skin, or cervical carcinoma in situ are not excluded; (16) history of deep vein thrombosis or pulmonary embolism within 12 weeks prior to or during Screening; (17) history of hemosiderosis or hemochromatosis; (18) history of prior organ transplantation (subjects with a history of failed kidney transplant or corneal transplants are not excluded); (19) scheduled organ transplant from a living donor and subjects on the kidney transplant wait-list who are expected to receive a transplant within 6 months; (20) history of a prior hematopoietic stem cell or bone marrow transplant (stem cell therapy for knee arthritis is not excluded); (21) known hypersensitivity to vadadustat, darbepoetin alfa, or any of their excipients; (22) use of an investigational medication within 30 days or 5 half-lives of the investigational medication (whichever is longer), prior to screening or during screening and any prior use of a hypoxia-inducible factor prolyl hydroxylase inhibitor. Subjects may participate in another concurrent trial only if that trial is a non-interventional, observational investigation; (23) subjects with bilateral native nephrectomy; and (24) any other reason, which in the opinion of the investigator, would make the subject not suitable for participation in the trial.

Example 4. A Randomized, Open-Label Active-Controlled Study Evaluating the Efficacy and Safety of Dose Conversion from a Long-Acting Erythropoiesis-Stimulating Agent (Mircera®) to Three Times Weekly Oral Vadadustat (Compound 1) for the Maintenance Treatment of Anemia in Hemodialysis Subjects The primary objective of the study is to demonstrate the efficacy and safety of vadadustat (compound 1) administered TIW compared to long acting ESA (Mircera) for the maintenance treatment of anemia in hemodialysis subjects.

The study population (approximately 450 subjects) consists of subjects ≥18 years of age and receiving chronic, outpatient in-center hemodialysis three times weekly (TIW), requiring erythropoiesis-stimulating agent (ESA) treatment and are on maintenance treatment currently receiving Mircera and with mean of 2 Screening hemoglobin (Hb) values between 8.5 and 11.0 g/dL (inclusive).

Efficacy Endpoints. Primary efficacy endpoint is mean change in Hb between Baseline (average pretreatment Hb) and the primary evaluation period (average Hb from Weeks 20 to 26, inclusive). Secondary efficacy endpoint is mean change in Hb between Baseline (average pretreatment Hb) and the secondary evaluation period (average Hb from Weeks 46 to 52, inclusive). Other endpoints include proportion of subjects having a Hb value within the target range (10.0 to 11.0 d/dL) during the primary evaluation period (Weeks 20-26) and during the secondary evaluation period (Weeks 46-52).

Safety Endpoints. Safety endpoints include treatment-emergent adverse events (AEs) and serious adverse events (SAEs), proportion of subjects receiving red blood cell (RBC) transfusions from baseline to week 26, proportion of subjects receiving RBC transfusions after week 26 to week 52, proportion of subjects with Hb>11.0, Hb>12.0, >13.0, or >14.0 g/dL, proportions of subjects with Hb<7.0, <8.0, <9.0, or <10.0 g/dL, proportions of subjects with Hb increase >1.0 g/dL within any 2-week interval or >2.0 g/dL within any 4-week interval.

Study Design. This is a multi-center, randomized, open-label, active-controlled study of the efficacy and safety of conversion from long-acting ESA (Mircera) to vadadustat TIW for the maintenance treatment of anemia in hemodialysis patients. Following a Screening period of up to 8 weeks (56 days), subjects who meet all inclusion and none of the exclusion criteria, Mircera will be discontinued and subjects will be randomized 1:1:1 to vadadustat 600 mg TIW, vadadustat 900 mg TIW, or to remain on Mircera according to the dialysis center's protocol. Randomization will be stratified by dialysis organization. Following randomization, there will be 2 periods during the study: (1) Conversion and Maintenance Period (weeks 0-52)—conversion to vadadustat TIW or to remain on Mircera (weeks 0-20). There will be a primary efficacy evaluation period (weeks 20-26) and a secondary efficacy evaluation period (weeks 46-52); and (2) Safety Follow-up Period (early termination [ET] and follow-up)—post treatment safety follow up visit (ET/End of treatment [EOT]+4 weeks) either in person or via telephone.

Study Duration. Individual subjects participate in the study for up to 64 weeks, including a Screening Period of up to 8 weeks, a 52-week Treatment Period and a 4-week Safety Follow-Up Period.

Key Inclusion and Exclusion Criteria. Subjects must meet the following inclusion criteria: (1) ≥18 years of age; (2) Receiving chronic, outpatient in-center hemodialysis TIW for end-stage kidney disease for at least 12 weeks prior to Screening Visit (SV)1; (3) Currently maintained on Mircera (≤250 μg/month) with at least 2 doses received within 8 weeks prior to SV2; (4) Mean screening Hb between 8.5 and 11.0 g/dL (inclusive), as determined by the average of 2 Hb values measured by the central laboratory at least 4 days apart between SV1 and SV2; (5) Serum ferritin ≥100 ng/mL and transferrin saturation (TSAT)≥20% during Screening; and (6) Folate and vitamin B12 measurements ≥lower limit of normal during Screening. Subjects must not meet any of the following exclusion criteria: (1) Anemia due to a cause other than CKD (e.g., sickle cell disease, myelodysplastic syndromes, bone marrow fibrosis, hematologic malignancy, myeloma, hemolytic anemia, thalassemia, or pure red cell aplasia); (2) Clinically meaningful bleeding event in opinion of investigator within 8 weeks prior to Baseline; (3) RBC transfusion within 8 weeks prior to Baseline; (4) Having received any doses of darbepoetin alfa (Aranesp®) within the past 4 weeks prior to Baseline; (5) Having any epoetin alfa (Epogen®) within the past 1 week prior to Baseline; (6) Anticipated to discontinue hemodialysis during the study; (7) Judged by the Investigator that the subject is likely to need rescue therapy (ESA administration or RBC transfusion) immediately after enrollment in the study; (8) History of chronic liver disease (e.g., chronic infectious hepatitis, chronic autoimmune liver disease, cirrhosis or fibrosis of the liver); (9) Aspartate aminotransferase (AST)/serum glutamic oxaloacetic transaminase (SGOT), alanine aminotransferase (ALT)/serum glutamic pyruvic transaminase (SGPT), or total bilirubin >2× upper limit of normal (ULN) during Screening. Subjects with a history of Gilbert's syndrome are not excluded; (10) Current uncontrolled hypertension as determined by the Investigator that would contraindicate the use of an ESA; (11) Acute coronary syndrome (hospitalization for unstable angina or myocardial infarction), surgical or percutaneous intervention for coronary, cerebrovascular or peripheral artery disease (aortic or lower extremity), surgical or percutaneous valvular replacement or repair, sustained ventricular tachycardia, hospitalization for heart failure (HF) or New York Heart Association Class IV HF, or stroke within 12 weeks prior to or during Screening; (12) Acute coronary syndrome (hospitalization for unstable angina or myocardial infarction), surgical or percutaneous intervention for coronary, cerebrovascular or peripheral artery disease (aortic or lower extremity), surgical or percutaneous valvular replacement or repair, sustained ventricular tachycardia, hospitalization for heart failure (HF) or New York Heart Association Class IV HF, or stroke within 12 weeks prior to or during Screening; (13) History of deep vein thrombosis or pulmonary embolism within 12 weeks prior to or during Screening; (14) History of hemosiderosis or hemochromatosis; (15) History of prior organ transplantation (subjects with a history of failed kidney transplant or corneal transplants are not excluded); (16) Scheduled organ transplant from a living donor and subjects on the kidney transplant wait-list who are expected to receive a transplant within 6 months; (17) History of a prior hematopoietic stem cell or bone marrow transplant (stem cell therapy for knee arthritis is not excluded); (18) Known hypersensitivity to vadadustat, Mircera, or any of their excipients; (19) Use of an investigational medication or participation in an investigational study within 30 days or 5 half-lives of the investigational medication (whichever is longer), prior to Screening (subjects may participate in another concurrent study only if that study is a non-interventional, observational investigation); (20) Current exposure to any hypoxia-inducible factor prolyl-hydroxylase (HIF-PH) inhibitor or prior exposure to vadadustat; (21) Subjects with bilateral native nephrectomy; (22) Noncompliance with dialysis session attendance defined as missing more than 1 dialysis session within 8 weeks prior to Baseline; (23) Active Severe Acute Respiratory Syndrome-Related Coronavirus (SARS-CoV-2) during Screening; (24) Females who are pregnant or breastfeeding during Screening or are planning to become pregnant and breastfeeding during the study period, and for 30 days after the final study drug administration; (25) Women of childbearing potential who are unable or unwilling to use 2 acceptable methods of contraception starting at Screening, throughout the study period and for 45 days after the final study drug administration; (26) Female subjects of childbearing potential who plan to donate ova during the study, and for 30 days after the last dose of study drug; (27) Non-vasectomized male subjects who are unable or unwilling to use an acceptable method of contraception from time of first dose of study drug until 30 days after the last dose of the study drug; (28) Male subjects who plan to donate sperm during the study and for at least 30 days after the last dose of study drug; and (29) Any other reason, which in the opinion of the Investigator, would make the subject not suitable for participation in the study.

Dosing. In this trial, 2 different vadadustat starting doses are explored. The starting doses of vadadustat are 600 mg TIW and 900 mg TIW in subjects converting from Mircera. The dose range for titration is 300 to 1200 mg TIW. Hb monitoring, a dose adjustment algorithm, and phlebotomy are implemented to mitigate the potential risk of a rapid Hb rise, as follows: Hb measurements are scheduled at least every 2 weeks to week 8 and thereafter every 4 weeks; the dose adjustment algorithm targets a narrow Hb range, 10.0-11.0 g/dL; and the protocol specifies that phlebotomy may be considered in the setting of high Hb levels (>14.0 g/dL) or a high Hb rate of rise, based on the investigator's judgment.

The aim is to achieve and maintain Hb levels within the target range of 10.0 to 11.0 g/dL inclusive, while targeting the middle of the range and minimizing excursions outside the target range. Dosing is initiated at Baseline and the first dose of vadadustat is administered at the hemodialysis unit after other Baseline procedures have been completed. Thereafter, vadadustat is anticipated to be administered at the hemodialysis unit. Subjects may take vadadustat with or without food and are instructed to swallow the tablet(s) whole. Subjects are to take vadadustat at roughly the same time each day. Mircera is administered IV at the hemodialysis unit based on according to the dialysis center's protocol.

For all subjects, it is recommended that no additional ESA doses will be administered after SV2 after the subject has met all eligibility criteria and before Baseline. For all subjects, it is required that a minimum of 14 days be observed between the last dose of Mircera and the Baseline visit. If an ESA other than Mircera was administered during the Screening period, the subject will be a screen failure. After discussion with the Medical Monitor, screening may be extended for an additional 2 to 4 weeks based on subject's Hb level or Hb trajectory or based on timing of last Mircera dose given during Screening and the Baseline visit. For subjects who are randomized to the Mircera treatment arm, the initial dosing regimen in the study (starting from Baseline) will be according to the dialysis center's protocol. The timing of randomization should align with next anticipated dose of Mircera.

Dose Adjustments. Dose adjustments are guided by central laboratory Hb concentrations throughout the study to determine if vadadustat or Mircera doses are adjusted, interrupted, or maintained. Mircera dosing is based on standard of care laboratory measures according to the dialysis center's protocol. Guidelines for vadadustat dose adjustments are as follows:

(1) Dose adjustments are based on the Investigator's clinical discretion, incorporating the protocol guidance below as well as the subject's current Hb level, trajectory, and variability; symptoms; CV risk; and other features of his/her clinical condition(s);

(2) If a dose increase or decrease is required to achieve and maintain Hb levels within the target range of 10.0 to 11.0 g/dL inclusive, dose is adjusted by 1 dose level (vadadustat 300 mg);

(3) A one-time dose increase after the first 2 weeks of dosing after randomization is allowed. Thereafter, in general, do not increase the dose more frequently than once every 4 weeks. A subject's dose may be increased by 1 dose level (300 mg TIW) if the subject has a decline in Hb≥0.5 g/dL from Baseline in the first 2-week period (the initial period from Baseline to Week 2 following conversion from Mircera) and if Hb is <10.0 g/dL;

(4) Reduce the dose in the setting of a rapid rise in Hb (defined as >1.0 g/dL in any 2-week period or >2.0 g/dL in any 4-week period);

(5) Reduce the dose in the setting of Hb>11.0 g/dL; and (6) Interrupt the dose in the setting of a Hb>12.0 g/dL until Hb value falls below 11.0 g/dL. After Hb falls below 11.0 g/dL, restart study drug at a lower dose.

The minimum dose of vadadustat will be 300 mg TIW (1 tablet TIW) and the maximum dose will be 1200 mg TIW. Subjects whose dose of vadadustat is interrupted due to elevated Hb will continue in the study. Unless contraindicated, treatment will be resumed whenever possible and assessed at every visit following study drug interruption. Mircera will be administered as standard of care. Dose adjustments will be made according to the dialysis center's protocol.

Iron Supplementation and Phosphate Binders. Investigators will prescribe iron supplementation (IV, oral or intradialytic) as needed throughout the study to maintain ferritin and TSAT according to the Schedule of Activities (SoA). The use of iron-based phosphate binders (e.g., ferric citrate) is permitted. Subjects already receiving oral iron supplementation as part of their treatment plan may continue their current treatment regimen. Because of the potential for oral iron and phosphate binders to reduce the bioavailability of vadadustat, the trial medication is not to be administered concurrently with an oral iron supplement (including multivitamins containing iron), iron-containing phosphate binders, non-iron-containing phosphate binders, or any oral medications containing iron. Subjects are instructed to take any non-iron-containing phosphate binders with a meal at least 2 hours before or 1 hour after the dose of vadadustat. Subjects are instructed to take iron-containing supplements and phosphate binders at least 1 hour after the dose of vadadustat. Investigators will prescribe IV iron as needed with dosing according to the dialysis center's protocol. Iron supplementation details will be captured in the appropriate electronic case report form (eCRF).

OATP1B1/1B3 Substrates (eg. Statins). Investigators should adjust the dose of these concomitant medication as follows: Simvastatin, maximum daily dose of 20 mg; Rosuvastatin, maximum daily dose of 10 mg.

Sulfasalazine. Other Breast Cancer Resistance Protein Substrates. and Probenecid. Exposures to sulfasalazine (moderately) and mesalamine (mildly) were increased with co-administration of vadadustat based on a study in healthy adults. In subjects taking vadadustat, sulfasalazine and other clinically relevant substrates of the breast cancer resistance protein (BCRP) transporter (e.g., sulfasalazine, methotrexate, mitoxantrone, imatinib, irinotecan, lapatinib, topotecan, tenofovir, glecaprevir, pibrentasvir, or sofosbuvir), caution should be taken during the study. Probenecid, an inhibitor of UDP-glucuronosyltransferase (UGT) and the organic anion transporter (OAT)1/3 transporters, increased vadadustat area under the curve and is prohibited during the study.

Statistical Considerations. The primary efficacy endpoint is defined as the mean change in Hb between Baseline (average pretreatment Hb) and the primary evaluation period (average Hb from Weeks 20 to 26, inclusive). The primary analysis of the primary endpoint will use the randomized population. Analysis of covariance (ANCOVA) with multiple imputation for missing data will be used to calculate the 95% confidence interval (CI) of the difference in mean change in Hb from baseline to the primary evaluation period between the vadadustat group and Mircera® control group, with a randomization stratification factor and Baseline Hb as covariates. Noninferiority of vadadustat is established if the lower limit of this CI is ≥−0.75 g/dL.

A hierarchical testing scheme is used to correct for the multiplicity of the 2 comparisons of the primary efficacy endpoint: comparison between vadadustat TIW 600 mg versus Mircera and comparison between vadadustat TIW 900 mg versus Mircera. Step 1: comparison between vadadustat TIW 900 mg versus Mircera. If the noninferiority of vadadustat is established in step 1, then move to step 2. Step 2: comparison between vadadustat TIW 600 mg versus Mircera.

For the primary efficacy analysis, it is assumed that the difference in mean change from Baseline in Hb for vadadustat is the same as the active control, Mircera, and the common standard deviation for the mean change from Baseline is assumed to be 1.2 g/dL. The noninferiority margin of −0.75 g/dL will be used (for vadadustat minus Mircera). With the 1:1:1 randomization ratio of vadadustat 600 mg TIW, vadadustat 900 mg TIW, and Mircera, approximately 150 subjects in each arm, the noninferiority test will have >90% power with consideration of a 30% drop out rate.

In addition to the final analysis which takes place when all subjects have completed study and includes all data collected, the 26-week efficacy and safety data may be summarized after the last patient completes the primary efficacy period (Week 26). As the study conduct and final analyses of primary efficacy endpoint is not modified by this analysis, no alpha adjustment is proposed. The decision about whether this 26-week analysis would be conducted and details about the analysis is described in the statistical analysis plan (SAP).

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

CERTAIN EXEMPLARY EMBODIMENTS

Additional exemplary embodiments are described in the following numbered paragraphs 1-382.

1. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

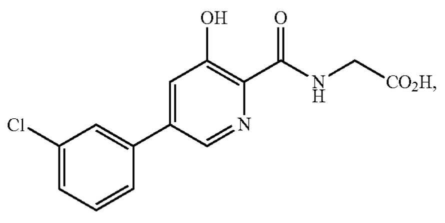

or a pharmaceutically acceptable salt, solvate, or hydrate thereof, wherein the dose comprises about 450 mg to about 1200 mg, or about 450 mg to about 1800 mg of Compound 1.

2. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

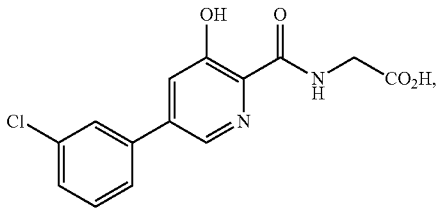

or a pharmaceutically acceptable salt, solvate, or hydrate thereof, wherein the dose comprises about 450 mg to about 1200 mg, or about 450 mg to about 1800 mg of Compound 1, and wherein the hemoglobin levels are increased to about at least 10 g/dL from a baseline hemoglobin level.

3. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

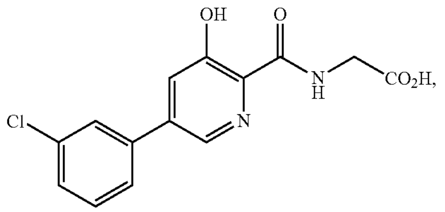

or a pharmaceutically acceptable salt, solvate, or hydrate thereof, wherein the dose comprises about 450 mg to about 1200 mg, or about 450 mg to about 1800 mg of Compound 1, and wherein the hemoglobin levels are maintained at about 10.0 g/dL to about 13.0 g/dL.

4. The method of any one of paragraphs 1-3, wherein the dose comprises about 600 mg to about 1200, or about 600 mg to about 1800 mg of Compound 1 three times weekly.

5. The method of any one of paragraphs 1-3, wherein the dose comprises about 750 mg to about 1200 mg, or about 750 mg to about 1800 mg of Compound 1 once daily.

6. The method of any one of paragraphs 1-5, wherein the dose is administered to the patient for at least about 12 weeks.

7. The method of any one of paragraphs 1-6, wherein the dose is administered to the patient for at least about 12-260 weeks.

8. The method of any one of paragraphs 1-7, wherein the patient has anemia secondary to or associated with chronic kidney disease (CKD).

9. The method of paragraph 8, wherein the CKD is dialysis-dependent CKD (DD-CKD).

10. The method of any one of paragraphs 1-9, wherein the patient previously has been treated with an erythropoietin stimulating agent (ESA).

11. The method of paragraph 10, wherein the ESA is epoetin, darbepoetin alfa (DA), and/or methoxy polyethylene glycol-epoetin beta (epoetin beta pegol).

12. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

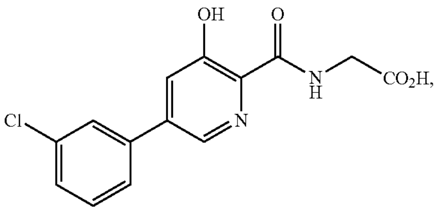

or a pharmaceutically acceptable salt, solvate, or hydrate thereof, wherein the dose comprises about 750 mg to about 1200 mg, or about 750 mg to about 1800 mg of Compound 1 once daily.

13. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

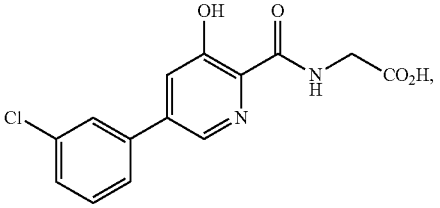

or a pharmaceutically acceptable salt, solvate, or hydrate thereof, wherein the dose comprises about 750 mg to about 1200 mg, or about 750 mg to about 1800 mg of Compound 1 once daily, and wherein the hemoglobin levels are increased to about at least 10 g/dL from a baseline hemoglobin level.

14. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

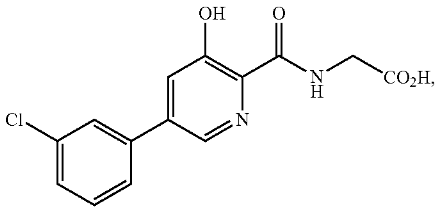

or a pharmaceutically acceptable salt, solvate, or hydrate thereof, wherein the dose comprises about 750 mg to about 1200 mg, or about 750 mg to about 1800 mg of Compound 1 once daily, and wherein the hemoglobin levels are maintained at about 10.0 g/dL to about 13.0 g/dL.

15. The method of any one of paragraphs 12-14, wherein the dose comprises about 750 mg to about 900 mg of Compound 1 once daily.

16. The method of any one of paragraphs 12-15, wherein the dose comprises about 750 mg of Compound 1 once daily.

17. The method of any one of paragraphs 12-15, wherein the dose comprises about 900 mg of Compound 1 once daily.

18. The method of any one of paragraphs 12-14, wherein the dose comprises about 1200 mg of Compound 1 once daily.

19. The method of any one of paragraphs 12-14, wherein the dose comprises about 1350, 1500, 1650, or 1800 mg of Compound 1 once daily.

20. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

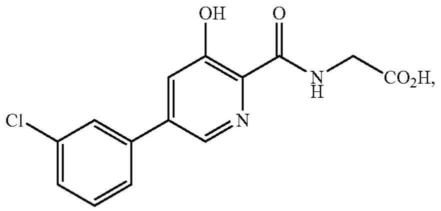

or a pharmaceutically acceptable salt, solvate, or hydrate thereof, wherein the dose comprises about 600 mg to about 1200 mg, or about 600 mg to about 1800 mg of Compound 1 three times weekly.

21. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

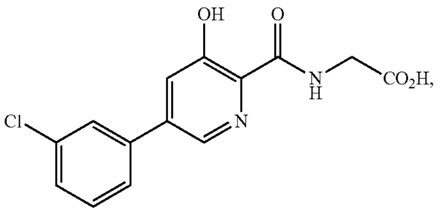

or a pharmaceutically acceptable salt, solvate, or hydrate thereof, wherein the dose comprises about 600 mg to about 1200 mg, or about 600 mg to about 1800 mg of Compound 1 three times weekly, and wherein the hemoglobin levels are increased to about at least 10 g/dL from a baseline hemoglobin level.

22. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

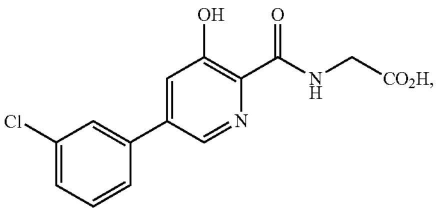

or a pharmaceutically acceptable salt, solvate, or hydrate thereof, wherein the dose comprises about 600 mg to about 1200, or about 600 mg to about 1800 mg of Compound 1 three times weekly, and wherein the hemoglobin levels are maintained at about 10.0-13.0 g/dL.

23. The method of any one of paragraphs 20-22, wherein the dose comprises about 600 mg to about 900 mg of Compound 1 three times weekly.

24. The method of any one of paragraphs 20-22, wherein the dose comprises about 750 mg to about 1200 mg of Compound 1 three times weekly.

25. The method of any one of paragraphs 20-23, wherein the dose comprises about 600 mg of Compound 1 three times weekly.

26. The method of any one of paragraphs 20-24, wherein the dose comprises about 750 mg of Compound 1 three times weekly.

27. The method of any one of paragraphs 20-24, wherein the dose comprises about 900 mg of Compound 1 three times weekly.

28. The method of any one of paragraphs 20-22 and 24, wherein the dose comprises about 1200 mg of Compound 1 three times weekly.

29. The method of any one of paragraphs 20-22, wherein the dose comprises about 1350, 1500, 1650, or 1800 mg of Compound 1 three times weekly.

30. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

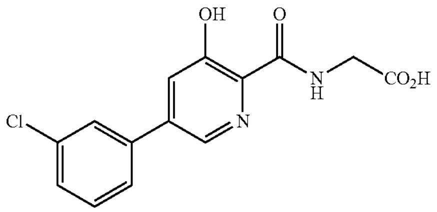

or a pharmaceutically acceptable salt, solvate, or hydrate thereof, wherein the dose comprises about 150 mg to about 1200 mg, or about 150 mg to about 1800 mg of the Compound 1 three times weekly, and wherein the patient was previously administered a daily dose of compound 1.

31. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

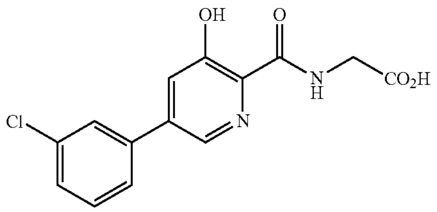

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, and wherein the hemoglobin levels are increased to about at least 10 g/dL from a baseline hemoglobin level.

32. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

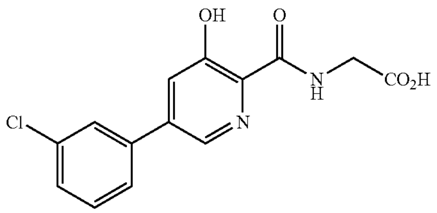

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, and wherein the hemoglobin levels are maintained at about 10.0-13.0 g/dL.

33. The method of any one of paragraphs 30-32, wherein the dose comprises about 150 mg to about 600 mg three times weekly.
34. The method of any one of paragraphs 30-32, wherein the dose comprises about 600 mg to about 1200 mg three times weekly.
35. The method of any one of paragraphs 30-32, wherein the dose comprises about 750 mg to about 1200 mg three times weekly.
36. The method of any one of paragraphs 30-33, wherein the dose comprises about 150 mg three times weekly.
37. The method of any one of paragraphs 30-33, wherein the dose comprises about 300 mg three times weekly.
38. The method of any one of paragraphs 30-33, wherein the dose comprises about 450 mg three times weekly.
39. The method of any one of paragraphs 30-34, wherein the dose comprises about 600 mg three times weekly.
40. The method of any one of paragraphs 30-32 and 34-35, wherein the dose comprises about 750 mg three times weekly.
41. The method of any one of paragraphs 30-32 and 34-35, wherein the dose comprises about 900 mg three times weekly.
42. The method of any one of paragraphs 30-32 and 34-35, wherein the dose comprises about 1200 mg three times weekly.
43. The method of any one of paragraphs 30-32, wherein the dose comprises about 1350, 1500, 1650, or 1800 mg three times weekly.
44. The method of any one of paragraphs 30-43, wherein the previously-administered daily dose comprises about 150 mg of Compound 1.
45. The method of any one of paragraphs 30-43, wherein the previously-administered daily dose comprises about 300 mg of Compound 1.
46. The method of any one of paragraphs 30-43, wherein the previously-administered daily dose comprises about 450 mg of Compound 1.
47. The method of any one of paragraphs 30-43, wherein the previously-administered daily dose comprises about 600 mg of Compound 1.
48. The method of any one of paragraphs 14, 22, or 32, wherein the hemoglobin levels are maintained at about 10.0 g/dL to about 12.0 g/dL.
49. The method of any one of paragraphs 14, 22, or 32, wherein the hemoglobin levels are maintained at about 11.0 g/dL to about 13.0 g/dL.
50. The method of paragraph 48 or 49, wherein the hemoglobin levels are maintained at about 11.0 g/dL to about 12.0 g/dL.
51. The method of paragraph 48, wherein the hemoglobin levels are maintained at about 10.0 g/dL to about 11.0 g/dL.
52. The method of any one of paragraphs 12-51, wherein the dose is administered to the patient for at least about 12-260 weeks.
53. The method of paragraph 52, wherein the dose is administered to the patient for at least about 12 weeks, for at least about 24 weeks, for at least about 28 weeks, for at least about 32 weeks, for at least about 36 weeks, for at least about 40 weeks, for at least about 44 weeks, for at least about 48 weeks, for at least about 52 weeks, for at least about 64 weeks, for at least about 76 weeks, for at least about 88 weeks, for at least about 104 weeks, for at least about 116 weeks, for at least about 128 weeks, for at least about 140 weeks, for at least about 156 weeks, for at least about 168 weeks, for at least about 180 weeks, for at least about 192 weeks, for at least about 208 weeks, or for at least about 260 weeks.
54. The method of any one of paragraphs 12-53, wherein anemia is anemia associated with or secondary to chronic kidney disease (CKD).
55. The method of paragraph 54, wherein chronic kidney disease is dialysis-dependent chronic kidney disease (DD-CKD).
56. The method of any one of paragraphs 12-55, wherein the patient previously has been treated with an erythropoiesis stimulating agent (ESA).
57. The method of paragraph 56, wherein the ESA is epoetin, darbepoetin alfa (DA), or methoxy polyethylene glycol-epoetin beta (epoetin beta pegol).
58. The method of paragraph 57, wherein the epoetin is epoetin alfa.
59. The method of paragraph 58, wherein the patient previously has been treated with epoetin alfa at a dose of about 10 U/kg of body weight to about 500 U/kg of body weight three times weekly.
60. The method of paragraph 59, wherein the patient previously has been treated with epoetin alfa at a dose of about 25 U/kg of body weight to about 300 U/kg of body weight three times weekly.
61. The method of paragraph 59 or 60, wherein the patient previously has been treated with epoetin alfa at a dose of about 50 U/kg of body weight to 200 U/kg of body weight three times weekly.
62. The method of paragraph 58, wherein the patient previously has been treated with about ≤90 U/kg/week epoetin alfa.
63. The method of paragraph 58, wherein the patient previously has been treated with about >90 U/kg/week to about <300 U/kg/week epoetin alfa, or wherein the patient previously has been treated with about ≥300 U/kg/week epoetin alfa, or wherein the patient previously has been treated with epoetin alfa at an amount of about 1,500 U/week to about 90,000 U/week.
64. The method of paragraph 63, wherein the patient previously has been treated with epoetin alfa at an amount of about 4,500 U/week.
65. The method of paragraph 57, wherein the ESA is darbepoetin alfa.
66. The method of paragraph 65, wherein the patient previously has been treated with DA at a dose of about 0.25 μg/kg of body weight to 0.75 μg/kg of body weight once weekly or once every two weeks.
67. The method of paragraph 66, wherein the patient previously has been treated with DA at a dose of about 0.45 μg/kg of body weight once weekly.
68. The method of paragraph 66, wherein the patient previously has been treated with DA at a dose of about 0.75 μg/kg of body weight once every two weeks.
69. The method of paragraph 65, wherein the patient previously has been treated with DA at an amount of about 6.25-200 μg/week.
70. The method of paragraph 65, wherein the patient previously has been treated with ≤0.45 μg/kg/week DA, or wherein the patient previously has been treated with >0.45 μg/kg/week and ≤1.5 μg/kg/week DA.
71. The method of paragraph 57, wherein the ESA is epoetin beta pegol.
72. The method of paragraph 71, wherein the patient previously has been treated with epoetin beta pegol at a dose of about 0.3 μg/kg of body weight to about 1.2

μg/kg of body weight once every two weeks or about 0.6 μg/kg of body weight to about 2.4 μg/kg of body weight once a month.

73. The method of paragraph 72, wherein the patient previously has been treated with epoetin beta pegol at a dose of about 0.6 μg/kg of body weight once every two weeks or about 1.2 μg/kg of body weight once a month.

74. The method of paragraph 71, wherein the patient previously has been treated with ≤250 μg/month epoetin beta pegol.

75. The method of any one of paragraphs 56-74, wherein the patient previously has been treated with an ESA for about ≥4 weeks.

76. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

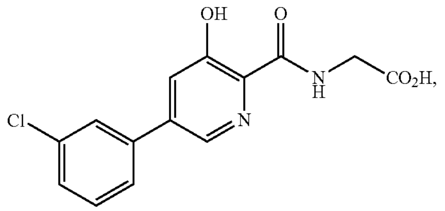

or a pharmaceutically acceptable salt, solvate, or hydrate thereof, for at least about 12 weeks, wherein the dose comprises about 750-1200 mg, or about 750-1800 mg of Compound 1 once daily.

77. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

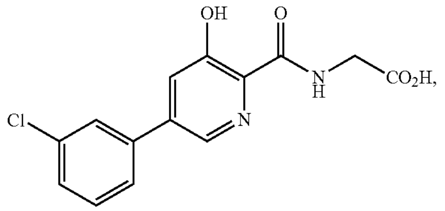

or a pharmaceutically acceptable salt, solvate, or hydrate thereof, for at least about 12 weeks, wherein the dose comprises about 750 mg to about 1200 mg, or about 750 to about 1800 mg of Compound 1 once daily, and wherein the hemoglobin levels are increased to about at least 10 g/dL from a baseline hemoglobin level.

78. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

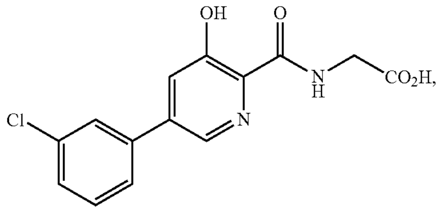

or a pharmaceutically acceptable salt, solvate, or hydrate thereof, for at least about 12 weeks, wherein the dose comprises about 750 mg to about 1200 mg, or about 750 to about 1800 mg of Compound 1 once daily, and wherein the hemoglobin levels are maintained at about 10.0-13.0 g/dL.

79. The method of any one of paragraphs 76-78, wherein the dose comprises about 750 mg to about 900 mg of Compound 1 once daily.

80. The method of any one of paragraphs 76-79, wherein the dose comprises about 750 mg of Compound 1 once daily.

81. The method of any one of paragraphs 76-79, wherein the dose comprises about 900 mg of Compound 1 once daily.

82. The method of any one of paragraphs 76-78, wherein the dose comprises about 1200 mg of Compound 1 once daily.

83. The method of any one of paragraphs 76-78, wherein the dose comprises about 1350, 1500, 1650, or 1800 mg of Compound 1 once daily.

84. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

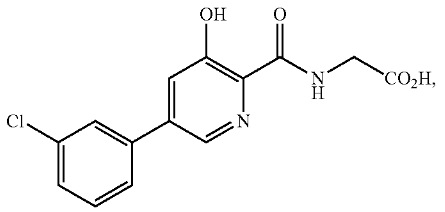

or a pharmaceutically acceptable salt, solvate, or hydrate thereof, for at least about 12 to about 260 weeks, wherein the dose comprises about 600-1200 mg, or about 600-1800 mg of Compound 1 three times weekly.

85. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

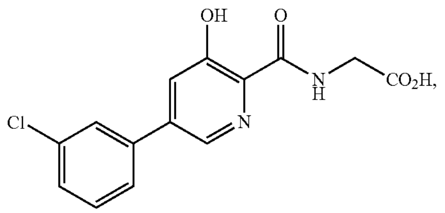

or a pharmaceutically acceptable salt, solvate, or hydrate thereof, for at least about 12 weeks, wherein the dose comprises about 600 mg to about 1200 mg, or about 600 mg to about 1800 mg of Compound 1 three times weekly, and wherein the hemoglobin levels are increased to about at least 10 g/dL from a baseline hemoglobin level.

86. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

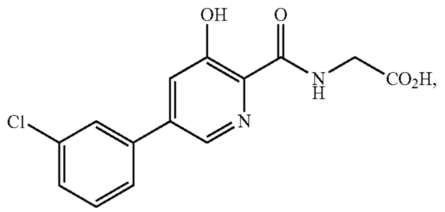

or a pharmaceutically acceptable salt, solvate, or hydrate thereof, for at least about 12 weeks, wherein the dose comprises about 600 mg to about 1200 mg, or about 600 mg to about 1800 mg of Compound 1 three times weekly, and wherein the hemoglobin levels are maintained at about 10.0-13.0 g/dL.

87. The method of any one of paragraphs 84-86, wherein the dose comprises about 600 mg to about 900 mg of Compound 1 three times weekly.

88. The method of any one of paragraphs 84-86, wherein the dose comprises about 750 mg to about 1200 mg of Compound 1 three times weekly.

89. The method of any one of paragraphs 84-87, wherein the dose comprises about 600 mg of Compound 1 three times weekly.

90. The method of any one of paragraphs 84-88, wherein the dose comprises about 750 mg of Compound 1 three times weekly.

91. The method of any one of paragraphs 84-88, wherein the dose comprises about 900 mg of Compound 1 three times weekly.

92. The method of any one of paragraphs 84-86 and 88, wherein the dose comprises about 1200 mg of Compound 1 three times weekly.

93. The method of any one of paragraphs 84-86, wherein the dose comprises about 1350, 1500, 1650, or 1800 mg of Compound 1 three times weekly.

94. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

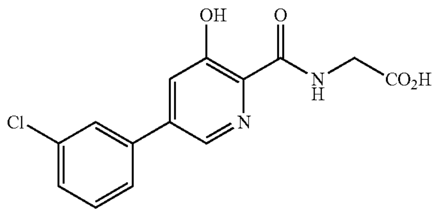

or a pharmaceutically acceptable salt, solvate, or hydrate thereof, for at least about 12 weeks, wherein the dose comprises about 150 mg to about 1200 mg, or about 150 mg to about 1800 mg of the Compound 1 three times weekly, and wherein the patient was previously administered a daily dose of compound 1.

95. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

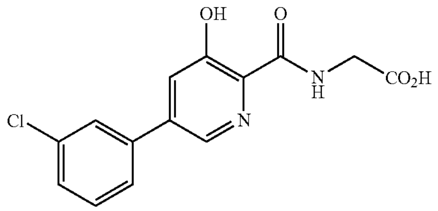

or a pharmaceutically acceptable salt, solvate, or hydrate thereof, for at least about 12 weeks, wherein the dose comprises about 150 mg to about 1200 mg, or about 150 mg to about 1800 mg of the Compound 1 three times weekly, wherein the patient was previously administered a daily dose of Compound 1, and wherein the hemoglobin levels are increased to about at least 10 g/dL from a baseline hemoglobin level.

96. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

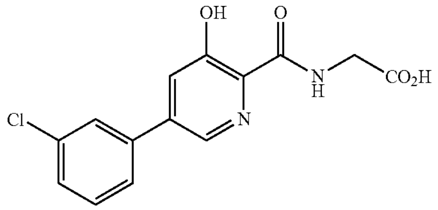

or a pharmaceutically acceptable salt, solvate, or hydrate thereof, for at least about 12 weeks, wherein the dose comprises about 150 mg to about 1200 mg, or about 150 mg to about 1800 mg of the Compound 1 three times weekly, wherein the patient was previously administered a daily dose of Compound 1, and wherein the hemoglobin levels are maintained at about 10.0-13.0 g/dL.

97. The method of any one of paragraphs 94-96, wherein the dose comprises about 150 mg to about 600 mg three times weekly.

98. The method of any one of paragraphs 94-96, wherein the dose comprises about 600 mg to about 1200 mg three times weekly.

99. The method of any one of paragraphs 94-96, wherein the dose comprises about 750 mg to about 1200 mg three times weekly.

100. The method of any one of paragraphs 94-97, wherein the dose comprises about 150 mg three times weekly.

101. The method of any one of paragraphs 94-97, wherein the dose comprises about 300 mg three times weekly.

102. The method of any one of paragraphs 94-97, wherein the dose comprises about 450 mg three times weekly.

103. The method of any one of paragraphs 94-98, wherein the dose comprises about 600 mg three times weekly.

104. The method of any one of paragraphs 94-96 and 98-99, wherein the dose comprises about 750 mg three times weekly.

105. The method of any one of paragraphs 94-96 and 98-99, wherein the dose comprises about 900 mg three times weekly.

106. The method of any one of paragraphs 94-96 and 98-99, wherein the dose comprises about 1200 mg three times weekly.

107. The method of any one of paragraphs 94-96, wherein the dose comprises about 1350, 1500, 1650, or 1800 mg three times weekly.

108. The method of any one of paragraphs 94-107, wherein the previously-administered daily dose comprises about 150 mg of Compound 1.

109. The method of any one of paragraphs 94-107, wherein the previously-administered daily dose comprises about 300 mg of Compound 1.

110. The method of any one of paragraphs 94-107, wherein the previously-administered daily dose comprises about 450 mg of Compound 1.

111. The method of any one of paragraphs 94-107, wherein the previously-administered daily dose comprises about 600 mg of Compound 1.

112. The method of any one of paragraphs 78, 86 or %, wherein the hemoglobin levels are maintained at about 10.0 g/dL to about 12.0 g/dL.

113. The method of any one of paragraphs 78, 86 or %, wherein the hemoglobin levels are maintained at about 11.0 g/dL to about 13.0 g/dL.

114. The method of any one of paragraphs 112-113, wherein the hemoglobin levels are maintained at about 11.0 g/dL to about 12.0 g/dL.

115. The method of paragraph 112, wherein the hemoglobin levels are maintained at about 10.0 g/dL to about 11.0 g/dL.

116. The method of any one of paragraphs 76-115, wherein the dose is administered to the patient for at least about 12 weeks, for at least about 24 weeks, for at least about 28 weeks, for at least about 32 weeks, for at least about 36 weeks, for at least about 40 weeks, for at least about 44 weeks, for at least about 48 weeks, for at least about 52 weeks, for at least about 64 weeks, for at least about 76 weeks, for at least about 88 weeks, for at least about 104 weeks, for at least about 116 weeks, for at least about 128 weeks, for at least about 140 weeks, for at least about 156 weeks, for at least about 168 weeks, for at least about 180 weeks, for at least about 192 weeks, for at least about 208 weeks, or for at least about 260 weeks.

117. The method of any one of paragraphs 76-116, wherein anemia is anemia associated with or secondary to chronic kidney disease (CKD).

118. The method of paragraph 117, wherein chronic kidney disease is dialysis-dependent chronic kidney disease (DD-CKD).

119. The method of any one of paragraphs 76-118, wherein the patient previously has been treated with an erythropoiesis stimulating agent (ESA).

120. The method of paragraph 119, wherein the ESA is epoetin, darbepoetin alfa (DA), or methoxy polyethylene glycol-epoetin beta (epoetin beta pegol).

121. The method of paragraph 120, wherein the epoetin is epoetin alfa.

122. The method of paragraph 121, wherein the patient previously has been treated with epoetin alfa at a dose of about 10 U/kg of body weight to about 500 U/kg of body weight three times weekly.

123. The method of paragraph 121, wherein the patient previously has been treated with epoetin alfa at a dose of about 25 U/kg of body weight to about 300 U/kg of body weight three times weekly.

124. The method of paragraph 122 or 123, wherein the patient previously has been treated with epoetin alfa at a dose of about 50 U/kg of body weight to 200 U/kg of body weight three times weekly.

125. The method of paragraph 121, wherein the patient previously has been treated with about ≤90 U/kg/week epoetin alfa.

126. The method of paragraph 121, wherein the patient previously has been treated with about >90 U/kg/week to about <300 U/kg/week epoetin alfa, or wherein the patient previously has been treated with about ≥300 U/kg/week epoetin alfa, or wherein the patient previously has been treated with epoetin alfa at an amount of about 1,500 U/week to about 90,000 U/week.

127. The method of paragraph 126, wherein the patient previously has been treated with epoetin alfa at an amount of about 4,500 U/week.

128. The method of paragraph 120, wherein the ESA is darbepoetin alfa.

129. The method of paragraph 128, wherein the patient previously has been treated with DA at a dose of about 0.25 μg/kg of body weight to 0.75 μg/kg of body weight once weekly or once every two weeks.

130. The method of paragraph 129, wherein the patient previously has been treated with DA at a dose of about 0.45 μg/kg of body weight once weekly.

131. The method of paragraph 129, wherein the patient previously has been treated with DA at a dose of about 0.75 μg/kg of body weight once every two weeks.

132. The method of paragraph 128, wherein the patient previously has been treated with DA at an amount of about 6.25-200 μg/week.

133. The method of paragraph 128, wherein the patient previously has been treated with ≤0.45 μg/kg/week DA, or wherein the patient previously has been treated with >0.45 μg/kg/week and ≤1.5 μg/kg/week DA.

134. The method of paragraph 120, wherein the ESA is epoetin beta pegol.

135. The method of paragraph 134, wherein the patient previously has been treated with epoetin beta pegol at a dose of about 0.3 μg/kg of body weight to about 1.2 μg/kg of body weight once every two weeks or about 0.6 μg/kg of body weight to about 2.4 μg/kg of body weight once a month.

136. The method of paragraph 135, wherein the patient previously has been treated with epoetin beta pegol at a dose of about 0.6 μg/kg of body weight once every two weeks or about 1.2 μg/kg of body weight once a month.

137. The method of paragraph 134, wherein the patient previously has been treated with ≤250 μg/month epoetin beta pegol.

138. The method of any one of paragraphs 119-137, wherein the patient previously has been treated with an ESA for about ≥4 weeks.

139. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

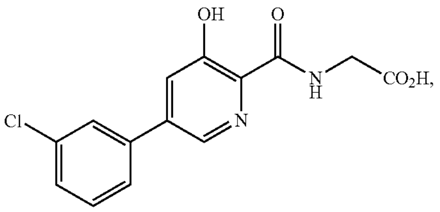

or a pharmaceutically acceptable salt, solvate, or hydrate thereof, wherein the dose comprises about 750-1200 mg, or about 750-1800 mg of Compound 1 once daily, and wherein the patient was previously treated with an erythropoietin stimulating agent (ESA).

140. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

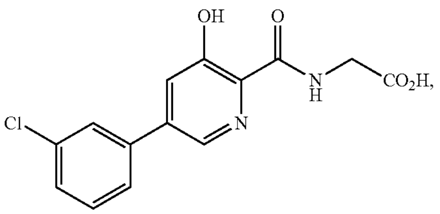

or a pharmaceutically acceptable salt, solvate, or hydrate thereof, wherein the dose comprises about 750 mg to about 1200 mg, or about 750 mg to about 1800 mg of Compound 1 once daily, and wherein the patient was previously treated with an erythropoietin stimulating agent (ESA), and wherein the hemoglobin levels are increased to about at least 10 g/dL from a baseline hemoglobin level.

141. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

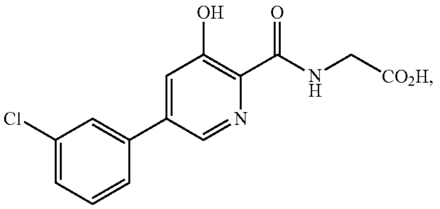

or a pharmaceutically acceptable salt, solvate, or hydrate thereof, wherein the dose comprises about 750 mg to about 1200 mg, or about 750 mg to about 1800 mg of Compound 1 once daily, wherein the patient was previously treated with an erythropoietin stimulating agent (ESA), and wherein the hemoglobin levels are maintained at about 10.0-13.0 g/dL.

142. The method of any one of paragraphs 139-141, wherein the dose comprises about 750 mg to about 900 mg of Compound 1 once daily.

143. The method of any one of paragraphs 139-142, wherein the dose comprises about 750 mg of Compound 1 once daily.

144. The method of any one of paragraphs 139-142, wherein the dose comprises about 900 mg of Compound 1 once daily.

145. The method of any one of paragraphs 139-141, wherein the dose comprises about 1200 mg of Compound 1 once daily.

146. The method of any one of paragraphs 139-141, wherein the dose comprises about 1350, 1500, 1650, or 1800 mg of Compound 1 once daily.

147. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

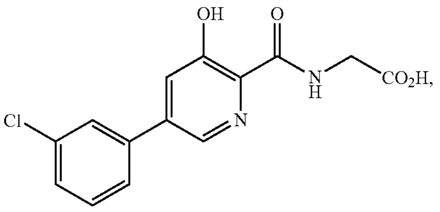

or a pharmaceutically acceptable salt, solvate, or hydrate thereof, wherein the dose comprises about 600-1200 mg, or about 600-1800 mg of Compound 1 three times weekly, and wherein the patient was previously treated with an erythropoietin stimulating agent (ESA).

148. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

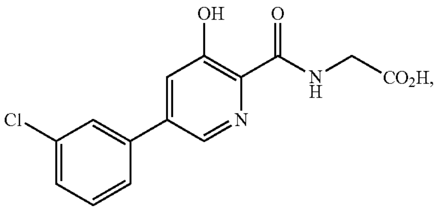

or a pharmaceutically acceptable salt, solvate, or hydrate thereof, wherein the dose comprises about 600 mg to about 1200 mg, or about 600 mg to about 1800 mg of Compound 1 three times weekly, wherein the patient was previously treated with an erythropoietin stimulating agent (ESA), and wherein the hemoglobin levels are increased to about at least 10 g/dL from a baseline hemoglobin level.

149. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

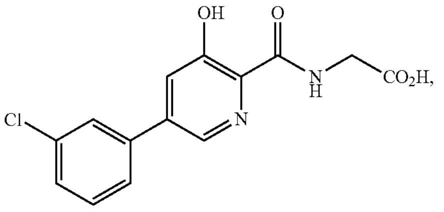

or a pharmaceutically acceptable salt, solvate, or hydrate thereof, wherein the dose comprises about 600 mg to about 1200 mg, or about 600 mg to about 1800 mg of Compound 1 three times weekly, wherein the patient was previously treated with an erythropoietin stimulating agent (ESA), and wherein the hemoglobin levels are maintained at about 10.0-13.0 g/dL.

150. The method of any one of paragraphs 147-149, wherein the dose comprises about 600 mg to about 900 mg of Compound 1 three times weekly.

151. The method of any one of paragraphs 147-149, wherein the dose comprises about 750 mg to about 1200 mg of Compound 1 three times weekly.

152. The method of any one of paragraphs 147-150, wherein the dose comprises about 600 mg of Compound 1 three times weekly.

153. The method of any one of paragraphs 147-151, wherein the dose comprises about 750 mg of Compound 1 three times weekly.

154. The method of any one of paragraphs 147-151, wherein the dose comprises about 900 mg of Compound 1 three times weekly.

155. The method of any one of paragraphs 147-149 and 151, wherein the dose comprises about 1200 mg of Compound 1 three times weekly.

156. The method of any one of paragraphs 147-149, wherein the dose comprises about 1350, 1500, 1650, or 1800 mg of Compound 1 three times weekly.

157. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

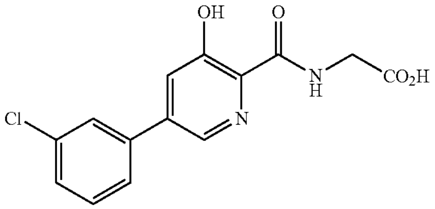

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, and wherein the patient was previously treated with an erythropoietin stimulating agent (ESA).

158. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

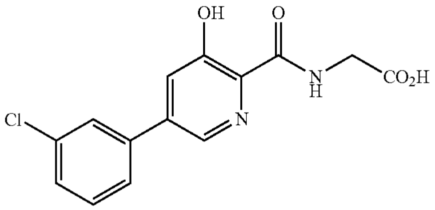

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein the patient was previously treated with an erythropoietin stimulating agent (ESA), and wherein the hemoglobin levels are increased to about at least 10 g/dL from a baseline hemoglobin level.

159. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

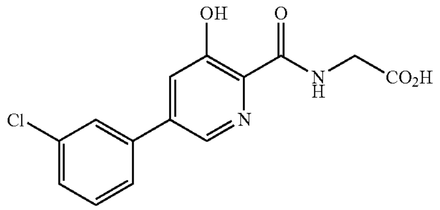

or a pharmaceutically acceptable salt, solvate, or hydrate thereof, wherein the dose comprises about 150-1200 mg, or about 150-1800 mg of the Compound 1 three times weekly, wherein the patient was previously administered a daily dose of Compound 1, wherein the patient was previously treated with an erythropoietin stimulating agent (ESA), and wherein the hemoglobin levels are maintained at about 10.0-13.0 g/dL.

160. The method of any one of paragraphs 157-159, wherein the dose comprises about 150 mg to about 600 mg three times weekly.

161. The method of any one of paragraphs 157-159, wherein the dose comprises about 600 mg to about 1200 mg three times weekly.

162. The method of any one of paragraphs 157-159, wherein the dose comprises about 750 mg to about 1200 mg three times weekly.

163. The method of any one of paragraphs 157-160, wherein the dose comprises about 150 mg three times weekly.

164. The method of any one of paragraphs 157-160, wherein the dose comprises about 300 mg three times weekly.

165. The method of any one of paragraphs 157-160, wherein the dose comprises about 450 mg three times weekly.

166. The method of any one of paragraphs 157-161, wherein the dose comprises about 600 mg three times weekly.

167. The method of any one of paragraphs 157-159 and 161-162, wherein the dose comprises about 750 mg three times weekly.

168. The method of any one of paragraphs 157-159 and 161-162, wherein the dose comprises about 900 mg three times weekly.

169. The method of any one of paragraphs 157-159 and 161-162, wherein the dose comprises about 1200 mg three times weekly.

170. The method of any one of paragraphs 157-159, wherein the dose comprises about 1350, 1500, 1650, or 1800 mg three times weekly.

171. The method of any one of paragraphs 157-170, wherein the patient was previously administered a daily dose comprises about 150 mg of Compound 1.

172. The method of any one of paragraphs 157-170, wherein the patient was previously administered a daily dose comprises about 300 mg of Compound 1.

173. The method of any one of paragraphs 157-170, wherein the patient was previously administered a daily dose comprises about 450 mg of Compound 1.

174. The method of any one of paragraphs 157-170, wherein the patient was previously administered a daily dose comprises about 600 mg of Compound 1.

175. The method of paragraph 141, 149 or 159, wherein the hemoglobin levels are maintained at about 10.0 g/dL to about 12.0 g/dL.

176. The method of paragraph 141, 149 or 159, wherein the hemoglobin levels are maintained at about 11.0 g/dL to about 13.0 g/dL.

177. The method of any one of paragraphs 175-176, wherein the hemoglobin levels are maintained at about 11.0 g/dL to about 12.0 g/dL.

178. The method of paragraph 176, wherein the hemoglobin levels are maintained at about 10.0 g/dL to about 11.0 g/dL.

179. The method of any one of paragraphs 139-178, wherein the dose is administered to the patient for at least about 12-260 weeks.

180. The method of paragraph 179, wherein the dose is administered to the patient for at least about 12 weeks, for at least about 24 weeks, for at least about 28 weeks, for at least about 32 weeks, for at least about 36 weeks, for at least about 40 weeks, for at least about 44 weeks, for at least about 48 weeks, for at least about 52 weeks, for at least about 64 weeks, for at least about 76 weeks, for at least about 88 weeks, for at least about 104 weeks, for at least about 116 weeks, for at least about 128 weeks, for at least about 140 weeks, for at least about 156 weeks, for at least about 168 weeks, for at least about 180 weeks, for at least about 192 weeks, for at least about 208 weeks, or for at least about 260 weeks.

181. The method of any one of paragraphs 139-180, wherein anemia is anemia associated with or secondary to chronic kidney disease (CKD).

182. The method of paragraph 181, wherein chronic kidney disease is dialysis-dependent chronic kidney disease (DD-CKD).

183. The method of any one of paragraphs 139-182, wherein the patient previously has been treated with an erythropoiesis stimulating agent (ESA) that comprises epoetin, darbepoetin alfa (DA), or methoxy polyethylene glycol-epoetin beta (epoetin beta pegol).

184. The method of paragraph 183, wherein the epoetin is epoetin alfa.

185. The method of paragraph 184, wherein the patient previously has been treated with epoetin alfa at a dose of about 10 U/kg of body weight to about 500 U/kg of body weight three times weekly.

186. The method of paragraph 185, wherein the patient previously has been treated with epoetin alfa at a dose of about 25 U/kg of body weight to about 300 U/kg of body weight three times weekly.

187. The method of paragraph 185 or 186, wherein the patient previously has been treated with epoetin alfa at a dose of about 50 U/kg of body weight to 200 U/kg of body weight three times weekly.

188. The method of paragraph 184, wherein the patient previously has been treated with about ≤90 U/kg/week epoetin alfa.

189. The method of paragraph 184, wherein the patient previously has been treated with about >90 U/kg/week to about <300 U/kg/week epoetin alfa, or wherein the patient previously has been treated with about ≥300 U/kg/week epoetin alfa, or wherein the patient previously has been treated with epoetin alfa at an amount of about 1,500 U/week to about 90,000 U/week.

190. The method of paragraph 189, wherein the patient previously has been treated with epoetin alfa at an amount of about 4,500 U/week.

191. The method of paragraph 183, wherein the ESA is darbepoetin alfa.

192. The method of paragraph 191, wherein the patient previously has been treated with DA at a dose of about 0.25 μg/kg of body weight to 0.75 μg/kg of body weight once weekly or once every two weeks.

193. The method of paragraph 192, wherein the patient previously has been treated with DA at a dose of about 0.45 μg/kg of body weight once weekly.

194. The method of paragraph 192, wherein the patient previously has been treated with DA at a dose of about 0.75 μg/kg of body weight once every two weeks.

195. The method of paragraph 191, wherein the patient previously has been treated with DA at an amount of about 6.25-200 μg/week.

196. The method of paragraph 191, wherein the patient previously has been treated with ≤0.45 μg/kg/week DA, or wherein the patient previously has been treated with >0.45 μg/kg/week and ≤1.5 μg/kg/week DA.

197. The method of paragraph 183, wherein the ESA is epoetin beta pegol.

198. The method of paragraph 197, wherein the patient previously has been treated with epoetin beta pegol at a dose of about 0.3 μg/kg of body weight to about 1.2 μg/kg of body weight once every two weeks or about 0.6 μg/kg of body weight to about 2.4 μg/kg of body weight once a month.

199. The method of paragraph 198, wherein the patient previously has been treated with epoetin beta pegol at a dose of about 0.6 μg/kg of body weight once every two weeks or about 1.2 μg/kg of body weight once a month.

200. The method of paragraph 198, wherein the patient previously has been treated with ≤250 μg/month epoetin beta pegol.

201. The method of any one of paragraphs 139-200, wherein the patient previously has been treated with an ESA for about ≥4 weeks.

202. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

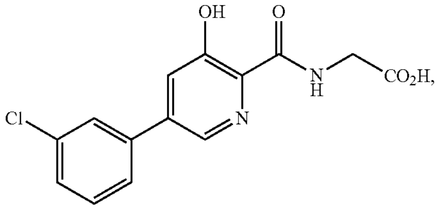

or a pharmaceutically acceptable salt, solvate, or hydrate thereof, wherein the dose comprises about 750-1200 mg, or about 750-1800 mg of Compound 1 once daily, and wherein anemia is anemia associated with or secondary to dialysis-dependent chronic kidney disease (DD-CKD).

203. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

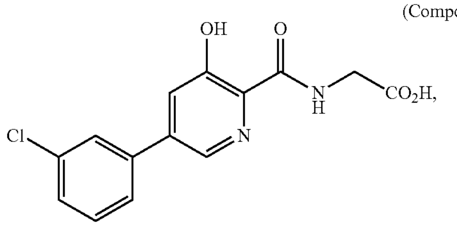

or a pharmaceutically acceptable salt, solvate, or hydrate thereof, wherein the dose comprises about 750 mg to about 1200 mg, or about 750 mg to about 1800 mg of Compound 1 once daily, wherein anemia is anemia associated with or secondary to dialysis-dependent chronic kidney disease (DD-CKD), and wherein the hemoglobin levels are increased to about at least 10 g/dL from a baseline hemoglobin level.

204. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

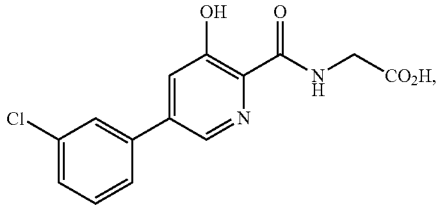

or a pharmaceutically acceptable salt, solvate, or hydrate thereof, wherein the dose comprises about 750 mg to about 1200 mg, or about 750 mg to about 1800 mg of Compound 1 once daily, wherein anemia is anemia associated with or secondary to dialysis-dependent chronic kidney disease (DD-CKD), and wherein the hemoglobin levels are maintained at about 10.0-13.0 g/dL.

205. The method of any one of paragraphs 202-204, wherein the dose comprises about 750 mg to about 900 mg of Compound 1 once daily.

206. The method of any one of paragraphs 202-205, wherein the dose comprises about 750 mg of Compound 1 once daily.

207. The method of any one of paragraphs 202-205, wherein the dose comprises about 900 mg of Compound 1 once daily.

208. The method of any one of paragraphs 202-204, wherein the dose comprises about 1200 mg of Compound 1 once daily.

209. The method of any one of paragraphs 202-204, wherein the dose comprises about 1350, 1500, 1650, or 1800 mg of Compound 1 once daily.

210. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

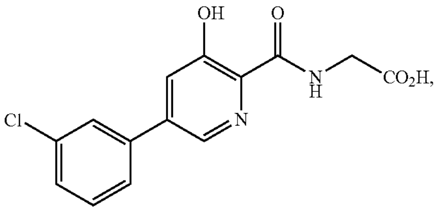

or a pharmaceutically acceptable salt, solvate, or hydrate thereof, wherein the dose comprises about 600-1200 mg, or about 600-1800 mg of Compound 1 three times weekly, and wherein anemia is anemia associated with or secondary to dialysis-dependent chronic kidney disease (DD-CKD).

211. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

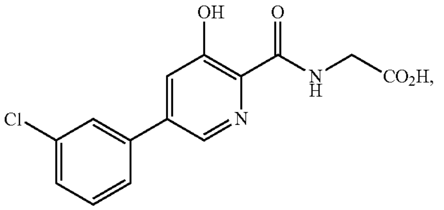

or a pharmaceutically acceptable salt, solvate, or hydrate thereof, wherein the dose comprises about 600 mg to about 1200 mg, or about 600 mg to about 1800 mg of Compound 1 three times weekly, wherein anemia is anemia associated with or secondary to dialysis-dependent chronic kidney disease (DD-CKD), and wherein the hemoglobin levels are increased to about at least 10 g/dL from a baseline hemoglobin level.

212. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

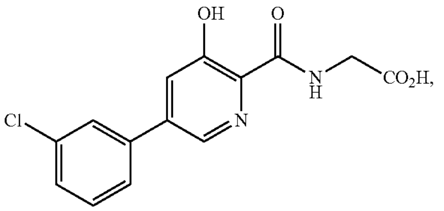

or a pharmaceutically acceptable salt, solvate, or hydrate thereof, wherein the dose comprises about 600 mg to about 1200 mg, or about 600 mg to about 1800 mg of Compound 1 three times weekly, wherein anemia is anemia associated with or secondary to dialysis-dependent chronic kidney disease (DD-CKD), and wherein the hemoglobin levels are maintained at about 10.0-13.0 g/dL.

213. The method of any one of paragraphs 210-212, wherein the dose comprises about 600 mg to about 900 mg of Compound 1 three times weekly.

214. The method of any one of paragraphs 210-212, wherein the dose comprises about 750 mg to about 1200 mg of Compound 1 three times weekly.

215. The method of any one of paragraphs 210-213, wherein the dose comprises about 600 mg of Compound 1 three times weekly.

216. The method of any one of paragraphs 210-214, wherein the dose comprises about 750 mg of Compound 1 three times weekly.

217. The method of any one of paragraphs 210-214, wherein the dose comprises about 900 mg of Compound 1 three times weekly.

218. The method of any one of paragraphs 210-212 and 214, wherein the dose comprises about 1200 mg of Compound 1 three times weekly.

219. The method of any one of paragraphs 210-212, wherein the dose comprises about 1350, 1500, 1650, or 1800 mg of Compound 1 three times weekly.

220. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

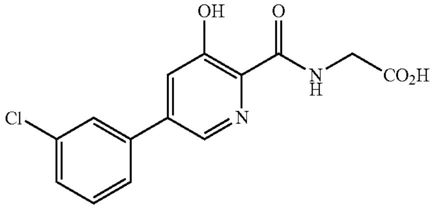

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, and wherein anemia is anemia associated with or secondary to dialysis-dependent chronic kidney disease (DD-CKD).

221. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

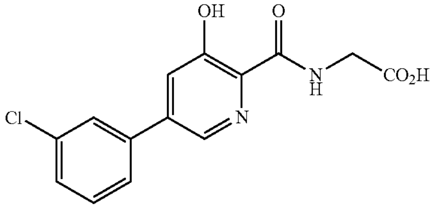

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein anemia is anemia associated with or secondary to dialysis-dependent chronic kidney disease (DD-CKD), and wherein the hemoglobin levels are increased to about at least 10 g/dL from a baseline hemoglobin level.

222. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

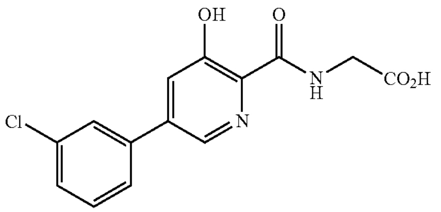

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein anemia is anemia associated with or secondary to dialysis-dependent chronic kidney disease (DD-CKD), and wherein the hemoglobin levels are maintained at about 10.0-13.0 g/dL.

223. The method of any one of paragraphs 220-222, wherein the dose comprises about 150 mg to about 600 mg three times weekly.

224. The method of any one of paragraphs 220-222, wherein the dose comprises about 600 mg to about 1200 mg three times weekly.

225. The method of any one of paragraphs 220-222, wherein the dose comprises about 750 mg to about 1200 mg three times weekly.

226. The method of any one of paragraphs 220-223, wherein the dose comprises about 150 mg three times weekly.

227. The method of any one of paragraphs 220-223, wherein the dose comprises about 300 mg three times weekly.

228. The method of any one of paragraphs 220-223, wherein the dose comprises about 450 mg three times weekly.

229. The method of any one of paragraphs 220-224, wherein the dose comprises about 600 mg three times weekly.

230. The method of any one of paragraphs 220-222 and 223-225, wherein the dose comprises about 750 mg three times weekly.

231. The method of any one of paragraphs 220-222 and 223-225, wherein the dose comprises about 900 mg three times weekly.

232. The method of any one of paragraphs 220-222 and 223-225, wherein the dose comprises about 1200 mg three times weekly.

233. The method of any one of paragraphs 220-222, wherein the dose comprises about 1350, 1500, 1650, or 1800 mg three times weekly.

234. The method of any one of paragraphs 220-233, wherein the previously-administered daily dose comprises about 150 mg of Compound 1.

235. The method of any one of paragraphs 220-233, wherein the previously-administered daily dose comprises about 300 mg of Compound 1.

236. The method of any one of paragraphs 220-233, wherein the previously-administered daily dose comprises about 450 mg of Compound 1.

237. The method of any one of paragraphs 220-233, wherein the previously-administered daily dose comprises about 600 mg of Compound 1.

238. The method of any one of paragraphs 204, 212, or 222, wherein the hemoglobin levels are maintained at about 10.0 g/dL to about 12.0 g/dL.

239. The method of any one of paragraphs 204, 212, or 222, wherein the hemoglobin levels are maintained at about 11.0 g/dL to about 13.0 g/dL.

240. The method of any one of paragraphs 238-239, wherein the hemoglobin levels are maintained at about 11.0 g/dL to about 12.0 g/dL.

241. The method of paragraph 238, wherein the hemoglobin levels are maintained at about 10.0 g/dL to about 11.0 g/dL.

242. The method of any one of paragraphs 202-241, wherein the dose is administered to the patient for at least about 12-260 weeks.

243. The method of paragraph 230, wherein the dose is administered to the patient for at least about 12 weeks, for at least about 24 weeks, for at least about 28 weeks, for at least about 32 weeks, for at least about 36 weeks, for at least about 40 weeks, for at least about 44 weeks, for at least about 48 weeks, for at least about 52 weeks, for at least about 64 weeks, for at least about 76 weeks, for at least about 88 weeks, for at least about 104 weeks, for at least about 116 weeks, for at least about 128 weeks, for at least about 140 weeks, for at least about 156 weeks, for at least about 168 weeks, for at least about 180 weeks, for at least about 192 weeks, for at least about 208 weeks, or for at least about 260 weeks.

244. The method of any one of paragraphs 202-243, wherein the patient previously has been treated with an erythropoiesis stimulating agent (ESA).

245. The method of paragraph 244, wherein the ESA is epoetin, darbepoetin alfa (DA), or methoxy polyethylene glycol-epoetin beta (epoetin beta pegol).

246. The method of paragraph 245, wherein the epoetin is epoetin alfa.

247. The method of paragraph 246, wherein the patient previously has been treated with epoetin alfa at a dose of about 10 U/kg of body weight to about 500 U/kg of body weight three times weekly.

248. The method of paragraph 247, wherein the patient previously has been treated with epoetin alfa at a dose of about 25 U/kg of body weight to about 300 U/kg of body weight three times weekly.

249. The method of paragraph 247 or 248, wherein the patient previously has been treated with epoetin alfa at a dose of about 50 U/kg of body weight to 200 U/kg of body weight three times weekly.

250. The method of paragraph 246, wherein the patient previously has been treated with about ≤90 U/kg/week epoetin alfa.

251. The method of paragraph 246, wherein the patient previously has been treated with about >90 U/kg/week to about <300 U/kg/week epoetin alfa, or wherein the patient previously has been treated with about ≥300 U/kg/week epoetin alfa, or wherein the patient previously has been treated with epoetin alfa at an amount of about 1,500 U/week to about 90,000 U/week.

252. The method of paragraph 251, wherein the patient previously has been treated with epoetin alfa at an amount of about 4,500 U/week.

253. The method of paragraph 245, wherein the ESA is darbepoetin alfa.

254. The method of paragraph 253, wherein the patient previously has been treated with DA at a dose of about 0.25 μg/kg of body weight to 0.75 μg/kg of body weight once weekly or once every two weeks.

255. The method of paragraph 254, wherein the patient previously has been treated with DA at a dose of about 0.45 μg/kg of body weight once weekly.

256. The method of paragraph 255, wherein the patient previously has been treated with DA at a dose of about 0.75 μg/kg of body weight once every two weeks.

257. The method of paragraph 254, wherein the patient previously has been treated with DA at an amount of about 6.25-200 μg/week.

258. The method of paragraph 254, wherein the patient previously has been treated with ≤0.45 μg/kg/week DA, or wherein the patient previously has been treated with >0.45 μg/kg/week and ≤1.5 μg/kg/week DA.

259. The method of paragraph 245, wherein the ESA is epoetin beta pegol.

260. The method of paragraph 259, wherein the patient previously has been treated with epoetin beta pegol at a dose of about 0.3 μg/kg of body weight to about 1.2 μg/kg of body weight once every two weeks or about 0.6 μg/kg of body weight to about 2.4 μg/kg of body weight once a month.

261. The method of paragraph 260, wherein the patient previously has been treated with epoetin beta pegol at a dose of about 0.6 μg/kg of body weight once every two weeks or about 1.2 μg/kg of body weight once a month.

262. The method of paragraph 261, wherein the patient previously has been treated with ≤250 μg/month epoetin beta pegol.

263. The method of any one of paragraphs 245-262, wherein the patient previously has been treated with an ESA for about ≥4 weeks.

264. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

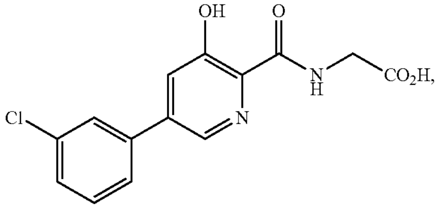

or a pharmaceutically acceptable salt, solvate, or hydrate thereof, wherein the dose comprises about 750-1200 mg, or about 750-1800 mg of Compound 1 once daily, wherein the patient was previously treated with an erythropoietin stimulating agent (ESA), and wherein anemia is anemia associated with or secondary to dialysis-dependent chronic kidney disease (DD-CKD).

265. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

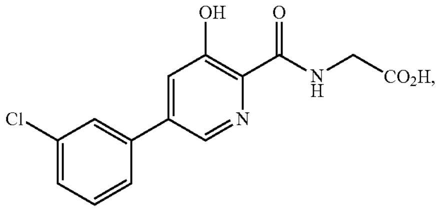

or a pharmaceutically acceptable salt, solvate, or hydrate thereof, wherein the dose comprises about 750 mg to about 1200 mg, or about 750 mg to about 1800 mg of Compound 1 once daily, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

266. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

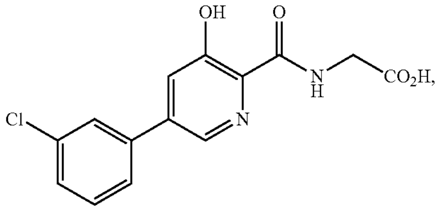

or a pharmaceutically acceptable salt, solvate, or hydrate thereof, wherein the dose comprises about 750 mg to about 1200 mg, or about 750 mg to about 1800 mg of Compound 1 once daily, wherein the patient was previously treated with an erythropoietin stimulating agent (ESA), wherein anemia is anemia associated with or secondary to dialysis-dependent chronic kidney disease (DD-CKD), and wherein the hemoglobin levels are maintained at about 10.0-13.0 g/dL.

267. The method of any one of paragraphs 264-266, wherein the dose comprises about 750 mg to about 900 mg of Compound 1 once daily.

268. The method of any one of paragraphs 264-267, wherein the dose comprises about 750 mg of Compound 1 once daily.
269. The method of any one of paragraphs 264-267, wherein the dose comprises about 900 mg of Compound 1 once daily.
270. The method of any one of paragraphs 264-266, wherein the dose comprises about 1200 mg of Compound 1 once daily.
271. The method of any one of paragraphs 264-266, wherein the dose comprises about 1350, 1500, 1650, or 1800 mg of Compound 1 once daily.
272. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

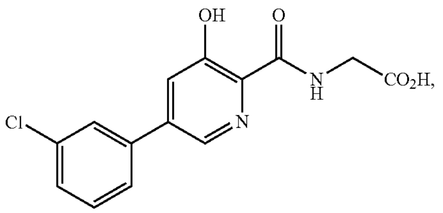

or a pharmaceutically acceptable salt, solvate, or hydrate thereof, wherein the dose comprises about 600-1200 mg, or about 600-1800 mg of Compound 1 three times weekly, wherein the patient was previously treated with an erythropoietin stimulating agent (ESA), and wherein anemia is anemia associated with or secondary to dialysis-dependent chronic kidney disease (DD-CKD).
273. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

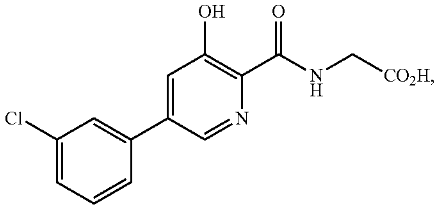

or a pharmaceutically acceptable salt, solvate, or hydrate thereof, wherein the dose comprises about 600 mg to about 1200 mg, or about 600 mg to about 1800 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.
274. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

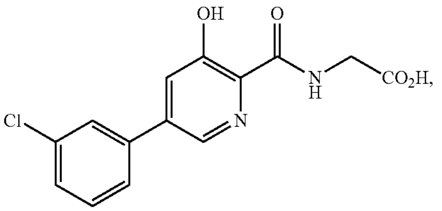

or a pharmaceutically acceptable salt, solvate, or hydrate thereof, wherein the dose comprises about 600 mg to about 1200 mg, or about 600 mg to about 1800 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels are maintained at about 10.0-13.0 g/dL.
275. The method of any one of paragraphs 272-274, wherein the dose comprises about 600 mg to about 900 mg of Compound 1 three times weekly.
276. The method of any one of paragraphs 272-274, wherein the dose comprises about 750 mg to about 1200 mg of Compound 1 three times weekly.
277. The method of any one of paragraphs 272-275, wherein the dose comprises about 600 mg of Compound 1 three times weekly.
278. The method of any one of paragraphs 272-276, wherein the dose comprises about 750 mg of Compound 1 three times weekly.
279. The method of any one of paragraphs 272-276, wherein the dose comprises about 900 mg of Compound 1 three times weekly.
280. The method of any one of paragraphs 272-274 and 276, wherein the dose comprises about 1200 mg of Compound 1 three times weekly.
281. The method of any one of paragraphs 272-274, wherein the dose comprises about 1350, 1500, 1650, or 1800 mg of Compound 1 three times weekly.
282. A method for treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

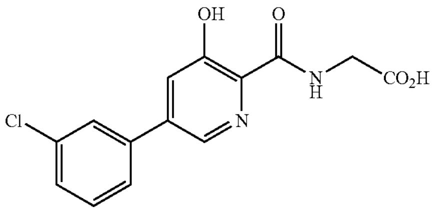

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein the patient was previously treated with an erythropoietin stimulating agent (ESA), and wherein anemia is anemia associated with or secondary to dialysis-dependent chronic kidney disease (DD-CKD).

283. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

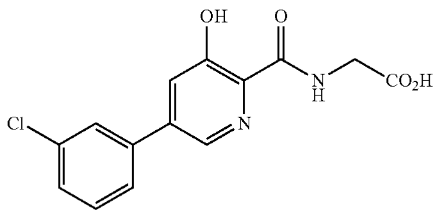

or a pharmaceutically acceptable salt, solvate, or hydrate thereof, wherein the dose comprises about 150-1200 mg, or about 150-1800 mg of the Compound 1 three times weekly, wherein the patient was previously administered a daily dose of Compound 1, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

284. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

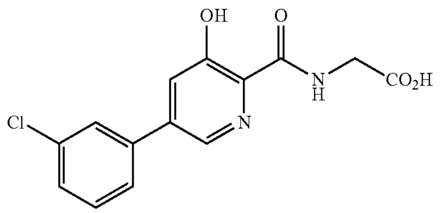

or a pharmaceutically acceptable salt, solvate, or hydrate thereof, wherein the dose comprises about 150 mg to about 1200 mg, or about 150 mg to about 1800 mg of the Compound 1 three times weekly, wherein the patient was previously administered a daily dose of Compound 1, wherein the patient was previously treated with an erythropoietin stimulating agent (ESA), wherein anemia is anemia associated with or secondary to dialysis-dependent chronic kidney disease (DD-CKD), and wherein the hemoglobin levels are maintained at about 10.0-13.0 g/dL.

285. The method of any one of paragraphs 282-284, wherein the dose comprises about 150 mg to about 600 mg three times weekly.

286. The method of any one of paragraphs 282-284, wherein the dose comprises about 600 mg to about 1200 mg three times weekly.

287. The method of any one of paragraphs 282-284, wherein the dose comprises about 750 mg to about 1200 mg three times weekly.

288. The method of any one of paragraphs 282-285, wherein the dose comprises about 150 mg three times weekly.

289. The method of any one of paragraphs 282-285, wherein the dose comprises about 300 mg three times weekly.

290. The method of any one of paragraphs 282-285, wherein the dose comprises about 450 mg three times weekly.

291. The method of any one of paragraphs 282-286, wherein the dose comprises about 600 mg three times weekly.

292. The method of any one of paragraphs 282-284 and 286-287, wherein the dose comprises about 750 mg three times weekly.

293. The method of any one of paragraphs 282-284 and 286-287, wherein the dose comprises about 900 mg three times weekly.

294. The method of any one of paragraphs 282-284 and 286-287, wherein the dose comprises about 1200 mg three times weekly.

295. The method of any one of paragraphs 282-284, wherein the dose comprises about 1350, 1500, 1650, or 1800 mg three times weekly.

296. The method of any one of paragraphs 282-295, wherein the previously-administered daily dose comprises about 150 mg of Compound 1.

297. The method of any one of paragraphs 282-295, wherein the previously-administered daily dose comprises about 300 mg of Compound 1.

298. The method of any one of paragraphs 282-295, wherein the previously-administered daily dose comprises about 450 mg of Compound 1.

299. The method of any one of paragraphs 282-295, wherein the previously-administered daily dose comprises about 600 mg of Compound 1.

300. The method of any one of paragraphs 266, 274, or 284, wherein the hemoglobin levels are maintained at about 10.0 g/dL to about 12.0 g/dL.

301. The method of any one of paragraphs 66 274, or 284, wherein the hemoglobin levels are maintained at about 11.0 g/dL to about 13.0 g/dL.

302. The method of any one of paragraphs 300-301, wherein the hemoglobin levels are maintained at about 11.0 g/dL to about 12.0 g/dL.

303. The method of paragraph 300, wherein the hemoglobin levels are maintained at about 10.0 g/dL to about 11.0 g/dL.

304. The method of any one of paragraphs 264-303, wherein the dose is administered to the patient for at least about 12-260 weeks.

305. The method of paragraph 304, wherein the dose is administered to the patient for at least about 12 weeks, for at least about 24 weeks, for at least about 28 weeks, for at least about 32 weeks, for at least about 36 weeks, for at least about 40 weeks, for at least about 44 weeks, for at least about 48 weeks, for at least about 52 weeks, for at least about 64 weeks, for at least about 76 weeks, for at least about 88 weeks, for at least about 104 weeks, for at least about 116 weeks, for at least about 128 weeks, for at least about 140 weeks, for at least about 156 weeks, for at least about 168 weeks, for at least about 180 weeks, for at least about 192 weeks, for at least about 208 weeks, or for at least about 260 weeks.

306. The method of any one of paragraphs 264-305, wherein the patient previously has been treated with an erythropoiesis stimulating agent (ESA) that comprises epoetin, darbepoetin alfa (DA), or methoxy polyethylene glycol-epoetin beta (epoetin beta pegol).

307. The method of paragraph 306, wherein the epoetin is epoetin alfa.

308. The method of paragraph 307, wherein the patient previously has been treated with epoetin alfa at a dose of about 10 U/kg of body weight to about 500 U/kg of body weight three times weekly.

309. The method of paragraph 308, wherein the patient previously has been treated with epoetin alfa at a dose of about 25 U/kg of body weight to about 300 U/kg of body weight three times weekly.

310. The method of paragraph 308 or 309, wherein the patient previously has been treated with epoetin alfa at a dose of about 50 U/kg of body weight to 200 U/kg of body weight three times weekly.

311. The method of paragraph 307, wherein the patient previously has been treated with about ≤90 U/kg/week epoetin alfa.

312. The method of paragraph 307, wherein the patient previously has been treated with about >90 U/kg/week to about <300 U/kg/week epoetin alfa, or wherein the patient previously has been treated with about ≥300 U/kg/week epoetin alfa, or wherein the patient previously has been treated with epoetin alfa at an amount of about 1,500 U/week to about 90,000 U/week.

313. The method of paragraph 312, wherein the patient previously has been treated with epoetin alfa at an amount of about 4,500 U/week.

314. The method of paragraph 306, wherein the ESA is darbepoetin alfa.

315. The method of paragraph 314, wherein the patient previously has been treated with DA at a dose of about 0.25 μg/kg of body weight to 0.75 μg/kg of body weight once weekly or once every two weeks.

316. The method of paragraph 315, wherein the patient previously has been treated with DA at a dose of about 0.45 μg/kg of body weight once weekly.

317. The method of paragraph 315, wherein the patient previously has been treated with DA at a dose of about 0.75 μg/kg of body weight once every two weeks.

318. The method of paragraph 314, wherein the patient previously has been treated with DA at an amount of about 6.25-200 μg/week.

319. The method of paragraph 314, wherein the patient previously has been treated with ≤0.45 μg/kg/week DA, or wherein the patient previously has been treated with >0.45 μg/kg/week and ≤1.5 μg/kg/week DA.

320. The method of paragraph 306, wherein the ESA is epoetin beta pegol.

321. The method of paragraph 320, wherein the patient previously has been treated with epoetin beta pegol at a dose of about 0.3 μg/kg of body weight to about 1.2 μg/kg of body weight once every two weeks or about 0.6 μg/kg of body weight to about 2.4 μg/kg of body weight once a month.

322. The method of paragraph 321, wherein the patient previously has been treated with epoetin beta pegol at a dose of about 0.6 μg/kg of body weight once every two weeks or about 1.2 μg/kg of body weight once a month.

323. The method of paragraph 320, wherein the patient previously has been treated with ≤250 μg/month epoetin beta pegol.

324. The method of any one of paragraphs 264-323, wherein the patient previously has been treated with an ESA for about ≥4 weeks.

325. A method of treating anemia, comprising administering to a patient having anemia a starting dose of a compound that is {[5-(3-chlorophenyl)-3-hydroxypyridine-2-carbonyl]amino}acetic acid having the structure of Compound 1, (Compound 1)

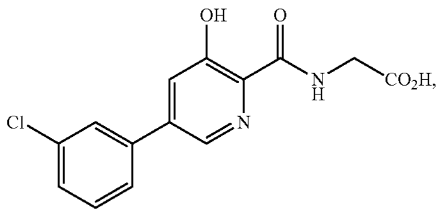

or a pharmaceutically acceptable salt, solvate, or hydrate thereof, wherein the starting dose comprises about 750 mg to about 1200 mg or about 750 mg to about 1800 mg of Compound 1 once daily, or about 600 mg to about 1200 mg or about 600 mg to about 1800 mg of Compound 1 three times weekly; and adjusting the dose by about 150 mg to about 300 mg of Compound 1 if the patient has a hemoglobin level of <10.0 g/dL or >11.0 g/dL following administration of the starting dose.

326. The method of paragraph 325, wherein adjusting comprises adjusting the dose by about 150 mg of Compound 1 if the patient has a hemoglobin level of <10.0 g/dL or >11.0 g/dL following administration of the starting dose.

327. The method of paragraph 325, wherein adjusting comprises adjusting the dose by about 300 mg of Compound 1 if the patient has a hemoglobin level of <10.0 g/dL or >11.0 g/dL following administration of the starting dose.

328. The method of paragraph 325, wherein adjusting comprises increasing the dose by about 150 mg of Compound 1 if the patient has a hemoglobin level of <10.0 g/dL following administration of the starting dose.

329. The method of paragraph 325, wherein adjusting comprises increasing the dose by about 300 mg of Compound 1 if the patient has a hemoglobin level of <10.0 g/dL following administration of the starting dose.

330. The method of paragraph 325, wherein adjusting comprises decreasing the dose by about 150 mg of Compound 1 if the patient has a hemoglobin level of >11.0 g/dL following administration of the starting dose.

331. The method of paragraph 325, wherein adjusting comprises decreasing the dose by about 300 mg of Compound 1 if the patient has a hemoglobin level of >11.0 g/dL following administration of the starting dose.

332. A method of treating anemia, comprising administering to a patient having anemia a starting dose of a compound that is {[5-(3-chlorophenyl)-3-hydroxypyridine-2-carbonyl]amino}acetic acid having the structure of Compound 1, (Compound 1)

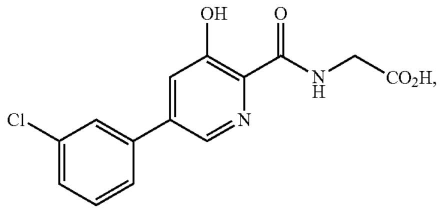

or a pharmaceutically acceptable salt, solvate, or hydrate thereof, wherein the starting dose comprises about 750 mg to about 1200 mg or about 750 mg to about 1800 mg of Compound 1 once daily, or about 600-1200 mg or about 600-1800 mg three times weekly, and decreasing the starting dose by 150-300 mg of Compound 1 if the patient's hemoglobin level increases by >1.0 g/dL within a 2-week period.

333. The method of paragraph 332, further comprises decreasing the dose by about 150 mg of Compound 1 if the patient's hemoglobin level increases by >1.0 g/dL within a 2-week period.

334. The method of paragraph 332, further comprises decreasing the dose by about 300 mg of Compound 1 if the patient's hemoglobin level increases by >1.0 g/dL within a 2-week period.

335. The method of any one of paragraphs 325-334, wherein the starting dose comprises about 750 mg to about 1200 mg of Compound 1 once daily.

336. The method of paragraph 335, wherein the starting dose comprises about 750 mg of Compound 1 once daily.

337. The method of paragraph 336, wherein the starting dose comprises about 900 mg of Compound 1 once daily.

338. The method of any one of paragraphs 325-335, wherein the starting dose comprises about 600 mg to about 1200 mg of Compound 1 three times weekly.

339. The method of paragraph 338, wherein the starting dose comprises about 600 mg of Compound 1 three times weekly.

340. The method of paragraph 338, wherein the starting dose comprises about 750 mg of Compound 1 three times weekly.

341. The method of paragraph 339, wherein the starting dose comprises about 900 mg of Compound 1 three times weekly.

342. The method of any one of paragraphs 325-341, wherein the starting dose is administered to the patient for about ≥4 weeks.

343. The method of any one of paragraphs 325-342, wherein anemia is anemia associated with or secondary to chronic kidney disease (CKD).

344. The method of paragraph 343, wherein chronic kidney disease is dialysis-dependent chronic kidney disease (DD-CKD).

345. The method of any one of paragraphs 325-344, wherein the patient previously has been treated with an erythropoiesis stimulating agent (ESA).

346. The method of paragraph 345, wherein the ESA is epoetin, darbepoetin alfa (DA), or methoxy polyethylene glycol-epoetin beta (epoetin beta pegol).

347. The method of paragraph 346, wherein the epoetin is epoetin alfa.

348. The method of paragraph 347, wherein the patient previously has been treated with epoetin alfa at a dose of about 10 U/kg of body weight to about 500 U/kg of body weight three times weekly.

349. The method of paragraph 348, wherein the patient previously has been treated with epoetin alfa at a dose of about 25 U/kg of body weight to about 300 U/kg of body weight three times weekly.

350. The method of paragraph 348 or 349, wherein the patient previously has been treated with epoetin alfa at a dose of about 50 U/kg of body weight to 200 U/kg of body weight three times weekly.

351. The method of paragraph 347, wherein the patient previously has been treated with about ≤90 U/kg/week epoetin alfa.

352. The method of paragraph 347, wherein the patient previously has been treated with about >90 U/kg/week to about <300 U/kg/week epoetin alfa, or wherein the patient previously has been treated with about ≥300 U/kg/week epoetin alfa, or wherein the patient previously has been treated with epoetin alfa at an amount of about 1,500 U/week to about 90,000 U/week.

353. The method of paragraph 347, wherein the patient previously has been treated with epoetin alfa at an amount of about 4,500 U/week.

354. The method of paragraph 346, wherein the ESA is darbepoetin alfa.

355. The method of paragraph 354, wherein the patient previously has been treated with DA at a dose of about 0.25 μg/kg of body weight to 0.75 μg/kg of body weight once weekly or once every two weeks.

356. The method of paragraph 355, wherein the patient previously has been treated with DA at a dose of about 0.45 μg/kg of body weight once weekly.

357. The method of paragraph 355, wherein the patient previously has been treated with DA at a dose of about 0.75 μg/kg of body weight once every two weeks.

358. The method of paragraph 354, wherein the patient previously has been treated with DA at an amount of about 6.25-200 μg/week.

359. The method of paragraph 354, wherein the patient previously has been treated with ≤0.45 μg/kg/week DA, or wherein the patient previously has been treated with >0.45 μg/kg/week and ≤1.5 μg/kg/week DA.

360. The method of paragraph 346, wherein the ESA is epoetin beta pegol.

361. The method of paragraph 360, wherein the patient previously has been treated with epoetin beta pegol at a dose of about 0.3 μg/kg of body weight to about 1.2 μg/kg of body weight once every two weeks or about 0.6 μg/kg of body weight to about 2.4 μg/kg of body weight once a month.

362. The method of paragraph 361, wherein the patient previously has been treated with epoetin beta pegol at a dose of about 0.6 μg/kg of body weight once every two weeks or about 1.2 μg/kg of body weight once a month.

363. The method of paragraph 360, wherein the patient previously has been treated with ≤250 μg/month epoetin beta pegol.

364. The method of any one of paragraphs 345-363, wherein the patient previously has been treated with an ESA for about ≥4 weeks.

365. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

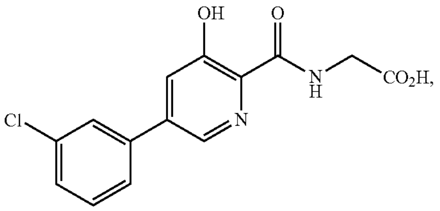

or a pharmaceutically acceptable salt, solvate, or hydrate thereof, wherein the dose comprises about 750 mg of Compound 1 once daily, wherein the patient was previously treated with an erythropoietin stimulating agent (ESA), and wherein anemia is anemia associated with or secondary to dialysis-dependent chronic kidney disease (DD-CKD).

366. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

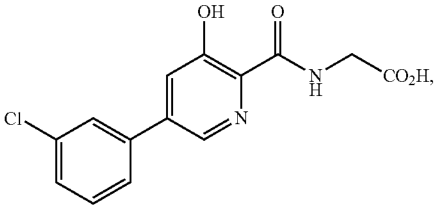

or a pharmaceutically acceptable salt, solvate, or hydrate thereof, wherein the dose comprises about 750 mg of Compound 1 once daily, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

367. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

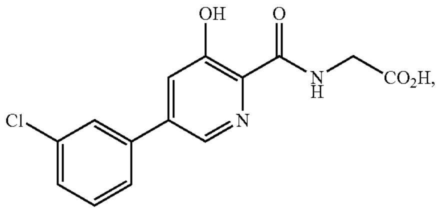

or a pharmaceutically acceptable salt, solvate, or hydrate thereof, wherein the dose comprises about 750 mg of Compound 1 once daily, wherein the patient was previously treated with an erythropoietin stimulating agent (ESA), wherein anemia is anemia associated with or secondary to dialysis-dependent chronic kidney disease (DD-CKD), and wherein the hemoglobin levels maintained at about 10.0-13.0 g/dL.

368. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

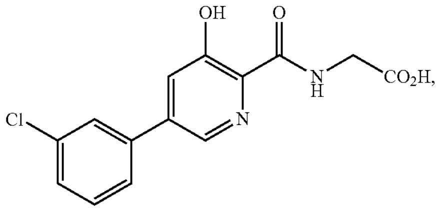

or a pharmaceutically acceptable salt, solvate, or hydrate thereof, wherein the dose comprises about 900 mg of Compound 1 once daily, wherein the patient was previously treated with an erythropoietin stimulating agent (ESA), wherein anemia is anemia associated with or secondary to dialysis-dependent chronic kidney disease (DD-CKD).

369. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

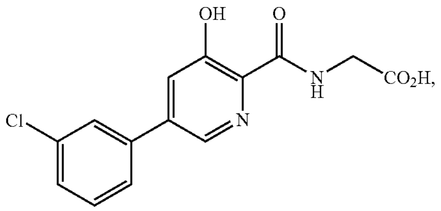

or a pharmaceutically acceptable salt, solvate, or hydrate thereof, wherein the dose comprises about 900 mg of Compound 1 once daily, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

370. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

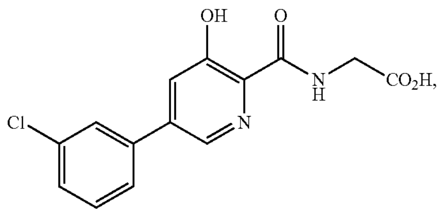

or a pharmaceutically acceptable salt, solvate, or hydrate thereof, wherein the dose comprises about 900 mg of Compound 1 once daily, wherein the patient was previously treated with an erythropoietin stimulating agent (ESA), wherein anemia is anemia associated with or secondary to dialysis-dependent chronic kidney disease (DD-CKD), and wherein the hemoglobin levels maintained at about 10.0-13.0 g/dL.

371. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

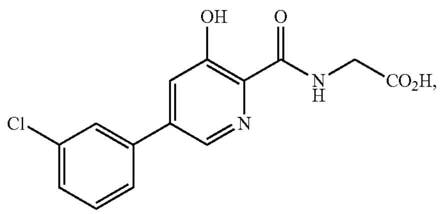

or a pharmaceutically acceptable salt, solvate, or hydrate thereof, wherein the dose comprises about 600 mg of Compound 1 three times weekly, wherein the patient was previously treated with an erythropoietin stimulating agent (ESA), wherein anemia is anemia associated with or secondary to dialysis-dependent chronic kidney disease (DD-CKD).

372. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

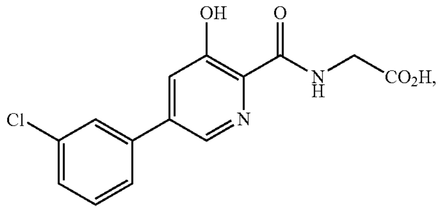

or a pharmaceutically acceptable salt, solvate, or hydrate thereof, wherein the dose comprises about 600 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

373. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

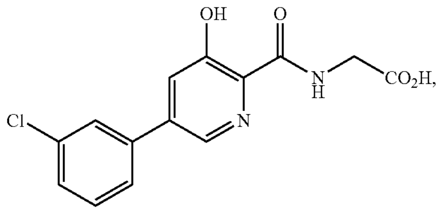

or a pharmaceutically acceptable salt, solvate, or hydrate thereof, wherein the dose comprises about 600 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels maintained at about 10.0-13.0 g/dL.

374. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

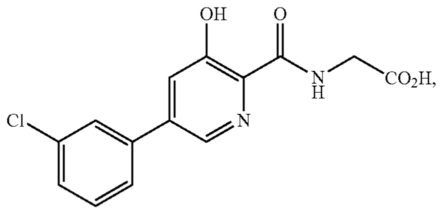

or a pharmaceutically acceptable salt, solvate, or hydrate thereof, wherein the dose comprises about 750 mg of Compound 1 three times weekly, wherein the patient was previously treated with an erythropoietin stimulating agent (ESA), wherein anemia is anemia associated with or secondary to dialysis-dependent chronic kidney disease (DD-CKD).

375. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

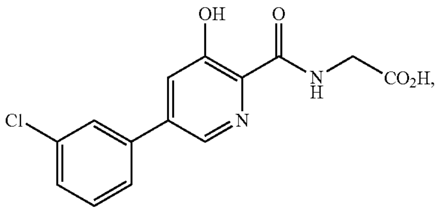

or a pharmaceutically acceptable salt, solvate, or hydrate thereof, wherein the dose comprises about 750 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

376. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

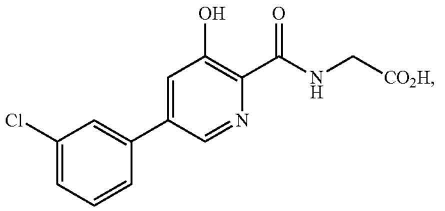

or a pharmaceutically acceptable salt, solvate, or hydrate thereof, wherein the dose comprises about 750 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels maintained at about 10.0-13.0 g/dL 377. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

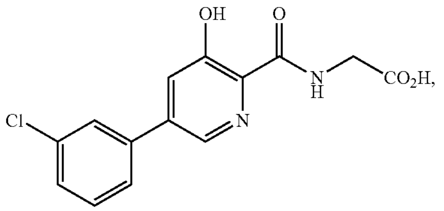

or a pharmaceutically acceptable salt, solvate, or hydrate thereof, wherein the dose comprises about 900 mg of Compound 1 three times weekly, wherein the patient was previously treated with an erythropoietin stimulating agent (ESA), wherein anemia is anemia associated with or secondary to dialysis-dependent chronic kidney disease (DD-CKD).

378. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

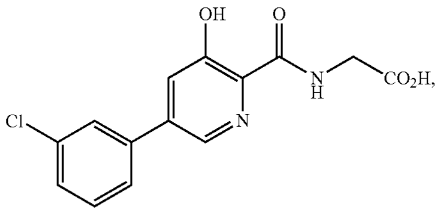

or a pharmaceutically acceptable salt, solvate, or hydrate thereof, wherein the dose comprises about 900 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

379. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

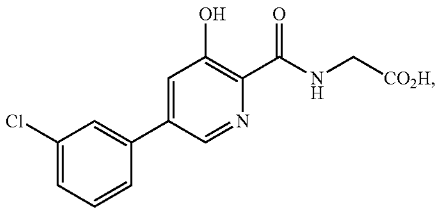

or a pharmaceutically acceptable salt, solvate, or hydrate thereof, wherein the dose comprises about 900 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels maintained at about 10.0-13.0 g/dL 380. A method of treating anemia, comprising administering to a patient having anemia a dose of a compound that is {[5-(3-chlorophenyl)-3-hydroxypyridine-2-carbonyl]amino}acetic acid having the structure of Compound 1, (Compound 1)

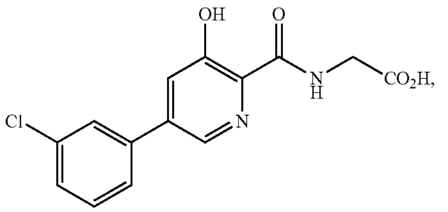

or a pharmaceutically acceptable salt, solvate, or hydrate thereof, wherein the dose comprises about 1200 mg of Compound 1 three times weekly, wherein the patient was previously treated with an erythropoietin stimulating agent (ESA), wherein anemia is anemia associated with or secondary to dialysis-dependent chronic kidney disease (DD-CKD).

381. A method of increasing hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

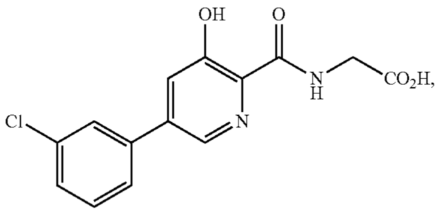

or a pharmaceutically acceptable salt, solvate, or hydrate thereof, wherein the dose comprises about 1200 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels are increased to about at least 10 g/dL from a baseline hemoglobin level.

382. A method of maintaining hemoglobin levels in a patient having anemia, comprising administering to the patient a dose of a compound that is {[5-(3-chlorophenyl)-3-hydroxypyridine-2-carbonyl]amino}acetic acid having the structure of Compound 1, (Compound 1)

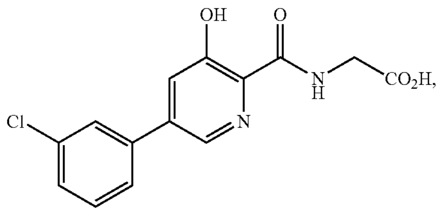

or a pharmaceutically acceptable salt, solvate, or hydrate thereof, wherein the dose comprises about 1200 mg of Compound 1 three times weekly, wherein the patient was previously treated with an erythropoietin stimulating agent (ESA), wherein anemia is anemia associated with or secondary to dialysis-dependent chronic kidney disease (DD-CKD), and wherein the hemoglobin levels maintained at about 10.0-13.0 g/dL

What is claimed is:

1. A method of treating anemia, comprising administering to a patient having anemia a dose of a compound that is {[5-(3-chlorophenyl)-3-hydroxypyridine-2-carbonyl] amino}acetic acid having the structure of Compound 1, (Compound 1)

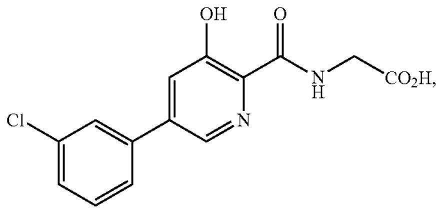

or a pharmaceutically acceptable salt, solvate, or hydrate thereof, wherein the dose comprises about 750 mg to about 1800 mg of Compound 1 three times weekly.

2. The method according to claim 1, wherein the hemoglobin levels are increased to about at least 10 g/dL from a baseline hemoglobin level.

3. The method according to claim 1, wherein the hemoglobin levels are maintained at about 10.0 g/dL to about 13.0 g/dL.

4. The method of claim 1, wherein the patient has anemia secondary to or associated with chronic kidney disease (CKD).

5. The method of claim 4, wherein the CKD is dialysis-dependent CKD (DD-CKD).

6. The method of claim 1, wherein the patient previously has been treated with an erythropoietin stimulating agent (ESA), wherein the ESA is epoetin, darbepoetin alfa (DA), or methoxy polyethylene glycol-epoetin beta (epoetin beta pegol).

7. The method of claim 1, wherein hemoglobin levels are maintained at about 10.0 g/dL to about 12.0 g/dL, or the hemoglobin levels are maintained at about 11.0 g/dL to about 13.0 g/dL.

8. The method of claim 7, wherein the hemoglobin levels are maintained at about 11.0 g/dL to about 12.0 g/dL, or the hemoglobin levels are maintained at about 10.0 g/dL to about 11.0 g/dL.

9. The method of claim 8, wherein the dose is administered to the patient for at least about 12-260 weeks.

10. The method of claim 9, wherein the dose is administered to the patient for at least about 12 weeks, for at least about 24 weeks, for at least about 28 weeks, for at least about 32 weeks, for at least about 36 weeks, for at least about 40 weeks, for at least about 44 weeks, for at least about 48 weeks, for at least about 52 weeks, for at least about 64 weeks, for at least about 76 weeks, for at least about 88 weeks, for at least about 104 weeks, for at least about 116 weeks, for at least about 128 weeks, for at least about 140 weeks, for at least about 156 weeks, for at least about 168 weeks, for at least about 180 weeks, for at least about 192 weeks, for at least about 208 weeks, or for at least about 260 weeks.

11. The method of claim 1, wherein the dose comprises about 750 mg to about 1200 mg of Compound 1 three times weekly.

12. The method of claim 1, wherein the dose comprises about 750, 900, 1200, 1350, 1500, 1650, or 1800 mg of Compound 1 three times weekly.

13. The method of claim 4, wherein the CKD is non-dialysis dependent CKD (NDD-CKD).

14. A method of treating anemia, comprising administering to a patient having anemia a dose of a compound that is {[5-(3-chlorophenyl)-3-hydroxypyridine-2-carbonyl] amino}acetic acid having the structure of Compound 1, (Compound 1)

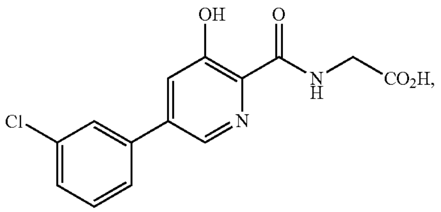

or a pharmaceutically acceptable salt, solvate, or hydrate thereof, for at least about 12 to about 260 weeks, wherein the dose comprises about 750 mg-1800 mg of Compound 1 three times weekly.

15. The method of claim 14, wherein the hemoglobin levels are increased to about at least 10 g/dL from a baseline hemoglobin level.

16. The method of claim 15, wherein the hemoglobin levels are maintained at about 10.0-13.0 g/dL.

17. The method of claim 14, wherein the dose comprises about 750-1200 mg of Compound 1 three times weekly.

18. A method of treating anemia, comprising administering to a patient having anemia a dose of a compound that is {[5-(3-chlorophenyl)-3-hydroxypyridine-2-carbonyl] amino}acetic acid having the structure of Compound 1, (Compound 1)

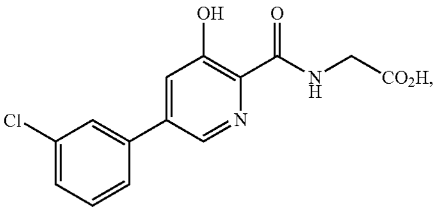

or a pharmaceutically acceptable salt, solvate, or hydrate thereof, wherein the dose comprises about 750 mg-1800 mg of Compound 1 three times weekly, wherein the patient was previously treated with an erythropoietin stimulating agent (ESA), and wherein anemia is anemia associated with or secondary to dialysis-dependent chronic kidney disease (DD-CKD).

19. The method of claim 18, wherein the hemoglobin levels are increased to about at least 10 g/dL from a baseline hemoglobin level.

20. The method of claim 19, wherein hemoglobin levels are maintained at about 10.0-13.0 g/dL.

21. The method of claim 18, wherein the dose comprises about 750-1200 mg of Compound 1 three times weekly.

* * * * *